US006916643B2

(12) United States Patent
Neelam et al.

(10) Patent No.: US 6,916,643 B2
(45) Date of Patent: Jul. 12, 2005

(54) ISOLATED HUMAN KINASE PROTEINS, NUCLEIC ACID MOLECULES ENCODING HUMAN KINASE PROTEINS, AND USES THEREOF

(75) Inventors: Beena Neelam, Gaithersburg, MD (US); Xianghe Yan, Gaithersburg, MD (US); Chunhua Yan, Boyds, MD (US)

(73) Assignee: Applera Corporation, Norwalk, CT (US)

( * ) Notice: Subject to any disclaimer, the term of this patent is extended or adjusted under 35 U.S.C. 154(b) by 131 days.

(21) Appl. No.: 10/427,923

(22) Filed: May 2, 2003

(65) Prior Publication Data

US 2003/0207311 A1 Nov. 6, 2003

Related U.S. Application Data

(60) Provisional application No. 60/377,592, filed on May 6, 2002.

(51) Int. Cl.[7] ............................ C12N 9/12; C12N 1/20; C12N 15/00; C12N 5/00; C07H 21/04

(52) U.S. Cl. ................. 435/194; 435/252.3; 435/320.1; 435/325; 435/6; 536/23.2

(58) Field of Search ............................. 435/194, 252.3, 435/325, 320.1, 6; 536/23.2

(56) References Cited

PUBLICATIONS

Sulston et al. "Toward a Complete Human Genome Sequence." The Sanger Centre and the Wasing University Genome Sequencing Center. Genome Research. Nov. 1998, vol. 8, No. 11, pp. 1097–1108.

Rappold G.A. "*H.sapiens* mRNA for Protein Kinase PKX1." Database Genecore on STN, AN X85545. Institute of Human Genetics. Jun. 5, 1997.

Klink et al. "The Human Protein Kinase Gene PKX1 on Xp22.3 Displays Xp/Yp Homology and is a Site of Chromosomal Instability." Database Genecore on STN, AN P51817. Human Mol. Genet. 1995, 4:869–878.

Li et al. "PRKX, A Phylogenetically and Functionally Distinct cAMP–Dependant Protein Kinase, Activities Renal Epithelial Cell Migration and Morphogenesis." Proc Natl Acad Sci USA. Jul. 9, 2002, vol. 99, No. 14, pp. 9260–9265.

Ausubel et al. "Short Protocols in Molecular Biology." 3rd Edition, Wiley & Sons Inc. 1995.

International Search report dated Nov. 6, 2003.

Results of BLAST Search of SEQ ID No:2 against Derwent (FastAlertP and GENESEQP) and NCBI (pataa) protein patent databases on Sep. 8, 2004 (13 pages).

*Primary Examiner*—Maryam Monshipouri
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

16 Claims, 56 Drawing Sheets

```
  1 ATGGAGGCGC CCGGGCTGGC CCAGGCGGCC GCGGCGGAGA GCGACTCCCG
 51 CAAGGTGGCG GAGGAGACCC CCGACGGGGC GCCCGCGCTC TGCCCCAGCC
101 CTGAGGCGCT GTCGCCGGAG CCGCCTGTGT ACAGCCTGCA GGACTTTGAC
151 ACGCTGGCCA CCGTGGGCAC TGGGACGTTC GGGCGGGTGC ACCTGGTGAA
201 GGAGAAGACA GCCAAGCATT TCTTCGCCCT CAAGGTGATG AGCATTCCCG
251 ACGTCATCCG CCTAAAGCAG GAGCAACACG TACACAATGA GAAGTCTGTC
301 CTGAAGGAAG TCAGCCACCC GTTCCTCATC AGGCTGTTCT GGACGTGGCA
351 TGACGAGCGC TTCCTCTACA TGCTCATGGA GTACGTGCCG GGCGGCGAGC
401 TCTTCAGCTA CCTGCGCAAC CGGGGGCGCT TCTCCAGCAC CACGGGGCTC
451 TTCTACTCTG CAGAGATCAT CTGTGCCATC GAGTACCTGC ACTCCAAAGA
501 GATCGTCTAC AGGGACTTGA AGCCAGAGAA CATCCTGCTG GATAGGGATG
551 GCCACATTAA GCTCACGGAC TTTGGGTTCG CCAAGAAGCT GGTAGACAGG
601 TTTCCTCCGT TTTTTGATGA CAACCCGTTT GGCATTTATC AGAAAATTCT
651 TGCAGGCAAA ATAGATTTCC CCAGACATTT GGATTTCCAT GTAAAAGACC
701 TCATTAAGAA ACTGCTCGTG GTTGACAGAA CAAGGCGATT AGGAAACATG
751 AAGAACGGGG CGAATGATGT GAAGCATCAT CGGTGGTTCC GCTCCGTGGA
801 CTGGGAAGCT GTTCCGCAGA GAAAACTGAA GCCTCCCATC GTGCCCAAGA
851 TAGCTGGTGA CGGCGACACT TCCAACTTCG AAACTTACCC TGAGAATGAC
901 TGGGACACAG CCGCGCCCGT GCCGCAGAAG GATTTAGAAA TCTTCAAGAA
951 TTTCTGA   (SEQ ID NO:1)
```

FEATURES:
Start Codon: 1
Stop Codon: 955

Homologous proteins:
Top 10 BLAST Hits

| | Score | E |
|---|---|---|
| CRA\|18000005009324 /altid=gi\|4826948 /def=ref\|NP_005035.1\| (NM_... | 645 | 0.0 |
| CRA\|60000046840853 /altid=gi\|13905166 /def=gb\|AAH06875.1\|AAH068... | 469 | e-131 |
| CRA\|1000682331899 /altid=gi\|6010221 /def=emb\|CAB57279.1\| (AJ238... | 459 | e-128 |
| CRA\|18000005121587 /altid=gi\|10835065 /def=ref\|NP_002751.1\| (NM... | 418 | e-115 |
| CRA\|222000008308820 /altid=gi\|17737603 /def=ref\|NP_524097.1\| (N... | 347 | 3e-94 |
| CRA\|222000011473317 /altid=gi\|18602357 /def=ref\|XP_090978.1\| (X... | 311 | 3e-83 |
| CRA\|222000011471094 /altid=gi\|18602355 /def=ref\|XP_090977.1\| (X... | 305 | 2e-81 |

Blast hits to dbEST:

| CRA Number | gi Number | Score | Expect |
|---|---|---|---|
| CRA\|1000492598774 | gi\|5674073 | 1102 bits (556) | 0.0 |
| CRA\|1000693107729 | gi\|6658851 | 1100 bits (555) | 0.0 |
| CRA\|335001036957930 | gi\|10036298 | 1084 bits (547) | 0.0 |
| CRA\|44000020408659 | gi\|7040833 | 1057 bits (533) | 0.0 |
| CRA\|3000000984691 | gi\|2437086 | 1055 bits (532) | 0.0 |
| CRA\|157000140853372 | gi\|13451463 | 783 bits (395) | 0.0 |
| CRA\|3000001205919 | gi\|3231096 | 674 bits (340) | 0.0 |
| CRA\|1000480886357 | gi\|3872449 | 640 bits (323) | 0.0 |
| CRA\|116000043583132 | gi\|11446247 | 636 bits (321) | 1e-180 |
| CRA\|1000483333637 | gi\|4260790 | 630 bits (318) | 1e-178 |
| CRA\|113000119346682 | gi\|14407823 | 571 bits (288) | 1e-160 |
| CRA\|223000024525471 | gi\|19184248 | 527 bits (266) | 1e-147 |
| CRA\|157000141183110 | gi\|13466408 | 486 bits (245) | 1e-135 |
| CRA\|1000480173836 | gi\|3770530 | 462 bits (233) | 1e-127 |
| CRA\|117000088061231 | gi\|12412029 | 410 bits (207) | 1e-112 |
| CRA\|1000480032287 | gi\|3753457 | 387 bits (195) | 1e-105 |
| CRA\|45000033602934 | gi\|8263238 | 339 bits (171) | 1e-90 |

FIGURE 1A

EXPRESSION INFORMATION FOR MODULATORY USE:

library source:

| gi Number | Organ | Tissue Type |
|---|---|---|
| gi\|5674073 | lung | squamous cell carcinoma, poorly differentiated (4 pooled tumors, including primary and metastatic) |
| gi\|6658851 | kidney | (none) |
| gi\|10036298 | (none) | B-cell, chronic lymphotic leukemia |
| gi\|7040833 | kidney | 2 pooled tumors (clear cell type) |
| gi\|2437086 | (none) | breast |
| gi\|13451463 | lung | large cell carcinoma |
| gi\|3231096 | (none) | (none) |
| gi\|3872449 | kidney | (none) |
| gi\|11446247 | ovary | fibrotheoma |
| gi\|4260790 | brain | anaplastic oligodendroglioma |
| gi\|14407823 | head_normal | (none) |
| gi\|19184248 | Stomach | Stomach\|7 |
| gi\|13466408 | testis | embryonal carcinoma |
| gi\|3770530 | (none) | (none) |
| gi\|12412029 | lymph | lymphoma, cell line |
| gi\|3753457 | (none) | (none) |
| gi\|8263238 | breast_normal | (none) |

FIGURE 1B

```
  1 MEAPGLAQAA AAESDSRKVA EETPDGAPAL CPSPEALSPE PPVYSLQDFD
 51 TLATVGTGTF GRVHLVKEKT AKHFFALKVM SIPDVIRLKQ EQHVHNEKSV
101 LKEVSHPFLI RLFWTWHDER FLYMLMEYVP GGELFSYLRN RGRFSSTTGL
151 FYSAEIICAI EYLHSKEIVY RDLKPENILL DRDGHIKLTD FGFAKKLVDR
201 FPPFFDDNPF GIYQKILAGK IDFPRHLDFH VKDLIKKLLV VDRTRRLGNM
251 KNGANDVKHH RWFRSVDWEA VPQRKLKPPI VPKIAGDGDT SNFETYPEND
301 WDTAAPVPQK DLEIFKNF . (SEQ ID NO:2)
```

FEATURES:

Functional domains and key regions:

Prosite results:

PDOC00005 PS00005 PKC_PHOSPHO_SITE
Protein kinase C phosphorylation site
Number of matches: 3

| | | |
|---|---|---|
| 1 | 16-18 | SRK |
| 2 | 70-72 | TAK |
| 3 | 244-246 | TRR |

PDOC00006 PS00006 CK2_PHOSPHO_SITE
Casein kinase II phosphorylation site
Number of matches: 5

| | | |
|---|---|---|
| 1 | 45-48 | SLQD |
| 2 | 81-84 | SIPD |
| 3 | 115-118 | TWHD |
| 4 | 291-294 | SNFE |
| 5 | 295-298 | TYPE |

PDOC00008 PS00008 MYRISTYL
N-myristoylation site
Number of matches: 3

| | | |
|---|---|---|
| 1 | 5-10 | GLAQAA |
| 2 | 149-154 | GLFYSA |
| 3 | 248-253 | GNMKNG |

PDOC00100 PS00107 PROTEIN_KINASE_ATP
Protein kinases ATP-binding region signature
55-78 VGTGTFGRVHLVKEKTAKHFFALK PDOC00100 PS00108 PROTEIN_KINASE_ST
Serine/Threonine protein kinases active-site signature
168-180 IVYRDLKPENILL Membrane spanning structure and domains:

| Helix | Begin | End | Score | Certainty |
|---|---|---|---|---|
| 1 | 144 | 164 | 0.735 | Putative |

FIGURE 2A

```
BLAST Alignment to Top Hit:
>CRA|18000005009324 /altid=gi|4826948 /def=ref|NP_005035.1|
          (NM_005044) protein kinase, X-linked [Homo sapiens]
          /org=Homo sapiens /taxon=9606 /div=PRI /dataset=nraa
          /length=358
        Length = 358

 Score =  645 bits (1646), Expect = 0.0
 Identities = 318/358 (88%), Positives = 318/358 (88%), Gaps = 40/358 (11%)
 Frame = +1

Query: 388  MEAPGLAQAAAAESDSRKVAEETPDGAPALCPSPEALSPEPPVYSLQDFDTLATVGTGTF 567
           MEAPGLAQAAAAESDSRKVAEETPDGAPALCPSPEALSPEPPVYSLQDFDTLATVGTGTF
Sbjct: 1    MEAPGLAQAAAAESDSRKVAEETPDGAPALCPSPEALSPEPPVYSLQDFDTLATVGTGTF 60

Query: 568  GRVHLVKEKTAKHFFALKVMSIPDVIRLKQEQHVHNEKSVLKEVSHPFLIRLFWTWHDER 747
           GRVHLVKEKTAKHFFALKVMSIPDVIRLKQEQHVHNEKSVLKEVSHPFLIRLFWTWHDER
Sbjct: 61   GRVHLVKEKTAKHFFALKVMSIPDVIRLKQEQHVHNEKSVLKEVSHPFLIRLFWTWHDER 120

Query: 748  FLYMLMEYVPGGELFSYLRNRGRFSSTTGLFYSAEIICAIEYLHSKEIVYRDLKPENILL 927
           FLYMLMEYVPGGELFSYLRNRGRFSSTTGLFYSAEIICAIEYLHSKEIVYRDLKPENILL
Sbjct: 121  FLYMLMEYVPGGELFSYLRNRGRFSSTTGLFYSAEIICAIEYLHSKEIVYRDLKPENILL 180

Query: 928  DRDGHIKLTDFGFAKKLVDR---------------------------------------- 987
           DRDGHIKLTDFGFAKKLVDR
Sbjct: 181  DRDGHIKLTDFGFAKKLVDRTWTLCGTPEYLAPEVIQSKGHGRAVDWWALGILIFEMLSG 240

Query: 988  FPPFFDDNPFGIYQKILAGKIDFPRHLDFHVKDLIKKLLVVDRTRRLGNMKNGANDVKHH 1167
           FPPFFDDNPFGIYQKILAGKIDFPRHLDFHVKDLIKKLLVVDRTRRLGNMKNGANDVKHH
Sbjct: 241  FPPFFDDNPFGIYQKILAGKIDFPRHLDFHVKDLIKKLLVVDRTRRLGNMKNGANDVKHH 300

Query: 1168 RWFRSVDWEAVPQRKLKPPIVPKIAGDGDTSNFETYPENDWDTAAPVPQKDLEIFKNF 1341  (residues
1-318 of SEQ ID NO:2)
           RWFRSVDWEAVPQRKLKPPIVPKIAGDGDTSNFETYPENDWDTAAPVPQKDLEIFKNF
Sbjct: 301  RWFRSVDWEAVPQRKLKPPIVPKIAGDGDTSNFETYPENDWDTAAPVPQKDLEIFKNF 358  (SEQ ID
NO:4)
```

Hmmer search results (Pfam):

Scores for sequence family classification (score includes all domains):

| Model | Description | Score | E-value | N |
|---|---|---|---|---|
| pkinase | Protein kinase domain | 186.8 | 3.4e-52 | 2 |
| pkinase_C | Protein kinase C terminal domain | 25.8 | 1.1e-06 | 1 |

Parsed for domains:

| Model | Domain | seq-f | seq-t | | hmm-f | hmm-t | | score | E-value |
|---|---|---|---|---|---|---|---|---|---|
| pkinase | 1/2 | 49 | 197 | .. | 1 | 141 | [. | 168.5 | 1.1e-46 |
| pkinase | 2/2 | 202 | 263 | .. | 213 | 278 | .] | 21.5 | 7.2e-05 |
| pkinase_C | 1/1 | 264 | 294 | .. | 1 | 31 | [. | 25.8 | 1.1e-06 |

FIGURE 2B

```
Support for alternative splice region:
CHGI:
>CRA|232000027924897 /altid=TA|1171945 /dataset=chgi_v5 /def=NOT
           ASSIGNED /taxon=9606 /org=Homo sapiens
           /fasta_sequence_orientation_wrt_asm=Reverse
           /predicted_transcript_orientation_wrt_asm=Reverse
         Length = 1065

 Score = 1742 bits (879), Expect = 0.0
 Identities = 934/947 (98%), Gaps = 5/947 (0%)
 Strand = Plus / Plus

Query: 423  ggagagcgactcccgcaaggtggcggaggagacccccgacggggcgcccgcgctctgccc 482
             ||||||||||||||||||||||||||||||||||||||||||  |||||||| |||||||
Sbjct: 5    ggagagcgactcccgcaaggtggcggaggagacccccgacggt-cgcccgcg-tctgccc 62

Query: 483  cagccctgaggcgctgtcgccggagccgcctgtgtacagcctgcaggactttgacacgct 542
             |||||||||| |||||||||  |  |||||||| ||||||||||||||||||||||||||
Sbjct: 63   cagccctgag-cgctgtcgcggatgccgcctgcgtacagcctgcaggactttgacacgct 121

Query: 543  ggccaccgtgggcactgggacgttcgggcgggtgcacctggtgaaggagaagacagccaa 602
             ||||||||||||||||||||||||||||||||||||||||||||||||||||||||||||
Sbjct: 122  ggccaccgtgggcactgggacgttcgggcgggtgcacctggtgaaggagaagacagccaa 181

Query: 603  gcatttcttcgccctcaaggtgatgagcattcccgacgtcatccgcctaaagcaggagca 662
             ||||||||||||||||||||||||||||||||||||||||||||||||||||||||||||
Sbjct: 182  gcatttcttcgccctcaaggtgatgagcattcccgacgtcatccgcctaaagcaggagca 241

Query: 663  acacgtacacaatgagaagtctgtcctgaaggaagtcagccacccgttcctcatcaggct 722
             ||||||||||||||||||||||||||||||||||||||||||||||||||||||||||||
Sbjct: 242  acacgtacacaatgagaagtctgtcctgaaggaagtcagccacccgttcctcatcaggct 301

Query: 723  gttctggacgtggcatgacgagcgcttcctctacatgctcatggagtacgtgccgggcgg 782
             ||||||||||||||||||||||||||||||||||||||||||||||||||||||||||||
Sbjct: 302  gttctggacgtggcatgacgagcgcttcctctacatgctcatggagtacgtgccgggcgg 361

Query: 783  cgagctcttcagctacctgcgcaaccgggggcgcttctccagcaccacggggctcttcta 842
             ||||||||||||||||||||||||||||||||||||||||||||||||||||||||||||
Sbjct: 362  cgagctcttcagctacctgcgcaaccgggggcgcttctccagcaccacggggctcttcta 421

Query: 843  ctctgcagagatcatctgtgccatcgagtacctgcactccaaagagatcgtctacaggga 902
             ||||||||||||||||||||||||||||||||||||||||||||||||||||||||||||
Sbjct: 422  ctctgcagagatcatctgtgccatcgagtacctgcactccaaagagatcgtctacaggga 481

Query: 903  cttgaagccagagaacatcctgctggatagggatggccacattaagctcacggactttgg 962
             ||||||||||||||||||||||||||||||||||||||||||||||||||||||||||||
Sbjct: 482  cttgaagccagagaacatcctgctggatagggatggccacattaagctcacggactttgg 541
```

FIGURE 2C

```
Query: 963  gttcgccaagaagctggtagacaggtttcctccgtttttgatgacaacccgtttggcat 1022
            ||||||||||||||||||||||||||||||||||||||||||||||||||||||||||||
Sbjct: 542  gttcgccaagaagctggtagacaggtttcctccgtttttgatgacaacccgtttggcat 601

Query: 1023 ttatcagaaaattcttgcaggcaaaatagatttccccagacatttggatttccatgtaaa 1082
            |||||||||||||| ||||||||||||||| |||||||||||||||||||||||||||||
Sbjct: 602  ttatcagaaaattcktgcaggcaaaatagatktccccagacatttggatttccatgtaaa 661

Query: 1083 agacctcattaagaaactgctcgtggttgacagaacaaggcgattaggaaacatgaagaa 1142
            ||||||||||||||||||||||||||||||||||||||||||||||||||||||||||||
Sbjct: 662  agacctcattaagaaactgctcgtggttgacagaacaaggcgattaggaaacatgaagaa 721

Query: 1143 cggggcgaatgatgtga-agcatcatcggtggttccgctccgtggactgggaagctgttc 1201
            ||||||||||||||||| ||||||||||||||||||||||||||||||||||||||||||
Sbjct: 722  cggggcgaatgatgtgacagcatcatcggtggttccgctccgtggactgggaagctgttc 781

Query: 1202 cgcagagaaaactgaagcctcccatcgtgcccaagatagctggtgacggcgacacttcca 1261
            ||||||||||||||||||||||||||||||||||||||||||||||||||||||||||||
Sbjct: 782  cgcagagaaaactgaagcctcccatcgtgcccaagatagctggtgacggcgacacttcca 841

Query: 1262 acttcgaaacttaccctgagaatgactgggacacagccgcgcccgtgccgcagaagga-t 1320
            |||||||||||||||||||||||||||||||||||||||||||||||||||||||||| |
Sbjct: 842  acttcgaaacttaccctgagaatgactgggacacagccgcgcccgtgccgcagaaggact 901

Query: 1321 ttagaaatcttcaagaatttctgaggacaggagctcacatctggaag 1367  (SEQ ID NO:5)
            ||| |||||||||||||||||||||||||||||||||||||||||||
Sbjct: 902  ttacaaatcttcaagaatttctgaggacaggagctcacatctggaag 948   (SEQ ID NO:6)
```

```
dbEST:
>CRA|3000000984691 /altid=gi|2437086 /dataset=dbest /taxon=9606
          /org=Homo sapiens /date=10/08/1997
          /altid=gb_acc|AA603225.1 /organ= /tissue_type=breast
          /length=559 /clone_end=3' /def=np45h11.s1 NCI_CGAP_Br1.1
          Homo sapiens cDNA clone IMAGE:1129317 3' similar to
          SW:KDC2_DROME P16912 PROTEIN KINASE DC2 ;, mRNA sequence.
        Length = 559

 Score = 1055 bits (532), Expect = 0.0
 Identities = 551/556 (99%), Gaps = 1/556 (0%)
 Strand = Plus / Plus

Query: 476  tctgccccagccctgaggcgctgtcgccggagccgcctgtgtacagcctgcaggactttg 535
            |||||||||||||||| ||||||||| | ||||||| |||||||||||||||||||||||
Sbjct: 5    tctgccccagccctgag-cgctgtcgcggatgccgcctgcgtacagcctgcaggactttg 63

Query: 536  acacgctggccaccgtgggcactgggacgttcgggcgggtgcacctggtgaaggagaaga 595
            ||||||||||||||||||||||||||||||||||||||||||||||||||||||||||||
Sbjct: 64   acacgctggccaccgtgggcactgggacgttcgggcgggtgcacctggtgaaggagaaga 123
```

FIGURE 2D

```
Query: 596  cagccaagcatttcttcgccctcaaggtgatgagcattcccgacgtcatccgcctaaagc 655
            ||||||||||||||||||||||||||||||||||||||||||||||||||||||||||||
Sbjct: 124  cagccaagcatttcttcgccctcaaggtgatgagcattcccgacgtcatccgcctaaagc 183

Query: 656  aggagcaacacgtacacaatgagaagtctgtcctgaaggaagtcagccacccgttcctca 715
            ||||||||||||||||||||||||||||||||||||||||||||||||||||||||||||
Sbjct: 184  aggagcaacacgtacacaatgagaagtctgtcctgaaggaagtcagccacccgttcctca 243

Query: 716  tcaggctgttctggacgtggcatgacgagcgcttcctctacatgctcatggagtacgtgc 775
            ||||||||||||||||||||||||||||||||||||||||||||||||||||||||||||
Sbjct: 244  tcaggctgttctggacgtggcatgacgagcgcttcctctacatgctcatggagtacgtgc 303

Query: 776  cgggcggcgagctcttcagctacctgcgcaaccgggggcgcttctccagcaccacggggc 835
            ||||||||||||||||||||||||||||||||||||||||||||||||||||||||||||
Sbjct: 304  cgggcggcgagctcttcagctacctgcgcaaccgggggcgcttctccagcaccacggggc 363

Query: 836  tcttctactctgcagagatcatctgtgccatcgagtacctgcactccaaagagatcgtct 895
            ||||||||||||||||||||||||||||||||||||||||||||||||||||||||||||
Sbjct: 364  tcttctactctgcagagatcatctgtgccatcgagtacctgcactccaaagagatcgtct 423

Query: 896  acagggacttgaagccagagaacatcctgctggatagggatggccacattaagctcacgg 955
            ||||||||||||||||||||||||||||||||||||||||||||||||||||||||||||
Sbjct: 424  acagggacttgaagccagagaacatcctgctggatagggatggccacattaagctcacgg 483

Query: 956  actttgggttcgccaagaagctggtagacaggtttcctccgtttttgatgacaacccgt 1015
            ||||||||||||||||||||||||||||||||||||||||||||||||||||||||||||
Sbjct: 484  actttgggttcgccaagaagctggtagacaggtttcctccgtttttgatgacaacccgt 543

Query: 1016 ttggcatttatcagaa 1031  (SEQ ID NO:7)
            ||||||||||||||||
Sbjct: 544  ttggcatttatcagaa 559  (SEQ ID NO:8)
```

FIGURE 2E

```
   1 CAAGCAAGGT GTTGTGAAAC GTGCAGGGTC TATTTATAAG AAGAGGTAGC
  51 TATGCGGTCA AGTTCAGGGT GGGTTCGGTG GAATCAGACC AACCAGCAGC
 101 TCAAGCAGAG TTTAACGCTG CAAATCTGTG CCACGTTCTT CTTCCTGCGT
 151 GCAATTTGCA GGCAAGGACA TCTGCTTAAT TGGGTGTGAA ACCCGGGCCT
 201 TGATTAAAAG GACTTTATGA GGCCGCAGCC TTGCATTTCC AAGGTCAGGC
 251 CCTAGTGGAG AGGGCGCGCG TTCCGCGGGG AGACACGAAC TTTTCCTGAG
 301 TGCGCGTTCC TTGCTGGCCC TGAACCCCTC GGCCAGGCAG GGCTTGGCAG
 351 GGCCGTTTCC TGTCCTAACC AGGATCAAGG GATTGCGCGG CTTGCTGGTG
 401 AAGCTTGGCA GGGCCGTGAC CTGTCCTAAC CAGGCTCAGG GGATGGCAGG
 451 GGCCTGCTGG TGTCGCATAT GTTTTGCATT CCAGCTCAGG ATTTTGCAGA
 501 GCATAGGGAG CGGGTGTCAC CCCCGGGGGG AAATGCCACC CACAAAATGC
 551 AGGTGGAGGC TGGGCGAGGC TGGCAGCCAG GGGCCAGAAA TCCAAAGCCT
 601 GAGCCAGGTT CAGACTTCCT GACTCCCCCT CCCCGTTAGC TGTGGAAGGA
 651 TGGCTCGGCC TGGTCCCCCT AAAAATGTGT CCGTTCTGAC TTAGAGGCCG
 701 CTTTGGCTCT CGGAAAGCCC CCCTGACCTG CGGACTGAGG GACTGGAGAC
 751 CCCCTCCAAT CGCAGAATCG CTGAGATCCC TCAAAACAAA GGCGTTTGCA
 801 GTTTGACCCC TTGCTGCTCA AACTGTGGTC GGCGAACCGG CAGCCTGGGC
 851 CGCCCTGGTC GCGGGTCAGG GGCGCAGCGT CCAGGCCGTG CCAGGCCCGC
 901 AAGTTAAGCA CTGTCTGCAT TTCCCTGGGG AAAGGGGTGA CCAAATATCT
 951 AGCTATATTT GCATTTCAAA TCCACACGGA TATGGGTTTT AAATATAAGT
1001 ATGTCCAACT ATTGCCTGAG CCACACTTAA GCCAGGAAAA AAAAATCTTT
1051 GGGGTTTCTG AAATTGAAAT GCCTCTGCAC AATTCTTTAT AGGGTTGTCG
1101 CCGGGGTGTT TGAAACAGTG ACCAATCAAG TTTCACGCAC TACATTTGGT
1151 CGGGCGATCT CTCAAATCTG TCTTTCCCTA GTTTTTTAAA GGAATGTTTA
1201 TTTGTAAAGA ATTCTAGATC CACAGGAAGC TGCAAAGAAA CGCACAGGGT
1251 CGAGCCCGCC CTTCCCCGCC CCTTCCAAGT AGAAATCTAG AATCACCAGA
1301 GTCCTACAGC AAAACCAGGA CGCTGAACTC ATCCCGAAGA CCCGGCAGCC
1351 CCTCTTGGGG ATCCGCCCTC ATTCCAAATT CTCTCAGGTC CCAAACAAGC
1401 ACCCGCAGGA GTACTGAACT TTTTGGGGGG AGGGCAGAGG GGATCTGTAT
1451 GCAGATTGCC AGCTGAGCAA TCCTATTTTC TATGACTTAA AGCCAATCAG
1501 AGGCTGGGCG TGGTGGCTTA TACCTGTAGT CCCAGCACTT TGGGAGAACG
1551 AGGCAGGCGG TTCACTTGTG CTCAGGAGTT CCAGACCAGC CTGGCCAACA
1601 TGGTGAAACC CTGTCTCTAC TGAGAAAATA CAAAAATTAG CCGGGCTAAT
1651 CCGAGCCCCT CTCTTCACCA AACGCCAGTT TCACTTTTTA GTTTTGAACT
1701 TCACTTCTGC TGAGCTACGC CCTCCCTGTC CCCGGGCCCC CTCGCCTCCC
1751 CATCTTCCGG GCTTGGGTGC AGCGACGCGG GTGGCCCGCC AGTGCGTCCC
1801 CGAGGAGAAG TCAGCCTGGG TCCCACCCCA GGGGTGCCCC GGGCGCGGAG
1851 GGGGCGTGGG CACCTCCCCA GCGCCGCACG CCCGGGTCTC CGGCTCCTGG
1901 GCTGGGTCGG GGCGGGGGCG GACGCGCGCG CGAAGGCGAC GCCCCCCAGC
1951 CCCGCGGCCG GGTTAGGGCG GGGAGAGGCG CGGTCACGCC CAGGCGGCTT
2001 CCGCCCGCCC CAACAGCGCG CACGCGGCTA CCGAGCTGGA GGAGGCGGCG
2051 GGCGCGAGAC CCGGAATGCG CAGGGCCCCC GCCTCGCCCC CCCCAGCCCG
2101 GGCCGCGGCC CCCGCCTTCC CCGCAGTCGT CCCGCACTCG GTGCCCGCCC
2151 CCCGAGGCCG GCGGCTGCTC CCACTCGGGG CCGTTGCTGC TTGTGCCGTG
2201 AGCGCCGCCC AGCCATTGTC CCCGTCGCTC CGTCAGCCGC GCCGGACCGC
2251 GCACCAGGAG GCGAGAGCGC GCATGGGGAG CCTCTGTTGA TGCCGCCGCC
2301 GCGCCGCCCT CCGAGGCTGC GTCCCGGGAA GCCCGGCTCC CCGAGCGCTC
2351 CGGCCTGGCC CGGTGCCCCG GACCTGAGTG CGTCCCCATG GAGGCGCCCG
2401 GGCTGGCCCA GGCGGCCGCG GCGGAGAGCG ACTCCCGCAA GGTGGCGGAG
2451 GAGACCCCCG ACGGGGCGCC CGCGCTCTGC CCCAGCCCTG AGGCGCTGTC
2501 GCCGGAGCCG CCTGTGTACA GCCTGCAGGA CTTTGACACG CTGGCCACCG
2551 TGGGTGAGTG AGTGCGGGCG GGGACTCGGC CCACAGGGGC GCGCGGCGTG
2601 GCCGGGACGT TGTAGTAGGA CAAAGGGCCC TGGGTGCCGA CCTCCTGGGG
2651 AGGGCCCTGA CCCGCTACTT CGGCTCGGAG TCCCCGTGCG GGGCTGCACC
2701 TGCGCCCCGG GTCTTCCCGG GTGGAGCGCA CTCCCCAGCC CCCCAGCCCA
2751 GGCAAGTACC CCCGACCGGC CGGGTGCCTA ACCTGAAATG CCGACGGCTC
2801 CTCTCGGAGA CCACCCTCCA CCCCCAGCAC ACACAGCACT CTGGGGCCTG
2851 GGCCGTCCGA CGTCACAAAA CCTCCTGCGG GTCACCTCGC CTGGGGGACC
2901 TCGTGCTCCC TCCCTGGCAG CGGCCCCAGG GACACTGGCG CGGGGTGCGA
```

FIGURE 3A

```
2951 AGACCCCTGC AGGCCTCCCC TAGGCCAGCC TCCCTGTGTG CCCAGAGGCA
3001 GGGAATGTAC AGATTTCTCC AGGGGCTGCA GGAGCAGCTG GGCTGTGGGG
3051 GACAGGTGTC CCGGGGCGCT GTGGGGACGA GGACGGCAGC GCTGGGGACG
3101 GATCCTAACA TGTCCTGACA CCGCCTGTGC TCTTCGTCTT GTGCCTCTGA
3151 AATGGGTAAT TCTTGTATCG GACGCTTTAT CCGTTTCCTT TGTCCTCTGT
3201 CTTTGAACTT AACCCCGAAT GGGCAGCTTG ACAGAGAGGT TTCGAGTTCT
3251 CGGTGCTCTT GCATCCGGAC ACGCGCTGCT TTATGGAGCA GCCCTGAGTG
3301 GGTCAGAATA TCCCAACTGA ACGTGGGCGC TGGATTTAAA CAGTTGTCAT
3351 CGGCCCGCCT GTGCCACTTA GGGACTCCGT ATGGCTAAGT GGGGTGTTGG
3401 CTGTCAAGAA AATAAATGGG AGAGTAGAGG GGGCTGTCCT GGGTGTGTTG
3451 GTGAGGCGTC GGCTCTCAGG CCCTCTAACT CCTGTTTGTC CTCATTTTGG
3501 AAAGGAGGAA GCTGGGCTGG GAAGCCCAAG GGCTCGAGGC CATAGCTTAT
3551 GACTTAGGAA GACCAGCGGG CATAGCCAGT GGGGCCTTTA GAACCGCTGA
3601 GGAAGAGGGG ACTTAGCTTC CTTCAGTGAC CTCTTTGCCA CTTAGACCTT
3651 GAGGAAGGGC CCACGAGGAA AGCCTGAATT TGGAAGGACA GAGTGGGAGG
3701 AGGCCCTCTC TCTTTCTCCT CTCCCTCCCT CCTCCTCTTT ATCTCATTCT
3751 CTCTCTCTTT TCTCTGTTTC TCTTCTCTCT CCCTCTTTCT GTCTCTGTTC
3801 AAGTCTCTCT GCATTTCTCC TCCTCTGTCT CTTGGTGTCT CTCTCCCTGT
3851 CCCCTTCCGG TCTTGGTTTT TCTGTCTCCC TCCCTCCTCT CTCTCTGCCT
3901 TCCCCCTTGT CTTGGTCCCC CCGGAAAGCT GTCCTGGTCT AATCTTAGAG
3951 CTGGGTGTGT TTTGCGCGGA AGAAGGGTGG GGCAGGAACC CTGACTGGCG
4001 CAGCCGCCAC AGTAGGTGGA AATACAACTC GACAATGGAA AATTGATGAG
4051 GTCCAGCCGT TCCTTGGCAC TCAGCACCAG CGTTTGTCAT TCTTTGGGGC
4101 ACCCACATGG GTCCCTTGGG AAAGGTGGAG CTGGGGCTGG AGGCCGGGGC
4151 AGAGAGCAGG ATGCGGGCAG GAGGGCGGCA GAGGTGAGGG GTTCTGGTGT
4201 CACAGGGGGC CACTCAGTTT GACGTCAAGT CAGCTTAGGG TGCCCAGCGG
4251 GTAACCTCAT CTTTAAAAAT AGAGTGTCGC TGCCTCTGGG GACCAAGCTG
4301 GCTGGGCGGG GAGTCAGCTT TTTTTTTCAG TCCAGTCAGT GCTCTCTTAA
4351 TGAGGATGAG GATGATGCTC CTTTCTCAAG GATAACTTCC TGTGAGCTCC
4401 AACGATGTGA CAGGAGGGCT AGGTATCCCA CACTCATTGG ACAGCAGGGG
4451 ACCAGGACCC AGGGGTGTGT GTGTGTATGT TTGCATGCAC GTCTGGAACA
4501 CTCTCTCATG ACAACTGCAC AGCTTTGGTG ACATTATCTG CAACCTTTTA
4551 TCCAAGCCCG TTTCTTTATT GTTGGTTAAA GAGCAATCTG AGTGTGATTC
4601 ACCTAAAATA ATACATTTTA TAAAATCCTA AGCCTTTTAG ATCCTTCACG
4651 ATTGTGTCTC TAAGCCACAA TCTACAGCAG CTTTGGACTG TTTTCCAAGG
4701 CGTGATGGAG AATAGTGAGG GGTGAGCTTG AGTCTCAGTC TGGAGTTGAA
4751 ACCCAGTCTG GGTGGGTGTG ACCTCTCTTC ATCCTAAACT GTCACTACAG
4801 GAACATAAGT TTGCTTTTAA GTGCTCTTTC GCCCTCATTC CGAATTCTCT
4851 CAGGCCCCAA ACAAGCACCC GCAGGAGTAC TGAACTTTTT GGGGGGTGGG
4901 CAGAGGGGAT CTGTATGCAG ATTGCCAGCT GAGCAATCCT ATTTTCTATG
4951 ACTTAAAGCC AATCACAGGC TGGGCGTGGT GGCTCATACC TGTAGTCCCA
5001 GCACTTTGGG AGGCCGAGGC AGGCGGATCA CTTGTGCTCA GGAGTTCCAG
5051 ACCAGCCTGG CCAACATGGT GAAACCCTGT CTCTACTGAG AAAATACAAA
5101 AATTAGCCGG GCGTGGTGGC GGGCGCCTGT AATCCCAGCT TCTCAGGAGG
5151 CTGAGGCAGA GGAATTGCTT GCACCCAGGA GGCAGAGGTT GCAGTAAGCC
5201 AAGATCACAC CACTGCGCTC CAGCCTGGGC GACAGAGAGA AAAAGAAACT
5251 TGTCAGCGTT CTAGATTGAC CAGTTTTCCT CAAGGTCAGG TAGTTAGGAA
5301 GAAAGAGTGC AGTTTGCAGT TGTGAAAAGT CTGATAATGG ATTCTTTTTT
5351 TCTTTTTTAT GCGTGAAGGG ATTCTGGAGT ACGTCTGGTC TAAAGGCCGA
5401 TTTCGTTTTA GGAACTTTGG ATCAGAACAG TCATACTAGT CCTCAGAGAA
5451 AAAATGGTTT TCAATCTGGT TCTTCAAATT TCTTGTTCAT ATAACCAAGC
5501 CATGCTTGTT CCTATGATGG AGAACAATTG TGCTTTAAAA AAAGAAATTT
5551 CAGGGCCAGG TACAGTGGTG CGTGCCTGTA GTCCCAGCTA TTTGGGAGGT
5601 CGCGGTGGGA GGATGACTTG AGGCCGGGAG TTCCAGACCA GCCTGGGCAA
5651 TATAGTGAGA CCCTCATCTC TTAAAAAAAA TAGTAGTAAT AGTTAGCTGG
5701 GCATGGTGGC GCATACCTGA GTTACCTGGG AAGCTGAGGC AAGAGGATCA
5751 CTTGAGCCCA GGAGGTCAAG GCTGCAGTCA ACCACAATCG CGCCACCGTA
5801 CTCCAGCCTG GGTGATAGAG CGAGATCCTC TCTATAAAAA ATAAAATAAG
5851 AAAATGATAT TATGGAAATG AAAAACTCAC CCTATGTAGA GAGAAGAGGA
```

FIGURE 3B

```
5901 TGAATCTGTG CAGCCATCTA CCAGCCTTAT TTTACCAATT TCCTACTTAA
5951 AATGACCACT TGAGAATTCC TTTCTCTATA TATCAGATAA AAAATACTTG
6001 GGTTTTTTCC CAGAAGTGTC CTTATGGAAT CATTTGGCAT CTACAACCCA
6051 GTGCTTGCTT GTCATGGGTA CCCCAAGTGT TAACCTGTCA GGAAGGAGGT
6101 AATTCAACAG GTAAACCAGT GGCCAGGCCT TGGGTCCACA TTTCATTTTC
6151 CTTTTCTCAG CCTAGTTCTG CATTTACTCA TCTACAGAGG GAAATAATGA
6201 CGGAACCTGT CCTACACGAT GACGATGAGG AAGACTCCAA AGTTCCTAGA
6251 CCCCTATTAA AAATATATAT TTTTTGAAAT ACAGACTCAC AGGGGATTTC
6301 AAAAACAGTA CCTGGAGTCT CATGGACCCT TCAGCCAACT TCCCCATGGT
6351 GACGTCTTCA TATCCGTGGG ACAATATCAG AACCATGTCA TCGATGTTGG
6401 TATATCCTTA TTAAAGAGAA CACATACCTC GTTCAGCTTT TTTTTTTTTT
6451 TTTTTTTGAG ACAGGGTCTC ACTCTGTTGC CCAGTCTGGA GTGCAGTGGT
6501 GCGATCTCGG CTCACTCCAG CCTTGAACTC CTGGGCTCAA GCAATCCTCC
6551 TGCCTTGGCC TCCCAAAGTG CTGGGACTAT ATACAGGCAT GAGCCATCGT
6601 GCCCGGCTTG TTCAGGCTTT ATTAGTTTTC AAAAGGTGCT CATTTGTGTT
6651 TGCGAGTGTG TGTGTAGAGT TCTGTGCAGT TTTACCCAGT GTGTGGATTT
6701 GGCAGCTACC ACCCTCCAAA CCATGGTGCA GGATGAATTC CCTCACCACA
6751 GAACACCCCT CGGTCTTGCT CGACACTTTT TTTTTTTTTT TGAGACAGAG
6801 TTTCACTCTT GTTGCCCAGC CTGGAGTGTA TTGACCACAA CCTCTGCTTC
6851 CCGGGTTCAA GCGATTCTCC TGCCTCAGCC TCCCGAGGAG CTGGGATTAC
6901 AGGCATGTGC CACCATGCCT GGCTAATTTT ATATTTTTAG TAGAGATGGG
6951 GTTTCTCCAT GTTGATTAGG CTGGTCTCAA ACTCCTGACC TCAGGCGATC
7001 CGCCCGCCTT GGCCTCCCAA AGAGGTGGGA TTGCAGGTGT GAGCCACCGT
7051 GCCTGGCCAG ACACTTTTTT TTTTTTTAAA CTTTCACACA CTATACAATC
7101 TGAAAATATT TTATTTTCTT AAGAGCTAGG AGATCTTCAT AATTAATGAT
7151 ACATGGTTCT CAGATCTAAA GTGCTTATAC TGGTAGGTTT TCTCTTGTCC
7201 TTGGTTCTCC TGAATTGGCC AGAATTTCCT TTCCTCTCCT TGTTGCTGGG
7251 TTCTTATTAA TGCCTCAAGT TAGTCGGTTC AGGCAGTTGT AGCAAAACAC
7301 CACCGACTGG GTGGCTTATA AACCACAGAC ATTTATTCAC AGTTCAGAGG
7351 CTGGAGGTCC AAGATGAAGG CATGGCAGAT TTGGTGTCTG GTGGGGACCT
7401 GCTTCCTGGT TCATAGATGG TGCCTTCTCG CTGTGTCCTC ACATGGTGGA
7451 AGGGGTGAGG GAGCTCTCTG GGGCCCCTTT ATAAGGGCAG TGATCCCATT
7501 CATGAGGCTC CAACCTCACG ACCTCATCAC CTCCCTAGGG CCTCACCTCC
7551 TGACACCATT ACCTTGCAGG TGAGGATTTC AACACAGGAA TTTTAGGGGG
7601 ACACAGACAT TGAGTCCACG GCATCCCCAC CCTGTCTGTC ACACAGCATG
7651 CTGCCGGGAC GAATGGCATC TGAACTGGTG AGATTCTACT GTGTGCATAA
7701 ATCAGCAGCC TTGTGGGCAG TGTTGACATA GCAATTAGGA GTGTTGTTTG
7751 TAGCCTAACA ATACACAGAA AGTGGAGCTC AGCCCTTTGA TCTTATTTAC
7801 CTTATGTGGG TGCTCCGTGT GAGACAGGCT CATGCATGTG TGAATGACAG
7851 TTTCCTTTAA GTGCATCACG CAAATGCCAA GAGATGAGAT CAAATATTAC
7901 ACATCAGAGA ACATTTCCAA GGATAGAAGT CCTGCCGGTT TCTCCTCTTC
7951 ATTGTTTATT TCATTTTATT TTTTTAATTT AAGTTAAAAT ACATGTTAAA
8001 TTAAATTTAA GTTAAATTAA GATACATGTG CAGGACTTAT TTTAAATAAA
8051 AGAGACAGGG TCTCGCTGTG TTGCCCAGGC TAGACTTGAA CCCCTGGGCT
8101 CAAGCATTCT GCCTGCCTCC GCTGCTGGCA CATAAATGCC AAGTGTGCAG
8151 GGACCTCTGT GTGTTGGAGC CACTTTCATC TCCCACATCC AAAGAACAGA
8201 CCCGGCACTT AGTGTGTGCC CAAGACCATC CACCGCATGA ATAGAGAAAT
8251 CAACCCTCCT CATGTGCCTG GGGTTTCCTG AGGTGGGAAA CCTTCAGTGC
8301 TAGCTGGGAG AGTCGCAGGC AGAGACAGGG ACAAGCTGGT CACTCTGTGT
8351 GTGAATAAAT AAATGAATGG ATGATGGCAT TATCGGCAGT TGTTCTTTAT
8401 GACACTCACT GATGCCAAGT ACTGGACGGG TACAATATGT ACATTAGTTT
8451 CTCTATGGGC AGAAGCTCCA CCATGACAAC ATTAGTGTTA TTTTCTTTTT
8501 GCTTTTTTGT TTAGAGACAG GGTCTTACTC TGTCGCCCAG GCTGGGGTGC
8551 CGTGGTGCAA TCAACAGCTC ACTGCAGCCT CGACCTCCCA GGCTCAAGCA
8601 ATCTTCCCAC CTCAGTCTCC CAAGTAGCTG GGACTGCAGA CGTGCACCAC
8651 CACACTCAGC TAATTTATGT ATTTATTTTT GTAGAGATGG GCATTGCTAT
8701 GTTGCCCAGG CTGGTCTCGA GCTCCTGGGC TCAAGTGATC CTCCCGCCTC
8751 AGCCTCCCAC GTAGCTGGGA CTACAGGTGC ATCCACCATG CTTGTAGCCT
8801 TATTTTCTTA ATGGGAAAGA GGGTCTGAGA GAAGGGATGC TGTGTGCCCA
```

FIGURE 3C

8851 ATGGGTTTCG CCTGCAGCAC GCTGCCTCCT CCCCGGGAAA GCAGGGCGTG
8901 CACATTGGGA TTGGACGACA AAAGCAGAGT CATCTACAGT TCATGGGCAC
8951 GCTGCAAAGA AGGGAGACGT TAAACTCTCG AAAGCAGCAG ACACCCCCCA
9001 CCAGGAAGAG ACATACTTGT AAAAATCAAA GGAGGGCGAA GGCATGAGAA
9051 TCGCTTGAGC CCAGGAGGTT GAGGTTGCAG TGGGCTGAGA TCGTGCTACT
9101 GCATTCCAGC CTGGGTGACA GAGACCTTGT CTCAAAAAAT AAAAATTCAA
9151 GGGAGGCCAG GTGTGGAGGC TCACGCCTGT ACCCAGCACT TTGGGACTCT
9201 GAGGTGGGAG GATCACTTGA GCCCAAGAGC TCAAGATCTG TCTGGACAAT
9251 ATAGCACTAC CCCATCGCTA CAAAAAAAAA TTTTTTTAAG TAGCTGGGTG
9301 TGATGGAATG CACCTGTAGT CCCAGCTACT AGGGAGGCTG AGGCAGGAGG
9351 ATTGCTTGAG CCCAGGAGGT GGAGACTGCA CTGAGCCATG ATGGTGCCAC
9401 TGTGTTCCAG CCTGGGCAAC AGAGCAAGAC CCTATGTCAA AAATAAAGAA
9451 AGTATCAAGG GAGATGAGTA CACAGTGCCT GGCACACTGT AGGGTCTCCA
9501 AAAAGTAAAC CTTTTCTATC CATCAGTTTC CTCTTCTCTC CAGCATGAAA
9551 TCGCATATGT AAAGTTGAAA AAAAGAGTGA GAGATATATC TTAAAAAGGT
9601 AGTAATGTTG ATGACATTGT GGTTTTTTTT TTTTTTTTAA AGAAAAACCG
9651 GCCGGGTGCG GTGGCTCATG CCTGTAATCC CAGCACTTTG GGAGGCTGAG
9701 GCAGGCGGGT CATGAAGTGT CAGGAGATCG AGACCATCCT GGCTAACACG
9751 GTGAAACCCC GTCTCTACTA AAAATACAAA AAAAAATTAG CCGGGTGTGG
9801 TGGCGGGCGC CTGTTAGTCC CAGCTGCTGG GGAGGCTGAG GCAGCGGAAT
9851 GGCATGAACC CGGGAGGTGG AGCTTGCAGT GAGCCGAGAT CACACCACTG
9901 CACTCCAGCC TGGGCGACAG AGCAAGACTC TGTCTCAAAA AAAAAAAAAG
9951 AAAAGAAAAA CCTTGGGGGA AATACAGAGG AAGCCCTAAG GCATCCCTTC
10001 CAAAAAGCTG AAAGTGCTTT ACTTAGAATT GTGACCTCGT TTTCCCTGTT
10051 AGAAAAGTCT GTGGTTAGAA GCTTCCTGGT AAGCCCAGTG TGAGAAGGTG
10101 GAACCGATGT TTCTGTGTGA CGGGTTCCCT CTGCCTGTTT CTCCAGGTGG
10151 CCTCCCCGTG GTCCTCTACT GTGGTGGGTC CAGTCCCAAA ACCAAGTCTG
10201 GGGCCACCAT CATCATATTT GTGTCCCCCA CCCCAAGATT CTTATGTCAA
10251 AACCCTAATC CCCAAGGTAA TGGTGTTAGG AGGTGGGGCT TTTAGGAGGT
10301 GATGGGGTCA CTAGGGTGGG GTCTCATGAA TGGGATCAAT GTCCTTATAA
10351 AAGGGACCCC AGAGAGCTCC CTCACCCCTT CCACTATATG AGGACACAGT
10401 GAGATGGCAC CGTCTGTTAA TTAGAAAGCC GGTCCCCACC AAACTCTGAA
10451 TCTCCCATAC CTTCATCTTG GACTTGTAGC CTCCAGGACT GACAGCGGTA
10501 AATGTCTGTT GTTTCTAAGC CCCAGTCTGC CGTGTTTTGT GATGGCAGCC
10551 GAAATGGATT TAGATGGGGC TCTATTCACC CCACGCGGCA GGGTCCATGG
10601 AAAGGCAGCT GCAATGCGCT GGTCTATCAT TACCTCTTTT ATGCTCTTTC
10651 ACACTGTCTT AGTCTTGCGT GGCTGCTGGA ATGAAGGACC GCAAATATAG
10701 TAGCTTAAAA CCACATACAG TGAAGAGATA CCTGCACTCC CAGGTTCACT
10751 GCAGCACGAG TCACACAACA GCCAAGATAG GGCAACAACC CACTTGCCCG
10801 TCAGCAGATG ACTGGGTGAA GAAAATGTGG TCTCTACACA ATGGAGTACT
10851 ATTCAGCCTG TAAAAAGAAT AAAGTCCTGT CATTTGCAAC AATGTAGATG
10901 CAACTGGAGG TCATTATGCT CTGAGAAATG AGCCAGGCAC AGAGAGACAA
10951 ATACGGCATT ATCTCACTCC TTTTTTTTTT GGACAGGGTC TCACTCGGAC
11001 ACCCAGGCTG GAGTGCAGTG ACGTGGTGTC ACTGCAGCAT TGACGTCCCA
11051 GGCTCAAGGG ATCCTCTCAC CTCAGCCTCC TGAGGAGCTG GGACTGCAGG
11101 TGTGCATCAC CACGCCAGGC TATTGTTTTG ATTTNNNNNN NNNNNNNNNN
11151 NNNNNNNNNN NNNNNNNNNN NNNNNNNNNN NNNNNNNNNN NNNNNNNNNN
11201 NNNNNNNNNN NNNNNNNNNN NNNNNNNNNN NNNNNNNNNN NNNNNNNNNN
11251 NNNNNNNNNN NNNNNNNNNN NNNNNNNNNN NNNNNNNNNN NNNNNNNNNN
11301 NNNNNNNNNN NNNNNNNNNN NNNNNNNNNN NNNNNNNNNN NNNNNNNNNN
11351 NNNNNNNNNN NNNNNNNNNN NNNNNNNNNN NNNNNNNNNN NNNNNNNNNN
11401 NNNNNNNNNN NNNNNNNNNN NNNNNNNNNN NNNNNNNNNN NNNNNNNNNN
11451 NNNNNNNNNN NNNNNNNNNN NNNNNNNNNN NNNNNNNNNN NNNNNNNNNN
11501 NNNNNNNNNN NNNNNNNNNN NNNNNNNNNN NNNNNNNNNN NNNNNNNNNN
11551 NNNNNNNNNN NNNNNNNNNN NNNNNNNNNN NNNNNNNNNN NNNNNNNNNN
11601 NNNNNNNNNN NNNNNNNNNN NNNNNNNNNN NNNNNNNNNN NNNNNNNNNN
11651 NNNNNNNNNN NNNNNNNNNN NNNNNNNNNN NNNNNNNNNN NNNNNNNNNN
11701 NNNNNNNNNN NNNNNNNNNN NNNNNNNNNN NNNNNNNNNN NNNNNNNNNN
11751 NNNNNNNNNN NNNNNNNNNN NNNNNNNNNN NNNNNNNNNN NNNNNNNNNN

FIGURE 3D

```
11801 NNNNNNNNNN NNNNNNNNNN NNNNNNNNNN NNNNNNNNNN NNNNNNNNNN
11851 NNNNNNNNNN NNNNNNNNNN NNNNNNNNNN NNNNNNNNNN NNNNNNNNNN
11901 NNNNNNNNNN NNNNNNNNNN NNNNNNNNNN NNNNNNNNNN NNNNNNNNNN
11951 NNNNNNNNNN NNNNNNNNNN NNNNNNNNNN NNNNNNNNNN NNNNNNNNNN
12001 NNNNNNNNNN NNNNNNNNNN NNNNNNNNNN NNNNNNNNNN NNNNNNNNNN
12051 NNNNNNNNNN NNNNNNNNNN NNNNNNNNNN NNNNNNNNNN NNNNNNNNNN
12101 NNNNNNNNNN NNNNNNNNNN NNNNNNNNNN NNNNNNNNNN NNNNNNNNNN
12151 NNNNNNNNNN NNNNNNNNNN NNNNNNNNNN NNNNNNNNNN NNNNNNNNNN
12201 NNNNNNNNNN NNNNNNNNNN NNNNNNNNNN NNNNNNNNNN NNNNNNNNNN
12251 NNNNNNNNNN NNNNNNNNNN NNNNNNNNNN NNNNNNNNNN NNNNNNNNNN
12301 NNNNNNNNNN NNNNNNNNNN NNNNNNNNNN NNNNNNNNNN NNNNNNNNNN
12351 NNNNNNNNNN NNNNNNNNNN NNNNNNNNNN NNNNNNNNNN NNNNNNNNNN
12401 NNNNNNNNNN NNNNNNNNNN NNNNNNNNNN NNNNNNNNNN NNNNNNNNNN
12451 NNNNNNNNNN NNNNNNNNNN NNNNNNNNNN NNNNNNNNNN NNNNNNNNNN
12501 NNNNNNNNNN NNNNNNNNNN NNNNNNNNNN NNNNNNNNNN NNNNNNNNNN
12551 NNNNNNNNNN NNNNNNNNNN NNNNNNNNNN NNNNNNNNNN NNNNNNNNNN
12601 NNNNNNNNNN NNNNNNNNNN NNNNNNNNNN NNNNNNNNNN NNNNNNNNNN
12651 NNNNNNNNNN NNNNNNNNNN NNNNNNNNNN NNNNNNNNNN NNNNNNNNNN
12701 NNNNNNNNNN NNNNNNNNNN NNNNNNNNNN NNNNNNNNNN NNNNNNNNNN
12751 NNNNNNNNNN NNNNNNNNNN NNNNNNNNNN NNNNNNNNNN NNNNNNNNNN
12801 NNNNNNNNNN NNNNNNNNNN NNNNNNNNNN NNNNNNNNNN NNNGACAACC
12851 AGAGTCACTC TTGTCACCAT CTTGGTTTGG GTGGGATTTG GCCAGCTTCT
12901 TTACCGCAAC CTGTTTTATC AGCAAGCTCC TTATGACCGG CATCTTGTGC
12951 TGACCTCCTA TCTCATCCCG TGACTTAGAA TGCCTTAACC ATCTGGGCAT
13001 GCAGCCCAAC AGGCTTCAGC TTCATTTTAC CCAGCTCCTC TTCAAGATGG
13051 AGTTGCTCTG GTTCAGATGC CGCTGACAGA ACTAGCTTAT GGTTGGAGAC
13101 AATGTCATAG GGAATTATTC TTCAAAGATC GCAAAATCCA GCTTGGATGA
13151 GATTCCAAAA ATCAAAAGGT GCTGAGAAAG CAACTTGTCT AGAATTTCCT
13201 CTTCATGGGC TGGTTGATTT TGTTTACAAT GACACCTTCA GAAAAAGTAG
13251 GCGACACACA GTGGCTCACG CCTATAATCC TAGTGCTTTG GGAGGTCAAG
13301 GAGGGAGAAT CATTTGAGGC TAGCAGTTCT AGACTAGCCT GGACAACATA
13351 GTGAGACCTT GTCTTTACAA AAAATAAAAT CAGCCGTGTG TGGTGGCGCA
13401 TACCTATAAT CCCAGCTGTT CAGGAGGCTG AGGCAGGAGG ATCATTTGAG
13451 CCCAGGAGTT GGAGGCTGCA GTGAGCTATG ATGGCGCCAC TGCACTCCAG
13501 CCTTAGTGAC AGAGCAACAT TCTGAAAGAA AAGAAAGAAA AGAAAAAAAG
13551 AAAAGGAAAT AAAAGATGAA GAAAGAAAAC AGAAGAAAAA AATAATTTAT
13601 ATAGAAAAAA AGTCCATAAT GACTCAAAAT ATTCCCTGGA CACTGGAATA
13651 GAATGATTTT GTTTATTAAA GCTTTTCTTT AGTTCGTCCT TAAACAGTTT
13701 AGTATTTTCT TTTGAAAACA GATTGTGTCT TGTCAACTTC ATTGATTTTC
13751 GGGCTGGGCT TGGTGGCTGA ACACCTGTAA TCCCCCAACA CTTTGGGAGG
13801 TTGAGGTGGG TGGAGCGCTT GAGGCCAGGG GTTCGAGACT AGCCTCTAGC
13851 CTCGGCAACA TGGTGAAAAC CTGTCTCTAC AAACAACAAC AACAACAACA
13901 ACAAACAATT AGCTGGGCGT GGTGGCACGT GCCTGTAGTC CCAGCAACTT
13951 GGGAGGCCGA GGTGGGAGGA TCACTTGAGC CCAAGAGGTC GAGGTCGAAG
14001 TGAGCTATGA TTGCACCATT GTACTCCAGC CTGGGTGACA GAGTGAGACC
14051 ATGAAAGAAA AGAAAGAAAA GAAAAAAGAG AAAGAAGAAG GAAAAAAAAA
14101 GAGAAGAAAA AAGTAAAAGA AAAACATAGA AAAAAAATCA GTAACGACTC
14151 AAAATATTCC CTGGATAGTT GAATACAAAT AGTTGTTGTT GGACGTGATT
14201 TTATGTATTA AGGCTTTTGT TTAGTTTATC CTTAAATAGG TTAGGATTTT
14251 ATTTTGAGAA TAGATTCTGG TTTATCAATT TCATCAGTCT TTGCAAAGAA
14301 ACAGCTTAGG GTTTCCTTTA TGTTTCTCCG TTAACTTCCT GTTTTCAGTT
14351 ACATTGCGTT TTGCTCTGGT TTTTCTTTCG TTTTTTCCAC TCGTTTTAGG
14401 TTTCTGGAAT TTCCTGAAAC ATTGTATTTT GATACAGATT CTGAGCTGGT
14451 GCTTTGGCTG TCACAAGCCA GAGGGTCCTA GAAGAAGTAG AATTGTAACC
14501 GAGGAAAACT GTTAGGAAAC TCCATCCCTT TTGACCTTCA AAGGTCACCG
14551 CCTAATTTTG GTGTTTTGTA GTCTGATGTG TTCATAGCTT GTGACTATTA
14601 GGCTCTGATT GAGCTCTGCT TTTTTTTAAG TTTCTCTTAC TCAGCTGGTG
14651 CTGTTTTAGC TCCAGCTTCC TCCTCTGTGT AATCAACACT CCCAGTCTCC
14701 TCTTCACCCA AAAAGCCACA GAAATAAGTG CAGAAAACAA GGCAGCCGCC
```

FIGURE 3E

14751 ACCTGCTACA GAGGCATGTC CTTAAATACG ATGCATTTCA GGACAGCTGT
14801 GTGAGTTCCG GGAGCTTGTC TTCCTTCAAA GGGAAAAGTA AAAATAAACA
14851 GGAAGGTTGC ACTGAAAGCA TTCTCAATTG AAATTGTGCC ATTTGGCTGT
14901 AGTGTTTCTG ATGCTCATTT AGAACTTTGG AAGTTGTGGG ATGGTGGGCA
14951 AGTGTGTGAC CTGGGATGGA GATTCTCTAC CTCTTTAAGA GTGAAACCCT
15001 GGCTGGGCGC CGTGGCTCAC TCCTGTCATC CCAGCACTTT GGGAGGCCAA
15051 GGCGGGTGGA TCACCTGAGG TCAGGAGTTT GAGACCATCC TGGCCATAAT
15101 GGTGAAACCC CGTCTCTACT AAAAATACAA AAAAATAGCT GGGCGTGGTG
15151 GCAGGTGCTT GTAATCCCAG CTACTTGGGA GGCTGACGTG AGAGAATCAC
15201 TTGAACCCGG CAGGCGGTGG TTGCAGTGAG CTGAGATTGT GCCACTGCAC
15251 TCCAGCCTGG GTGACAGAGT GAGACTCCAC CTCAAAAAAA GAAAAGAAAA
15301 AGAAAAACTT TAAAAAATGC CGGGCACGGT GGCTCCCGCC TGTAATCCCA
15351 GCACTTTGGG AGGCTGAGGT GGGTGGATTG CCTGAGCTTA GGAGTTTGAG
15401 ACCAGCCTGG GCAACATGGT GAAACCCCGT CTCTCCTAAA ATGCAAAAAA
15451 TTAGCCGGGC GTAGTGGTGC ACGCCTGTAG TCCCAGCTGC TTGGGAAGCT
15501 GAGGCAGGAG AATTGCTTGA ACCTGGGAGG CAGAGATTGC AGTGAACCGA
15551 GATGGTGCCG CTGTACTCCA GCCTGGGCGA CAGAGTGACA CTCTGTCTCA
15601 AAAAAAAAAA TAAAATAAAA ATTAGCTGGG CGTGGTGGCA CACATCTGTG
15651 ACAGAGCGAG ACTCCATCTC AAAAAAAAAA AAAAAAGAAT TTTGGAAGTT
15701 GTGGGATGGT GGGCGAGTGT GTGGTCTGGG ATAGATTCTC CACCTCTCTA
15751 AAAGTGAAAA CCTGGTTGGG TGGGGTGGCT CACATCTGTA ATCCCAGCAC
15801 TTTGGGAAGC TGAGGTGGGC GGATCACTTG AAGTCAGGAG TTTGAGACCA
15851 GCCTGGCCAA CATGGTGAAA CTCTGTCTCT ACCAAAACTA CAAAAATTAG
15901 CCGGGTGTGT GGTGGCGGGC ATCTGTAATC CCAGCTACTC GGGAGGCTGA
15951 GACACGAAAA TCGCTTCAAC CCGGAAGGCG GAGGTTGCAG TGAGCCGAGA
16001 TCACACCACT GTGTATGCCA CTGCACTCCA GCCTGAGCGG CAGTGAGACC
16051 CTGTCTCAAA AAATACACAC ACACACAAAA ACAAAAAACA AAACACATGT
16101 AGAAAAAACC ACAAAGACAA AAACAAAACA ACAACAACAA CAACAAAAAG
16151 TGAAAACCTA CTTCTTTTTC TGGACACGGT GGCTCATGCC TGTAATTGCA
16201 CCATTTTGGG AGGCCGAGGT GGGAGGATCA CTCTCACCTT TCAAGGCCCA
16251 GGAGTTCGAG ACCAGCCTGG GCAACACAGC AAAACCCCAT CTCTCTAAAA
16301 ATAAAAAAGA GAAAAAGAGA AAAATTGCTT CTTTCTATGT AGTTGGTGAG
16351 TTTTTTCAGT AGGATGCTTT GCATTTCTTC CTGCGTCTGT GGCTCTGTGG
16401 TATGCCAGCA TATACGATAG TCACTACAAG ATCCGTAGTT GTACACCCAG
16451 CCATACGCAT CACAGGTTTT TGGCTGATTT CATGACAACG CTTAAGGCTG
16501 CTGAAAACAC TCTAATTCTT TGGATGTTGG CAAATGTTCA GATGAAACTA
16551 AGCGGCTGGC CCACCCACCT GCTCAGGAAA GAATGGCCGC ATTGTGTGGG
16601 AAAGGAATCC TCTGTTCCCT AGCTGGCTGC CTGGTGTTCT TGTTGAGTGA
16651 GCAGAACAGA GAGTGCCCCT GGGTAGACCT GTGTGTGCTC CAAAAGGCGA
16701 TTTTGTCAAT TGTTCCCTTG GGATGCCCTT GTTCCAGAAA GCATGTTCTG
16751 TGTGACTCTC AGCTGGGGTT CCCAGACTGT GTAAAGAAAA CATGGTGATT
16801 CATGGCTGTG TGCGGTTGCC CATGCCTGTC ATCCCAGCAT TTTGCGCGGC
16851 CGAGGCGGGA GGACTGCTTG AGCCTGGGAG GTCAACGCCA GCCTAGGCAA
16901 CACAGTAAGA ACCTGTCTCT ACAAAAACAA AACAAAAAAA GTGTAGCCGG
16951 GCATGGCGAC GAGCACCTGT GGTCCCAGCT ACTCAGGAGG CTGACGCAGG
17001 ACGATCGCCT GAGCCTGGAA GTTGGAACTG CAGTGAGCCA TAATCACACC
17051 ACTCTACTCC AGCCTGGGTG ACAGAGTGAG ACCGCATCTT AAAAAAAAAA
17101 GAAAAAAAAA AGGACATTGT GATTAATGAA AACAAACATT GCCTGGTGAT
17151 AAGGAAAGTA AGAAGTAGGA TTGTTCTCAG ATTAGTGACC CAGGAGATAA
17201 AGGAGTAACA GAGTGTGCAG GAAGCAGGTC TCCAATTTAA TAGCAGGATG
17251 GTGAAGATAG AGCAAGTGAC TTCTTTCTAT TTTTTTTAGA AACTGGGTGT
17301 TGCTTTGTCA CCCAGGCTGG AGTGCAGTGG CGTAATCATA GCTGACTGCA
17351 GCCTTCACCT CCTGGGCTCA AGCAGTCCTC GTGCCGCACC TTCCCGAGTA
17401 GCTGAGACTA CAGGCACATA CCACCATACT TGGTTAATTT TTTGTATTTT
17451 TAGTAGACAT GGGGGTGTGG GGATGGTTTG CCGTATTATC CAAGCTGGTC
17501 TCAGACTTCT GGCCTCAAAT AATCCTCCTG CCTCGGCCTC CCAAAGTGTT
17551 GGGATTACAG GCATGAGCCA CTGTGCCTGG TGAGTAGGTA GCTTTTTGTT
17601 TGTCTGTTTG TTTGTTCTGT TTGTTTGTTT TTGAGACAGT CTCGCTCTGT
17651 CGCCCAGGCT GGAGTGCAGT GATGCAATCT TGGCTCACCC CAACCTCCAC

FIGURE 3F

```
17701 CTCCCGGGTT CAAGTGATTC TCGTGCCTCA GCCTCTCAAG TAGGTGGGAT
17751 TACAGGCACA TGCCACCATG CTTGGCTATT TTTTGTTTTT TTAGTAGGGA
17801 CAGAGTTTTG CCTTGTTGGC CAGGCTGGTC TCAAACTCCT GACCTCAAGT
17851 GATCCGCCTC CCTCGGCCTC CCAAAGAGCT GGGATTACAG TTGTGAGCCA
17901 CCGTGTCCAG CCAAACAAAA AAAAGTCTGT CTTATAAAGA AGATCCCTAA
17951 TTTATGATGA TTCCATTTAT GATGGTTTGA GTTATGGTAG TTTGAGTTAG
18001 GATAGTTCGA TTGAAGATTT TTTGATTTTA CGATGGTGAG AAAGACACAG
18051 TCCGTGGAAC CCGGGCTTCG AGTACCCATG CAACTGTTCT GTTTTTAACT
18101 TGCAGTGCAG TATTCAGTAA ATTACATGAG GCATTCAATA CTTGATTGTA
18151 AACTAGGCTT CACGTTAGGT GATTTTGCCC AGTTGTAGGC TAATGTAAAT
18201 GTTGCGAGCA CGTTTAGGGC AGGCTGGGCT AAGCTGTGAT GTTCGTAAGT
18251 TAGGTGTATT CGATGCATTT TTGACTTACC ATATTTTCAA CTTACAAAGG
18301 GTTTATGGGG TGTAATGTCA TCATTGTAAG TTGAGGAGTG TCTGTATCAT
18351 AGACTGGGGG GCTTAAACAG ACATTTATTG CTCCCAGTTC TGGAGGCTGG
18401 GAGTCACAGA TCAAGGCGTG GCACATTCGG TGTCTGGTGA GGGCTTCCTG
18451 GTTCATAGAC GGCGCCTTCT CACTGTGTCC TCACATGGTG GAAAGGGTGA
18501 GGGAGCTCTC TAGGGTCCCT TTAATAAGGA CATTGATCCC ATTCATGAGG
18551 CTCCACCCTC ATGACCTCAA CACCTCCCAA AGGCCCCACC TGCTAACATC
18601 ATCATCTTGG GGATGAGGAT TCAACACGGG AATTTTGGGA GGATGCAAGC
18651 TTTCACCAGT AGGGTTTTCT TTGTAAAGAA ATAGAAGGAA ATGAAAAGGC
18701 AGGCACTGGG TAGGAGAGAG CTACAGAAGA CAGCGGGGTG GTGGCACTCC
18751 AGGATAGTGC TGTCCCCCAG CATCATTTAC ACCGAAGAAA CCTGAGGCAG
18801 TCTTTCTGAT GTGTCATTCT TAGGAAAACC ACCATGAATC TGGCATCTAG
18851 CTATCAGTGA AACTGTGGGA GAGCTTAATG GAAGTAAAGA CATGTGGTCC
18901 CAGAAATGAC AGATCATTCG GAGAACCTAA GAGAGGATTA AAAGCAAAAG
18951 GGGGTCATGT GCGCTGTGAC TCAAACTTTG GGAGGTCGAG TGGGAAGATT
19001 GCTTGAGCCC AGAAGTTTGA GACCAGCCTG GGCAACATAG GGAGACCCTA
19051 TCTCTACAAA AAATACAAAA ATTAGCTGAG TGTGGTGGCA CACACCTTAG
19101 TCCCAGCTAC TCAGGAGTCT GAGGTGGGAG GATTGCTTGA GCCTGGGAGT
19151 TCAAGGCTGC ACTGAGCTAA GATTGCGCCA CTGCACTCCA GCCTGGGCGA
19201 CAGAACAAGA TCCTGTCTCA AAAACAAAAA CAAAAGCAAA ACAAAACAAG
19251 AAAATCCAAA AGGGAAATAT AAGAGAAAAC AAAAAATCTC ACTTTGAGAC
19301 ATCTTTTTTG AAGAGTTGGA GAGGATATTG TCTCCATCCA CAAAAATAGG
19351 ATGTTACAAT AAAAGAGAAA GAGGAAGGAA GAGCTTTATA TGGGACTGCT
19401 GAAAGTTAAA AGAAAAACAT TGCATTAAAT AAATTAGAAG GGTGATCTCA
19451 TCTGTGCCTG TGACTTCAGT TATCATCTTA AGGCTTTGGG TCTCAAAGCA
19501 CACATCTAGT TTAGACCTTT CTTAGGAGCC CTGAAGGGTG CATTGCCAAC
19551 TACTGCCCGT TGGAGGGTCC ATTTTTCCCA AGATATCCAG CAACACTCTT
19601 ATATGAGTGT CCTGCTCCAT TGTCTCAAAT TACCATAAAC TGGGGAACGC
19651 AAGCAACAGA AATTTATGCT CTCCCAGGCC TGGACACCAG GAGTCTGAAA
19701 TCAAAGTGCA GGCAGGATTG TGCTCCCTCT GGAGGCTCTG GGGGAGGAAG
19751 CTTCCTGCCT CTCCCGGCTC CTGGGGGCTC CAGGCATCCC TGGGCTTGTG
19801 GCCACAGCAC TCCAGTCTCT GCCTCTGTCT CCACGTGGCC TTCTCATCTG
19851 TGCCTGTGTC TCCTCTTCTG TCTCTTAGAA GTACACTGGT CATTGGATTT
19901 AGGGCCCACC CTTTTCCAGC GCGATCTCAT CTCAAGATCC CTAGCTTAAT
19951 CACGTTTGCA AAGTTCCTTA TTTCCAAATA AGTTCCCATT CCAGGTTCTG
20001 GACATGAGGA TGTGAATATA TCTTTGTGGG GACCACAGTT CAGTCTACTA
20051 GAGTTGTATG CAGTTCCTTC TGGAGGCTCT AGGGGAGGAT CCTTTCTGCA
20101 TCTCCCAGCT CCTGGGGGCT CCAGGCATCC CTGGGCTTGT GGCTGTATCA
20151 CTCCAGTCTG CCTCCGTCTC CATGTGGCCT TCTCCTCTGT GTCTGTGTCT
20201 CCTCATCTGG CTCTTTATTT TTTTAAATTA TTTATTTATT TATTTATTTT
20251 TTATTTTTTT TGGTGACGGA GTTTCGCTCT TTTGCCCAGG CTGGAGTGCA
20301 GTGGCATCAT CTCGGCTCAC TGTAACCTCT GCCTCCCGGG TTCAAATGAT
20351 TCTCCTGCCT CAGCCTCCTC AGTAGCTGGG ATTATAGGCA CCCGACACCA
20401 CGCCTGGCTT ATTTTTTATG TTTTTAGTGG AGACGGGATT TCACCATGTT
20451 GGCCAGGCTG GTCTCGAACT CCTGTCCTCA GGTGATCCGC CCGCCTTGGC
20501 CTCCCAAAGT GCTGGGATTA CAGGTGTGAG CCACCATGCT CACTGGCCAT
20551 TTTTTATTAT TACTCTTTTT TCCTCTTCTG TCTCTTAGAA GGACACCCGT
20601 TGTTGGATTT AGGTCCCACC CTAAATCCAG GATGGCCTTA TCTGGAGATT
```

FIGURE 3G

```
20651 GTTTACTTAA TAGAAACTAC AAAGACCCTA TTTTCTTTTC TTTTTTTTTT
20701 TTTTTTTTTT GAGACGGAGT CTCCCTCTGT TGTCCAGGCT GGAGTGCAGT
20751 GGCGCAATCT CGGCTCACTG CAAGCTCCAC CTCCCGGGTT CACGCCATTC
20801 TCCTGCCTCA GCCTCCCAAG TAGCTGGGAC TACAGGCACC CGCCACCACA
20851 CCCGGCTAAT TTTTTTTTGT ATTTTTAGTA GAGACGCGGT TTCACCTCGT
20901 TAGCCAGGAT GGTCTCTATC TCCTGACCTC GTGATCCGTC CGCCTCGGCC
20951 TCCCAAAGTG CTGGGATTAC AGGCGTGAGC CACCGCGCCC GGCCTCAAAA
21001 ACCCTATTTT CAAATAAGAC GCCATTCACA GGCACCAGGG GTTAGGATGT
21051 AGACATATTT TTGGGGGGCA CCATTCAACC TAGTCTATCC CTCAATCTCA
21101 ATACATCCCC TGGGTTAAAC ATGAAATGTG TCCCCTTCTT CCCCCAAATC
21151 AAAGCAACCC AAAAGACCCC TGTGCACCTG CACACCTTGC CTAAGTCGGC
21201 AGCACTCACT GCGTAGATGC CCAAACCCTA AGCTGTGATC ATCTCCACCC
21251 TCCCTCTTGC AGCCTAATTG AGCCCATTCT CTGCCCAAGC ACCTTATGAA
21301 CAGGACTTTA ACCCTCCATC TCCACCACCT TCCCATTTTC ACTGGAAATT
21351 TTACTTCTTA AAGAGGCCTT CCCTGACCCC TTGACCAAGG TTAGATGCAT
21401 CCCAATGTTC TCCTATGGAT ATGTTGTTTG AAGTCCTCAA GTCTGAACAA
21451 ACTCATGTGA GGTCACCCAA GTTGTTAGAC TTACTGTCAT TAATGCTTCC
21501 TGCCCTCCTT CCAGCCCGAC TGGAACTAAA CAAAACTAAA TGAGGGACCA
21551 ACCTTGTGTT GTTCATTGCA GTTTCTCGGA GGTAGACAGC ACCTGAGACC
21601 CAGGAAAATA TCAATCATGA TGGAAGTGAT GCATTCATTT ATTATATTGA
21651 CTCCTTTTTT TTCCCAAAAG CTATTTTGTG TTCAAAACCT GGACTGCATA
21701 AACCACTTCA TTGTGGTTAT GGAGTGTTAG AAGCCGACAC CTAATCAAAG
21751 AATTCAGTGT GTCTCAGTGG TAGGAACTCT AAAGCCATCT AACATTAAAT
21801 GCAATAAAAG TTCAGTTGCT TACGACCTGG CGCCGTGGCT CACGCCTGTA
21851 ATCCCAGCAC TTTGGGAGGC TGAGGCGGGT GGACCACGAG GTCAGGAGAT
21901 TGAGACCATC CTGGCTAACG TGGTGAAACT CTGTCTCTAC TAGAAATACA
21951 AAAAATTAGC CAGGCGTGGT GGTGGGTGCC TGTAGTCCCA GCTACTCAGG
22001 AGGCTGAGGC AGGAGAATGG CGTGAACCTG GGAGACGGAG CTTGCAGTGA
22051 GCTGAGATCG CGCCACTGCA CTCCAGCCTG GGTGACAGAG CGAGACTCCG
22101 TCTCAAAAAA AAAAAAAAAA AAGTTCAGTT GCTTACTCTC CATAGCCTCA
22151 ATTCAAATCC TCAGTAGCCA CTTGTGAGCT TGTGGCTACC ATTTTGGACA
22201 GTGCAGATAG AGAACATTCC TATCATTGCA GGCGATACTA CGGGCAGTGC
22251 TTGCTCCAAA ACAGGGGGTC TCAACTGGGG GCCGGCCTTC CCCCACAGGG
22301 CACTTGACAG TGTCTGGGGA CAGTTGTGGT TGTCACTACT GGGGGTGGAT
22351 GCTGATGGCG TGTGGTGAGT GGAGCCCAGG GACGCCGCTC TGCAGGTTTG
22401 CAGTGCACAG GATGGCCCTA CAGAGAATCA TCCAGCCTCA AATGTCGGCA
22451 GTGCTAGGCT GAGAGAACCT GCTTTAGCGT GAGAGTCAGT CTCTCTCTTT
22501 CTGTCTCTCT CTCTCTCTCC CCCTCTCTCC CCTCCCCACT CTCGCTCTCC
22551 CTCCCTCCCC CCTCCACCCA TCCCATCTGT TATCTACCTA CCTACCTACC
22601 TATCAATTAT CTAACCATCC TAATTATCTA TGTATCACCT ATCTATCCTA
22651 TCTGTTACCT ATCTACCTAC CCACCTACCC ATCCATCCAT CCATCCAATC
22701 AATTAATCAG TGTATCATCT TTCTCTTTCC ATGTATGTAT CATACCCATT
22751 GTCCATCCAT CCATCCATCC ATCCAGTCAG TCATTCAATC AATCAATCAA
22801 TCATCTTTCT ATCTATCCAT CTATCTGTCT ATCATACCCA TCTACCTATC
22851 TTTCTATCTG TCTGTGGCAG AGATTCTCTG CCAATGGCAA TTCAGCTCCA
22901 TCAGGGAGAT ACTTCTTCCC TGGACAAGTC TGGAGACATT TTTGTTGTCA
22951 CAGCTCAGGT AGGTGCTACT GATAACAGGT GGGTGGAGTC CAGGGTCACT
23001 GCTTGCCACC TTACAGTGCA CAGGATGGCC CCACCACAGA GAATCATCCA
23051 GCTCCAAATG TTAATGGACT CAGTTTGAGA AGCTGATCTC AAGGGTAATT
23101 CGGGGGAGTC CTGCGGGATT GTTGCATCCT ATTGAAGGGG AAATTAATGA
23151 ATTTTGTAAG TGTAATGGGG CGGGGGGACT GGGTTAAGAG AGAATACTAA
23201 CTGCTTATCC CTCCTCTATG CCCAGAGAGG CTTATCTGTG TTCCATCGTT
23251 TTACATTCCT TGAGGCACGG CGAGTTCTTG CTTCCCTCCC TAGTGCAGCT
23301 GTAAAGTCAC AAGGTTGACA AGCAATTGCT GCAAAAGTAT GTATTCCCAA
23351 GAATGTAAGA CGTACGGTGT AACAAATGCA AAAGAGTAAT TAACTGCCTT
23401 TGTTCTCGCT TCTGCAAGTA TGCTTTCTGC AGCACGTAAC TCCCGCCACA
23451 AACTGCTTAA AAGGTGATTG ATCCCTCTGT ACGGGGCTCA GACTTTCTAG
23501 ACCCTAGTCC GACTGAGCTG GTGATCACCT TAATAATTAT AATTATAATG
23551 GTCATCTCCT AACTGTGCTC GGTCTCTACC GTCTCTGATT TATCCCGCAA
```

FIGURE 3H

```
23601 CACTATCGTG GAGGTAGGCT AGGATGTATC TTTAACCTGG CTGGATTGTA
23651 TTGTAGATGT GTGAAAACCA GCCCTTGTTT TTCTTGGTAG AGTTGCACTC
23701 AAATGTTATT GAAAGCTGCA CATACTGTGC TTGTATAAAT ACACTGAGCC
23751 AGAAATCACG AACCTTTCCC TGGCTTCACA TCTGTTAGTG TTGTGGGAGA
23801 AGATGAGAAT TTCTTGTTTT TCTTTTCACT TCTGTGATTA TACATTTTGT
23851 ATTTTGTTGT TGTTTTTTGG GACAGGGTCT CGCTCTGTCA CCTAGGCTGG
23901 AGTGCAGTGG TGTGATCATA GCTCACTGCA ACCCCCGCCC CCAGGCTCAA
23951 GTGATCCTCC TGCCTCAGCC TCCCAAGTAG CTGGGACTAT AGTCGCATGC
24001 CACCATGCCT GGCTGTTTTT TGTGTTTTTA GTAGAGATGG GGTTTTGCTT
24051 TGTTGTCTAG CCTGGTCTTG AACTCCTGTG CTCAAGTGAT CCGCCCACCT
24101 TGGCTTCCCA ACTGTGGGGA TTACAGGTGT GAGCCACTAC TCACGGCCAC
24151 ATTTTGTATT TCTGATGAGA AAGTGTAATT TAATACACTG TACATCGGAG
24201 AGTGTAGTTC TGAAACATCT GCATCTTTTA AATTAGGACA GTGTAAAAAT
24251 GGAATGTTGT TTGACTCAGC AAAATTTTGA GGGAGTTTGT TTCCAACTGT
24301 CTAGACCAGT GAACTCACCA AACTATCTAC CACACACTGC TTGGCTGAAT
24351 TGGCTCTACT GTTTTTAACT GAAGTTTGAA GTAAATATTC CAAGCTTAAA
24401 AATATATCTT GTTCCTCCCC CACCCACTGG TTATAGCAGC AATATAAATA
24451 AAAAATACCT TCCCAAGAAT ATCCAAAGCA TACATTCTTT TCTAAAGTAA
24501 ACATTGTTTA TAGAGATACA ATTTCTATAC CATAAGATTC ACCCTTTAAA
24551 AACACATAGT TCTTTAGTTT TCAGTTTATT CACAGAGTAA GCACACTGTT
24601 TTTTGTTTGT TTTGTTTTTT TCGAGACAGA GTCTTGCTCT GTCACGCAGG
24651 CTGGAGTGCA GTGGTGCCAT CTCGGCTCAC TGCAAGCTCT GCCTCCCGGG
24701 TTCACGCCAT CCTCCTGCCC CAGCCTCCCG AGTAGCTGGG ACTACAGGCT
24751 TCCGCCACCA CACTCGGCTA ATTTTTTGTA TTTTTAGTGG AGACAGGGTT
24801 TCACCGTGTT AGCCAGGATG GTCTCGATCT CCTGACCTTG TGATCCGCCC
24851 GCCTTGGCCT CCCAAAGTGT TGGGATTACA GGTGTGAGCC ACCGCGCCCA
24901 GCCCATTCAT TCATTTTTTG AGACAGAGTC TTGCTCTCTC ACCCAAGTTA
24951 GAGCACAGGG GTGCGATCAC TACTCACTGC TGTCTTGAAC TCCTGGGCTC
25001 AAGTGATCCT CCTGCCTCAG CTTCCCAGGT AACTTGGACT GCAGGTGTGT
25051 AACCACCACG CCCTGCTAAT TTTTTGATCT TTTAATAGAG ACGGGGTCTC
25101 GTTATGTTAC CCAGGCTGGT CTAGGACTCC TGAACTGATG TCCTTCCGTG
25151 GCCTCCCAAA GTTCTGGGAT TATAGGCACG AGCCACCATG CCTGGCAACA
25201 CACACTCTTT TTTAAAAATA CTTTTTAACA GCTTTTTTTC CTGTCTATAA
25251 AATAGAAGGT CATTATACTT GTTTGCAGCA GTAATTCCAA AAATCGACTT
25301 CGTAAAGAAG AACTGCGTGT TTCACACACT TATTTCCTCC ATGGTAGCAT
25351 TTAATGTTCT TTTATTGATT TTACCCAGGG GGGAAAATGT CAAGGAAAAG
25401 AACTGAGTTT GAGGATGATA AATGTGTACG TTCTGATATC ATTATTTTGA
25451 AACAATTATT TAATGCAATG CGTCGGTTTC ACTTATCAAT TTAACATAAA
25501 TTGAACCTAT GTTGATGAAC TATTTCTATA GTCATAAATT TTAAAAGGTG
25551 AGAAAGTTAT ATAGTGAAAT GCATCTGTTT TTGTGCCTCA CCTGTGCAGA
25601 ATTTGCCCTC TCCTTCCACC CAGGTGCCCA TATTAATGTG TCTTGTATAT
25651 TTCTCCAAAG TCCTTTCTCA ATATAGAAGC AAATTATCAC TTATGGAGAA
25701 GAGCCTCACT TTTTTTTTTT TTTTTTAAAC AGATGGGGGT CCCGCTCTTT
25751 TGCCCAGGCT GGAATGCAGT GGTACTATCA TAATTCACTG CAGCCTCCAA
25801 CTCCCGGGCT CAAGCAATTC TCCCATCTCT GCCTCATGAG TAGCTGGGAC
25851 TACTGGAGCA TACCACCACA CCCGGCTCAT TAAAAAAAAT TTTTTTTTTT
25901 TATAGATGGT GTCTGGCTAT GTTGCCCAGG CTAGTCTCGA TCTCCTGGGC
25951 TCAAGTGATC CTTCTGCTTC AGCCTTCTAA AGTGCTGGGA TTACAGGCAT
26001 GAGCCACTGC TCCTGGCCTC CACCCATCTA TAGGTGTGGA ACAAGAGCAT
26051 GTTCCCTCCC AAGCTAATGT GGCAGGTAAC TGGCCTCCCA GGCTGTAGAC
26101 AAGATGGATG GGGGCTGTGC CCACTTCTTG AGTTAACCTT TTTTTTTTCT
26151 TTGGAGACAG AGTCTCGCTC TGTCGCCCAG GCTGGAATGC AGTGGTGTGA
26201 TCTTGGCTCA CTGCAGCCTC CGCTTCCCAG GTTTAAGCAA TTCTCCTGCC
26251 TCAGCCTCCT GAGTAGCTGG GGTTACAGGT GCCTGCCACC ATGCCCGGCT
26301 AATCGTTGTA TTTTTAGTAG AGATGGGGTT TCACCATGTT GGCTGGGCTG
26351 GTCTCGAACT CTTGGCCTCA GATCATCCAC CTGCCTCGGC CTCCCAAAGT
26401 GCTGGGATTA CAGGCGTGAG CCAGCGCGCC CAGCTGGGTT TTACCTTTTT
26451 TGTTTGTTTG TTTTTTGAGA CAGAGTCTTG CTCTGTCGCC CAGGCTGGAG
26501 TGCAGTGGTG TGATCTTGCC TCATTGTAGT CTCTGCCTCC TGGGTTCAAG
```

FIGURE 3I

```
26551 CAATTCTCCT GCCTCAGCCT CCCAAGTAGC TGGGATTACA GGCATGTGCT
26601 GTCACGCCCA GCCAATTTTT TGTATTTTTA GTAGAGATGG GGTTTTCCCA
26651 TGTTGGCCAG GATGGGGTTT TACCTTTTTT GAAGTGTATT TTCCATGTAG
26701 CCACCTCTCT TGGAGTGTCC ATGAGGAACA CGATGCTGTC CTTGGTGTCT
26751 CAGCGGAGCC ACTGTGACGC TCTCCTCTTG CAAAGATTTC TGGTCATGAT
26801 GTCTCAACAT TGGCCTGTTT GGGGTTTTTT TTCTCCTGCA TTTTAGGGAG
26851 AATTAGGGCT CATCCACCCT CACCTTCTCT CCCCCATTGA ATTGGTGCAT
26901 CCTGTTTTTT TTTAGCCCCT GGGATGCCCA TGTTCAAGAT TCCTTAAGCA
26951 TCACAGTTTA AGGAAAGAAA TGCAGATTAT TTAAAATATG TGGGGTGAGT
27001 GTGCAGGGTG GTGATGGACA ATGCATGTGT TTAATTCAGG GACTGTTGTG
27051 CCAGCTGTGT TTGAGCCTTA GGAATTCTTA TAGTTGACTG GCATTTACAG
27101 TTTATTAAGG CACTTACCTC TTAGGTGTAT AATCCTCAAA ACATCTAAAA
27151 AATTAGTGAT TTTTGTTATC CAAGTTACTT TGACATCAGC CATTTGCTGT
27201 CTCACCCACA TGATTTCTCA TTATGTTACC TTATTATTGG CTAAGTTAAT
27251 CTGCTTACTG AGGACCTGCA TGTGACTTTT CCCATTAAAA GTAAGTTAAG
27301 TCTGGGCGCA GTGGCTCATG CCTGTAATTC TAGCACTTTG GGAGGCTGAG
27351 GTGGGAGGAT CCCTTGACTT TGAGACCAGC CTGGGTGAAA AAGTGAGATC
27401 TCAAAAACAA AATTAGCCAG ACATGGTGGC GCATGCCTGT AGTACCAGCT
27451 ACTTGGGAGG CTGAGGTGGG CTGATGGCTT GAGCCCAGGA GTTTATGCTG
27501 CAGTGAGCCG AGATTGCATC ACTGCACTCT AGCCTGTGGC ACAGAGTGAG
27551 ACCTGTCTCT TAAAAAAAAT TAATTAATTA ATTAAAAATA AATAAAAGTA
27601 AGTCCAAGTG GAGATGGTTG GTGGTGTTGG TTGGATAACA TTGTGAATGT
27651 ATTTAACACC GTTAATCTGT ACACTTCAAA ATGGTTAATT AAGATGGTAA
27701 ATTTTATGTT GTGCGTATTT TACCATAATT AAAAAATAGA TTTGGTCTGC
27751 GTGATGGCTC ACGCCTGTGA TCCCAGCACT TTGGGAGGCG AGGTGGGCGG
27801 ATCACCTGAG GTCAGGAGTT GGAGACCAGC CTGGCCAACA TGGTGAAACC
27851 CCGTGTCTAC TAAAACTACA AGAATTAGTC GGGCGTAGTG GCAGGCACCT
27901 GTAATCCCAG CTACTCTGGA GGCTGAGGCA GAAAAATCGC TTGAACCCAG
27951 GAGGTGGAGG TTGCAGTGAG CTGAGATCGC GCCACTGAAC TCCAGCCTGG
28001 GTGACAGAAT GAGACTCTGT CTCAAAAAAA AAAAAAGATT TAAAACAAAG
28051 TAACTATGTT CAAGGCCAGG TGTAGTGGCT CACGCTTGCA ATTCTGACAC
28101 TTTGGGGCGC TGAGGTGGAA GATTGCTTGA AGCCAGGAGT TCAAGACCAG
28151 CCTGGGCAAC AGAGTGAGAC CCCATGTCCA AAAAAAAAAA AAAAATCATC
28201 AGCTTTCATT CTGGGATCGT AAGTAGAGAC ATTGTTTCCC AGACCTGGTA
28251 CAGATGGAAC CTGCCTACGT GTCTTCAATG GGCATCTTAA GACTTATGTT
28301 TTGGACATAT CAGACTTTTG GAATAAAGGA GCTGAGTTGG GAGTACAAAC
28351 TCCTCTTCTT ATCCATTTCC CTGTGGCAGG AGATTTTGCT CTCAGCCCCC
28401 ACTTACTGGT GTGAGATCCT TGATTCTGGA AGGTGAGCTG TGCTGTTCAG
28451 CCCACAGGTC CTCATGAATG TCTACATTCA GTGCCACGCA GAATAAGAAG
28501 AAACACACAC CAGCTCTGCT TCTGTGAAGC TTACTTTTTG TTGTTGTTGT
28551 TGAGAGGGGG TCTTGCTCTG TCTCCCAGGC TGGAGTGCAG TGGTGCAGTC
28601 ATGGCACTCA TTGCAGCCTC TACCTCCTGG GCTCAAGAGA TCCTCCCTGC
28651 TCAGCCTCCT GCGTAACTGG GACCACAGAT GTGCGCCACC ATGCCCAGCT
28701 AATTTTTAAA TTTTTTGTAG AGACAGGGTT TCACCATGTT GCCTGGGCTG
28751 GTCTTGGACG CCTGGGCTCC AGTGATCCAC CTGCCTTGGC CTTCCAAAGT
28801 GCTGGGATTA CAGACATGCG CCACCGAGCC TGGTTTTGCT TACTTTTTCT
28851 TTTTTTTTTT AAATTCCTCT TAGCCTATCT TGGGGGAGGC GGGTCAGTGT
28901 TATTCCGGTG TACATACAAC AAAATCACCC ATTTGAAGTG CACACTGGGA
28951 GGAGTCCTTG CCAAATGGAT AGGGCTGGGT AACCACTGCC ACATGGGACA
29001 TTTGGGAAGC CGATGTTTGA ATGTTTTCAC GCTTACAGAT GCATTCATTT
29051 ACTACGTTTA TTATTCTGTG TGATGTGCTT TCTGTGTGTT ATTTCACTTA
29101 AACCCAGTGG GGGTAAAGAT TATGATCCCT ATTTGGTAGA TGAATTTTAG
29151 AGAGGTTAGG GGGCTTGTCA AGGTCACACA GCTTTTAACC GTGATGGGAT
29201 GACGCCTCTT GAATGAGGCT TAGTAGTGAG ATGGCTGAGG AAGGAAAAAA
29251 GTAGGAAGGA GAGAAAGAGA GAAGGAGGGA AGGAAGAAAG TAGGGAGAAA
29301 GGAAGGAAAG GAGAGGGAAG GAAGGGAGAA AGGAGGATGG AAAGATGGAA
29351 TGAGAGGAAA GAAGGAAGGA AACCGATGAA AGAAGGAGGG AAGGGCTGAA
29401 GGAAGGAACA GGTGCCCTGT TCAGGTGGGT TTATCCTCAG GAAGGACCCA
29451 AGATGGAAAG TGTGTATGCA AGAATTATTT TAGGCCAGGC GTTGTGGCTC
```

FIGURE 3J

```
29501 ATGCGTGTAA TCCCAGCACT TTGAGAGGCT GAGGCAGGCG AATCACTTGA
29551 GGTCAGGAGT TTGAGACCAG CCTGGCCAAC ATGGTTAAAC CCCATCTCTA
29601 CTAAAAATAC AAAAATTAGC TGGCTGTGGT GGCACATGCC TGTAATCCCA
29651 GCTACTTGGG AGGCTGAGGC CGGAGGATCG CTTGAACCCA GGAGGTGGAG
29701 GTTGCAGTGA GCTGTGATCG TGCCACTACA CTCCAGTCTG GGCCACAGAG
29751 CAGGACTCTA TCTCACAAAG TAGAAATAAA TAAAAAATAA ATAAAAACAG
29801 AGATGAGGAC ACAGACGCAC ATAGAGGACG ACCCTGTGAG GACACAGGGA
29851 GAAGATGGCA TCGACAAGCC TAGGAGAGAG GCCTCAGGAG GAACCAGCCC
29901 TGCCCACACC TGGGTCTCCG ACTTCCAGCC TCCAGGACTG TGAGAGAAGA
29951 AAGTTCTCTT TAAGTCCTCC AGTCTGTGTT AGGTTATTAC AGTAGTTCGA
30001 GCAAAGTACT TTATTTACAT AGAAGTCTGC CACAATTATG AGCCCTGAAA
30051 CCCTTTCCCA GGATGAACCG AGGTCAGAGT GTAATTAATA GGTACTTTTT
30101 TTCATTTACG TTTAGCCACT AGATTTTTTT TTTCAACAGA GAGTAGCGAA
30151 TACTGCAGAA GCTGAATGAG ATGAAGCTTA AGTCAGATCT TTATGCACCT
30201 CAGAATATTT GTACTGATGA AAAGAAATAA CCAACACTTG ATAGAGGGAA
30251 AGATTGAGAC CCAGAAAGTA ATCTCTCCCT GTGACCACTC CTACCAAATT
30301 CTTGCTTAAC TACCTTATTT TGTTCGTTTG TTTGTTTTTG TTTTTTTGAG
30351 ACGGAGTCTC GCTCTGTTGC CCAGGCTGGA GTGCAGTGGC GCAATCTTGG
30401 CTCACTGTAA CCTCCACCTC CCGGGTTCAA GCGATTCTCC TGTCTCAGCC
30451 TCCTGAGTAG CTGGGATTAC AGGAGCGCGC CACTACCACC CGGCTAATTT
30501 TTGTATTTTT AGTAGAGACG GGGTTTCACC ATGTTGGTCA GGCTGATCTT
30551 GAACTCCTGA CCTTGTGATC CACCTGCCTT GGCCTCCCGA AGTGCTGGGA
30601 TTACAGGTGT GAGCCACTGT GCCTGGCCAA CTACCTTGTT TTTTTTGGAT
30651 GAAAATGTGG TTCTTACCTC AGTAAAGATT ATGAAGGGAT TTATGTACAG
30701 ATGACTAAAA TATCAGCCAT TAGTTTCCTA TTTGTTTTTG TTGTTGTCAT
30751 TTTTTGTTTT GAGACAGGGT CTTGCTCTGT TGCCCAGGCT GGAGTGCAGT
30801 GATGCGATCT TAGCTCACTG CAGCCTCGAC CTCCCAGGCT CAGGCAATCC
30851 TCCCACCTCA GCCTCCCAAG TAGTTGGGAC GACGGCTGTG CACCACCACA
30901 CCTGGGTAAT TTTTTATTTT TATTTTTGTA GCTGGGATCT CGCTATGTTG
30951 CCCAGGCAGG TCTTGAACTC CCGGCCTCAA GTGATCCCAC CATCTAGGCC
31001 TCCCAAAGTG CTGGACTTAC AAGCGTGAGC CACCCTGCCC AGCCTAGTTT
31051 ACAATTTGAA CTTGGTTTTT CATCTCGGCT CCTTTGAAGA CTTCTGTCTT
31101 CTCCCATGTT TGGGGCAGCT GTGTGTTGTG GACATTCCTT AGTGATCGGC
31151 CTGGGAAGGC TCAGACATGT CTAGGCTGCC TTTGTAGGAA TAGGGATTAG
31201 TAGCTCCTTA GCCCCACTCT TTCCTGGGAT GTTGCTGTTT GCTGAGGTCT
31251 GCACAGTTCA GACCACCCTG GAAGCCTCTC TCAGGTTCTC AGAGATGGTG
31301 GAGTTATACC TTTGACCGTG AGCTCGCAGC ATTGCTAGGG AATGTACTTG
31351 GCTAAATTTG GAACTATTTG GTTGAATTTG TACCCCTTGG GCATATTTGC
31401 TTTGGTAACA TACCACAGAC TGGGTGCCTT AAAATAACAG AAGTTAATTG
31451 TTTCACAGTC CTGGAGACCA CAACTCTGAA GTGCAGATGC GGCAGGGCTG
31501 TGCTCCCTCT GCGGGCTCTA GGGGAGGCTC CTTCCTGCCT CTCCCAGCTC
31551 CTGGGGGCTC CAGGCGTCCC TGAGCTTGTG GCCGCATCAC TGCGGTCTCT
31601 GCCTCCGTCT CCACATGGCC TTCTCCTCTG TGTCTGTGTC TTCTCTTCTT
31651 CTCTTACAGG AACACCCGTC ATTGTGTTTA GGGTCCACTC CAATTTTGGA
31701 TGACCTCACC TTGAGATCTT TAACTTAATT ACATCTGCAA AGACCCTTTT
31751 CCCAAATGAG GTCTCATTTA CAGGTTCTGT GGGTCAGGAC ATGGACATAT
31801 CTTTCTGGGA GACCATAGTT CAGTCCACTA CAGTTGTATC CAGTTGTTTC
31851 TGGAGGCTCC AGGGGAAGCT CCTTCCTGCC TCTCCCAGCT GCTGGGGGCT
31901 CCAAGTGTCC CTGGGCTTGT GGCCGCATCA CTGTACTCTC TGCCTCTTTC
31951 TCCACGTGGC CTTCCCCTCT GCGTCTGTGT CTCCTTATTA GTTCACCACT
32001 CATATTGCAC CACCTTCAGG ATGACCTCAC CTTAATATAT ACCTTTTTTT
32051 TTATTTCATT TTTTAAAAAA GTGGAGCTGA GGTCTTGCTG TGTTGCCCAG
32101 GCTGGTCTCA AACTCCTGTG CTGGGATTAC AGGGGTGAGC CACTGTGCCC
32151 AGCCTTTGTG TATATCTTAA TCACATCTGC AAAGACCCTG TTTGCAACTA
32201 AGGTCCCATT CACAGGTACC AAGGATTAGG ATGTCAACGT ATCTTTTCCA
32251 GGGCACCCCA TTCAATGCAC ACAAAGTGGG GAGAGGGGAG ATTGGCTGTG
32301 TTTAGGTGAC CTGTGAAAGG CCGAGCTAGC TGTGCGGCGT TGCTCTTGCA
32351 GCACAGAGGA AGAACTGGGC TCAGATGGTG TCAGCTGTTG GTGTCTGAGA
32401 TCATCCGTGA ATCTACTCCC GGGAATGTGC TGCAGTGAGA CACGGTCCTT
```

FIGURE 3K

32451 CTCCCGTCAC CTTCCTGACC CCATCCCATA TACCCACGGA CCCCAAGGGA
32501 AAGTACTCAG GGTTGGTTGG TTTCTTTTCC GTTTTGTGAC CGCGTGAAAT
32551 TCCATGTCAC GGTCCCTGTG TTTATTCCAT ACAGCTCTCC TGAAGTGTTT
32601 TGAGTTCTAG CAAAATTTAA AAATATAACC AAAGAAACTT AAATCCGTGT
32651 TTCTCCTCTT TCTGGACACT TCTTTAGTAT GAATGGGCAT CGTGATGATA
32701 AACACGGTGG CCTGCTGTCT TTGCTTCTCT CTCTGCTGGC CGCCTCCTTC
32751 CTTCCCTCCA AAGTCACAGG CAAGAGGGAT TTAGGGTTTG CTGGGCTTGA
32801 GGAAGAGAGG AAAAGGCCAT CTCTTTTCAC AGTGAGAAAT GTGTTTTCTG
32851 TTCTTTCTCA TACCTCGCTT TGTACATTTA AAAAAATTAT TTCTCTTTAG
32901 ATTTTTGAAC CAAGAGAGAT ATATTTATTA TTTAAAAAAA ATTTTTTTTT
32951 GAGACAAAAT CTCCCTCTGT TGCCCAGGCT GCAGTGCAGT GGTGCAATCT
33001 CAGCTCTCTG CAACCTCCTG CTCCCTGGTT CAAGACATTC TCATGCCTTT
33051 GGAGTAGCTG GGATTACAGG TACCCGCCAC CATGCCTGGC TAATTTTTTT
33101 GTATTTTTAG TAGAGGCTGG GGTCTCACTG TGTTGTCCAG GCTGATCTCA
33151 AACTCCTGGG CTCAAGCGAT CCTCCCATGT TGGCCTCCCA AAGCACTGGG
33201 ATTACAGGTG TGAGCTACTG TGCCCGGCCT ATTTCTTTTC TAAATAGAGG
33251 CAGGGTCTCA CTATGTTGCC CTGGCTGGTC TCAACCTCCT GGGCTCAAGC
33301 AATCCTCCTG CTTCGGCCTC TTGAGCAGTT GGGACTCCAG GTGCACACAA
33351 CCATGCCTGG CTAATTTTTG TATTTTTTCG TAGAGATAGG GATCTCACCA
33401 TGTTGCCCAG GCTGGTCGGG AATTCCTGGG CTCAAGCAGT CCTCTGACCT
33451 CAGCCTTCCA GTGTGCTGGG ATTACAGGTG TGCACCACTG TGCCTGGCCT
33501 TATTTATTTT TTATTTATTT ATTTTTGGAG ACAGGGTTTC ATTCTGTTGC
33551 CCAGACTGCA GTGCGGTGGC AACCATAGCT CACTGCAGCC TCCACCTCCT
33601 GGGCTCAAGT GATCCTCCCA CTTCAGCCTC CCCAGTAGCT GGGACTGCAG
33651 GAGTGCATCA TGACTCCTGG CTAATTTCTT TTAATAGGGA TGAGATCTCT
33701 ATGTTTTTGT AGACAAGGGG CTCTCGCTGT GTTGCCCAAG CTGGTCGAGA
33751 ACTCCTGGCC TGAAGCCATC CTCTTGCCTT GGCCTCCCAA AGTGCTGGGA
33801 TTACAGTTGC GAGCTACGGT GCCTGGCTGT AGATTCCCCC CAGCCCCCAA
33851 GCCGCCAGTT GTGAGTCTTC ACTAACAAGG GAACCTTTCA GCATTTTCCA
33901 TGGTCATGGT GATTCACCTA ATATTTTAGT TCTGCTGAGT TGTCTAAACA
33951 TTCGGGATAA AGGCTGTCAT TTTTTGGTGA CCGTAATGTG TATGTGTATG
34001 TTTACAGTTA CACATGCCTG TATTTGGGTG GAGCTCAGAA GATGCCCATG
34051 GCATTTTTCT GGGAAAGTTG AAGTTTATGA TGTTTGCTCT TTATTGGGAG
34101 TGTGGAGGTC GTCTTTCTCC TTCTTCCCAT CCCTCCAGAC AGAAAGCTGG
34151 GATGTGGCCA GGTGCAGTGG CTCATGCCTG TACTCCTAGC ACTTTGGGAG
34201 GCCGAGGTGG GTGGATCACT TGAGGTCAGG AGTTTGAGAC CAGCCTGGCC
34251 AACATGGTGA AACCCTGTCA CTACTAAAAA TACAAAAATT AGCCAGGCGG
34301 GGTGGCGGGC ACCGGTAATC CCAGCTACTT TGGAGGCTGA GGCAGGAGAA
34351 TCGCTTGAAC CCAGGAGGCA GAGGTTGCAG TGAACTGAGA TTGCGCCATT
34401 GCACTCCAGC CTGGGCGACA GAGTGAGACT CTGTAACAAC AACAACAACA
34451 ACAACAACAA CAACAACAGG CCAGGATGTG TTTGTGTGTG AGTTGGACCC
34501 AAGGGCTTGG GAAGGATGGA TAGGGTAGGG GAGGAGGGAT AGATGGATGA
34551 GGGAATGCAG AGAGAGTGGC CACACTGTCA GAGGCTTTCA AAAAGCAGGA
34601 GGTTCTCCAG TGGGAGAGAG GAGACCTGAG TCCACCCCGC ATTAATGTTT
34651 ACAGATCAGA ATTGCACACA TAGAATGGCT CATAAATCTG ATCCACCTTC
34701 CTCGTCTGGC ACTTGGCTGG AGAAACAACT CTTTGAATGT TGGAGGAAAA
34751 GCCCACTGTA TTGCACCTGC TATAAAAAGG GCGTGCCCAC CTTAAAAGTA
34801 GCCACACCTT CCCGAGATTG CCATGGTCCT TCTAAGTCTC TGAAATGTAT
34851 AGATCAGGTA TATTTGGGAA TTTGGGGATT TTTCTAAATT TGGGATGAGA
34901 ATGGGTGCAT GTCCTTTTTA ATTATACAAC ACCCTCAGCA GAGTCTGGGC
34951 TGGATGTTGT TATCAAGACA AGAATATTTC TGTAGTGAAA TAGGTAGATA
35001 TTCACCCCAA GGAGGATCAA GCCTGAACAG TCTCACGTTA GGCAAGGTCC
35051 AGTTTTGCGG CCAGGTGTGT TGATGAAGAC ACTTTGAGTA TTCAGAGCCT
35101 TTAGCTTTAG CCACTGTGGG TAAGGGATTG TAGAACCCAT ACTTAAGCTT
35151 TCCCCTTAAA GCTTTGACTT TAATCTCCAC ATTGCAGCCC TGCAAAAGAA
35201 CAGAATCGTG TCCTTTGCAG CAAAGTGGAT GCAGCTGGAG GCTGCTATCC
35251 TAAACAAATT CATGCAAAAA ATCGAGAGCC AGATATTGCA TGTTCTCACT
35301 TATAAGTGGG ATCTAAACAC TGAGTACTTC ATGGACACAA AGATGGGAAC
35351 AATAAACACT GGGGATTCCA AAAAGAGGAA GGGAGGGAGT GGGGAAAAGA

FIGURE 3L

35401 CTGAAAAACT TCCTATTAGA AACTGTTTAC TACTTGGGCA ACGGGATCAT
35451 TAGAAGCCGA AACCTCAGCA TCATGCAATA TACCCATGTA ATGAACCTGC
35501 ACATGGACCC CCTGAATCTA AAATTAAAAG AAAAGACATA AACTCCACAT
35551 CTGATTTCCC TCGTGCATAA CACTACTACT TAGCTTGGAG AGAGATGGAG
35601 GGGATCTCTA GGGTGGGGAA TGGACCACTT ACCTTCAAGA TCTCCCTTAT
35651 CAGGAAGGAA AGAGCTGACC TGCCTAGAAA CACTTGAAAA CACTCTTTTT
35701 TTATGTCTTA TTGGGCAAAG CTGGGTCAGA TGGCCACCCT TAGCTGCAGA
35751 GAAGGCTACA AATAGACATT TTCTCCTCAA GTGGGATAAT GATAACTGGG
35801 GAATGTGTAC TGGAGAGCCT TCCAACACCA AGCGGGGAAG ATCTACCAGC
35851 ACCATTAAAT GTTGCCTTTG TCTTCTGTGC ACTTAAGCTG ATAAACCTTA
35901 AACATTACAG CATGCCACTT CTGTCTGCTT TGAATAAGGT TGTTTACCGA
35951 CATACTTCTG CAGTCTGATT GTGGCGTTGG CGGGACTGAC AATATCTCCC
36001 AGGGTAGCGC AAAGATCCGC TGCAGTGCAT AAGTAACGTG TTTTGAGTTT
36051 TGTATGTTTA TAATGCACAC AGCTCAGAGA AAGCTTTAAA GAAGTCACAG
36101 AAGTGTAAAA AATCTGTTGA GTCATAGCTG TTGTTCTTAA AGTAGGCATG
36151 GAGAATTCTC TCTGTTGAGG GTCAAATACA AGTACTAAGA CAGAATGTTA
36201 TGCAGTAAAC ACAGCCAAGT AATGAATGGG TTCCTTGGGG TGGGTGATAG
36251 AGAAAGATAA ATAAGGAGGA AGGAACCAGA TAGAGGAAGA AAAGTCAAGG
36301 ACCATATTCA TTGCATTATT AGAATTTTAG GGTGTGGCAA GAATTTAATG
36351 TTTCCTAATA ATATGCAAGT TCTGTTGGAA AGAAGAGCAA CAGGAGACTA
36401 AAAGGTTAAA AGGTTACTCT GTTGCCCATT TCATAGGTCC AATGGCAGGA
36451 TAAGCTTGGG TTGGATGCCA GTGTTCCTGA TTCCTAATTG TGTTTTATCC
36501 AATTGAAACA TCAGTGGCCA TAGTCAAACA CCTAAACTGT ATCAGTTCAC
36551 AGTCCTCAAA GCCCTTCTCC CACTTCCTGT CTTTGACCTG ATTCCACCTA
36601 ATTTTGTCCA CACCATGTTG TACTGTAATA AAACCTATTT TATTTCCAAA
36651 TTAACTAAGA GAATATACTT TAAAAATGTG TTACTATTTC ATTATTTGTT
36701 TACTTTTTTT AAAGAAATAT TTAACACCTG TCAGCTATTG ACATTGTTTC
36751 CTTCTTACAC TTTTTCTTTA TCTTGTAGTT CACTTTCTAT TTCTGCCATA
36801 ATAAAATATT CAGTATCGGA AACTTCACTT AAAAAGCAAA GGTTACTTCT
36851 CCTCCTCCCT TCCCAGTCTG CCCTATAAGC TAGTAAATTC ATCATTCATT
36901 AGCTTAGATA TTTTACAACA TGGGGATTTT AGTTTACAGC AAATACTCTA
36951 AGTAAAATTG GTAGCTTAAG TACAACTTTT TCTTTTCACG TTACCATGTG
37001 CAATCAATGG CATTCCAGAC TCTTGGAAGG AAATCCATTG TATGGTTGTG
37051 GTCTTTTTTT TTCCTTCTCA AACCAGTCAA AAATACCCAG TCACAATTTA
37101 AAAAATTATC CGCCCTTGGT GGTGCACGCC TGTAGTCCCA ACTATTTGGG
37151 CTGAGGTGGG AGGGTCACTT GAGCCTGGCA GGTCAAGGCT GCAGTGAGCT
37201 ATTGATTGTG CCATTGCACT TCAGCCTGGG CAACAGAGAG AGACCCTGTC
37251 TCAAAAAAAA AAAAAAAAAA AGACAAAACA ATATAATGTG ATCTACCCTC
37301 TAAGCAAATT TTCATATATA CAATTTTACT ATTGTATATG TGAGCTATTT
37351 ATATATAAAA TTTCATTTAT CAGTTCAGTA TTGTTAACTA TATGAACTAG
37401 GTGTATGGTA GATCTCCATG GTTTATCTTG TTCAACTAAA ACTTTGTATC
37451 CTTTGACCAA TATATTTCCC CTTCCCCCTC AAGCCCTACC CTCTGATAAC
37501 TACCTCTCTA CTCTCTGCTT CTATGAGTTT GACTATTGTA GATTCTGCAT
37551 TAGTCCATTC TCATGCTGTT AATGAAGACA TACCTGAGAC TGGTTAATTT
37601 ATAAAGGAAA GAGGTTTAAT GGACTCACAG TTCCACATGG CTGCGGAGGT
37651 TCCGACAGTC ATGGCAGAAG GTAAAAGGAG GAGCAAAGTC ACGTCTTACA
37701 TGACAGCAGG CAAGAAGAGA GCCCGAGCAG GGAAACTCCC ATTTATTAAA
37751 ACATCTGATC TCGTGAGACT TATTCACTAT CAGGAGGACA GCATGGGAAA
37801 ACCCACCCCC ATGATTCAGT TACCTCCCAC CTGGTCTCTC CCACAACACG
37851 TGGGGATTAT GGGAGCCACA CTTCAAGATT AGACTTGGGT GGGGACACAG
37901 CCAAGCCATG TCAGATTCCT TGTATAAGTG AGATCATGCA ATATTTAATA
37951 TTTGTTTTTC TGTGCCTATC TTATTTCACT GAACATAATG GCCTCCAGTT
38001 CCATCCATGT TGCTGCAAAT GCCAGAGTTT CCTTCTTTTT TAGGGCTGAA
38051 TGGTATTCCA TCGTGTATAT GTACCATGTT TTCTTTATCC ATTTGCCCTT
38101 GGACGGACAC TGAGGTTGTT TCCACGCCTT GGCTGTTGTG AATAGTGCTG
38151 TCATAAACAT GGGAGTGCAG GTGTCTGGAA GATCCTGGTT CTCTTGGGTT
38201 TTGCAATCTA GCATAAAGCA GGCACAGGAG TACCAGCCAA TGAATGGATA
38251 GGTAAATGGA TCAATATTGA TCGGTGAGAT TTGCTCGTCA ACAGATGTTG
38301 GTTCCTCAGA AGGATACACT TCCAAACCAT CCTTTCTCTG AATGTCAGTT

FIGURE 3M

38351 TCTGAGAAGC CTCTCTGCTG TTTGGGGTGG GTGTGATCAC ATAATACGGG
38401 AGGGCAGTTT TGTTTTAGTT GCTCATCTCT GTCTGCAGCT GTGAATGCGT
38451 TGTTTAAAAA TATTGCTGAG GAATGACTTG CATGTCAGTA AGGGGCTGCT
38501 GACGCTGGGA TCAAGGTACG TCAAAGGCAA TTTAGGGATA CTCTAGAAAT
38551 CCTGCATCAG TTGCAGTGGC TCATGCCTGT AGTCCCAGCA CTTTGGGAGG
38601 CCGAAGCAGG AGGATCACTT GAGCCCAGGA GTTCAAGGCT AGCCTGAGCA
38651 ACGCAGTGTG ACCCCCTCTT TACAAAAAGT ACAAAAATTA ACTGGGTAGG
38701 CTGAGGCGGG AAGATTGCTT GAGCCCAGGA GGTAGAGGCT ACAGTGAGCT
38751 GTGATGGCGC CACTGCACTA TTCGTTCCAT TAACCCAAGA ACATTTATGC
38801 TACGTGAAGA ATATTTCAAT ATGTGCGTGA ACACGTGCAC ACCTTGTAGG
38851 ATCAGTGTGT TACAGGAAGA GGAGGAGGAT GAAGAGGAAG AAGAGGAGAG
38901 GGAGGAGGAG AAAGGAGGAG GAGGAACAAG CAAAGCTTGT TTAGAGATTT
38951 TGATTTTCTT TTATATCTCA TTGACTATTA GATTTCTTCA TTTACATGCA
39001 CCCCAGTGGG AGGAAGAGGA GGGAGAGGAG GAGGAGATGG AGGAGGAGGA
39051 AGAAGTGGAA AAGAAAAGGA TGTAGAGGAG AAGGAAGAGA TGAAAGAGAA
39101 GGAGGAGAAG ATTGAGGAAG AGAAAAAAGA GAAGGAAGAG ATGGAGGAGG
39151 GGAAGGAGGA GAAGAGAGTG TTTGGATTGA AAATGTCCCA GCAGAATACA
39201 GTAGAGCTAT TGGTTTTCTT TTATATTTGT AGTGGTTGCA GTTGTTGTTG
39251 TTGTTTTGTT TTCTGTTTGT GGGCACCTAT ATAGCACTTC ATCCCAACCC
39301 ACGCCAGATT GTAGAATACG GACTCCGTAC TTTGAGCAAG CCTTAATGTG
39351 CGTTAAGGAA ACAGCCGTGT TGAGGAGGGC TGTGTGTTTT ACACCCTGTC
39401 TGTATTTCTG ATAAAACCAG AGAGCCTGAA GAGAAAAAGG CATGTTATAT
39451 AAATACATTT ACTATTACTC TAATGCTTCT CCATGTGGGT GTGTGGGGCG
39501 TGTGGGTGTG CTGTGTGCGA AGACTGATCT GCAGAAATTA TGGCCAGTTT
39551 GTCCCCAAAT TGAGGAACCA TTCAGAGGCA GATGGCTCTC TCTGTCTCCC
39601 TCTCTCTCCC TCTTTCTCTC TCTGCAATTT CTGTATTCAG TGGAAAATTC
39651 CAGGTGAGCG CCTCTCACTA AATGCCATCA GCCCACGTGC ACCATGACAC
39701 AAAGTCTCTG AAAGTTTCAC TTGGGGTCTG TGTTTGCCGT CCTGGTGCAG
39751 CCCCCCGCTG ATTGCATGGC TGTGGTGGTT TCTTCCTTTG TCGGAAGACT
39801 TAATGACCTC TGTCGATTTC TTCTCTCTCC AGGCACTGGG ACGTTCGGGC
39851 GGGTGCACCT GGTGAAGGAG AAGACAGCCA AGCATTTCTT CGCCCTCAAG
39901 GTGATGAGCA TTCCCGACGT CATCCGCCTA AAGCAGGAGC AACACGTACA
39951 CAATGAGAAG TCTGTCCTGA AGGAAGTCAG CCACCCGTTC CTCATCAGGC
40001 TGTGAGTCCC CTCCTGAAGC CTCTCCCCAC GCACTCTCCC TAGACCCCTG
40051 TGTGTCTCTT CTTATAAGAA GCTGGGTGGG CCGAGACCAT GGCCTGCGTG
40101 CAAAGCCTTA GGCCACAGCA GTCTCCACCT GTCAGGTCTT ATCAGCCTCT
40151 GATCTTAGAG CTGGAATACC TCCAGGGCTC CTGACCTCCA TGGCTGACCA
40201 GGTCCAAAAA GAAACGCTCT GTGTTCAGAA GTCCGTGCCC AAGGCCCCTT
40251 GCTCCTCTCC TGGGTGAACC AAGTATCTCT GCCCGGAAAA GGATGCAGAA
40301 ATCTTTGTCT CCTCACCTCC TTGGGTTCTG CATCTATAGC TCTCGGCAGA
40351 ACTGGTTAAG TTGGTTTTTA AGGGACCACA GTCACGTGGA CGGGGCTGGG
40401 CTTCAGGTTT CGTTGGGTTT CTGGTTGACT GTGGATGAGA GATACCCCGT
40451 TGAGATGCAG CCCACACACT TCCAGCTGAT GGTACACAAC AGTCTTATGT
40501 CCTAGGGTAG GTGTGATAGT CCATTCAGGC TGCTATAACA AAGGATCTTA
40551 GACTCGGTAA TTTACAAATG ACAGACATTT GCCTCATGGT TCTGGAGGCT
40601 GGAAAGTCCA AGATCAAGAC ACGGTGGATT CAGTGTCTGG CGAGGACCCG
40651 CTTCCTGGTT CATAGATGGC GCCTTTTTCAC TGTGTCCTCA CATGGTGGAA
40701 GGGGTGAGGG ATCTCTCTGG GGTCCCTTTT ATAAGGGCAC TCGTCCCATT
40751 CATGAGACTT CACCCTCATG ACCTCCCAAA GGACACAACA CCTAACACCA
40801 TCACCTTGGG GGTGAGGATC CAACATAGGG ATTTGGGAGG ACACAAGATA
40851 TTCAGACCAT TCCAGCAGGG TAATTCCATT TCCACCCAGA TGCCTTAGAC
40901 AAGGATGTCC TGCGTGTCTC TCCTTTCCCT CCATGGGTGC CTTCCATCCA
40951 ATTCCCACGT CTTCCCTCCG CCATCTTGCT ACCATGCCTC TCCTGTCCAC
41001 CTATCCATCT TCTGCTTTAT CTGGGTCCCG TCTCTCTGCC CTGATTTTCT
41051 GTACTGGCTT CCCTCCTACC TGGTCTTTCT CTCCCAGCCT TGCTCCCCTT
41101 GAAGACATTC CTCACTTTAT AGCCTCACTG GTCCTCCCAG GTACCTCTGC
41151 AATGACCTGC CTCTCTCCTT TCATCCTCAG GGTACTCCTG AAGTATCCCA
41201 TATAAAGCCC CAGCAATGCA GCATCCTCCT ACCAGTATCC TCGTGGACTG
41251 GCCCCCTGCC ACCACCTCCC TACAGGAGAA GGTAGAAGGT GCTGTTCACA

FIGURE 3N

41301 CACTCATTCC GGGGCTTCTC CCAGGCCACC CTTCTTTGAC AGGCCTCCTT
41351 CTTTGCTCTC ATCATTGTCC TTCACTTCCC CCATCTAAGA AACACCTACC
41401 TGTTTTCCCT CATTCACCTG CTGTCCCCGG GACACAGGGT GCCTCCCATC
41451 ATGTTCTTGA AGCACCTCGT GTGTACTGGA ACAAGTGCAC CTGCCTTCTC
41501 CTCTAGACCC AATGCTGCCT AAGCTCCGAA CAAAATCATA TGCAGAGGAT
41551 GGGCGCGGTG GCTCCCTTCC TCCCTTCCTT TCTTCCTTTC TGCATTTCTC
41601 TTTCTTTCTT GACAGGGTCT CACTCCTTCT TGCCCAGGCT GGAATTCAGT
41651 GGCACAATCA TGGCCCACTG CAGCCTCTGC CGCCTCCCAA CTAGTTGAGA
41701 CTACAGGTAT ATGCCACCAT GCCTGACCAA CTTTTAAAAG TTTTTGTAGG
41751 ATGAAGTCTT GCTGTGTTGC CCAGGCTGGT CTCAAACTCC TGGCCTGAAG
41801 CAGTCCTCCA GCCTCAGCCT CCCAAAGTGC TGGGATTGCA GGTGTCAGCC
41851 CCTGCACCTG GACTGAGAAT GCATGTCTGT TGTCTGCCGC GTCCCTCCAC
41901 CCCAACCCCC AGTTTGTGGT ACTTTGTTAA TGATAGCCCT GAGGAACTCA
41951 CACACACCCC CTGCGCCTCC TGGAGCAGGA GAGCAGCCGA GACGATGGGC
42001 TCCTGAGTAC TCTACAGTTC AGAAATCTAA AATCCCACAG AAGAACCGCA
42051 TGGACATGGG AGTGGGTGGA GTATACAAGT GAGAGAATTC CCCAGGATGG
42101 AATTCTTGAG CTCCCGCAAG TTAAAAAATA GGGAGGAGCT TGTAGAACAG
42151 AGCTTTAGTT AGGTAGTTCT CCTTTCTTCA AGGCAGGATA GCTCAAGACT
42201 GTTTTCCTTG GCAGATAAGG TGCATTCCTG CAGGGACGTG GATTCTGATT
42251 TTGATATTCC CTGCTTTCAA TTAAGGAACA AAGTCGTTTA TATTTCTTAA
42301 GTCTTATATA AAGCCCTAGA GACTTTAGAA ATTCTATTCA AAGTTACCTA
42351 TGTTGGTTTA TTTTTATCTT TTATATAAAA AAGTATATAT ATAGATTTAC
42401 ATTTAGAGAC GGGTTTTGCT CTGTGGCCCA TCTTGGAGTG CAACGGTGCA
42451 ATCACAGCTC ACTGCGGCCC CAACCTCCCG GGCTTAAGCC ATCCTCCTTC
42501 CTCAGCCTCC AGAGTAGCCG GGACTACAGG CACCCATCAC TACACCCTGC
42551 TAATGTTTTT ATTTATTTTT AATTTTTAAA AAACATATGT ATATATTTTT
42601 CACAACCTCT TTGGTGAAGA TAATGTTTTT GTTTTTTCTC TATGAACAGG
42651 GTCTTGCTAT GTTGCCCAGG CTGGTCTTGA ACTTTAGGCT GCAAGCAATC
42701 CACTTGCCTT GGCCTCCTGA CATGCTGGGA TTACAGGTGT GCACCACCAC
42751 ACCTACCTCA TTTTAAAATT TTCTGTAGAG ATGGGATCTT ACTTTGCTGC
42801 CCAGGCTAGT CTCAAACTCC TGGGCTCAAA TGATCTTCCC ACCTCGGCCT
42851 CCCAACATGC TGAGATTATA GATGTGAGCC ACCGTGCCTG GCCTATTTCT
42901 AACTTTTAAG GAGTGAAATT TCTCTGCACC GTGACAGCTT TTGAAGAGGA
42951 CATTTTGGAT GCTTCATGGG TTGTCCTTTG CCCGTACAGC TCACCGGCTC
43001 CTCCGAGTGC TGGTTACAGT CGAATGTGAG CTGTTATTTG TATGTCAGGT
43051 CCGCCTGGTG GTGTTGCCAA AAAGCATGAA TTTTTCCTCA TCATTTAAAG
43101 TCTACATGGA ATTTAAGGCC ACTTTCGATA TTATTCTTGG GAGGATTTTA
43151 TTCAGTGTTT TGGGAGAACA TGGCAGGGGC TCATTTCAGA ATTCTCTGAT
43201 TTGGGGCCGA GCTCGGTGGC TCACACCTGT AATCCCTGCA TTTTTGGAGG
43251 CCAAGGCGGA AGGATCACTT GAGACCAGGA GTTCCAGACC AGCCTGGGCA
43301 ACATAGTGAG ATCTCGTCTC TTAAGAAAAA AAATTAAAAA GAAAATTCTA
43351 GCCTGGCCAA TATGGGGAAA CCCTGTCTCT ACTAAAAATA CAAAAATTAG
43401 CTGGGCGTGG TGGCGCACGT CTATAACCCA GCTACTTGGG AGGCTGGGGC
43451 ACTAGAATCT CTTGAGCCTG GGAGGCAGAG CTTGCAGTGA GCCAAGATCG
43501 TGCCACTGCA CTGCAGCCTG GGTGACAGAG CAAGACTTTG TCTCAAAAAA
43551 TAATAATAAA TAAAAATAAA TAAATAAATA CAGTTCTTTG ATTTTGAAAT
43601 AGTGCAGAAA ACAAGGCAGG CCCTGAAGTC CACAGCTCTC ATGAAAAGTT
43651 TTGGATCTAG GGAAGTGATT GTCAACAATG AGCCTTTAAA GACTTAATGG
43701 TGATAGCAAT TTACAGGTGA CTTTTCCCAA AAAATGACAG AAAATGAGTT
43751 TGCCACTTGG GCATGTTGAC TCACACTTAT AATCCCAGCA TTTTAGGAAG
43801 CTGAGGTGGG AGTGTCCCTT GCACCCAGGA GTTTGAGACC AGCCTGGGCA
43851 ACATGGCAAG ACCCTGTCTC TACAAAAAGT ACAAAAATTA GCTGGGTGTG
43901 GTGGGGGGGC CTGTAGTCCC TGCTACTCAG GAGGCTGAGG TAGGGGGATC
43951 GCTTGATCCT GGGAGGCGGA GATTGCAGTG AGCCGAGATT GTGCCACTGC
44001 ACTCCAGCCT GGGGGACAGA GCAAGACCCT GTCTCAAAAA AGAATCCGAA
44051 AAACAATGTA GACTTGGAGG GGGTGATGTA ACTTAGCCCA TGAGACCGCC
44101 TTAGTGACTT GCTGATAATT GATCTTTCGG TGCCCTGCAG TATTATGATA
44151 ACCTGCTATA GCATTTTGCT TTTTCTGTGC ATTAACACTT TAGGGACCAA
44201 GTGGCTTTAA GAACTGGATT AAAGTTGATC CAGTGCATTC AGACACTTGG

FIGURE 3O

```
44251 CATTCCCTGT ACATAACACG AGAGAGCACG CCGGGTCTGG CCAGCCCCAT
44301 GGATAAGATG CTGGAGGGTG TCCAACGTTG CATGCTGAGG AGCATGTCTT
44351 AGAGGAGAAT CCTAGATCCT CTGTGAAGAA TGAATTTCAT CCTCCCAGCT
44401 GTGCAGCTTC TCTTCTAAAT GTAAGTTGCC TTGCTCAACA TCTGCTTCCC
44451 ATACGGGCAG TTTTAGGCCT TGGACTTCTT GATGAAGGTA TAAAACGAGG
44501 ACTTTCAGCG GAGGTGCCTC CCATTTATGG CTGGAGGAGT CTCTGGGGTG
44551 GGGCCGTCCT GCACACTTCA GGGTGTTGGG GAGTGTCCCT GGGCTCCACC
44601 CACCAGCGGC CAGGAGCAGC AACCTCAGTT ATGAAAAGCA GAAATGTCTC
44651 CATACATAAC CAAGTGTTCC TTCAGGGAGG GAGGGCAAAG TTTTCTCCAC
44701 TAGTGAACCA CTGTGATAGA CAGACGACGG ACAGAGAGAG ATGATAGATA
44751 CGATAGGTAG GTATATGTTG AGATGGATAG GTGATAGATA ATAGATATTA
44801 AGATAGGTGT AAATGATGGG TGATTGATAG GTGAGTAGAT AGATGATGGG
44851 TAGCTAATAG ATGATATTAA GATAGGTGAT AGATAATAGA TACTAATATA
44901 TACAGCTATA GATGATAGAT GATATTGAGG TGGGTAGGTG ATTGATTGAT
44951 AGATTAATGA CCGATTGCAT GTAGGCAGAG CTCTCATGCT AAAAGAGAGT
45001 TTCTCAACCT CAGCAGTGCT GACACATGGG GCGGGATCAT GGAGGACTCT
45051 GTGGTGGGGC ATCCTGTGCA CTGTAGGGTG TTGAGCAGCG TCCCTGGACT
45101 CCACCCAGCA GATGCCAAGA GCACCCATCC CATCTATGAC GAGTATCTAA
45151 AGATGTCTCT AGATACTGCT AAGTTCCCCC TATGGGGGGA CAAAAAGTTA
45201 TCCCCAGTTG TGAACCACTG TGACAGATAG TTGATGGATG GATGGATGGA
45251 TGGATGGATG GATGGATGGA TGGATGGAGA TCAACATTGA GACAGATATT
45301 TGATAGATGA CAGATATTGA GGTAGATGAT AGCTATAGAT GATAGATGGT
45351 TGATAGATAT TAGATAAGTG ATTGATAGAT GATAGCTATA GATGATAGCT
45401 GATTGATAGA TAGCTGGTAG CTATAGATGG TAGATGGTTG ATAGATATTG
45451 AGATAGATAG GTGATTGATT GATAGATTGA TGATGGAACG TATTAGTAGA
45501 GTTTCTCAAC CTCAGCACTG CTGACATTTG GGGCTGGAGG ATTCTCTGCG
45551 GTGGAACCGC CCTGTGCACT GTAGGGTGCT GAGCAATGTC TCTGGGCTCC
45601 ACCCACCAGA TGCCTCTAGC ACCCCCACTC CAGCGTGACA GCCAAAGATG
45651 TCTCCAGACA TTGTCCAGTG TTTATTGTGG GGAGCAGAAT CAGCTCCATT
45701 GACACCCACT GTAGCGGATG CACAGACAGA TAAATACCTG TGCGTGTGGA
45751 GTCCCTTTCT CCCTTTTCTG CCCCAGCCCC TGAGCCTGCA GCCCCACTCT
45801 TCTGTCATGA TTGATTGGCT TATGGGCCAA ACAGTGGTTC CAGTGCCATA
45851 TTATCTATGG CACAGCAGCC GAGCCAAGCC AGTGGGTTTG GTCTGTGGTT
45901 GCAGGGCTTA GCCAGCTTTC TTCTACAGAA CTTGGAAGGC AAGAGGTCTC
45951 TCCACTCCGG GCCACATCCT TCTAGTTCCT GGATGACCGC TCGTTTCTCC
46001 ATGGAGAGGA GTTCATGCCA GAACCTCTTC TTCGGGGAGA GTGGATGCAT
46051 CTCTTGGAAA CATCTTTTTT TAAAGTCTGC AGACTTGAGT GTGGTCCCCA
46101 TTGTCATTGG TACTTGTTGG GGGTAGGAGT AAAATCATTC CTTTGTTTTA
46151 CTGAGAGTTC AGGAAGAAAG AACACCATGT TCTCTCCTTT TATTTATTTA
46201 TTTATTTTGC TCTCTATTTG AATTTTAAAG GCAAAAATCT AGAAATAGCG
46251 CTTCTTGCTC TGTCATCACT GCCTGCAAAG CACAGAGACC AGAGTGAAGG
46301 CAGGCAGCTC CTGGGTCTTC TCTTCCTCTT CTTTGTCCAA AAAATGATAC
46351 ATTGCATGTT TAGTATTTGG GGCAAAGCAG ACGCTTCAAA AAGGGAGGCT
46401 TATTTTATTA TCTATATTTT TCTTTTTTAT TATTTTTTAC CTTGATTCCC
46451 TTTTTCTATG TATGAAAAGG GAGGTTTAAG TTCTTGCAAG AGAATGCAAC
46501 TGTAGTGTCT TCTGAATGGA GTTTTCCATT TGATGCCAAG CCTTCCAGTG
46551 CCTTGGTCTA AGGAGAACTG CGTAGGGTGA GAAGAGTCCC AGCGATACGT
46601 GGAAAAGGGG CCTTACCAGC TCTGGAGGGC AAGAGGTAGG GGGTGAAGAC
46651 GCAGTGGACA CCTAAGGAGA ATTTTGCAGG AGGAGTAGGG GTTTATTGGC
46701 TGAAAGGGGT GGGTGGTGGA AACTCATTCT AGACAGGGAG TGACACGGAA
46751 GCCATGGGTC ACTACGGGGC AGGAGGGACA TGGGGGAGAA ACTCAAATCT
46801 GAGTTCAGCC AGGAGGTGGA CACAGGAATG CAGTGAACCC AGATGTGTAG
46851 GAGACTGCCA TGGGGACTGG GGTATGAGGA AGGACTGGCT CTGGCTCGGC
46901 TGTGCATATA AGGAAGGACT GGCTCTGGCT CAGCTGTGCA TTTGGGCTGC
46951 TGGACAGTGA GGAGATCCAG GGAGAGAGAG TGCATTCCAA TTTGGGAAAC
47001 TTTGAGGGCA AAACATCTGC AGCAACTGTC TCAGAAGAGA GCCTGAGGCA
47051 GGGTCCTTGG AGGGAGGAAG CCACAGGTGG ATGGAGCCAC CGAGGGCTGC
47101 TAGGTCACCT TGGTTAAGGG CTAGTTGCAG TGCAGCCAGG TCGGAAAGTA
47151 GAGCCGTTCT GGAGCCTCAC GTGGCATAGA TGTTGGAGGA GATGGGATGA
```

FIGURE 3P

```
47201 GGATGGCTCA TTTTCTTCTT CTCACCACAA AAGCCCAGCT TTATGGCGGG
47251 CTCTGGAGAG AGGAGGACCA ACTTCTACGG TAAGGCGTCT CCAAATTAGT
47301 GAGGCTGATT TGCCTGTTCA TAAAAACAAA AACAAAAGCA AAAAAATCCC
47351 TTAGAGGACA AGCCATCCCC GCAGACCCTG CAAATAAAAG ACTGCAGATC
47401 AGCTTCGCGG ATGGAAAAGT GCTGCTGTCA GCTAAAGATG AGGACAGAGC
47451 TGCTCAGCTG AGGTCACTGG AGAGGATGGG GAGGGGACTT GGAAACCTCC
47501 CTTGTCTCAG TCGTTGTTGA CGACATTGAC TCTTTCTTCA TGTTGACTTT
47551 CCCCCCGTTC ATAGATTCAT AGATTGCTCT CTATGCTGGA AAACATTCTT
47601 TAAAATTTAA TTTTTTTATT TTGTTAACAT ATATCACATA ACAGTTTACT
47651 ATTTTAACTT CCTTTTTTTT TTTTTTTTTT TTTAAAAGAA ATGAGGTCTT
47701 GCTCTGTTGC CCAGGCTGCA GTGTACTGGT GCAATCATGG CCCACTGCAG
47751 CCTCAACCTC CTGGGCTCAG GTGATCCTCC TGCCTCAGCC TCCCAAGTAG
47801 CTGGGACTAC AGGTGCGCAC TACCACGCCT GGCTAATTTT TTAATTTTTG
47851 GTAGAGACAG GGTCTCGCTG TGTTGCACAG GCTGATCTCC AACTACCAGG
47901 CTCAAGCAGT CCTCCTACCT CAGGCTCTCA AGTTGAGCTG GGACTATAGG
47951 CACATGCCAC CATGCCCAGT TAATATTTTA ATTTTTGGCA AACATGTGAT
48001 CTTGCTTTGT TGCCCAGGCT GTTCTCAAAC TCCTGATCTC ACTCAATCCT
48051 CCTGCCTTGG CCTCTCAAAG TGCTGAGATT ACAGGCATGA GCGTCCATGC
48101 CCGGCCTCAT TTTAACCATT TTTAAAATGT ACAGTTCACG GCTGGGCGTG
48151 GTGGCTCACG CCTGTAATCC CAGCACTTTG GGAGGCCGAG GTGGACGGAT
48201 CACGAGGTCA GGAGATCAAG ACCATCCTGG CTAACACAGT GAGACCCCGT
48251 CTCTACTAAA AATACAAAAA AATTAGCTGG GCGTGGTGGC GGGTGCCTGT
48301 AGTCCTCAGC TACTTGGGAG GCTGAGGCAG GAGAACGGCA TGAACCTGGG
48351 AGGCAGAGTT TGCAGTGAGC CAAGATCGCA CCACTGCACT CCAGCCTGAG
48401 TAACAGAGCG AGACTCTGTC TCAAAAAAAA AAAAAAAAAA AATGTACAGT
48451 TCACTACTCG GGAGGCTGAG GCAGGAGGAT CACTTCAACC CAGGAGGCGG
48501 AGATTGCAGT GAGCTGAGAT TGTGTCGCTG CACTCTATCC TGGGCAACAG
48551 AGTAAGACTC TGTCTCAAAA AAAAAAAACA GAAAACAAAA AAAACAAAAC
48601 ACTGTTTAGT GGCATGGAGC ACATTCATGT TTCTGTGCAA CCGCCACCCC
48651 ATCCCCATCC CCATCCCCAT CCATCTCCAG AACTCCTTTT CATCTTCCCC
48701 AACTGAAACT CTGTCCTCAT GAAACACGCC TTATTGCCCC TCCCTCCAGC
48751 CCTGCCCTGG CAACCTCCCT CGTACTCTCT GCTCTATGAA TTTGGTGATT
48801 CTAGGAGCCT TATATAGGCA GAATCATACG GCATTTGTCC TTTTGCGACT
48851 GGCTTCTTTC AGTTACTGTA ATGTCCTTCA GATTCCCCCG TCCTGTAGAA
48901 AGGAATTTCC CTCCTTTCTA AGCCTGAGTA CTATTCCATC GTATAGAGGA
48951 TACAGCATGT TGTGTTTACC CATTCATTCA TCCTTGGACA CTGGGGTGCC
49001 TTCCACCTCT TGGCTGTAGT GAATAATGCT GCTATGAACA AGGTTTGGCA
49051 AATATCTGTC CAGTGCCTGA TTTCAGCTGC TTGAATACAT TGTTTTAATT
49101 TATTATTATT ATTTTTTAGA GATGGAGTCT CGCTCTGTCA CCCCAGCTGG
49151 AGTGCAGTGT TGTGATCTTG GGTCACTGCA ACCTGTGCCT CCTGGGTTCA
49201 AGCGATTCTT CCAACTCAGC CTCCTGAGTA GCTGGGATTA CAGGCATGCA
49251 CCACCACCCC CAGCTAATTT TGTACTTTTA GTAAATATGG GTTTTCACCT
49301 TGTTGACTGG GCTGATCTGG AATTCCTCAT TGCCAGGTAA CTATTTCACA
49351 GCCTGGTATG GATCCTTCTG TACTTTTCTT TGTGTTAAAA AAGCCCCCTC
49401 ACACAAACGC ACACACACAA GCACGCACAC ACACAAGCAC ACACACGTGC
49451 ACGTGCACAC ACACATGCAC GCACACATAT ATGCATGCAC ACACACACAC
49501 GCGCGCGCCC CGTGCAGTTT TGGCCTCATG CCACTAGAGT ATGCATCATT
49551 TTTGTCTCTT GTTTTCTTGG AGATCCCTCT GGGGTATTTT GAGGAGGAGA
49601 AGTTGTATTA TTATTGTGTT GTTGTTAATC TTTAGACATT CAGGGATACA
49651 CGTGGACGTT TGGTACATGG ATGTATCATG TTATGGTGAG CTTTGGGCTT
49701 CTAGGGTACC CCTTACCCGA ATAGTGAACA TTGTACCCAA TAGGTTATTT
49751 CTCAGCCCTC AACCCCTTCC CAGCCTTCCC CTTTTGGGAG TCCCCGTATC
49801 TGTTATTTCC ATTTCTGTGT CCATGTGGAC CCACTGTTGA GCTCCTACTT
49851 TTGAGTGAGA CTATGCGGTA TTTGACTTTC TGTGTCTCAG TTATTTTACT
49901 TAGGATAGTG GTTTCCAGTT CCATCCCTGT CGTTGCAAAA GACATGATTT
49951 TATTTTTTAT GGTGGTGTCG ATATACTACA TTTTCTGTGA CTTTTATATA
50001 CTAAATTTTC TTTATCCAGT CATCTATTGG AATGGCTGTT ACAAAAACTC
50051 AAAAAAATCC AGGCATGGTG GCCCACGCCT ATAATCCCAG CACTTTGAGA
50101 GACCCAGGCA GGAGGATCGC TTGAGCCCAG GAGTTTTAGA ACAGCCTGGG
```

FIGURE 3Q

```
50151 CAATATAGGG AGACCCTGTC TCTACAAAAA GCTCGAAGAA ATAGCGAGGG
50201 ATGGTGTTGC ACGCCTATAG TCACAGTTCT TCAGGAGGCT GAGGTGGGAG
50251 AATTGCTCGA GCTCAGGAGT TGAAGGTTGC AGTGATCTAT GGTTGCGCCA
50301 CTGCACTCCA GCCTATGCAA CAACAGAGCG AGACCCTATC TAGGAAAAAA
50351 ACAAAAAAGT AAGAAAACAA CAGATGTTGG TGTGGAAGTG GAGGAAAGGG
50401 GCCATGGATG CGCTGCTGGT GCGGAGGAGG TCTTCCAGTG CGTGCAGCAG
50451 GGGAGGTGAC CTCACTTCTC CTCGAGAGGA GCTCAGCTGT GCAAGGCAGT
50501 GTTGCAGAGG ATGGGAGGGT GCATGTGACC CTAGGAGCAA GGCTGTGTGC
50551 CTGTGGGCAT GTACTTCCTG GTGACGTTTC CTTGGACCCC ACAGTGGGAA
50601 ACAGGAGCCC CTCTGCCCTC TCATTCCTCT TTCTCTGTAT TTGCATTCGC
50651 TGTCTTGCTG GTCTCAAGAT TCCCAAGCGC TGCTGCCAGC CCACCCCTTC
50701 AGCCTGCCAA GCTACATGTG TGCGCCCACT TGACCACTCT CTGAGCCTTC
50751 TGCTCAGATG CCTCTCACCA AAAATGAGTT CCTGCTCTTC CTCCTTGCCC
50801 CTCAGCCCTA ATCAGTTCCT CATTTGCACT TCCCCATTTC ATAGGTGGTC
50851 CTTCCAGCTC TTGGGGCTCA CCCAGGAACC ATTTTTTATT CCTTTTCTTT
50901 GACTCTGCAT TCACTGTAAT CCTGAGTCCT GCCCTTTTAA CTTTTTTTTT
50951 TTTTTTTTTT TTTAAGAGAT GTGGTCTTGC CGTCTCATCC AGGCTGGAGT
51001 GCAGTGGTGC AATCATGGCT CACTGCATCC TTGACCTCCT GGGCTCAAGA
51051 GATCCTCCCA CCTCAGCCTC CCAAGTAGCT GGGACCACAA GTGCACACCA
51101 CTATGTCCAG CTAATTGAAT TTTTGTGTGT GTGTGTGTGT GTGTGTGTGT
51151 GTGTGTGTGT GTGTGTGTAG GGACAAGATC TCACTGTGTT GCTCAGGCTG
51201 GTCTCAAACT CATAATTTCA AGCATTTCCC CTGCCTCAGC CTCCTAAGTA
51251 GCTAGGATTA TAGGTGCACA CCGCCATGCC TTGCCCCTTT CCAATTCTCA
51301 AACACATCTC CAGAGCCCAT CCACATCAAT GATGTCTTCA CAGAAGCTGC
51351 CATAGCTTAT CTAAATTCCC TCCCCTTCTC TCCACTGATC TCTGATCTCT
51401 GCTGAACTCA CCCCTTCCTG CTGTATCAGC CCAAACGTTT CTGATGTGAA
51451 AATAGGCAGG GCGTAGTGGC TCATGCCTAT AATCTCAGCA CTGTCAGAGG
51501 CTGAGGTGAG AGGATTGCTT GAGGCCAGGA GTTTGAGACC AACCTGGGCA
51551 TCTTAGTGAG ACCCCATCTC TAATTTTTTT TTTTTTTTTT TTTTTAAAGA
51601 CAGGGCCTTT CTCTGTTGCC CAAGATGGAG TGCAGTGGTG CCATCATAGT
51651 TCACTGCAGC CTCATTCTCC TGGGCCCAAG TTATCCTCCC ACCTCAGCCT
51701 CCCAGATAGT TGGGACTACA GGCCTGCACC ACCAAGCCTG GCTGATTTTT
51751 AAATTTTGGG GGTCTTGCTA TGTTGCCCAG GCTGATCTTG AACTCCTGGG
51801 CACAAGTGAT TCTGCTACCT CTGTCTCTCA AGTAGATAGG AGTACAGGTG
51851 CATATCACCA TGCCCACCTA ATTTTTAATT TTTTTTTTTT TTTTTTTTTG
51901 AGATGGAGTC TCACTCTGTC CCCCAGGCTG GAGTGCAGTG GTGTGATCTT
51951 GGTTCACTGC AAGCTCCGCC TCCCAGGTTC ACGCCATTCT CCTGCCTCAG
52001 CCTCCCAAGT AGCTGGGACT ACAGGCGCCC GCCACCACAT CCAGCTAATA
52051 CTTTGTATTT TTAGTAGAGA TGGGGTTTCA CCATGTTAGC CAGGATGGTC
52101 TCGATCTCCT GACCTCGTGA TCCACCTACC TTGGCCTCCC AAAGTGCTGG
52151 GATTACAGGC ATGAGCCACT GCGCCTGGCC CTAATTTTTA ATTTTTTGTA
52201 GAGACGTGAT CTTGCTTTGT TGCCTAGGCT GGTTTTGAGC TCCTGGGCTC
52251 AAGCGATCTG CCACCTTGGC CCCGCAAAGT GCCGGAATTA CAGACGTGAG
52301 CCACCGCACC TGGCCTCCAG CTCTTTTGTG TCCCTCCCCA ATCTTCCTTT
52351 GGCCTTCAGC TGTGGGGACA GAGATGCCCC CTGCCTCCCT GTCCCCACCT
52401 TCTACCTGGT CTTACAGGAC CCCCTCCAGC CATCCTTCCA AGTTTACTAT
52451 GTAATGTCTG TTCCACATCA AGCCTGCAAA GCTCATGACA GTCACAAGAT
52501 CTGCCGTTCC TGATACTATG TACCGAGAAC ATTACTTGGC ACATAAGGGG
52551 CCCTTGTCCA AAACATTTGG AAACCAATAA AGAATGTGGC TGGTGAGTTA
52601 CTGATTAATG TGTTGATGAA TTCATTGATT GCTGAGGCTA GTATGTACAG
52651 TAAGTGTTAG ATCTTGAACA TACTTCTCAT ATCCATTGTG ATAAACCCTC
52701 TTATCTTCTA TTGCTTTTGA ACTTTTATAG ACTTGATGTC AGGGGCAGAG
52751 TCCCTCAGGT AACTGGAATC ATTGAACTGA TGCATTGGTT TCTAATTTTC
52801 TAAGCTCAGA TTTGAAATCA CCTGTGGTCA CTAAACTCGT CCTATCCCAC
52851 AGCCCCTGCA CATGATGACT TAAGTTTTGT GAATGTTTTT TGGAGATAGT
52901 AAAGTCAGTA TCTCTTTCAA CATTTTGTTC CTTATCTTTA GTGATACCCA
52951 GCTCTGTACA AATTCTGTCC ACGTAAGCAA AGTCTTTTTT TTTTTTTCCA
53001 GATAGGGTCT GGCTCTGTCA CTGAGGCTGG AGTGCAGAGG TTCAGTCATA
53051 GCTTCAACTC CTGGGCTCAG GCTGTCCTGC TGCCTCAGCC TCTTAAGTAC
```

FIGURE 3R

```
53101 CTGGGACTAC AGGCCTGCAC AACCACACCT AGCTAATCTT TTTATTTTTT
53151 GCAGAGACAG AGTCTCCCTA TTTTGCCCAG GCTAGTCTCA AACTCTTGGT
53201 CTCAAGTGAT CCTCCTGCCT CAGTTTCCCA AAGTGCTGGG ATTACAGGTG
53251 TGAGCCACCA CACTCGCCTG CAAAGTCTTA CTGATAAAAG ATTTGAAGGA
53301 AGGATGTGTC AGAGAACTTC TTTTTTCTTA TAATATTTAC TTAATCTTAT
53351 TGGTTTGGGG AAGGGCAAGA GAATCCCAGT TATCTAGATT TTTCTTTTTC
53401 TTAAAGGAGT ATGTTTTTAC TTGCTAACTC TCTTTGTAAA CTGTTACTTC
53451 TTAAAGATGC TGAAGGGTGA TCCCGCATTA GTGTATAGGT AAAAATGATG
53501 TCTCCATTTC ATATATACTG ATAAGGTGAC TTTATTAAGC CTTGTGGTTT
53551 GTTGATGTTG ATTTTACTGA GACACTTGTG GAACAGATGT ATTTTCATAC
53601 AACCTTACAC ATCTCAGTAG TTTTCCCCAC TCGTGCAGTA ACTTTTTCTC
53651 CCCTGCTTTC TCTCCTCCTC TCCCCACCTC TTCTTCCTTC CCCTCCTCTC
53701 CTCGTCCCTT CCCTCCTCTT CTCATTTGAT ACAAAGCCCT AACTCTCTTC
53751 CTCTACAGAT CATCCTACCC ATGGTTGAAA TTGCAACTTC CCCTGCAAGC
53801 CAAGTGACCG AACCTGAGAT GTTTGTATTG TCAGGGCTTG CGTATTCTAC
53851 ATGCCTGTGT AATCCTCAAA GTTCTTTCAT TCCTTGCTTC TAACCTACCC
53901 AAATCCTTCT AATCTCCCAC CATGGTTAAT TATCTCTGAT GCTCCTGAAA
53951 GGTGACCTGC TGCTACATTG TGACAAGGTG ATGCATTATT CTTAAGAGGA
54001 TCTGTGCAGA TTATTATCCC AGAGTGAGGT AGATGGGGGA GGATACAGGA
54051 TATATCCAAA AATGTGTTGC AAGCTAATTG ATAGAGAGAG AGAGAGTGTG
54101 TTTGTATGTG TGTGTGTAAG CATGCGTCCA TCTTTTTCTT ACATATTTGA
54151 GCCATAGGGA AGTAGAGCCA TGTATATTCT CTTCAACCAA ATTAACAGTT
54201 GTAGACAGTG GTCTTGCTAT TGCTTTGACT ATTAATGGTA TTTTCAAGAG
54251 CTCAGTGTTA CCCCCAAATG TTCAGTATCA CACCTTGGCT GGTCAGTCGT
54301 AGCTAAATTT TCCTTCCACC TTGCGCCCTG AAGAAATTTA GAAAGTCACC
54351 AGCTGACACA GAAGTTTATT GTAAAAGTTC ACTAGTACGA TAGTATTTGG
54401 ACCTTGGAAA ATATTTCCCC ACCAGAACAG TGAAATCATG AAATCATGGT
54451 TGTCTTCTAA GCTCATCCAC AAAAGTACAG TTTGACTGTC ATGCATTTGA
54501 GATGCCATGT GCTTAATCAC GAAATATTAC TGAGAGGAAC ACTCTTGCCC
54551 AACCAATAAC GGTGCAAAGC AGAAAAACAG GGCATTTAGC TGGGAGAAAA
54601 TGAGTCGAGA TGTCAGTGAT AAGATGGAAG GAATGTGGGT ATGTGCTGGG
54651 TCTTTTAGAA CTCCAGCAGA TTGCTCTGGA AAACAGCCAC TACATACCAA
54701 AAGTAGCCGG TCATGGTGGC ATGCGCCTGT AATCCCAGCT ACTCGGGAGG
54751 CTGAGGCGGG AGAATCACTT GAACTCGGGA GGCGGAGGTT GCAGTGAGCC
54801 AAGATCGTGC CATTGCACTC CAAGCCTGGG TGACAGAGCA AGACTGTCTC
54851 AAAAAAAAAA AAAACAAAAA AAAAAACAAA AAAAACACCA CTCCAACAAA
54901 ATACTTCTCC TTCCTCATAT AGTGTCCCTG CTTCCCTTTA TGCCTCAAGA
54951 CCACACATTT TGAACTTGCT GAGCTATAAG AAGTGAATGG AGAGGTGGGA
55001 CACAGGTGCA CAGCCTTCAG TAACTGAAGG AAAAAAAACA GAAGAAATGT
55051 CTAACCCTGA GCTTCCTGAG CTCCCTTCAG CCACCCAGCT GCTGAGGGGC
55101 AGGAATCCAG CAGCAAGGTG GAGAGCAGAA GGCATTCCTG CAACCTGTAT
55151 GTGTGGGTCA TTAGTCCCCC ACCTCCAGCA TCATTGCAGA ATCTGCAAAT
55201 TTAAAAGTGC GTTAGGTAAG AGCCTTTTTT ATAAGAGGCC CATATTTTTG
55251 CTAATACATA AAAACATTGT GATTAGTCAA ATAAATGTTC ATTTAAAATT
55301 CACAGTAGCA TGTGTCTATT TTTTTTTTTT TTTCCTTTTA GAAATGAGGT
55351 CTTGCTCTGT CACCCAGGTT GGAGTACAGT GATGTTGTGA TCATAGCTCA
55401 CTGCAGCCTC CAATTCCTGG GCTCAAATGA TCTTCCCACC TCAGCCTCCC
55451 GAATTGCTGG GATGCCACCA TGCCTGGCTG ATTCTTTTAT TGTAGAGACG
55501 GGATCTTGCT GTGCTGCTCA TGCTGCTTTC CAACACCTGG CCTCAAGTGA
55551 TCCTCCTGCC TTGGCTTCCC AAAGTGCTGG AATGACAGGC ATTGAGCCGC
55601 CGTGCCCAGC CTATGATTTT TCTTAGCATT AATCTCTGTG TCATTGCAAG
55651 CTGTCTCCCA CGTCCTTGCC TTCATTCTAC ATTGTTTTGG TGGAATGGCC
55701 TGTGCTAGCA GACAAGACCA TCCGGTCGAC CTTGAGCATC CTTCCCTGTC
55751 CTCAGGGAAG GTTTCCTGGG CCTCATTTTG TTTTCTTTGT ATACCAGCGG
55801 GGTGCAGCTC ATTTGAATGA GCTTGCAGGG GAGCATCTGT GATAGCATCA
55851 TGATCAGATG AGACAAAACT GGCACGGGTC CTGGTCATGG TTGAAGACCT
55901 TTATGCTCCT GATTCTATTG GGTGTCTTCT ACTGGTGAAG GCTCATGTGC
55951 TCATGGGAAC ACGGGCATGC TGGTGTCTTC CGAGTCCTCT CCAAAAACAA
56001 AGCCCAGGTC AGGTACAGTG GCTCACGTTT GTAATCCCAG CACTTCGGGA
```

FIGURE 3S

```
56051 GGATGAGGCG GGAGGATTGC TGGAGCCCTG GAGTTCAAAA CCAGCCTGGG
56101 CAACACAGTG AGACCCTGTC TCTACAAATA ACAGTAAATA AAAATTAGCC
56151 AGGCATGGTG GCATGCACCT GTAGTCCTAG CTACTTGGGA GGCTGAGGTG
56201 AGAGGATTGC TCGAGCCCGG GAAGTTGAGG CTGCATGAGC CTTACCTGCA
56251 CCACTGCACT CCAGCCTGGC AGACAGAATA AGAACCTGTT TCAGAAACAA
56301 ACAGACCGGG CACGGTGGCT CATGCCTGTA ATCCCAGCAT TTCTGGAGGC
56351 CGAGGCGGGT GGATCGCCTG AGGTCAGGAG TTCGAGACCG GCCTGGCCAA
56401 CATGGTGAAG CCCCATCTCT ACTAAAAATA CAAAAATTAG CTGGGCGTGG
56451 TGGTGGGCGC CTATAATCCC AACTACTTGG GAGGCTGAGG CAGGAGAATC
56501 GCTTGCACCC AGGAGGCGGA GGTTGCAGTG AGCCGAGATT GCACCGTTGC
56551 ACTCCAGCCT GGGCAACAAG AGCAAAACTC TCTGAAAAAC AAACAAACAA
56601 AAATCCCAAA GCCCTTAGTT CCAAATCTTG CCTCATACCC CACCCGTCCC
56651 ATCTTTAGGT GAAAACGTTC TTTCATTATC AGTGCGTATC TCTCCAAACT
56701 GTATTTGTAA CTTGTGCTGA GATGTTGAAT GCACAGACGC ACCTCAGTAT
56751 CTTCTGTTCC TTCTTTCATC CCTACCCCCA CCTTCCTCAA TCTCTCATTG
56801 CTGCGTTTTC TTCCATTAAT CAACACCTTT GTAAGGAGAA GCACCTCAGG
56851 CAAGCTCCCA CAAGCAAGTG CTTCGAAATA CTTCATTTGG GGCTTTTTAA
56901 AAGGGCTACC TTTTCCTAGC AGGTTTGGGA TGCAGTCTGC TAGTTTATTG
56951 TTAATTCTCA GGCTTAATGA TAGTTCCAGG TTACTGAATC AGGTGTGATC
57001 TCTGAAGATG TGTGTGTTGT AGGTTAGTTA GTTAGTGCTG CCATAACAAA
57051 GTAGCATAGA CGGTGTGGAT TAAACAACAC TGATTTATTG TTTTATAATT
57101 TTTGAGGCTA GAATTTTGAG AAGAACGTCT TAACAGGGCT GGTGCCTCCT
57151 GAGCCCTCTC TCCTTGGCTT GCAGACGCTG TCTTCTCCCT GTGTCCTCAC
57201 GTGGTCGTCC CTCTGTGTGT GTCTGTGTCC TCATCTCCTC TTCTTAGGAC
57251 TCCAGTCCTG TTGGAATAGG GCCCATTCTA GTGACCACAT TTTACCGTAA
57301 TCACCTGTTT ACATGACCTG TCTCCAAATA CAGTGGATAT TGGAAGGACA
57351 CAGTTCAGCC CATAGCATAC TGTTGGCTGG TTTATTATGA GACCATGATA
57401 TTTACTATTC ATTCATCCCA AGACAATGAG ACCTTTTACC CATGTCCCAG
57451 GATACACATA TCTTAACATC TGCTGTTGTC TGAATACGTC CTTTCCAAAT
57501 TCATATATTG AGACAGTAAC CCCCAAAGCT ATGGAATTAA AAGGTGGAGC
57551 TTTGGGGGAA GTGATTAGAT CGTGAGGGTG AAGCCGCTGA ACAGGACCAG
57601 TGCCCTCGGT GAAGGGGCCT GAGGGAGCCC GTTTCCCCTT GGTCCATGGG
57651 AGGACAGCGA GAAGGGCCCT TCCCTCAGGA ATGGGCCCTT ACCACGCAGT
57701 TCATCAGCAG GCGCCCCGAC CTCGGACTTC CAGCCTCCAG AACTGAGGGT
57751 AATACATTTT TCTTATTTGT AAGACCCCCT AGTATATGGT ATTTTTGTGA
57801 TAGCAGCCAG AATGGACTAA GACAACATCT ATGTAACATC TGTGGAACTT
57851 GTACTTTAAT GTCCATCTAT ATGCTTATCC CAGTATCTGA TTATACACCT
57901 CTTAACATCT ACACACGTCT TAGCATCTAC CTATACTGAT GAATTACACC
57951 TTTCTATATG CAGACCTCAG CACCTGTCTA TACCTGTAGA GTCACATCTA
58001 CACACACGCA TATCCTAACA TCTGTCTGTA TGCACACCTT AGCATCTGTC
58051 TATCACATAT ATTAGCATCT ATCTACACCT ACATATTAAC ATCTACTTCC
58101 ACCCATATCC TAATATCTGT CTGCACCCAC AGAGCAACAC CGGTCTACAC
58151 GTCTATACCC ATATCCTAAC ATCTCTCTAT ACCTCTGTTA ATATCTATCT
58201 ACGTTCATAT TCTAACATCT GTCTTTACGT GTATATTAAC ATCTCTCTAC
58251 ACCCATATCC TACTATCCAT CTACACCCAT ATTGTAACAT CTGTCTCTTC
58301 CTATATGTTA ACATCTCTCT ACACCCATAT TCTAACATCT ATGTCCATAT
58351 ATTAACCTCT GTCTACACCC GTATCCTGAC ATCCATCTAC ACCCATATTG
58401 TAACATCTAT ACGTATAGAT ATCATCTGTC TTCACCTATA TTGTAACATT
58451 GATCTCTATC CATATTCTAA CGTCTGCCTA CATCCATATC CTAACATCTA
58501 TACCTACATA TTAACATCTG TCTACACCTA TATTCCAACA TTTATCTATC
58551 TGTATTTTAT TTGTCTATGC CCATACATTA ACACCTGTCT ACACCCATAA
58601 TCTAACATCC ATCTGCACCC ATATACTAAC ACCTGTCTAC ATCCATCTAC
58651 ACCCATATAT TAATACCTGT CTACATCCAT CTACACCCAT ATCCTAACAT
58701 CTCTCTATAC CTACATATTA ACATCTGTCT ACACCTGTAT TCCAACACTT
58751 ATCCATATCC ATATTGTAAT ATCTGTCTGC AACCATATCC TAACATCTAT
58801 CTATAACTAC ATATTAACAT CTTTCTATAC CTATATGCTA ACATATATCT
58851 ATATCCATAT TTAATACCAT ATGGTAACAC TGTTTACACC CATGTATCAG
58901 CCCCGATGTA CACCCATATC CTAACATCTG TCTCTAAGCA CATCGTAACA
58951 TCTGTATGTA CGTGCATTCG AACACCTATC TGTACCCATA TATTAACATC
```

FIGURE 3T

59001 CGTCTTTACC CATGTGCTGA TATCTGTGTG CTCCATGTCC CGACATCTGT
59051 CCCCAGCTAT TACTGTCTGT CTGTACACAC ATTTTGGTAT CTAGCTGCAT
59101 CTGTACCCCA ACACCTAGCT GACGGCGTAC CCCCTGCCCT GCCTTGGCGG
59151 GGCCCTGAGC ATGTGCTGTC TGTCCCCGCA GGTTCTGGAC GTGGCATGAC
59201 GAGCGCTTCC TCTACATGCT CATGGAGTAC GTGCCGGGCG GCGAGCTCTT
59251 CAGCTACCTG CGCAACCGGG GGCGCTTCTC CAGCACCACG GGGCTCTTCT
59301 ACTCTGCAGA GATCATCTGT GCCATCGAGT ACCTGCACTC CAAAGAGATC
59351 GTCTACAGGG ACTTGAAGCC AGAGAACATC CTGCTGGATA GGGATGGCCA
59401 CATTAAGCTC ACGGACTTTG GGTTCGCCAA GAAGCTGGTA GACAGGTAAG
59451 AGGAACGTGA ACTCCGATGG AATCTACACT GCTTGGCAAT GAGAAAGGTG
59501 GTGGTAGTTG TGGCAGGTCA GGCAGGGAAA GATTGGGAAC CAGAGTTTAA
59551 CTCTCATGTG TAGGAGACAC TTGCAACCAG GGATGAGAGA GCCAGGTTGA
59601 CCCACAGCTC GTTTTAGGTG GGCTGCGATT GCTGGCAAAG AGCCAGTGGG
59651 CAGGAAGTCA GTCTCCTTCA CTGGCACCGT GGAGGAAATC AGAACACCAC
59701 ATATCCGCTA TTGATCCGAA ATGATGAGGA AATGAGTCAT ATCCAAGTTT
59751 GAATTGCCCT GACTATAAAA TAGATCTGCA TCGAATAGGA TACAATATCT
59801 CTTAAAATTA AATGCCAGGT GCTGTGGCTC ACACCTGTAA TCCCAGCACT
59851 TTGGGACGCC GAGGTGGGAG AATCATTTGA GCCCAGGAGT TTGAGACCAC
59901 TGTGGACAAC CTAGTGAGAC CCCGTCTCTA CAGAAATATA TATATTTAAA
59951 AAAAAGTTGA TTATGGTGGT GGATCCCTGT AGTCCCAGCT ACTTAGGAGG
60001 CTGAGGTTGG AGGATTATTT GAGCCCCGGA AGTTGAGGCT GCAGTGAGCT
60051 GTGATTATAC CACTGCACTC CAGCCTGGGT AAAAGAGCAA GATCCTATCT
60101 CAAAAAAAAA CAAAACAAAA AAAAAAAAAA AAAAAACCAA ATTGAATATT
60151 CCATACACAC CTGCTCACAC ACACGTGCAC TTATTTTTTT CTGTTATCTA
60201 TATTTCTATT ATGTATATAT ATATTTCCAC TATATATGTA TATTAAATAG
60251 AAATATATAT AATACTATAT TATTGTATAT AACATATAGT ATATTTTATG
60301 TACATATGAT ATAGTATTAT ATATGTATAG TATATATTAT ACTATATATT
60351 ATATAGTATA CAATGACTAT GATATAGTAT CATATAGGTA TACTATATAT
60401 TATAATATAT AATATATATT ATATAGCATA CCTATATCAT ACTATATCAT
60451 ACATATCACT ATACTCTATA TAGTATATAT TATACGTATT ATATATTACA
60501 CATACTACAT ATATATATTA TATAGTATAT TATACTATAT AATATATATA
60551 ATATATATAT TACATAGTAT ATAATATATA TAGTATATAT CACATAGTAT
60601 ATAATATATA TAATATATAT ATCACATAGT ATATAATATA TATTATATAT
60651 ATCACATAGT ATATAATATA TATTATATAT ATCACATAGT ATATAATATA
60701 TATAATATAT ATATCACATA GTATATAATA TATAATATAT ATATCACATA
60751 GTATATAATA TATAATATAT ATATCACATA GTATATAATA TATATTATAT
60801 ATATCACATA GTATATAATA TATATTATAT ATATCACATA GTATATTATA
60851 TATATTATAT ATATCACATA GTATATTATA TATATTATAT ATATCACATA
60901 GTATATTATA TATATTATAT ATATCACATA GTATATTATA TATATTATAT
60951 ATATCACATA GTATATTATA TATAATATAT ATATTACATA GTATATAATA
61001 TATATAGTAT ACCTATATCA TACTATATGA CATGTATGAT ATATGTGTTT
61051 CTTTTCTGGA AACACACAGA CATACCCCAA AACAGTGTTT GAACAAACAT
61101 CTGGGCACCC CACGGCCCAT CAACACATGA AACAAACCAT TACATGTCGT
61151 CTCAGCCAGT GCGGGCTGCA CTAACACACA CTCATAGACT GGGCAGCCTC
61201 AACAGCAGAC ATTCATGGCT CACAGCTCTG GAGGCTGGAA GTCCGAGATC
61251 GAGGTGCGAC AGATTCTGTA CCTGGAGGGA ACCAGCTTCC TGGTTCGTAG
61301 ACGGCGCCTT CTCGCTGTGT CCTCACATGG TGGAAGGGGC GAGGGGGCTC
61351 TCTGGGGCCC CTTTTGTAAG GGCACTCATC CCATTCATGA GACTCCACCT
61401 TTGTGACCTC ATCACCTCCC AAAGGCCCCA CCTCCTAATC CTATCACTTT
61451 GGGGATGATG ATTTCAACAT AGGAATTTTG GCGGGGGGCA CATACATTCA
61501 GCTTATAATA CATGTATATG TATTTTTTTT TCCATGATTG GATTCATTTA
61551 ACCAGTCTGT CTTGACAAAA GACCACACAC TGGGCATTTT AAAGAATAGA
61601 CCTTTTCCTC TCACTGTCAT GGAGGCTAAG GTCTGAGATC CAGGTGTGGG
61651 CAGGGCTGGT TCCTCCTGAA GCCTCTCTCC TTGGCTTGGA GACGCTGTCT
61701 CCTCCCTGTG TCCTCACAGG ATTGTCCTCT GTGCATGTCT GTATCCTCAT
61751 CTCCTCTTCT TATGAGGACA CCAGTCCTCT TGGATCAGGA CCCACCCTAG
61801 TGACCTCGTT TTACCTTAAT GACCTCTTTA AAGATGCTCT TTCCCATATA
61851 GTCACATTCT GAAGTTCTGG GGGTTAGGAC TGCAGCATAT AAGGTTTAAG
61901 GGATACATTT CAGCCTGGAA CAAGTATATA TAGATATGTT TCCGTACACA

FIGURE 3U

```
61951 CACATACTCC ATTGAGGAGA AAACAGTTAT CCTTTTTTGT TTGTTTTTTT
62001 GTTTTTTTTT GGGACGAAGT CTCGCTCTGT CGTCCAGGCT GGAGTGCAGT
62051 GGCACAATCT CGGCTCACTG CAACCTCCGC CTCCCAGATT CAAGTGATTC
62101 TCCTGCCTCA GCCTCCCAAG TAGCTGGGAT TACAGGTGCC CGCCACCAGG
62151 CCTAGCTAAC TTTTTTTTTT TTTTTTGAGA TGGAGTCTGG CTCTGTCGCC
62201 CAGGCTGGAG TATAGTGGCA TGATCTCAGC TCACTGCAAG CTCTGCCTCC
62251 CGAGTTCACG CCATTCTCCT GCCTCAGCCC CCCAAGTAGC TGGGACTACG
62301 GGCGCCCGCC ACCACGCCCG GCTAATTTTT TGTATTTTTA GTAGAGACGG
62351 GATTTCACTG TGTTAGCCAG GATGGTCTCA ATCTCCTGAC CTTGTGATGC
62401 GCCCACCTTG GCATCCCAAA GTGCTAGGAT TACAGGTGTG AGCCACCGCA
62451 CCCGGCCCCA GTATGTAGTC TTTTATCTCT CACCCACCTC CCACCCTTTA
62501 CCCCAAGTCC TTGAAGTCCG TTGTATGGTT CTTATGCCTC AGCGTCCTCA
62551 TAGCTTAGCT CCCAATGGAT CTTTAATTTA CATTCATAAA ATCAACAGTC
62601 ATAAAAAGTA AATTCACACG CCCAAGCTGC TGAAAAATAC TCAGAAAGAT
62651 TTTTGGTAAC TACACTGAGT GTCAGTTTTT CAATTAGATT AAATTAATGA
62701 AAGTAGAATT AGATAATGAC ATCCGTTCCT TGGTAGACAA GCTACATTTC
62751 AAATACCCAG GATTGCACAT GGCTATCGGC TTCTGTCTTG GTCAGACAAG
62801 CCTAGAAAAT ACATTTTATA TTTCCATATT CTTTGATGTG GTGGGGTTGG
62851 GTAAGGTGAT AATTACACTA ATTATACTCC TAACATTGTA AAACCGTCTG
62901 CATTTTGAGA AACTTGATGT GGGGGCAGTT TTACACTAAA TGACTCTCTT
62951 CTCTGGCAGC TTTTAGAAAA GGGCTCTCCT AGGAAAATTT TATGATGCGT
63001 TTACATTCAA TCTGATTTTC CCCTATAGTA TTTCTTGTAC TACATTTCCA
63051 AAAATAAGGC ACATGGAAAT TAGGTGCATT TTACATGGAG TAGGAAAGAT
63101 GCAGGATTTT TTAAAATATT GATTTATAGC ATCTGTGCTG CCCTCTCTTG
63151 GCAGCACACG GTATATTAGT AAATTCTTTT AAAGTCATTT TATTTGCAAG
63201 TCTAATTCAA AGAAAACAGA TAAAATATTT CATATATTCA CTTGTTTATA
63251 AGTTTGACAA ACCATGTTAC TGTCCAGTTA ATTCATCATA TCTATTTAAA
63301 TGGACGAAAA TGGTTTCGTA TATAACATGC AGCAATTATT TTACTTAATG
63351 AACATGTGAA AATCTTAGAA AATGTCTCAT TACCATATTG ATAGATTGCT
63401 TTTGCAAAGA ACTGCATCTT CCTCTGTATG GGTAGTGTAG CTTCTGGAAA
63451 CTTTTTTTTT GTGGGGGCTT TTTTCTCCTT TTTTTTTTTG ACCATCATTG
63501 TAACGAAGCA TCTCTCTGCT GGCCCGGCCC CAGGGAAGTT GTGTTCATGG
63551 GGGCAGATAC ATGGCCCTGC CTCTGATTCA GGATTCAAAC AGTACCTGTG
63601 CCTTTTGAAT AAAACTGAAA TTCACCACTG TATCGTGGAC CACTACAGAA
63651 TAGATGGAAC TAAACAGGGA GGCCTCATCT TGAATAATTT TTTTTTTTTT
63701 TTTTTTTTTT TTTTAAAGAC AGGGTCTTAC TCTGTCACTC AGGCTGGAGT
63751 GCAGTGGTGG GATCTTGGCT CACTGCAACC TTGGCCTCCT GGGCTCAAGC
63801 GATCCTCCCA TTTCAGCCTC CCAAGTAGCT GGGATTACAG GCATGTACCA
63851 CCACACCTGG CTAATTTTTG TATTTTTAGT AGAGACCTGG TTTCACCATG
63901 TTGCCTAGGC TGGTCTTGAA CAGCTGGCCT CAAGTGATCC ACCTGCCGCG
63951 ACCTTCCAAA GCATTGGGAT TACAGGCGTG AGCCACCGTG CCCGGCCTTG
64001 AATAACATTT TTGAACATAT CCCAGAAAGA AGTCTGTTTC TCATTTTTCT
64051 CTCTTTTTTT TTTTTTTTTT TTTGGAGAGG AGTCTCGCTC TGTCGCCCAG
64101 GCTGGAGTGC AGTGGTGCGA TCTCGGCTCA CTGCAAGCTC TGCCTCCCGG
64151 GTTCACGCCA TTCTCCTGCC TCAGCCTCCC AAGTAGCTGG GACTACAGGC
64201 GCCCACCACC ACGCCCGGCT AATTTTTTGT GTTTTTAGTA GAGACGGGGT
64251 TTCACTGTGT TAGCCAGGAT GGTCTCGATC TCCTGACCTC GTGATCCGCC
64301 CGCCTCGGCC TCCCAGAGTG CTGGGATTAC AGGCGTGAGC CACCGTGCCC
64351 CGCCATTTTT CTCTTATAGC ATGGGGTAAA AACATACTTA AGCATGTTGT
64401 AATGTAATCT ACTCACTACA TGAATTTCTT TCTTTGTTTT TTGTTTCTTT
64451 TTTGAGACAG GGTCTCACTC TGTCACCCAG GCTGGAGTGC AGTAGTGCAA
64501 CCATGGCTCA CCACAGCCTC GAACTTGCAG GCTCAAGCAA TCCTCCTGTC
64551 TCTCAGCCTC CCAAGTAGCT GCAACTACAG GCTTGCACAC CCTGCCTGGC
64601 TAATTTTTGG ATTTTTTGTA GAGACGGGGT TTCACTATGT TGCCAGGGCT
64651 GGTCTTGAAC TCCTAAACTG AAGCAGTCCT CCAACCTTGG CCCCCCAAAG
64701 TTTTGGGATT ACAGGCGGGA GCTACGGTAC TCAGCCTCTC CCTCCCTTCC
64751 TTCCTTCCTT CCTCCCTCCC TCCCTCCCTC CCTCCTTTCC TCTCCCTCCC
64801 CTCCCTCCCT TCCTTCCTCC CCTCCCCTCC CCTCCCATTC CTTCCCCTTC
64851 CCTCCCCTCC CATTCTTTCC CCTTCCCTCC CCTCCCATTC CTTCCCCTTC
```

FIGURE 3V

64901 CCTCCCCTCC CATTCCTTCG CCTCCCCTCC CCTCCTCTAT CCTCCCCTCC
64951 CCTCCCCTCG CCTCCTCTAA CCCTCCCCTC CCCTCCCCTC CCCTCCCCTC
65001 CCCTAGCAAC CCTGTTAACT GGATGACTTG TACCCTACTT ATTTTAAACC
65051 ACTGCTCTTG GTGACTTGAT TTCTGACTTT CCTAGGTTGT CAGTATGTTC
65101 AGATGGTGTT CTTTTGTGAC TTGCGTTCAC CAGGCTCTTG TTTTCTAACA
65151 GCAATATTAC GTTTGTATTG TAAATATTTT GCACACACAC TTTATGTTAT
65201 CTAGATAGCT CCCCTAAAAG ATTTGGTGGC AAACTAGAAT TATTTCTGGT
65251 TTTATGAAAT GGTCAAAATA AAATACTGAT GTGTTTAATT TGATTTTATA
65301 ATTCAAATGC ATAACACAAG CATCCCTTAC CTGAAATACT TCAGACCAGA
65351 ATTGTTTTGG ATTTTAGATT TTTTTCAGAT TGTGGAATAT TTGAATTACA
65401 CTTACCTGTG AGCATCCCTA ATTTGAAAAT CTGAAATCCA AGATGCTCCA
65451 GTGAGGATTT CCTTTGCGCT GTGAGCCTCA TGTCGGTGCT GGAAAAGTAT
65501 TGACTTTTGG AGCATTTGGG ATTTCAGATT TGGATTAAAG ATGCTCAACC
65551 TTTATACATC TGTCTTTAAA CCATAACAGA TGGTTTTCTT TCTCTGCAAC
65601 AGCTCTTTTT TGTTTGTTTT TGGTGTTTTT TATTTCTCTG CGACAGCTTT
65651 TTGTTTGTTT GTGTTTTTTT GTGTTTCTTT TGAGACAGGG TCCCACTATG
65701 TTGGCCAGGA TAGTCTTGAA CTCCTGGCCT CAAGCAATCC TTCCACCTCG
65751 GCCTCCCAAA GTGCCAGGAT GGTAGCCGTG AGCCACCATG CCAGGTGCAA
65801 CAGCTCTTTC CTAGTTCCTC TGTTGTAGCA TTTTAAATCC AGATGTTACA
65851 TTGATTACTG TCCTCTGGAT TTTTATTTCT AGCCTTATAG GGATAACATT
65901 GAACCTAGTC TTTCAAAATT ACTACTTACC CCTTTCACAC ACACACACAC
65951 ACACACACAC ACACACACAC ACACACACAC ACACACAGGA GTAGAGAGAG
66001 TAATTCACAT TGAAACCTTA TGGCCCCATC ACCCAGCTTC GATTGTTATC
66051 AAAGCTTTGT CACTTTGTTT TTTTTCTCTT TGCCCATTTG TTTCTTGAGT
66101 TATTTTAAAG CAGGTGCACT TTATCCTATC TTTAACAGAT AACTCCCTTT
66151 AAAAAAGAAC TTCAGTGCCA TTATCACATC TGACAACTAT TTAAAAAAAA
66201 AAAACCCAGC CTGGGTAACA TAGCAAGACC TCATCTCTAC AAAACATCAA
66251 AAACAAAAAA ATTAGCCTTG CATAGGTTAA ATCCAGCCCC CTATGTGTCT
66301 GTTAATAAAG TTTTATTGGA ACACAGTCAC ATCTTGGGGG CTTTTGAGCT
66351 ACCGTAGCAG AGCTGGATAT TTGTAACAGA GACCATGTGA TTCACAAGGC
66401 CTAAAATATT TGCCGTCTGG CTCTTTACAG AAAATATTTG CCCACCCCTG
66451 AGCCAGGCCA TTTGCTTTGT GAACTGGTTA AAATTGGCCA GGAGCTCTGT
66501 CTGTGCAGTG GAATATTATT TGGCCTTGAA AAGGAATATA ATTCTGACAC
66551 ATTCTACGCG TTGATAAACC TTGAAAACAT GATATTGGAC GAAATAAGCC
66601 AGACCAAAAA GGTCTCATGT CGTGTGATTC TACTTGTAGG AGGGCCCTAG
66651 ATTCTTCCAA ATCATAAGGA CAGAAAGTAG AATGGTGGGT GCCAGGGGCC
66701 GGGGAGGTGC AGGGAAGGGG AAGATGCTGT TTAATGAGGA TGGAGTTTCT
66751 GTTTGGAATG ATGAAGAAGT TCCAGCAGTG GACGGTAGGG AGGGTTGAAC
66801 ACGAAGGTCA GTGGACTTCC CACCACCGAA CTATACAATT AAAAATGCTT
66851 AAAATGGAAA ATTCTATGCT GTGTGTATTT TACCACATTA GAAAATCATA
66901 CATATAAAAT CATAATTATG TATATAATTA TAAATAACTA TATAATTGTA
66951 ATATTTACAC ATAAATAATA TATCCGACAT TAAATTTATA TATTTAAATA
67001 TATTTATCTC TTTAATATAT TAAATATTTT AGTATATTCA TATATAAATT
67051 TAATACATAA AGATATTAAT GTAATGTGTT AATTACTAAT ATAACAATGT
67101 ATGTATATAT TAATATACTA ATATATTCTA ATTATAATTA TATATTAAAT
67151 ATGTAATTTT TAGTTAAACA TAATTATATT TAAAAAATAA TTTAATACAA
67201 TTAAATATAT AATAAATGGA TACAGTTTTA TATTTAATAT TACATATTTA
67251 ATTTTATAAA CATGGCTACC AAATAATTAT ATGTGCTCAT AAATTATGGT
67301 ATAAATATGT TTAGAAAGTT ATATGTAGCT ATAATTATAC ATTATTATCC
67351 ATAGTTTTAT ATATAATTTT ATAAATATAT ATTTATTTTT AAAATTTAAA
67401 TTTATATATT AGTATGTGTT ACACATTTAG TGTTTAGATT ATAAGTTCAA
67451 ATTTAAACAT ATACATTTAT AAATACATAA TCGTTTTATA TATATTTCAT
67501 AACACCAGAA AAGTCTTTCT AGTTACTTTA GACCTTTTCC CCTAGCTTCT
67551 TACTTTGAGT ATTTAACGGA AGTCAAGGAG GGCCTGAGAT GTCGAGTCTG
67601 TTTGCAGTCG GTGTTGTTAC TTTCCCTTGA GCCCCTTTTA ATTTTGCTGT
67651 AGTTCATACT AGGACGTGGG TATTACTGTG CCGAGGTTGG TGACAGGCAC
67701 CCTTCTCCCT GCTGATCAGT GGTGCCTAGG AGCCATTGTC ACCGAGGAAA
67751 CCCCTCCCAG GGCCTGGGCT GGCCATCGGA AGCTGTCCCA TGCTCGCAAA
67801 CACACACCTT CTCCCTTCAC GGGCCTGAAA TTCTCAACTG TTTGTCCCCA

FIGURE 3W

67851 TCAGACAGTT CTAGGAACTG TGATTGTGTC CCCATAAAAA AAAAGATGAC
67901 AAAATCTTCC CTTTTTATGA AAAACCCCAC ACCCTGCTGC TTTATTGCAA
67951 CCCAAGATCC TATAAGAAAA GGCAATGTAG TATTTTCACC ATGAGTACTG
68001 AGCGAACATC TATTTCCTGC ATTACCAAAC CCAGACAAAA CACTGGCTCA
68051 TACTTTTCTG ATAAAAAGGG AAAAAATGCA TTTGTATCTG TAATCAAGTG
68101 TAAAAGCTGT AATCAGCTGT CCTTCCTCCT GAGCCCTACC ATGCCCCTGT
68151 TAGCTGAGTG ACATGCTCAC CATGTCATAA AGCCATGAGG AGAGACAGAA
68201 AGTGAGGCTG GTGACGCCAC CTGCTAGGAC GTAAGAGGGA CTGGACTGAA
68251 ACTCAGCTTG GAGATGTCAT CCGTTTCTCT CTGTCTCTCT CTCTTTTTTT
68301 TTGAGACGGA GTCTCACTCT GTTGCCCAGG CTGGAGTGCA GTGGTGCGAT
68351 CTCGGCTCAC TGCAACCTCT GCCACCCAGG TTCAAGTGAT TCTCCTGCCT
68401 CAGCCTCCGG AGTAGCTGGG ATTACAGGTG CCTGCCACCG CGCCCAGCTG
68451 ATTTTTGTAG TTTTTAGTAG AGACAGGGTT TCACCATCTT GGCCAGGCTG
68501 GTCTTGAACT CCTGTTCATG ATCCACTTGC CTCGGCCTCC CAAAGTGTTG
68551 GGATTATAGG CATGAACCAC CGTGCCTGGC CTCTTTTTCT CTTTTTATTG
68601 TGGTAAAATA CACTTAAAAT GTACCATCGT AACCATCTTT ATTAACATTT
68651 TTTATGTTTC AGAATAGGGT CTTCCTCTGT CAGCCAGGCT GGAGTGCAGT
68701 GGTACGATCA TGGCTCACTG CAGCTTCCAA TGCCTGGGCT GAAGCAATCC
68751 TCCTCCCTCA GCCTCCTGAG TACTTGAGAC TAGAGGTGTG AGCCACCATG
68801 ACTGGCTAAC TTTGAAATAT TTTTGTACAG ACAGGGTCTT GCTATGTTGC
68851 CTTGGCTGGT CTGGAACTCT GAGGCTCAAG TGATCCTCCC ACCTTGGCCT
68901 CCCAAAGCGT TGAGATTATA GGCATGAGCC ACTGTACCCA GCCTGTTTGA
68951 ACCATCTTGC CGTGCACAAT TGAGTGGCAT TTATTGCATT TACCATGTCG
69001 TGCAACCATC ACCTCTCTCT AGTTCCAGAA CATTTTCACG ATCCCAAAAG
69051 AGAACTTGTA TCTGTTAAGC AATTATTCCC CATCCTAAGC CAGGATGATC
69101 TCATCTTAAC TTGATTGCAG CTACAAAGAT CGTGTTTGCA CATAAGGTCC
69151 CACTCACAAA TACTGGGGTT TAGGACTTTG GGGGGTGCAC AGTTCAACCA
69201 GTGCAGGTGT GGCGGAAGGC GTGGGCATTA AGAACACAGG AGTCATTGGA
69251 TATCTATACT TTATAGATAA TCCTATCCTT AGCTCTGTTT CTCCTTCGTT
69301 AACATGGCCT CCTCCCTCCC CTCCCCCCGG CCATAGTGAA ACTAAGAACA
69351 GTGAGAAAAC TGAGAACAGC AGGTGTCACC TTCCTTCTAC CCAAAAGCCA
69401 GGTGAGCAAA AGGAGACAGG AGCAGGGAAG TGGATAATTC ACTGCCCAGA
69451 CCAGTGGTCT CGACATAACA CTCAGGCTGT CTCATCTCAT ATTCATTCAC
69501 GCAGTCAGCA TCTCTCCATA GCAGCGTATG TCTCTCTGTA CATTCAGCTA
69551 GGCGTTGGGG CTTTTTGCAG GAAGGAGTGA CTCTAACAGG GCAGGAGTCC
69601 TCCTGAGGCA AGTTAGAACC TGGATACTTA TACAGCCTCA TACAACCTCA
69651 GGTGTGTGTC CTTACCCTAA CACGGAGCCA AAAAGAGCCT CATCTTTCAA
69701 AAGGTAAGTG GAGAAGTTGC AGCTAATGCC TGTAGCATGA CCTGTGGCCT
69751 CTACCTGGGC TTCATATCAG CTAAGATCTA GGCTTTTAGC TACTTTCAGG
69801 CCACTTTGGA TGGGCTAGAA AGGTGGAAAT ACAAAACTAG CAGGCCAGTA
69851 AGTCGCTCGT CTTGCAGAAT GACAGAAGTG TCGTGCATTG AAGCAGCCAG
69901 GGTGTACTTG GAGTTGATTC AACTGCTGGG CAGGGCAGGG GAGAGCGTGT
69951 TTCTAAAATA GTGCGCATTG TACTTTCCAT TTGTAGACTT AATTCTAATG
70001 AGTGAGAAGC ACTTAACAGG ACCACAAGGT GGTCCCTGTT CCATACTTAG
70051 CTCTAACCTG CAGATAGAGA GTAAGTCCCT TCCACATGCT TCCATGGGAG
70101 GAGAACTCAA TTTCTCTCCT TGTCTTCTTT CCTGGTTTCC TGATTTATAT
70151 CTGCTACATC CTGCAGTAAT TTTTTTTTTT TTTTTTTTTT TTTGAGACAG
70201 TGTCTTGCTC TGTTGCTCAG GCTGGAGTAC AGTGACACTA TCATGCTCCC
70251 TGCAGTGTTG ACCTCCTGGG CTCAAGTGAT CCTTCCATCT CAGCCTCCCG
70301 ACTAGCTGAG ACTACAAGTG CACTTCAGCA CACCTGGCTT TTTTTTTTTT
70351 TTTTTTTTTG TAAAGGAGTG GTCTTGCTGT GTTGTCCAAG CTGGTCTGAA
70401 ACTCCTAGCC TAAAGCAATC CTCCTGCCTC AACCTCCCAA AGTACTAGGA
70451 TTACAGGTGT GAACTACCAT GCCTGACCTT GTGGTACTTT TATTTCATGG
70501 ATGGCCGACA GAATTTGAAA TTTGGATGGC AGCCAGTTTG TTGTTATCCC
70551 AAGGGCTTAC AGATTAGTGT GGAAAAGTCT GTTGTCTGGA AAGAGATGGG
70601 GTATGGAGGT GTGGTGGGGA AGGGAAGGAA AGATAACAGT AACAACATTT
70651 TGGGTGGGTT CCTGCAAGCA GGAAGCTGAG GAGCTGAAGC CAAGATACGT
70701 GCCCACACCA CTGCAAACAG TGCGGACTCA GGCAAGATGT GCTGGGTATA
70751 AAATAGGCTT TGCACATGCT TGATACATTG TGCAAAGAAC TTGAGAGTGG

FIGURE 3X

```
70801 ATAAACATGT ATATTACCAG ACTCTGTGGA ACTTGTTTTT TGTTCTCTTT
70851 ACATTCAACT TACAAAATAA GGGTTTCTTC TTTCATTGAT CTGAGTGGTG
70901 GGAGGGAAGG GTCTTTTGCA AAGCATCTAT ATATTTTTTC CCTCTGAGGG
70951 TGTTGCTTCT TTCTGCCTGT CTACAGACAG GCTCCACACA CCAGGGCAGC
71001 ACTTGGCAGG AAGGGTGGAT GTGGCCCGCA TTTGTGCTAC AGGTCTGAAT
71051 TGCTGAAAGC CCGAAGCGAC ATTCTACCCA GCAGTAGAGC GCCAATGGAG
71101 TACGGCCCAG ACAAGGCCCC CTCTCTGGGG TTACTGATAC TCAGCTCCTT
71151 TCCAGCCCAT GAGTCTTCCA GCTTCTGCTG CAGTCCTTGT TATCTTGCCC
71201 TGACTTTATT TAGCAGATTC TTCTGTAACC AAAATGCAGG TTCAGCCGCT
71251 CGCCGTTTGC AGAGTGCAAT TAGCAAGAGC GAGGTCTAGT GTAAAGAAAG
71301 TGATTTTTTA TTCCAGAGCT TTCTTAGGGG AAGAAGTACA GGCTTCCTGC
71351 TTGAGGCCAC CCCTTTGCTT TTGGAGCACA AAGCAGGCAC CTTTAAAGGA
71401 AAATGGTATG CAGGGGAGGA AGTGTATTTC TGTCTTTACA CTGGTTTCCA
71451 GGGGGCAAGA AATGTTTTTT TGGGGGGTGG GGGTGTAAAG AGCCAAAGAG
71501 AACATACGTA AGCTTTGCAA ACCATCCAGT CTCAGTTACA AGTACAAACC
71551 CAGCTCTTGC ACCTTTTTTT TTTTTTTTTT TTTTTTTTGA GAGAGAGTCT
71601 CACTCTGTCG CCCAGGTTGG AGTGTAAAGT GCAGTGGCGC ATTCTTGGCT
71651 CACTGCAACC TCCGCCTCCT GGGTTCAAAC ATTTCTCCTG CCTCAGCCTC
71701 CGGAGTAGCT TGGACTATAG GCATGCATCA CCATGCCTGG CTAATTTTGT
71751 ATTTTTAGTA GAGATGGGGT TTCACCATGT TGGCCAGGCT GGTCTTGAAC
71801 TCCTGGCCTC AAGTAATCTG CCCACCTTGG CTTCTCAAAG TGCTGGGATT
71851 ATAGGTGTGA GCCACCATGC CCGGCCTAAG CGAGTTCTTG AATTATTCTT
71901 TTCACTGCCA CTTTTTTTTT TGGATAAAGG ATTTTCTTTT TACTTAATTT
71951 TATTTATTTA TTTATTTAAA GAACTTTTAG GTTCAGGGGT ACACGTGCAG
72001 GTTTGTTACA TGGGTAAACT GTATGACACT TGGTGTACTG ATTATTTTGT
72051 CACCTGGGTA ATAAGCATCA TACCTGACAG GTAGATTTTC CATCCTCATC
72101 CTTCTCCTGT GCTTCTCCTT CCAGCGGCCA GGTGTCTGCT TTTCCCCCTC
72151 TCTGTGTCTG TGTGTCCCCA GTGTTTAGCT CCCACATACA AGTGAGAACA
72201 TGTGAGTCCA CTTAGGAGAA TGGCCTCTCC ACCTCCGTCC ATGTTGCTGC
72251 AGAGGACATG ATCTCGTTCT TTTTCCTTTA ATTAATTAAT TTTATTCTTT
72301 ATGATTTATA CTAAGGTATA AATAACTCAA AAAAAATGAG GTTTTTTTTT
72351 GCTTCTGAGT AACAGTGGTA ACAGTACCAG CAACAGGAGC AAGGATGATA
72401 AAACCAATTC TTAGCTTCCA AGCCCGTTAA GAAATGTTTC TATGGAAAGG
72451 AATCAGCGAA AACAATGTTA CTGTCTTTAC ACATTAAAAT ATGTGCACAG
72501 GAGGGTAAAC GGAGCGTGGT TTTACTCAAC GAAGTTATTG TAACAATCAG
72551 AGCTTCTAAG GTGACTGCAT TAGCCAAGCA CCACTGAGTG TTGTGGGGGC
72601 CTGTCTCTGT CGCCCATATA GGACTTGGAC CCTCTGTGGA ACACCCGGAG
72651 TACCTAGCCC CCGAAGTCAT TCAGAGCAAG GGCCACGGAA GGGCCGTGGA
72701 CTGGTGGGCC CTCGGCATCC TGATATTCGA GATGCTTTCG GGGTAAGTAG
72751 AGTCTCTGTA GAGAATCTTC ATCTTACAGG CCAGCACCCC CCTTCCCCCA
72801 CCCATTCGTC CACTCGGCAT TTCTGTAACC TTGAAAACAG TACGTGAGTG
72851 TCGCAAACAC ACAGTGTGGC TGCACACACA TCTGCTGCCC TGCTGAGGTT
72901 GGCAATGTGA ATTAGCAATT GAGCTTGTGT GAATAAGAGG CAAAAAACCC
72951 AAACTTGTGA AGGAACCACC CATGCATGCC CATTGAGATT TTTATATTGA
73001 AATATCCATA TCTTCTTTAA ATATACAATT AACATTCTGG GCTGCTCTGA
73051 AGGTAGTGAG TTATCTCAGT TGATTTTCAC AGTCAGCTAC AGATTGAACT
73101 CCTTGCTCTA CTCTTTTCCC CCCTTATCAC TTCTGCGCTT GTTTAGTCTT
73151 AAAAAGAATT TAAAAATTAA ATTAAAAAAT GAATCTTCTG CACAGACCCT
73201 TTCTGAAGTA ACCTGCAGAG CTCAGGGGGG CACAGGTTGG GTCAAGGTAA
73251 ATCAGCCAAA TACAGTTCAG TGGTTTCTGG ATGAACAGCT GGCAAGGAAG
73301 GCGAGAATAT GTTCTTTCCT AAAACCGTAT GTCTGTGGTA CAGGAAAGGG
73351 GTCCCGACCC ACACCCCAGC ACAGGGTTCT TGGATCTCTC GCAATAAAGA
73401 ATTTGGGGAA AGTCCATAAA GTGAAAGCAA GTTTATTAAG AAAGTAAAAG
73451 AATAAAAGTA TGGTTACTCC TTAGGCAGAG CAGCCCTGAG GGCTGCTGTT
73501 TGGCTATTTC GATGGTTATT TCTTGACTAT ATGCTAAACA AGGGGTGGAT
73551 TTTTCGTGAG TTTTCCGGGA AAGTGGTGGG CAATTCCTGG AGCTGAGGGT
73601 TCCTCCCCTT TTTAGAGCAT ACAGGGTAAC ATCCTGACCT TGTCATGGCA
73651 TTCGTAAACT GTCATGGCCC TTGTGGGAGT GTCTTTTAGT ACCTAATGCA
73701 TTATAATTAA TGTATAATGA GCCATGAAGA CGATCAGAGG TCACTTGTCG
```

FIGURE 3Y

```
73751 CCATCTTGGT TTTGGTGGCA TTTGGCCGGC TTTACTGCAG TCTGTTTTAT
73801 CAGCAGGGTC TTTGTGACCT GTATCTTGTG CTGACCTCCT ATCTTGTCCT
73851 GTGACTTAGA ATGCCTTAAC CGTCTGGGAG TGCAGCCCAG TAGGTCTCAG
73901 CCTCATTTTA CCCGGCCCCT GTTCAGGATG GAGTTACTCT CGTTCCAACG
73951 CCTGTGATAC CTGTGTTGGG TGAGATTTGG AAGTCAGGAG AGGTGCCATC
74001 CACCCTGCAA CCACATAACA GAGGTCGGTC ATTTGTTGGG ACGTCAGCAT
74051 GATTGAGTGT TCAAGTCTAG CATATGCCTG AGACAGCTCC ACTATGACTA
74101 GACCAGAAAC GCAAAGGAAG CACGCAACAC TTGGAAACCC AGGACGTGGG
74151 CGTCATCCTC GTTCCGTTGT TAGTGCTAAG ATGACACAGT AGCGTGGCAC
74201 TTTTCCAGAT AGGAACCTGT AGGAAGGAGT GAGCTACGTG TCAGAGGAAC
74251 TGTTGCACCA TGTGGCTCTG CACGAAAGGC TCTTCTCTCT GGGATGAAGA
74301 CGAGAGGAAG CCCAGCCAGC GAGGGCCCAG AACACCGGTT GGGGGAGCCT
74351 CTGCCGCGCT TTGCCACAGC CGACACTCTG CCTCCTAGGT TCTCTCTTTT
74401 CCTGTTTCCT TCTTTCTTCT GCTTGCCCCT GAGTCTCAAA GACAGACACC
74451 AGCGTATCCT CTGAGTGGCC TCCATTGTCG CAAAAGCCAG ATCCTCTCTC
74501 ACATCTCTCT GATTCCCTGC AGGGGGTAAA GACCAGAGTT TTACTGGGGA
74551 ACCTTCCCTT TCAGTTGGAA ACAAAGGAGG GAAGGAAGAG AGGCATTCTC
74601 CTGCCTGGAA GGCGTGTCTA AGCCAGGTCC TGCTGGTGGG GAGCACCGAG
74651 CGCTTGTTCC TGGGGGTGTG GAGCATGTGA CATTCTAACA TCCACCTCAG
74701 GAAATCCAGG CAGTCGCTGA CTTTGTTTGG GGAGCAGACA GGGGTCATCG
74751 TCCCATGTGC TTATCTCTGC CCTCTTTTAT AAAGAAAGTG AATCCGTTAA
74801 TTCCCACACT AGCTTAGGGA TCAGAACGAT GTTGAACAAG CACTACCAAA
74851 GAATTCCACC ACAAAACCGG AGCCTGAGAT GCCGCAGGAG GAGAGTGGAA
74901 CCCGTAAAAA CCTGTATTTC ATTGTCTAGC TATCCATGTG TATTGTTTAT
74951 CATCCATCCA TCCATCTACC CACCTGTCTA TTTATCTATG TTTATATACT
75001 TTTCCATCCA TCCACCCACC TACCCCCCAA CCCCTTCATC CATCCACCCA
75051 CCCACCCCGT CATCCATCCA CCCACCCACT CCTTCATCCA TCCATGTACC
75101 CACTCCCCCA CCCCCTACCC CTTCATCCAT CCACCCCCCC ACCCCTTCAT
75151 CCATCCACCC CCACCCCTTC ATCCATCCAT GCACCCACCC CCCCACCCCT
75201 CTACCCCTTC ATCCATCTAC CACCCCACCC CTTCATCCAT CCACCCCCAC
75251 CCCTTCATCC ATCTACCACC CCACCCCTTC ATCCATCCAC CCCCCGACCC
75301 CCCCACCCCT TCATCCATCC ATCCATCCAT CCATCCACCC ACCTACCCCT
75351 TCATCCATCC ACCCACCCAC CCCTTCATCC ATCCACCCAC CTGCCCACCC
75401 ACCGCTTCAT CCATCCACCC ACCCCTTCAT CCATCCATCC ATCCACCCAC
75451 CCTTCCATCC ATCCATCCAT CCACCCACCC ACCCACCCAC ACACCTATCC
75501 CTGTCTATCT CTATGGTCTA CCTATTTTGT AAGTATGTAT GTATCTGTTT
75551 ATCCATTTAT CCTTATCTAT CATCTAAGTT GTCATTTATA TATTTATATA
75601 TCCATCTCTC TCCATCTCTT TATCTCTACG ATCTTTTTAT CTGCCTACCT
75651 ACCTGTTATC TATGTATTTA CCTATCATCT ATCTGTCATT CATGTACCAA
75701 TCTATCCATC TACTTCCTAT TTATCTATGT GCCTATCCAT CTATTTATCA
75751 TCTGTCTTTC TATGTAACTG TTTACCTCCC TACCTATCCA TCTATCAATC
75801 ATCTATCTAC CTATTCATCT ATCTGCTTTT CTATATATCT ATGTATTTAT
75851 CAATCATCTA CTTACCTACC TATCCCTCTA TCTCTACCTT TCTGTCTATC
75901 TAGCTATCAA TAATCTACCT ACCTACCGGC CTGTTGGTCT TTTGAATTTT
75951 CCATTACTCT TTGCTGAGAC ATGCCTACAA GTCATATAGA ACCAAACTTC
76001 TCAATATGCA CCCTAGCCCA TTATGTCCTA GGCAAACCCA AAAGGTTAAA
76051 AATAACTTAG GCATATTGAT CAGCGTCCAC CCAAGGAAAA GCACCACATT
76101 TTCCTTCGGT GATAACACTG ACCACACGAG GGCAGCATTG CCTGAGGATC
76151 GTTGTATCCT GTAGTCTAAT GGTTTTAAAT AGAGTGAGGT TCGTGTGCCC
76201 CAAATTTTAT TGATTCTAGG ATAGAGTAGA CTATTATTAG AATACAATAT
76251 ACTATTAGGA CATAATATTG TTAGAATACA ACATAGAATT ATTAGACTAT
76301 AATTAAAACA GAATATTAGT CTCAGGGTAC GCTGAAGTTA AAAATACATA
76351 AAAATACATT TAAAAAGAAT AGAATATTAC ACTCTTAGAA TGACTGTATT
76401 CGAATTATAT AAAGTTACCA GAATTGTTAA TAGGCTATAA CATTGGAATA
76451 TTTAAATATA TTAGAATACA ATAGAATAGA AAATAACCTA ATTGTAATGT
76501 AATAAATCAT TAGGCTAATT GAAAATGAAT AATTAGGCCA GGCACCATGG
76551 CTCACACCTG TAATCCCAAC ACTTTGGGAG GCCGAGGTGG TTGGATCACC
76601 TGAGGTCAGG AGTTCGAGAC CAGCCTGGCC AAAATGGTAA AACCCCGTCT
76651 CTACTACACA TACAAAAAAA AGCCAGGCAT GGTGCCTGTA ATCCTAGCTA
```

FIGURE 3Z

76701 CTCGGGAGTC TGAGGCACGA GAATCGCTTG AACCTAGGAG GCGGGTAGGT
76751 TGCGGTGAGC CGAGATCGCA CCACTGCACT CCAGCCTGGG CAACAGAGGT
76801 GAGACTCCAT CTCAAAAAGA AAAAAAAAAA AAAGAAAGAA AATGAATAAT
76851 TAAATTAAAT GAATAACCGT CTCCCAATCA AAGCCCAGTC TGCTGACCTG
76901 TGCATTTCAT GAGGCAGGGA GCTATTGATT CACAGTAAGC CTATTTTTAT
76951 TTTCCTTTTT TCTAATTAGA GTCTATTTCT GGGTGAATAT TGTTTTTTCA
77001 ATTTCTCAGC AGCCCTGTGT CTCTTCACAT GGGTGGGTGT CTTGAGAGTT
77051 ACCAGCTTCG CCGACCCCAA CTCTCCCAGG CATTCCTGTG CTCTTCCCCA
77101 GCTCCAGCCG GCCTGAGCTC GCCTGGACCA CCCCAAGCCT TCTCAGTCTC
77151 CTGCATCCCC TCCTGCCTGC AGTACATTTT CCTGGAAGCA GCTGCAGGCA
77201 TCCTGTCCAC GTACCCATCA GCTGTGTCCC TATTCCCTGG GAGCCCGCTT
77251 GTTGCTTCCC GGATGACTGG AGCAGAATCG GAGGCTCGTT ATCATATGAG
77301 GTTCTGAGAC GGTCTGCCTG TGGGTTGTCC ACCCCTCTTA GACAACAGCC
77351 TGGCCCCTCC TTGTCTTCCC ACTGCTTTTT AAACGTGCCA GGAAGCCTGA
77401 CCTGTCCCCC TGCCCAAAGG CTGGCTTCCT TCCTCCTTCT TTTCTTTTTC
77451 CCTTTCCTTT CCTTCCCTTT CCTTTCCTCC CTCCCTCCCT CTCTCCTTCC
77501 TTCCTCTCTC CCTCCCTCTC TCTCTCTCTC TCCTTCCTCC CTTCCCTTTC
77551 CCTTCCCTTC TTCCTTTCCT TTTCCTTTCC CGTCTCCCTC TTCCTTTCCC
77601 CTTTCCCTTT TCCCCTTTCC CCTTTTTCCT TTCCTTTCCT TTCATTTCCT
77651 TTCCTTCTTC CTTTCCTTTC TGTTCCGCCT CGCTCTGTCA CCCAGGCTGG
77701 AGTGCAGTGG CACAATCTTG GCTCACTGTA ACCTCTGCTT TCTTGTCTCG
77751 CTCTGTCACC CAGGCTGGAC TGCAGTGGCG CAAATCTTGG TTCACTGCAA
77801 CCTCTGCTTC CCAGGTTCAA GCAATTCTCC TTCCTCAGCC TCCTGAGTAG
77851 CTGGGATTAC AGGTGTGCGC CACCACGCCC AGCTAATTTT TGTATTTTTA
77901 GTAGAGAGGG GGTTTCACCA TATTGGCCAG GCTGGCCTCA AACTCCTGAC
77951 CTCAAGTGAT CCACCTGCTT CGGCCTCCCA AAGTGCTGGG GTTACAGGCG
78001 TGAGCCACCA CACCCAGCCA GGGCTGGCCC TTTCTCTTCC ACTGCACATG
78051 CTGCAGGCTC ACCTGTCACC TGCTCCCACA GCCCTCTGGG GCCTCCCCTG
78101 TTCTCCTGGG CCATGCCCTG TCCGACCAGC CCATCTGTTT TCTTTATACT
78151 GATTAGCAGC TCTGAAACCA TCTAAATTTT GTATGTGTTG ACTGCCTCTG
78201 AGAGCAATGC TCCCAAGCTG CTCTCCTCAC CTCCTTGAAC CCAGAAACTT
78251 CTGGTGGCTG GAGGGAGGGC ACTGCTGCAC ATACAAGTGG AGCCGGCCTG
78301 CAGTCAGAGT CTTCCTGCTC CCTTCGCAGC CTGTGTCTGC ACCTTTCCTA
78351 TCGCAGCTCC ATTTGCTGGA TTCCCACTCT TAGCAGGATC AAGTGAGACT
78401 GTGCCTTGTC TGTGTTATTG CTTTAAGTGA TTATCTCAAT CTTCCACTAA
78451 GCACAGGGAA AACCATCTAT TTGGTAAAAT CTGCCATGTG ATTAGGAAGG
78501 AGATCATATC ATGATGCAGA TTTTATTTTC ATGGAATGAG ACATGTTTAG
78551 GTCAGATGAA AATTGTGTGG CACATTCTGG AACAAAATCA CTCATGCACT
78601 TTCCAAGGAC CCAAGCTCAG CTCCGATTTC TTCCATCCTA TTCTCTTTCC
78651 TCATCCATTT CTGTGGTTTT ATTCTCCCAG AGAGTTTAAC TCAAGAGTCA
78701 GGTAAAGGCT GGACGTGGTG GTTCATGCCT GTCATCCCAG CACTTTGGGA
78751 GGCTGAGACA GAAGAACTGC TTAAGCCCAA GAGTTCAAGA CCAGCCTGGG
78801 CAACATAGTG GGACCCCATC TCTACAAAAA ATAAAAATAA AACTAGCTGG
78851 GTGTGGTTGT ATGTTCCTGT AGTCCCAGCT ACTCAGGAGG CTGAGGTGGG
78901 AGGATTGCTT CAGCCCAGGA AGTCGAGGCT GCAGTGAGCT GAGATTGCAC
78951 CAGTGCACAT CAGCTTGGGT AACAGAGCAA GACACTGTCT CAGAAAAAGA
79001 AAAAAAAAAA TCAGCTAAAG CATCAAGAAC AAAACACAGG GACACACAAG
79051 ACATACAGCA GAGTGCAGGG TAAGAGAAAG CCCCTGGGCC ATCTTGTCTT
79101 AGTTGTGACA GCAGTGATTC TCAAAGTGGC ATCCCAGAGG ACTATGGGGT
79151 TCCCGAAGTG TGTTTCAGCA GATGAGTGAG ATCATTTTTC CAATGACAGA
79201 TCTGAATAGT GATGAATTTT CTTCATAGGT GTCAACTAAG ACAATACAGC
79251 ATAGCAGACA GGGTGCAGAA GATCCTAGAG AAGGTGGAAT TTGGCTGCAG
79301 TGGAGCCTCT TCCACGGGGA GCATTAGGCA TTGCGCAGTG GTTCTCAAAC
79351 ATGTTGGCCT CGGGAACCCT TCAACACACA GCTCAAAGTT ATTAACAACC
79401 CACAGAACTT TCATTTCTGT GTGTTACAGC TGTCCGCGCT GACTACATTT
79451 GAAATTAAAG TAGAGACTGA AATATAAACC AACAGAATAC ATAAATAATA
79501 TATATGAGAA GTTAAATAAT CAGAGGAGAA CATAAATAGC ATTTTTAAAT
79551 GAAAAAAATG TGTAACCACA CTTTCTAGAA TTAAAACCAT TCAGGCTGGA
79601 CATGGTGGCT CACGCCTGTA ATCCTAGCAC TTCAGGAGGC TGAGGTGGGA

FIGURE 3AA

```
79651 GGATCACTTG AGCCCAGGAG TTGGAGGCCA GCCTGGGCAA CATAGTGAGA
79701 CCCCATTTCT ACAAAAAATA AAATGAAATA AATAAACCAA TTAGCTGAGC
79751 ATGATGGTAC ACGCCCAGGG TCCCAGTACT TTGGGAGGCT GAGGTGGGAG
79801 GATCACTGAG GCTGGGAGGT CAACGCTGCG GTGAGCTGTG GTCTCGTCAC
79851 TACACTCCAG CCTGGGTGAC AGAGAGACCC TGTCTCTAAA AAGAGAGAAA
79901 ACATTTGTGA GGAGGTTGGC TGTATTTTCT GGGTTTTGTG AATCTCTTTA
79951 GTGTCCAGCT TTCACAAGGG CTGCTGGCCT CTCCTCCCTC TGTCTGCAGC
80001 CTGTCTGCTG TGCTGCGTGG CACGTTGTTT AGTTGAGGCA TAGGAGAAAA
80051 TTCATCACTA TTCTGAACTG GAGTCAGAAA AACGATCTCA GCCATCCCTA
80101 AACTGAGGTC GGGAAGCCAC CCTGGGACTC CACTTTGAGG GCCACTGCTG
80151 TGATGCCCAA GTCAACGTGC CCGGGGCTAT ATTTTCACCC TCTACTCTGC
80201 CCCAACCCTC ACACACCCCA GTGCCTGCTC CTTCCGCTTT AACTGGCCCT
80251 CAAGTTCCCC TTTCTCATCT CCCACCTCAG CCTCCCTGAT TCATCTGAGG
80301 AGCACAGATT TTATATTTAT TTATTAATTA TTATTATTTT TTTTCTTTAG
80351 AGGGACCCCT GCTCTGTCAC CCAGGCTGGA GTGTAGTGGC GCGATCTCGG
80401 CTCACTGCAA CCTCTGTCTC CTGGGTTCAA GCAATTCTCC TGCCTCAGCC
80451 TGCCGAGTAG CTGGGGTTAC AGGTGCGTGC CACCGTGCCT GGCTAATTTT
80501 TGTATTTTTA GTAGAGATGG GGTTTCGCCA TGTTGGCCAG CCTGCTCTCA
80551 AACTCCTGAC CTCGAGTGAT TCACCTGCCT CAGCCTCACA AAGTGCTGAG
80601 ATTACAGGTG TGAGCCACCA CGCCTGGCCT AAATTTTAGT TTTTAATCTG
80651 AAGGTATCGG GACAAGGATT TTTGAGGAAG AAGTCAAGGT GGGATGAAAT
80701 TCTAGTGAAA TTCTAGTGAC GGCTTTCTTC TTTTCTCTAA AAACCTCTGC
80751 CTTCCTTTTC TTGAATGCAT TTCCAAAGCA CCTGTCTTCC AAGGCCAGCC
80801 CCGGTCCTCA GAACTGGAGC AGGTAGTGTG TCAGCTGATA GTTTAGGAGG
80851 GTGTTTTTCC AGCTGAGTAG GAGGGAGAAC ATCAGCTCAC AGCGCCCAGG
80901 GTATCTCTGC CTGCACCATC CACTTTACTG GAAGATGTAA ATAGGCGGAA
80951 TGGTTACATT CAAATTTTAC TGGCAAATGA TAGAGCTAGT GGCACAATTG
81001 GTGTAAATTT TTTTCATTTT TCTTTTTTTG TTTTTGCAGA CAGTTTTGCT
81051 CTGTTGCCCA GTCAGGAGTG CAGTGGTGCA GTCACAGCTC ACTGCAGCCT
81101 GGACCTCCTG GGCTCAAGCA AACCCCCACC TCCGCCTCTT GAGTAGCTGG
81151 GATGACAGGT ACACGTCACT GTGCCTGGCT AAGTTTTTAA AATTTTTTTG
81201 TAGAGATAGG GTCTTGCTAT GTTACCCAGG CTGATTTCAA ATTCCTAGGC
81251 TCAAGTGATC CACCTGCCTC GGCCTCCCAA AGTGCTGGGA TGACAGCCGT
81301 GAGCCACTGC ATGAGCGTTT TTTTTGTTTT TTTTTTTTTT CTTTTGAGAC
81351 AGGGTCTTGT TCTGTGTCCA GATTGGAATG CAGTGGTGCA GTCATAGCTT
81401 ACTGAAGCCT CGACCTCCTG GGCTCAAGCG ATCCTCCTGC CTCAGCCTCC
81451 TGGGACTACA GAGGCTGTAG CTGGGGACCG CAGAGGCTGT AGCTGGGAAC
81501 ACAGGCACAC ACCAGCACGT CCAGATAATT TTTAAATTTT TTGTAGAGAC
81551 GAGGTCTCAC TGTGTTGTCC AGGCTGGTCT TGAACTCCTG GGCTCAAGCA
81601 GTCCTCCCGC GTTGGCCTCC CCAAATGCTG GGATGACAGG CATGAGCCAC
81651 TGTGCCTAGC CTGGGCATGA ATTTTTCAGG CGAAAATCTG GAGCTTGCAT
81701 TCATGCTGAT TAGCAGATTG TCCTTGCAAG TGTAGCTGTC ACCACAGATC
81751 AATTTAACTT GCTTAATAAT GCCAAATGCC ATATAATGAG AATTTATTCT
81801 CCACTTGGTA AGAATTGGAA GCAGTCTGTA TGTTTAGAGA CAGAAATTTG
81851 AGGGTTTCAG AGGGCACTGC CCAGGCGTCC GGGGGAGTGC TGTTTCTCAG
81901 ACACACACAC ACACTGTCTC TGCTTTTTCT TTCAGGCAAG ATCATCAGTT
81951 AGTGCTCACT TATTATTTAT CTTTTTCCGC TTATTAATAC CTTTCCCATG
82001 ATCTTATGTA ATGTCTACTG TCCAAGAGCA CTTCGTTTAA TATTCTCCAT
82051 AAATGTTTTT AGGTATGTAT GGCACATTTC CTCCTGGAGT TTAATGCTCC
82101 ATTCCTGTAT TTGTGCATTA TTCACACAGC TGAATGTATT CAGACAGGGT
82151 CGCCACCCAA ACCCAGAGAG AAACAGGAAT ACAACTCCCC CAACTACTGT
82201 TACAGAGAAC GCTGCGGGCA GGTGAGGGAG GACGGGCTCG GGAGGTTGTT
82251 AACGTCTGAG GCGGCAGGGT TGGCGCAGAT CGCATGAGTG TCTGTACTCA
82301 GAGCTCTGCT TCCCAGCCTG GCCTGGGTGG TTTTTCAGTA CGTTGTGGTG
82351 GCTCGTAACT CCAGGACCAG CGGCCCAAAG AGATACCCTA TTGGGAAACT
82401 CACCTTCATG CTAAAGTGCA AAACAAGCAA CTGAAATGTT ATTTAAGAAG
82451 GAAGAAATGC TGTGTTAGGG CCACGTCGCA CGCACCTAAT CATTTACCTT
82501 TCTCTGGTAA CTTTCATTTC CTCATGTAAC CCACCCCCAC TTCTCTGTCA
82551 CCTCTCCCAT TGATTTCCAT TTTTGTACTT CATATTTCTC CTCTTTGTTT
```

FIGURE 3BB

```
82601 TTCTTTGAAT TTTTCTCCAC TGCAGTGTAT TGGACAGTTC ATGTGTGTAG
82651 TTCTACGTAT GAATGTCCTG ACGCTGCTGT TAGAAACTAC CACAGACTGA
82701 AAGGTTTAAA CAAGAGAACT TTATCCTCTC TTAGTCCGGG AGACCAGAAG
82751 TTTGAGATCA AAGTGTCTCA GGACTGTACT CCAGGGAAGG ATCCTTTCTG
82801 CCTCTCCCAG TTCCTGGGGG CTCCAGCATC CCTGGGCTTG TGGCCACATC
82851 ACTGCAGTCT CTGCCTCCAC CTTCATGTGG CCTTCTCCTC TATGTCTCTG
82901 TCTCCTCTTC AGTCTCTTAG AAGGAAGGCC ACCTGTCATT GGATTTAGGG
82951 CCATCCTAAT CCAGGACGAT CTCATCTCAA GATCCTTCAA TTAATCACAT
83001 CTGCAAAGAC CCTATTGCTG AATAAGGTCT CATTCCAGGT CTGGGCATTA
83051 GGACGTGGAC AGATCTTTCT GAGGGCCACA GTTCAATCCA CTACACGTGT
83101 ATCCAGTTCC CTCTGGAGGC TCTAGGGGAG GATACTCCCT GCCTCTCCCA
83151 GCTCCTGGGG GCTCCAGGCA TCCCTGGGCT TGTGGCCGCA TCACTGCTGT
83201 CTCTGCCTCT GTCCCCATGT GGCCTTCTCC TCTGTGTGTG TGCCTCCTCT
83251 TGAGTCTCTT ATGAGGATAC CTGTCATTGG ATTTGGGCCT ACCCTGTTCC
83301 AGGATGATCT CATCTGAAGC TCCTTAATTC TATCTGTGAA AACCCTGTTT
83351 CCCAATAAGG TCCCATTCAC AGGTTGTTGG GGTAAGATCA TGGATGTATC
83401 TTTTTGGGGA CCTCTCATTC CGTCCACTCC ACTGAATTTT GTTAAGGTCA
83451 GGAAGTGATT TGGAATCTAC AGGAGAATTA TTTTTGCTCA TGGACATTTC
83501 TGATAATCAA TGAGGGTGTC ATTTGAAAGC TCCGTTTTAT AAGGTATTTC
83551 CGTTGCTAGC ATACCTGAAT TAGAATATCT TAAGTCAAAA GAAGCTAAAT
83601 GGAAAACATG ACTTTGAGCC AATATGAGTA TCTGTCCTGA TCAATATGAG
83651 AAAATCTCAG AAGTACAACT TGTGCCACGG ACATGTAAGT GTCTAGTATA
83701 CACTTACTGG TTGATGAAAT GGTTTGGCTT TGTGTCCCCA CCCAAATCTC
83751 ATGTTTAAAT GTAATCCCCA GTGTTGGAGG TGGGACCTGG TGAGAGGTGG
83801 TTGGATCATG GGAGTGGTTT CTGACAGTTT AGCAACATTG CCCTAGTACA
83851 GTCTCATGAT AGAGTTCTCA GGAGATCTGA TGGTTTTAAA GTGTAGTACT
83901 TGCCCCTTTG CTCGCTTTCA CTCATCTGCC ACCATGTAAA TGTGCCTTGC
83951 TTCCCCTTCG CCTTCCACCA TGATTGTAAG TTTCCTGAGG CCTCCCCAGC
84001 CATGCGGAAC TGTGAGTCAA CTCAATCTCT TTTCTTTTCT TTTTTGTTTT
84051 TTGAGACAGA GTCTTGCTCT GTCGCCCAGG CTCGAGTGCA GTGGCGTGAT
84101 CTCGGCTCAC TGCAAGCTCC GCCTCCCGGG TTCACGCCAT TCTGCTGCCT
84151 CAGCCTCCTG AGTGGCTGGG ATTACAGGCT TCCGCCACCA CGCCTGGCTA
84201 ATTTTTTGTA TTTTTAGTAG AGACAGGGTT TCACTGTGTT AGCCAGGATG
84251 GTCTCGATCT CCTGACCTCG TGATCCGCCC ACCTTGGCCT CCCAAAGTGT
84301 TGGGATTACA GGCGTGAGCC ACCGCACCTG GCCTAAATCT TTTTTCTTTA
84351 TAAATTACCC AGTCTCAGGT AGTTCTTTAT AGCAGACTGA AAATGGACTA
84401 ATACAGTTGA CTTCTAGATG TTCTTGGATT TATCTTGGTC TTTGCAGTTT
84451 TAAGTATATA TATTTTTTTA GTTTGTTTCA CATATTTTGA ACATTTCTAG
84501 GTATTAGTAA AGTCTGCTGG TTTCTGCAGC AGGACTGTAA TCTTTTTACT
84551 ACAGTCAACA AAGCATAGTA TGACAATCTT GTTTTTACAC ATGCACCATT
84601 TTCAAGGCTG TATTTGCATG TATTTCTGTC TTTTTCCTGG TCTCCAGGGG
84651 TCAAGAAATG GTTTTCTTGG GGCAAAGAGC TTCGGTCAGC TTTGCAGACT
84701 ACCCAGTCTC AGTTACAAGT ACAGACTCTG CTCCTGCACC TTAAAAAGTA
84751 GTCACATAGT GAGACCGCAT CCCTATAGAA AGTCAAAAAA TTAGCCAGAC
84801 ATGGTGGCAC ACACCTGTGG TCCCCGCTAC ATGGGAGCCT GAGGTGGGAG
84851 GATGGCCTCC TGGGGGAGGT CAAGGCTACA GTGAGCTATG ATTGCACCAC
84901 TGCACTCCAG CCTGGGTGAC AGAGTCAAAC CCTGTCTCAA AACAAAAGAA
84951 AAATATGATA TCTCAGGCTC TTTCATTTGG CCTGTACACA TTTATTGAGC
85001 ACCTGTTGTG TGCCACATAC TGTTCCATGA ATGAGGAATA TAAAGAAATT
85051 CAGTAATGGG TGTGGTGGCT CACATCTGTA GTCCCATTAC TTTGGAAGGC
85101 TGAAGTGGGA GGATCACTTG AGCCCAAGCG TTTGAGACCA GCCTGGGCAA
85151 CATAGTGAGA CCTTGTCTCT ACCAAAAATT AAAAAAAAAA AAAAAACAAA
85201 ACCCTGGCGT GGTGGTGCAG ACCTGTAGCC CCAGCTGCTC AGGAGGCTGA
85251 AGTAGGAGCA TAGCTTGAGC CCTGGAGGTG AAGGCTGAGT GCACTGAGCC
85301 AGGATCACGC TGCAGTACTC CAGCCTGGGG GCAACAGAGC AAGACCCTGT
85351 CTCAAAAAAA AAAAGTAGTT CACTGACATT CACTTGCAGT TTATTGAGGA
85401 TGCCTTATAG TGCCGTGCAA GCAGGCTCAG TACCGGGCTG GACATAATCA
85451 GGTATTGCTC GTGCTGTAGA GTGAAGGAAG CCTCGAGAAA GGTGTCCTGT
85501 TCTTGGCCAT AGTGGCGTAT TCACCACTGT AAACTTTATT TTAACAATTA
```

FIGURE 3CC

```
85551 TTTTATATTT CATTTCATTT ATGTACTCCA TCTCTCTCTG TCACCCAGGC
85601 TGGAGTGCAG TGGCACGATC TCAGCTCACT GCAACCTCTG CCTCTCAGGT
85651 TCAAGCAATT CTCCTGGCCC AGCCTCCTGA GTAGCTGAGA TTACAAGCAC
85701 CGGGGACCAT GCCCAGCTAA TTTTTGTATT TTTAGTAGAG ACGGGTTTCA
85751 CCATGTTGGC CAGGCTGGTC TGGAACTCCT GACCTAAAGT GACCTGCCTG
85801 CCTCAGCCTC TCAAAGTGTT GGGATTGCAG GCATGACCCA CAGCATCCAG
85851 CCTATTTTAT ATTTTATTTT ATTTTGAGAC AAGGTCTCAC TCTGTCACCC
85901 AGGCTGGAGT GTGGTGGTGT GATCACAGCT CACTGCAGCC TTGACCTCCT
85951 GTGCTCAAGC GATCCTCCCC CCTCAGCCTC CCAAGTAGCT GGGACCACAC
86001 ATATGCACCA CCACACTCAG CTAATATATA TTTTTTTAAG ACTGGGTTTT
86051 GCCATATTTC CCAGGCTTAT TTTATTTTTT AAATTGACAC ATAATAATTG
86101 TACATATTCA TGGGGTAGAC AGTGATGCTT TGATACAAAG AATGGAGTAA
86151 TCAGATCAGG GTAATTAGCA TATCCATTTC AATTATTTAC CATTTCTTTG
86201 TGTTAGGAAC ATTCAATATC CTCTATGTAT TTGAAACAAT ACGACATGTT
86251 ATTGCTAATT ATAGTCACCC TACAAGACTA TAGAACACTG GAACATATTC
86301 CTCCTATCTG CTTGTAATTT TGTATCCTTT AACAAACCTC TCCCTATCTC
86351 TCACTTCTTC CCTTCCCAGC GTCTAGTATC CTCTGTTCTT CTTTATCCTT
86401 TCAGGAGATC AGCTTTTTTT TAGCTTTCAT GTATGAGTAA GCACAAGTGC
86451 TGTTTAATGT TCTTTTCCTG GCTTATTTCA CCTAACATAA TGTCCTCCAG
86501 TTTCATCCAT GTTGCTGCCA GTCAGAGGAT TGTATTCCTT TTCATGGCTG
86551 AATAGTATTC TACTGTGTGT AGATACCACC TTTTCTTTAC CTATCTGCTC
86601 ATCTGTTGAT GGACATCTAC GCTGATTCCC TATCTTGGCT GTTGTGAATG
86651 GTGCTGTGGT AAACATGGGC GTGCCGATGT CTCTCCAGTA TCATGACTTC
86701 CTTTCCTTTG AACAGATACC TAGTAATGTG ATGGCTGGGT CATATGGGAG
86751 TTCTATTTCT AGCTTTTCTG AGGAACCTCC ATACTCTTCT CTATGGTGGC
86801 TCTACTAGTT TACGTTCCCA CCAACATTGC GTAAGAGTTC CCTTTTTGGC
86851 CAGGCACAGT GGCTCACGCT GGTAATCCTA GCACTTTGAG AGACCAAGCT
86901 GGGTGGATCA CTTGAGCCCA GGACTTCAAG ACCAGCCTAG GCAACATGGT
86951 GAAACCCCCG CTCTACAAAA AAAAATACAA AAATTAGCTG GCATGGTGGC
87001 AGATACCTGT GATCCCAGCT ACTTGGAAGG CTGAGGCAGG TAGATCGCTT
87051 GAGCCTGGGA GGCAGAGGTT GCAGTGAGCT GAGATTGCAC CGCTGCACTC
87101 CAGCCTGGGA GACAGAGCGA GATCCTGTCT CAAAAAAAAA AAGAGTTCCC
87151 TTTTCTCCAC ATCCTCACCA GCATTTCTTA TTTTTGTGTG TATGTGTCTT
87201 TTTTTTTTTT TTTTTTAATT TTTTTTGAGA CAGAGTTTCA CTCTTGTTTC
87251 CCAGGCTGAA GTGCAATGGC ATGATCTCGG CTCACTGCAA CCTCCACCTT
87301 CCGGGTTCAA GTGATTCTCC TGCCTCAGCC TCCCAAGTAG CTGGGATTAC
87351 GGACGCGTGC CACCACGCCT GGCTAATTTT TGTATTTTTA GTAGAGATGG
87401 GGTTTCACCA TGTCGGCCAG ACTGGTCTCA AACTCCTGAC GTCAGGTTAT
87451 CCACCCGCCT CGGCCTCCCA AAGTGCTGGG ATTACAGTGT CTTTTTGATA
87501 ATGGCCGTCT TAATTGGGTT GAGATGATTG ACACCTCATT GAGGTTTTGA
87551 TTTGCATTTC CCTGATGATT AGTGACGTTG AGCATTTTTT TTCATATACA
87601 TGTTGGCCTT TTCCATGTCT TCTTTTGAGA AATGTCTGTG AAGACCACCT
87651 GTCCATTTTT TAATTGGAGT GCTTATCTTT TCGCTCTTGA GACATTTGAG
87701 TTCCATGCTT GGTCATGGTG GTGGATTCAC CCCGGTAAAC ATGAGAGAGC
87751 ATTGCTGTCC AGTGTTTAGT GCACAGTTAA GGAATGGGCT GGTGGCCCCT
87801 CAATAAGATG CCCAAAGGAG TTGCCTTCTG CTCAGCAGAC GCCTCTCAAA
87851 TGGTCTTTAT ATTCTCTCCA AGGGAGCTTC CCCTGCATCG GACTGTGGCA
87901 CACGATGCCT TGCCTCTTAG AACCATCTGA CTGTCACGTG CTTTCAGATC
87951 GTGACAACTT CAGTGTGCGG GGAAGAGCAT GTGAAATAAA TTACCTTCTG
88001 CCTGTGTGAA GCAGAAATAG CTATCGTTAC AAAGCAGGGA TTTTTTTCCA
88051 TGCTTACTCC CCACTAAAAA TACATGTTTG TTTTTCTAAC AGGTTTCCTC
88101 CGTTTTTTGA TGACAACCCG TTTGGCATTT ATCAGAAAAT TCTTGCAGGC
88151 AAAATAGATT TCCCCAGACA TTTGGATTTC CATGTAAAGT AAGTAAACCG
88201 TTTGCCTCAT CATGAGGTGT GTTTATTTTT AAAGTGTCTA AAATCACCGT
88251 GAAAGCACGC ACTCAGCAGG ATACCATATT GTGTTATTAA ATGTGCTGCG
88301 CATAAACTAT TTTGGACAGT TGTCTTTTCC ACAAGAAAAG AAAAAGATTT
88351 TCAGTATTCT ACTTTAATGA TAGCTTCACA TTTTAATGAG TCTTGGCCGT
88401 ATTGTGTTCT TTTGGTGGTA TGTTATATTT AAAATGAGCC AATGAACGAG
88451 TTTGTCATCG TATTTTATAA GAGAGCAGTT TTGGAATTTG ACAAGAAGGA
```

FIGURE 3DD

88501 TCCTCCTAGT TCTGTGGCTA ACAGAACTGT TGATGGGTTT AGCAGAGTTT
88551 TATCCTTTCT CTCCTGCTTA AATTATGCTC AACCTCTAAG TCCTTTTTAA
88601 CGTCAACATT TTCAGTTCTG AGCATGTTGC TTCAAGGATA TTTACAGTTG
88651 CTGGATATTG GCAACTTTGG ATGCACATTT TATAAAGGTC GTGGCAGTAG
88701 GGAAAAAATA TATTATTTTC TTAAATATAA GAACGCGGCT GGGCGTGGTG
88751 GCTCATGCCT GTAATCCCAG CACTTTGGGA GGTTGAGGTG GGTGGAACAC
88801 GAGGTCAGGA GATCGAGACC ATCCTGGGAA ACACGGTGAA ACCTCGGCTC
88851 TACTGAAAAT ATAAAAAATT AGCTGGGTGT GGTGGTGGGC GCCTGTAGTC
88901 TCAGCTACTT GGGAGGCTGA GACAGCGGAA TCGCTTGAAC CCAGGAGGCG
88951 GAGGTTGCAG TGAGCTGAGA TCGCACCACT ACATTCCAGC CTGGGCGACA
89001 GAGCAAGATT CTGTCTCAAA AAAAAAAGAA TGCTTTTGGT TTTCTGGCTA
89051 CCTTACCCAA TCTGGTCAAC TGGTAGCCAT TTTTACTGTA ATAAGCACTG
89101 ATTTCTGTTT GTTTCACTGT ATTTTTCAGA TGAGTTGATG GGTGCACCAG
89151 CCCCCTGGGC ACAAACTAGA GCTAAATGCA TCTAGTTGAG AATTAAACTT
89201 TTTCTTTTCC ATGGTCTATT TTCTTATGAG CCGGTGGAAG TTCAGTTCAG
89251 AGAAGACTTA TTTCAGGGCG ATGGAGCAGG TTGTTTTGAA TATGCCCCTT
89301 ATGGGGCCAC TGGCTACGTT CAGTTGAGTT TCTTGGTGGT GAACGCACCC
89351 CATCCTAACC AGAGGTTCTT AGTCTGAACA GAAGATAAGG TCGTGTTTTA
89401 TTGGCTTGAG CATGTGTTGT GTTTGACACA CTAAGAGGCA GGCTTTAAAA
89451 GACTTTAGCA AGAAAACGAG GCTCCGCTTA ACAATGAGTC GCCTAGAAGG
89501 GACACCCTGT CCAGTGAATG GTAAGACAGG GAGGTGTCAG GGGAAACAGC
89551 ACCTCAGAAG CCGACTGCTC TGGAAGGAAA TAGAAAGGAT TATATAGAAC
89601 CTCTCTCTCA GGCCCCAAAT CCCATCTGAG TTGAGTGACA TTATATTAAG
89651 TGGATGGCAA AGCACTTTTA TGATCGAGTT TGGCCAGGTG AGGTGCTCAT
89701 GCCTGTAATC CCAGCACTTC AGGAGCAATC CGAAGTGGGA GGATTGCTTG
89751 GGGCCAATCC AATAGTTTGA GGCCAGCCTG GACAATGTAG CAAGACCCCA
89801 TGTCTACAAA AAATTTAAAA ATTAGCTGGG CATGGTAGCA AGTGCCTGTA
89851 GTCCCAGCTA CTAGGGAGGC TGAGATGGGA GGACTGCTTG AGCCCAGGAA
89901 GTCGAGGCTG CAGTGACCTA TGATTGCACC ACTGCACTCC AGACTGGATG
89951 AAAGAGTGAA ACTCTGTGTC AAGAAAAGAA AAAATAATAA AATTAAAAGA
90001 TATAATTATA TATATATATG GGGGGGGTTT CCAATGTTCT GTGGAAACAA
90051 CAACAAAAAA AGGAATTGCA GAAATAGAAT AAACCAGAAG CGTAATCAAA
90101 GTCTGGTCTC TTGCCACTTG TCCTTCTTTC TCTCCTAGTT TATCTTCTTT
90151 GAGAGTAGGG AACCAGCAGC GACCATCTTG GTACTGTCTG ATCTAACATG
90201 CCTCTCTTTA TGCAGCTCCC AGCCCCTTCC AGTGTTCCCC ACAGTGCCCC
90251 TGTTTCTTTA CATACCCAGT GTGGGTTCCC CAAGAGCAGA AACAGTGATA
90301 GATAGAAGTG AACTGACAGT TCACTTCTTC CCATTATTTG TTAAATCTTA
90351 TCAAATTGGC TGAGAAGCAA GACCTCAATG ACTCATATCT TTCCTTTTTT
90401 TGGTAGAGAT GGGTATGGGG ATCTTGCTGC ATTGCCTAGG CTGCTTTTGA
90451 ACTCCTGGGC TCAACTGATC CTCCTGCCTT GTCCTCCCCA AGTGTTGGGA
90501 TTACAGGCGT GAACCACTGC ACCTGGCCTT AATGAGGCAT TTTTCTTATC
90551 CAAATCACTG TCCCTGGTTG TCCATGATGC TAGAATTTTG ATTCTCTGCT
90601 TTTTAAAGTC ATATGTTGGT TCCTGCAACT TTTATCATTT GACCAGGTAA
90651 ACATGTCGCC TGGGCAAATG GCACATCAGG ATTGACATTC CTTATAGAAA
90701 TAAATATCAT TTAAAACAAA ACACCAAAAC AAAGCTTTGG GACTTGTTGC
90751 CAATTCAGTA GAGGTATTAT CTGCCGGTGT TTTTTACAAC ACCTGAAAGT
90801 ACCTGCATCT GAGAGGAGCC AGCTGGTGCC AGGATCGTAA ATAAAATGTA
90851 GAATTTTGGC TACAGTGCAT CAAAAGAGTG CCGGCAGATG TGTCGCTTAT
90901 CCCGGGGTCA AGGGACCCAT CTACAGCTGT GGACACTTCT GTCGTTCCTT
90951 TATAGGGCTT TGCATCTTCA GGGGCCTCTT CTCATCCATA CTCTTTACTT
91001 TCTAGACTGC TTTATAAGAG TTTGCTTTGG TATTTTACTT TTTCTTTTAA
91051 AGAGACGGGT GTCTTGCTCT GTCACCCCGG CTGGAGTGCA GTGGCACAAT
91101 CATAGCTCAC TGCAGCCTCG ACGTCCTGGG CTCAAATGAC ACTCCCACCT
91151 CAGCCTCCCG AGTAACTGGT GCTACAGGCA TGCACCACCA TGCCTGGCCA
91201 ATGTTTTGAT ATTTTGTAGA AACGAGGGTC TTACTATGTT GCCCATGCTG
91251 GTTTCGAACT CTTGGTCTCA CGTGGTCTTC CCACTTCAGC CCACTGCATA
91301 GCTGGGATTA CAAGCCACTG TCCCCTGTAT TTTAAATAAA TCTTCATTTT
91351 CTTACATGCC AAACACCAAA AAAATTTAAA AAAAAATTCA AGGTCATCAA
91401 ACATTTTGTT TTCTTACATG ACACACACAC ACACACACAC ACACACACAC

FIGURE 3EE

91451 ACACACGTTG AAATTTATCA GGTGATCACC AAAACATTCT GAAATAAACA
91501 TAGGGCTTTT TTTCCCCCCT ATAATTTACA CCACTGCCTG CCCCATTAGC
91551 GTATACACTT AAAGCTGATT GGACTGGGAT TATAAGAAAA CAAAGGTTTA
91601 TCTAAAATAT AAAAGCATAA ATAAACCTGT CTTATAATTG CACTCCAGTG
91651 AGCTTTAAGT GTGTGTGGTA AGGGGGCAGG CAGTGGTGTA AATCACGTGG
91701 GGGACGAAGC CCCACATTTA TTTGGGAATG TTTTGGGGGT ATAGTGTTTG
91751 ATAACCTTGA TTTTTTTTTG GCAGGGGGGA GCATGTCAAA ATAATGAAGG
91801 AGAAACTCAC TAAGTAGTGG AAAGGTTTCT AACTTTTAGG TGATTTTTAT
91851 ATTCCCCATC CTGCTCAAAG CTTTTCAGCC TTACAGGATG GATACAAAAT
91901 CCTAGCCTTA GGTGGGCGGA CAGATGGTCT CTGAGTTTTA CTTTGTGGCA
91951 GAGAAGCGGT GAAGTCTGAC AAGCATCCCA TCCTAATTCA GAAAGCATGG
92001 TGGCAGGAAA CTGTAAAATT TCCGATCAGA CAGCACTGGC GAGATTCACA
92051 ATCTAGATGG TGGAGTCTGA CCCTAGGACG TCACCTGGCT TGTCGGAGAC
92101 TCCACAGTCT GTCACAGAAC CTGGGAGTGG CTCAGTCCAA GTTCGTGCTA
92151 CTTACCTTGG GGCATAGTTT ATGCTGGGAA AGCCTAGACG CTTACACCGG
92201 GGTCATGGGT ATTGGATTGT TTTGGGGGAC TTCAATATAT TATATTATTA
92251 TATCATATTA TGTATGTTAT TATACATAAT GTACTCTGTG TATTTTATGT
92301 GTACACACAG ACACACATGA TCATTTCTAC TTCCATAAAT ATGCATCTTT
92351 TAGAACTCAC CTAATCTCCT GGAAGTCTTC AACATCATCT CCAACTACCC
92401 ATCCTAATTG AAGCAGCTTG CTGTTTTTTG TTGTCGTTGT TGTTGTTTGT
92451 TTTTGTTTTT TTTTGAGACT GACTCTACCT CTGTCACCCA GACTGGAGTG
92501 CAGTGGCTCA GTCTCAGCTC ACTGCAACCT TCGCCTCCTG GGTTCAAGCG
92551 GTTCTTGTGC CTCAGCCTCC CAAGTAGCTG GGACCACAGT TGTGTGCCAG
92601 CATGCCCAGC GAATTTCTTT TTCTTTTTTT TTGTAGAGAT GGGGTTTCAC
92651 CATGTTGGCC AGGCTGGTCT CAAACTCCTC ACGTCAAGTG ATCCACCCGC
92701 CTCGGCCTCC CCACAGTGCT GGGATTACTG GTGTGAGCCA GTATGCCCAA
92751 CCTCCCCACC TGCTGTACTT CTGACATGGT CTGTTATTTA AAAGGAAGAT
92801 TATAAGTGAA GAAGCAGACT TAGGAGACTC ATCCTAATGT GTGTGCTTAT
92851 GGGAAAGCCA GCCTTTTAAA ACAGGAATCC CATCAATAAG CAGACCCCCA
92901 GGACAGCGCG TGAGTGTTGA TGTTGGTGAA AGCAGATGTC TTCTATTTTG
92951 CAGGGACAGC CTGACAGGCA TGTTTACGTT AAGTGTCTGG ATCCTCCCTG
93001 CAGGCACATA TAAATTTCAC CCTTTTCTAC TCAGAGGTGT ATTTTCTTTA
93051 CAAAGATGTA ATCAACCCCC TTCCCTTAGC TTCAGCCTTG CACGGGGCAA
93101 CCCAGCCTTG CATAGGTGAT TTAAGAGCCG GTGATGGTAG GAAATAAGCA
93151 CTAGAAAGTG TTTTGCCAAA GTGGAAATTG AACTGCGGTC CTCATGTCAG
93201 ATAGATCTTA TCTCTGTTGC CATGCTGCGT TTGCTGATGT TGATATATAA
93251 TCTGTGTACT TTTTTTTTTT TTGTCTCCTT CCCCAACATA GAGACCTCAT
93301 TAAGAAACTG CTCGTGGTTG ACAGAACAAG GCGATTAGGA AACATGAAGG
93351 TCAGTATTTG ATCCCGTGGG TATTCAGTGG TACCCGATGT GCGTGTCTGC
93401 CGTCTAACAC CCACATTGGC ATGTGCAGGT ATAAACCAAG GCTTAGCGGT
93451 CGTATTTAAT CACTGCCCAA ATTTCAAATC TGGTGTTTTA TTTATTTTTT
93501 TAAATTTTAC TTGAAACTGC CAGGAAAGAT CTATCAAATC TCGGTTTCTG
93551 GGCCCACAAC GTCAAACTGG GTCTACACCG TATCTCCCCT CCCCTCAAGC
93601 AAGGTTAATA GAGCAATAAC AATGTATAAG TTATTACTCA TTATTTTGTT
93651 TACTTATTTA TTTTATTTTT TAAACAGTTT TACGGAGAGT GAATTCACAC
93701 GCCATGCCAT TTACCCATCT AAAATGTGCA ATTCGGTGGC TTTTAGTATA
93751 CACACGATTA TGTACAGCCA CCCCTGTGGT TAATCTTAGA ACATCTTCAT
93801 CAGTTCAAAA AAAGAAACCC TGCACCCTTC AGTTATCACT GTGCTATTCT
93851 TTCATCCTCT CTTGCCCTAA GCCAGCGGTC CCCGACCTTT TTGGCACCAG
93901 GGGCCAGTTT TGTGGAAGAC AGTTTTTCCA CAGACCGCAC AACCTAAATC
93951 CCTTAGTTGC GCAGTTCACA ATAGGGTGTG TGCTCCTATG AGAATCTAAT
94001 GCCACTGCTG ATCTGACAGG AGGCGGAGCT CAGGTGCTAA TGCCAGCCAT
94051 GGGGAGCAGC TGTCAGTACA GGTGAAGCTT CGCTCACCTG CCTGCTGCTC
94101 ACCTCCTGGT GTGCGGCCCA TTTTGGTTCC TCATAGGCCG TGGACCACTA
94151 CCAGTTTGTG GCCCAGGGGC TGGGGACCCC TACCCTAAGC AGCCACTAAT
94201 CTACTGACTT TCTCTGTAGG GTTCGGTGTT CTGGGCTCTG CTAAAAATGG
94251 AATTGTACAA AATGTAAGCT TTTGCCTCTG GCTTCTTTCT CTGAGCACGA
94301 TGTCTTCAAG GTTCATCCAG GCTGTAGCCC GTGTCAGAGC TTCCTTCCTT
94351 TTCCTGACTG CATAGTATTC GATTGTGTGG GCAGACCTCG TTTTGTTTAT

FIGURE 3FF

```
94401 CCATTCATCT ATGGATGGAC ATCTGGGCTG TTTCCACCTT TTGGCTTTTG
94451 TGAATGGTTC TGCCATGGAC ATGAGAGTAG GTGTTTTGTG TGCGCAGGTG
94501 ATGATTTTAA AAGTTGTGCA TCAGGTATGA TTTCCACAAA CTTTTTGTGT
94551 GGAGGCAAGT ATATAATTGA CAAACAGACT ATTCCTTAAG TAGTATCATA
94601 CCTGATATGC GTGTTTTGAC ATCCCTGAAT TTGACAGAAT TCATGGACTT
94651 TTTGTTGGCC ATTTCTAGCT CTGGACAACC TCAGAGGGAC TTATACATGG
94701 AGGAACTTCC ATATACGTCT TGACCCTGTA AATTACAGTC TGGAGAGACA
94751 CAGTACACCG GGGTGTGAGG CTTGAACCAC TTGGCTCTCT TGGGGCCCTC
94801 TGTGTGGTTT ACGAGTCTCC AGTAGCTGCC ATAAGAACTG ACCACAAACT
94851 AGGGGCTTAA ACAACAGGAA TTTCTGCTTT CCCCATCCTG GAGACGAGGA
94901 GTCTGAGATC AAGGTGTCTC AGGCCTCCAG AGGCTCTAGG GGAGGATCAT
94951 TCCTGCCTCT CCCAGCCCCT GGGGGCTCCG GGCATCCCTG GGCTTATGGC
95001 CGCATCACTC CAGTCTCTGT CTTTCTTCAC GTGGCCTTCT CTGTGTCTGT
95051 GTCTCCTCTT CTGTCTCTCA GAAGGATGCC TGTCATTGGG TTTAGGGTCA
95101 TCCTAATGCA GGATTATCTC TTCTCAAGAG CCTTCCCTTA ATTACATTTA
95151 CAAAGACCCT ATTTGCATGT AGGGTTCCAT TCCCAGGTAC TGGGAGTCAG
95201 GACATGGGCA TATATTTTGA GGGCCACTGC CCAATGTGTG ATAATTGTGT
95251 CTGCTTCCTG CTAGAGGCTC TAGTGGGGGA TCCTTCCTGC CTCTCCCAGC
95301 TCCTGGGGGC TCCAGGCATC CCTAGGCTTG TGGCCACACC ACTGCAGTCT
95351 CCACCTCCAT TTTCACATGG CCTTCTCTAT GTTTGTGTCT CCTCCTCTGT
95401 CTCTTATGAG GACACCTGTC ACTGGATTTA GGGCCCACCC TTCTCCAGGA
95451 TGATGTCATC TCAAGAACCT TAATTTAGTT ACATCTGCAA AGACCCTATT
95501 TCCAAATAAA GTGATATTCA CAGGCACTGG GGGATAGGGA TGTGCACATA
95551 TCTTTTTGAG GGACATTGTT TACCCTATAA CAGTAGTCAA GCTTCTGTCC
95601 TTTACATTAT TTGCGGACAG CAACGGGATA CCTTCAGGTC TCCGAGGAGC
95651 CTATCCAGCC AGGTTGCACG GTGTGGACTC ATCTGTGCCA CGGCTCTTCA
95701 TAAGATTGGA CGAGTCCTGT TTTAATGCCA CAGCCATTTA GAAAAGAGCT
95751 GGGTCTCTTG CTGGGACTGC AGGGAATCAC AGACGACCCA TATCTAGAAT
95801 CTGCTGGGAA TGGCGTAGTG ACCATCATAG GTACCTTCCA AGGGGGAAGA
95851 ACAAGTTTCC CAATCAAAGG AATTGGGGAA AAGCTCACAA ACTCCCAAGC
95901 TAGGTCTTAA AGTCTAGTTA AAGCTTCCTG ATATGGAGAT AAACTGAAAG
95951 AGACTCAAGA AAACACTGAC TTTATATTTT TTTTAAATTA ACACATGAAA
96001 ATGGTATTAT TTAGCATGTA CAACATGAAG TTTTGAAATA TGTACCCATT
96051 GTGGAATGGG TCCATTGAGT TCATTAACAT ATGCATTACC TCACATAATT
96101 ACCATTTATT TGTGGTGAGA ACACTTAAGA TCTACTCTTT GAAAAAAATT
96151 GTTTTTAAGA GTTGGGGTCT TGATGTGTTG CCCAGGCTGG TCTCGAGCTC
96201 CTGAGCTCAA GTGATCCGCC CACCTTGGCC TCATAAAGTG CTAGGATTAC
96251 AGGCAAGAGC CACTGCACCC AGCAAGATCT ACTCTTCCAG AGATTCTTGA
96301 GAATACATCA TTAGTTATAG TCACCGAGCT GTGCAAGCCA CTGACTGAAC
96351 TTGTTCCTCC TGTCTCTCTC ACTTTGTCTC TTTTGACCAA TGACTTCCCA
96401 TCTCAGCCCC TTCCCAGCCC CTGGTATCCA CCATTCTACT CTCTGCTTCT
96451 ATGAGTTCAA CTTTTTTAGA TTTCCCATGT AAGTGAGGTC AGGCGGTATT
96501 TGTCTATCTC TACCTGGCTT ATTTCTCTCT CTCTCTCTCT CTTTTTTTTT
96551 TTTTTTTTTG AGACACAGCA AGGCGGAGGT TGCAGTGAGC CAAGATGGCG
96601 CCATGCCCTC CAGCCTGGAT GATGGAGTGA AACTCTGTCC ATTGCCCCGC
96651 CCCCCCAAAA AGAACATAGA GTATAGTAAA TAGATAAACC AGGGACATAG
96701 TCATTTATTA TCATTACCAA GTATTAGGTG CCGTAGGTAA CGTATGTGTT
96751 AGACTGTTAC ACGCCTGGCA GCGTAACAGG AGGGATGCAT TGTCCTGTGG
96801 TTACAATGGC CATGGCGTCA CTAGGGGATA GGAGTTTTTA AGATCATTAT
96851 AATCTTACAG GAGCAACACT GTATATGTCA TCCATTGTTG ACTGAAGCAT
96901 CATTTTGAGG CTCATGACTG TAGATACACA CCCACACACA CACTTTTTTT
96951 ATTTTTATTT TTTCAAGACA GGATCTTGCT CTGTCATCCA GGCTGGAGTG
97001 CAGTGGTGCG ATCACAGCTC ACTGCAGCCT TGACCTCCTG GCGTCAAGTG
97051 ATCCTCCCAC CTCCGCCTCC CGAGTAGCTG GGACTCAGTG CATGCACCAC
97101 CAAGGCTGGC TAATTTTTTA TGTTTTTTTG TAGAGACCAG GTCTTACTTT
97151 GTTGCCCAGG TTAGTCTCAA ACTCCTGGGT TCAAGCAGTC CTCCTGCCTC
97201 GGCCTCCCAA AGTGCTGGAA TATAAACGTG AGCCACTGCT CCCACCCCCC
97251 TCACACACAC TTTATATAAC ACACACACAC TAGTTTGGAT ACTAATGTGA
97301 ATCTCGGTAT ATACATATAC TTTGTACTCT ACATATAAAG TGTGTAAAGT
```

FIGURE 3GG

97351 ACATATGTAT ATGTGTATAT ATATATATAA TACATGTGTA TATATTAACG
97401 TGTATGTATA TAAGTATGTG TATATTTAAT GTGTATATAT TAACGTGTGT
97451 ATGTATATAA GTATGTGTAT ATATAAATAT ATGTGTGTAT ATATTAACGT
97501 GTATATGTGT ATAAGTATGT ATATATTAAC GTGTGTATGT CTATAAGTAT
97551 GTGTATATAT TAATGTGTGT ATGTGTATAA GTATGTATAT ATCAATCTAT
97601 GTGTGTATAT ATGTATGTGT GTGTGTATAT ATTACTATGT ATGCATGTGA
97651 GTATATACAG ACACACACAT CCTTTAGTAT CCAAATTAGA ATTTTATCTG
97701 ATGGATAAAA TTTATTTTAT TCTCTTATTC ACAGCACTCT TATTTATTCT
97751 TATTCACAAC ATTGCTGAAG GGAAAACTCA ACAGCTATTG TTTGTTGCCT
97801 GACTTAGCTA TAGATCAAAA ATACCTGTTT TGCAATAAGA AAAGAAAAAG
97851 TTGTCAAAAC AACTGGATGG GAAAACAATA GAAAAAATTC ACATTACTGT
97901 TTCCTTTTGA AGATATGGTC GTGGACGTAT TCCTCTTTAA GGATAAGAAA
97951 TTTGAAACTA CAGTAATGCT AACTGATAGA CGCGTTAAAT TCAGATGTAC
98001 TGGCTTCTGT TTCATGGAAC CTACGTTTAT TTCTTCTGCT GTCCCACATT
98051 TAATTGATAA CGACATCACT ACAAGTATAA GAAAAGGAAG CAGAGTGAGG
98101 TTTACGGATG AGCACTTGGG AGGGATTTCA GAGGTCGTGA TGGCCACAGT
98151 GTGAGCCAGC GATGCCTGGT GCTACCCTTG AGCATGAAGC AGGCCGACTT
98201 GAACGCACCT TGTTAATTGC CAGGCCGTGC AATGTCGTTC CTAAGGTCTC
98251 TTAAACTGGA CATCCTTGGT TTGAGTTCCC AGTCTTGTTA TTTACTTGCT
98301 GGGTCCTACG GAGCAAATTA ACATCATTCC TTGAACCCTA GTTTCTATGT
98351 CTGTAAAATA CTGAGTAAGT TTGCCAAGAT GAAAACAGGA GACAAACTGA
98401 GAAACTACTG GCTGTCCAAT TTTATGTCGA GAGATGGAAT CGTATTTACC
98451 TTTTTCGTCT TTGGTCCGGA ATGCAAATGC ATTGCACAGG AGCAGAATGA
98501 CTGGATTTGT TTCTGCGGCA AAAAAGGGCA AACAAAACAC TAACAGCTTT
98551 GCTTGCAGGT TTTCCTGGCA GCTCACCCTC CAGGCACAGT TCTCCAAAAT
98601 GCAGCAAACT TGGTCTGTTT GTTTCAATAC TAAAATAATG TAGAGATTCT
98651 TTGGGGTATT TTTCTTTCCT GCCCTGTCAA AATTCTGTAC GCTGACGACA
98701 TGTGTTGTTT CTTTTGAAGA ACGGGGCGAA TGATGTGAAG CATCATCGGT
98751 GGTTCCGCTC CGTGGACTGG GAAGCTGTTC CGCAGAGAAA ACTGAAGGTA
98801 CAACACATAT CAGTGGGTGA CTCAGTATGC CCGAGCTCTT CCATTAGCAG
98851 GGACTGCCTC TGAATCCTGG GACTTCTTTA TTGATGGCTG ACATGTGATT
98901 AATTTATATA ATACAACTAT TTGTCTAAAA CTGTTCATAA GCCAAGTTCC
98951 CCACTCTTTG AGTGTCTTAG TGCTAACCAT CTACCTAGCT CCCACAAAGG
99001 CAGGAGCCAC CACACCCAGT CATATACCAC ATGTTCTTTG TCCATTCATC
99051 CCTGGATGGA CACTTATCCC AGATTTTGAA GCAGATTTTA GGAGACCTGG
99101 CCTGATTCCT GACTAGCTCT GTGACTGCTA AACCCTACTC CCTCCTCTTT
99151 AGTGGAAAGC GGTCAACAGG ATTACAGAGA TAAGCAAGCG TCTAGCACCA
99201 TGGTCATCAT TCAGTGATGG TGGTGTATTA CATGGAGAAT ATTCTTTGGA
99251 ACGTTTCTGG CCAAACTGCC TATTTTTAAA CATCTGGCTT TTTGGCTGGG
99301 TGCTGTGGCT CACGCCTATA ATTCCAGTAC TTTGAGAGGC CAACTCAGGC
99351 AGATCACTGG AACCCACGAG TTTGAGACTA GCCTGGGCAA TATGGTGAAA
99401 TCCCGCCTCT ACAGAAAATA CCAAAATTAG CCAGGCGTGG TGGCATATGC
99451 TTGTGGTACC AGCTACTTGG GAGGCTGAGG CACAAGAATT GCTTGATACC
99501 AGGAGGCGGA GGTTGCAGTG AGCCAAGATT ATGCCACTGC ACTCCAGCCT
99551 GGGCGACAGA GCCAGACCCT GTCTCAAAAA AAAAAAAAAA AAAAAAAAAA
99601 TCTGGCATTT TTTTCAATGT ATAATACTTG TCCATTTTAT AAATGAGGAG
99651 ACTGTGCTCA GAGAAGTTAA GCAATGTGTG GAAGGTTACA CAGCTGCTAA
99701 GCAGTGTAAC TATCACAGGT ACATATTTAT GGGGGTACAT GTTATATTTT
99751 GACACACGCA TAGAATGTGT AATGATCAAC TGAGGGTAAC CAGGGTATCC
99801 ATCAGCTCAA ACATTTATCA TTTTTATGGG TTGGGAATAT TGCAAATCTA
99851 GCTATTCTGA AATATACAAT ATATTGTTAA CTCTGCCCAC CCAACTATGC
99901 TGTCAAACAC TGGAACTTAT TCCTTTTATC TAACATTATG TTTATGCAAT
99951 ATTTCTTCAT CTCCCCTTCA TCCCCTAGCT ATACACACTT CCCACCCTCT
100001 GGTAACTATC ATTCTACTCT CAACCTTCAT GACATCCATT TTTTTAGCTC
100051 CCACATATGA GTGGGAACAC GCTGTGTTTC TCATTCTGCG TCTGGCTTAG
100101 TTTATTATTT ATTATTTATT TTTTGAGACA GCGTCTTGCT CTGTTGCCCA
100151 GGCTGGAGTG CAGTGGCACG ATCTTGCTCA CTGCAGCCTC CACCTCCTGG
100201 CTTCAAGCAG TTCTCATGCC TCAGCCCCCT GAGTAGCTGG GATTACAGAC
100251 GCCCAGCTAA TTTTTGTATT TTTACTAGAG ACGGGGTTTC ACCATGTTGG

FIGURE 3HH

```
100301 CCAGGCTGGT CTCAATCTCC TAACCTCAAG TGATCCACCA GCCTCAGTCT
100351 CCCAAAGAAG TGCTGGGATT ACAGGCATGA GCCGCTGCAC CCGGCCTGGC
100401 TTAGTTTACT TAACATGATG GTCTCCCATT CCATTCGTGG TGCTATAAAT
100451 GACAGGATTT CATTCCATTT TATGGCGGGA TAGTTTTTCA TTGTGTGTAT
100501 GGACCACACT TTCTTTATCC TTTCATCCAT TGGTGGACAC TTAGGTTGAT
100551 TCCATATCTT GGCTTTTGTG AACACTCTGA ACTGCATATG TTACTGATGG
100601 GAGTGGTCAA TGGTAGTGTT TTCACCTTTG CACTTCAGAG TTAAAAGAAT
100651 GGAGAATGCT TAGAAATGCT TATTCCTAGT CCTCAGCTCA GACCAGAGTT
100701 TCTGGGGCTG GAGCCTGGGA TGATACGCTT CTTTTTTTTT TTTTTTTTTT
100751 TTTTTTTGAG ATGGAGTCTC ACTTTGTCGC TCAGGCTCGG GGTGTAGTGC
100801 AGTGGAGTGA TCTCAACTCA CTGCAACCTC CACCTCTTGG ATTCAAGTGA
100851 TTCTTCTGCC TCAGCCTCCC AAGTAGCTGG GATTACAGGT GTGCGCCACC
100901 ACATCCAGCT AATTTTTTTG TGTGTTTTTA GAAGAGATGG GGTTTCACTA
100951 TGTTGGCCAG GCTGGTTTCG AACTCATGAC CTCAAATGAT CCACTCTCCT
101001 CGGCCTCCCA AAGTGCTGGG ATTACAGGTG TCAGCCACTG GGCCTGGGCT
101051 GATGCATCAT TTTGTTCAAA GTTTTACCTT TTCAAATACT TTATTGTATT
101101 AAATTGCATT AAAAAAACAA TTTGAATACG TTTTATCTAT CCACATTGGT
101151 CAAAAACCAA GTCAATATTA AAACAGATAT ATTGCCAAGT CTCCCTCTTA
101201 CCCCCTCCAA GCCACCTGTA GGTAATCACC TTTTATTGTT TTTCTGTGTA
101251 TCCTTCTAGA GTTTCTTTGT GCTAATAAAA ACCCACATGG ATACATGCAT
101301 TCTTATTTTT GCCACTCATT TATACAAATC TAGAGTAGCG TAGTATGTAC
101351 ATTATTATAG TCTTGCTTTT TGCACTTGAC TATATAATCT GGAGACCTGT
101401 CTACATACCT GGCTAGCTTC CTCATTTTTT TTTTTTTTTT TTTTTTTTTT
101451 TTTTTTTTTT TGAGACGAAG TCTTGCTCCG TTGCCCAGGC TGGAGTTCAG
101501 TGGTGCGATC TCGGCTCACT GCAACCTCCG CCTCCCAGGT TCAAGCGATT
101551 CTCCTGCCTC AGCCTCCCAA GTAGCTGGGA TTACAGGCAC CCACCACTAT
101601 GCCCGGCTAA TTTTTGTCTT TTCGGTAGAG ACAGGGTTTC TCCATGGGCC
101651 AGGCTGTTCT CGAACTCCTG ACCTCAGATG ATCCTCCCAC CTTGGCCTCC
101701 CAAAGTGCTG GGATTACAGG CATGAGCCAC TGCGCCTAGC CAGCTTCCTC
101751 ATTTTAAAAA ATACTGCATT GTATTCCATC ACATGACTGT ACCATAGCTT
101801 ACTTAATACT ATATATATAT ATTTTGAGAC AGGATCTCAC TCAGTCATTC
101851 AGGCTGGAAT GCAGTGGTGC AATCATGGCT CACTTGGAGT ATCGACCTCC
101901 TGGGCTCAAG CAGTTCTCCC ACCTCAGCCT ACTGAGTAGC TGAGACTGCA
101951 GGCACACAGC ACCACACCCG GCTAGTTGTA TTTTTTGTAG AGACAGGGGA
102001 CTCCCTGTGT TCCCCAGGCT GGTCTCAAAC TTCTGAGGCT CAAGCAACCC
102051 TCCCGCCTCA CCTTCTTAAA GTGTTGGGAT TACAGGTGTG AGTCCCCACA
102101 CGCAGCCTCA TTCACAATAT TTTAATTCAA AGATTGCCGC TTTCATAAAT
102151 GAAGGGAAGA CAGCTTTAGT GTTTTGCAAA TCATTTTCAT TTTTAGGTAC
102201 AGTGACAGAA ATAAAGCGGT GTGTGCAGCA TCCAAGTGTC CCGTCCCTTT
102251 CTAACCATGC CTTTGTGCTT CGGCCATGTC TCACAGCCTC CCATCGTGCC
102301 CAAGATAGCT GGTGACGGCG ACACTTCCAA CTTCGAAACT TACCCTGAGA
102351 ATGACTGGGA CACAGCCGCG CCCGTGCCGC AGAAGGATTT AGAAATCTTC
102401 AAGAATTTCT GAGGACAGGA GCTCACATCT GGAAGGTATA TCTTTATATT
102451 TAGTAATTCC CAAAAAATGA GACTGACTCG ACCCCACATC CAGGTGAGGC
102501 TGCGTTTACT GAGTGGGGCT TAACCTCATG CACACAGAGG TCAGCAGTGA
102551 AGCAGAGCAA AGGGGATTGA TTGCAAGGGT CAGCGAAATA AACACAGCCA
102601 TGCCTGTGAC TCCAGGTCAG CATGTGACCG TCAGAGGCAT CAGCATGACA
102651 GTCCAGAATC CATGTTCTGC ATCAGAACCT GCATGTCTAA ATAAGACCGC
102701 TAGGTGGTTT GTGTGTGCCT GAATATTTGA GAAGCCCAGC TCCTCTGGTC
102751 CCTGTTCCAG AAACCCTGAG TGACAGGCGA GCTTCCTTAG AATAATTAAC
102801 AAGTATTTTC AAAAGTCTCT TTAGGTCTCC TTTGGTTAAA AAATAAGAAG
102851 AAGAAATATG CCCTCATAGG AAATTTGCTA AGCTTAATTG AAGATGACTG
102901 GAAAAGGATT TTGAGTCTAT TACTTCTTTG AGCCTTTGAA GGTCTATTAT
102951 TAGTTTTTAA ATAATAATAA TATTTTTTAG AATCCCTCAT GAAATTTGCT
103001 AAGCTTTAAT TTAAGATGAC TGAAAAAGGG TTTTGACTGT GTTATTTCCT
103051 TGAGCCTTTG AAAATCTATT ATTAGTTTTT AAGTATGGAT TAAAAAGAGC
103101 TTTCAGTTAC TCCTCAATTC TAAATTGCTC GGTTATATGG CTTCAATTAG
103151 ATCTTTCTTC CTGTAACACA CGAGCAAGAA ACATACCAGT GAAGCAAAAT
103201 ATTGTCAGTG ATGTGTCTAT TCATTGACAT AGCTTGTTTT TCCCATTTTG
```

FIGURE 3II

103251 ATTTCCATTC CCGTAATTTT CCTGTAGTCT TCCCAGTTAT GTGAAGTGGA
103301 AAGCCAATTG GCTAACCAAC ACCATTCGAA ACAGACACCA AATGTCACAA
103351 TTGCTGACTG GGGAGAGGAA CCAACCTGCT GAAAGACGTG GTGAATGAGA
103401 GCCCTCCATC CTGGGCAGGT GTTTACATGG ATGTACCAAG AGGAAAGCTG
103451 GATACAAATT GAAATAATAG ACAACAAAAT GATAGAGGAA TAGGTGGCTA
103501 TGACCTCGAG AAGATAACCT GTCTCCATGG CATGGCTTCA CCTCTCAGTG
103551 TGTGATGAAC GCTTTCACAG TGGTGACTGG TTTGTATTAA CATGAGAGCG
103601 TGTAACTTTA CCAACTTCAT AAACGCTCAT GAAATCCAGT TGCGGGTTTT
103651 AAAAATCATA AGATGTTCCT GAATGTGTTT ACTTCTTTTT GTTTCTCTGC
103701 TCTACTCTGG GGCTTACATT TTAGCTGACT CGCCCATAAC ATCTTACAAA
103751 TTGTGTCTCT CCAGGAAATC TTTAAAATGA TGTAAAGACT TGGTTTGCTT
103801 TAGTATGAAG GACCCCTAGT TGATAAGCCA CAAAAATAGA ACCTTTCTCT
103851 AATAGAGACC CCTCAATTGT AAAATTTACT TAAAGAACAA AAAAGCTTCC
103901 ATTTGATGGA TTTTTGTCAT ATAATCAGTG AACAATTTCA TTACATCCTG
103951 TCCCCAGCTG CCCCTACTTT CCCTGAAAAA GATTCCACAC GTAGGAATAA
104001 CCTTTCTCCA TCTGGTATGC ATTGTTGAGA AAGTATGTGT AAGTAAGTAT
104051 TATTTTTGCT AAGTGGAATC ATTTTTAATA TAGTTTGGCT AGTGGTTGGG
104101 GCTCTGTTTA ATGAATTTTT TTTTCTTTTT GAGACAGAGT CTCGCTCGGT
104151 TGCCCAGGCT GGATTGCAGT GGTGCGATCT CAGCTCACTG CAACCTCCGC
104201 CTCCTGGGTT CAAGTGATTC TCCTGCCTCA GCCTCCCGAG TAGCTGGGAT
104251 TACAGGTGCC TGCCACCACA CCAGGCTAAT TGTTTTGTAT TTTTAGTAGA
104301 GATGGGTTTT GCCATGTTGG CCAGGCTGGT CTTGAACTCC TGAACTCAGG
104351 CAATCTGCCC ACCTCGGCCT CCCAAAGTGC TGGGATTACA GGCATGAGCC
104401 ACTGTGCCTG GCCCAGATGC AATATTTTAA TCCGTCTTAG TAATTTTATC
104451 AAGTAATTTG CACACCAAAC ACATCCCTGG CATTTTCAGC AACGAGCGAT
104501 TAGTTGCAGG AATTTTATGC AGGAAGATAT TTCTTCATGA AGCCAAATCT
104551 TCTCCTGTAA ATAAGACACC AGTTCAGATG AATCACTGCA CTTGAGGGCA
104601 GCTTAGAAAC TATGCTGTAG CCGTTCATCT TTGTTTGAAT CACCCTGTAT
104651 GCCTTTCTGA ATGTGGAGGA GGAATTTAAG AGAACTGACT CACTATGTCT
104701 TTTATTTTAC TTTGTAATAA AATATTTTCT GTCTTGCTGT AAGGTTCTCT
104751 GAGGAAGCAT GTTGAATTGG GGATCCCATT TTTCTTGTGC AGTTCATCAT
104801 CTATTGGTGG ATACATTTAT CTATTTATGG ATAAGCGTAT GATAGAACAT
104851 TCTTCAGGCT GGATGTGGTG GCTCCTACCT GTAATCCCGG CACTTTGGGA
104901 GGCCGAGTTG GGAGGCTCAC TTGAGGTCAG GAGTTTGAGA TCAAGCCTGG
104951 GCAACATAGT GAGACCCCAT CTCTACAAAA AATAAAAAAG TTAGCCAGGC
105001 GTAGTGATAC ATACCTATTG TCACAGCTAT TCTAGAGGCT GAGGTGAGAG
105051 GCTCGCTTGG GCCTGGAAAG TTGAGGCTGC AGTGAGCCGT GATTGTGCCT
105101 GTACTCCGGC CTGGATGGCA GAGTTAGACC TCATCTCAAA AATGAAAACA
105151 GGGCTGGGCG AGGTGGCTCA TGCCTGTAAT CCCAGCACCT TGGGAGGCCG
105201 AGGCGCATGG ATCATCTGAG GTCAGGAGTT CGAGACCAGC CTGGCAAACA
105251 TGGTGAAATC CCATCTCTAC CAAAAATACA AAAATTACCC AGGCGTGGTG
105301 GCGGGCACCT GTAACCCCAG CTACTCAGGA GGCTGAGGTA GGAGAATCAC
105351 TTGAACATGG AGGCGGAGGT TGCAGTGAGC TGAGATCACA CCACTGTACT
105401 CCAGCCTGGG CAA (SEQ ID NO:3)

FEATURES:

Genewise results:

Start: 2388
Exon: 2388-2553
Exon: 39833-40001
Exon: 59182-59445
Exon: 88093-88188
Exon: 93292-93349
Exon: 98720-98797
Exon: 102287-102409
Stop: 102410

Sim4 results:

Exon: 2388-2553, (Transcript Position: 1-166)

FIGURE 3JJ

Exon: 39833-40001, (Transcript Position: 167-335)
Exon: 59182-59445, (Transcript Position: 336-599)
Exon: 88093-88188, (Transcript Position: 600-695)
Exon: 93292-93349, (Transcript Position: 696-753)
Exon: 98720-98797, (Transcript Position: 754-831)
Exon: 102287-102412, (Transcript Position: 832-957)

CHROMOSOME MAP POSITION:
Chromosome X

ALLELIC VARIANTS (SNPs):

| DNA Position | Major | Minor | Domain |
|---|---|---|---|
| 2916 | G | A | Intron |
| 3308 | A | G | Intron |
| 4840 | C | G | Intron |
| 4874 | G | A | Intron |
| 5255 | G | A | Intron |
| 6268 | T | C | Intron |
| 6438 | - | T | Intron |
| 6457 | - | T | Intron |
| 8486 | T | C | Intron |
| 8534 | C | T | Intron |
| 8995 | C | G | Intron |
| 9623 | T | - | Intron |
| 13172 | C | T | Intron |
| 14802 | C | T | Intron |
| 20393 | C | T | Intron |
| 22234 | G | A | Intron |
| 22253 | G | T | Intron |
| 25890 | A | T | Intron |
| 25891 | A | T | Intron |
| 25894 | T | C | Intron |
| 27386 | T | C | Intron |
| 28861 | - | T A | Intron |
| 30916 | G | A | Intron |
| 30959 | A | G | Intron |
| 34435 | - | A | Intron |
| 36813 | G | T | Intron |
| 37063 | C | T | Intron |
| 37569 | C | T | Intron |
| 37905 | A | G | Intron |
| 41617 | T | G | Intron |
| 42444 | C | T | Intron |
| 46230 | G | A | Intron |
| 48604 | T | A G | Intron |
| 48867 | T | C | Intron |
| 51123 | T | G | Intron |
| 51212 | A | G | Intron |
| 52308 | C | T A | Intron |
| 52333 | C | T | Intron |
| 53079 | G | C | Intron |
| 62141 | T | C | Intron |
| 70339 | - | T | Intron |
| 70379 | A | G | Intron |
| 76074 | C | T | Intron |
| 77336 | C | T | Intron |

FIGURE 3KK

| | | | |
|---|---|---|---|
| 77582 | G | C | Intron |
| 78010 | C | T A | Intron |
| 78011 | A | G C | Intron |
| 79557 | G | A | Intron |
| 79617 | T | C | Intron |
| 84900 | C | G | Intron |
| 100529 | A | G | Intron |
| 100997 | - | T | Intron |
| 101864 | C | G | Intron |
| 101915 | C | T | Intron |
| 102141 | G | T | Intron |
| 102459 | A | C | Intron |
| 102724 | C | T | Intron |

Context:

DNA
Position

2916

TAGGACAAAGGGCCCTGGGTGCCGACCTCCTGGGGAGGGCCCTGACCCGCTACTTCGGCT
CGGAGTCCCCGTGCGGGGCTGCACCTGCGCCCCGGGTCTTCCCGGGTGGAGCGCACTCCC
CAGCCCCCCAGCCCAGGCAAGTACCCCCGACCGGCCGGGTGCCTAACCTGAAATGCCGAC
GGCTCCTCTCGGAGACCACCCTCCACCCCCAGCACACACAGCACTCTGGGGCCTGGGCCG
TCCGACGTCACAAAACCTCCTGCGGGTCACCTCGCCTGGGGGACCTCGTGCTCCCTCCCT
[G,A]
GCAGCGGCCCCAGGGACACTGGCGCGGGGTGCGAAGACCCCTGCAGGCCTCCCCTAGGCC
AGCCTCCCTGTGTGCCCAGAGGCAGGGAATGTACAGATTTCTCCAGGGGCTGCAGGAGCA
GCTGGGCTGTGGGGGACAGGTGTCCCGGGGCGCTGTGGGGACGAGGACGGCAGCGCTGGG
GACGGATCCTAACATGTCCTGACACCGCCTGTGCTCTTCGTCTTGTGCCTCTGAAATGGG
TAATTCTTGTATCGGACGCTTTATCCGTTTCCTTTGTCCTCTGTCTTTGAACTTAACCCC

3308

TACAGATTTCTCCAGGGGCTGCAGGAGCAGCTGGGCTGTGGGGGACAGGTGTCCCGGGGC
GCTGTGGGGACGAGGACGGCAGCGCTGGGGACGGATCCTAACATGTCCTGACACCGCCTG
TGCTCTTCGTCTTGTGCCTCTGAAATGGGTAATTCTTGTATCGGACGCTTTATCCGTTTC
CTTTGTCCTCTGTCTTTGAACTTAACCCCGAATGGGCAGCTTGACAGAGAGGTTTCGAGT
TCTCGGTGCTCTTGCATCCGGACACGCGCTGCTTTATGGAGCAGCCCTGAGTGGGTCAGA
[A,G]
TATCCCAACTGAACGTGGGCGCTGGATTTAAACAGTTGTCATCGGCCCGCCTGTGCCACT
TAGGGACTCCGTATGGCTAAGTGGGGTGTTGGCTGTCAAGAAAATAAATGGGAGAGTAGA
GGGGGCTGTCCTGGGTGTGTTGGTGAGGCGTCGGCTCTCAGGCCCTCTAACTCCTGTTTG
TCCTCATTTTGGAAAGGAGGAAGCTGGGCTGGGAAGCCCAAGGGCTCGAGGCCATAGCTT
ATGACTTAGGAAGACCAGCGGGCATAGCCAGTGGGGCCTTTAGAACCGCTGAGGAAGAGG

4840

GCAACCTTTTATCCAAGCCCGTTTCTTTATTGTTGGTTAAAGAGCAATCTGAGTGTGATT
CACCTAAAATAATACATTTTATAAAATCCTAAGCCTTTTAGATCCTTCACGATTGTGTCT
CTAAGCCACAATCTACAGCAGCTTTGGACTGTTTTCCAAGGCGTGATGGAGAATAGTGAG
GGGTGAGCTTGAGTCTCAGTCTGGAGTTGAAACCCAGTCTGGGTGGGTGTGACCTCTCTT
CATCCTAAACTGTCACTACAGGAACATAAGTTTGCTTTTAAGTGCTCTTTCGCCCTCATT
[C,G]
CGAATTCTCTCAGGCCCCAAACAAGCACCCGCAGGAGTACTGAACTTTTTGGGGGGTGGG
CAGAGGGGATCTGTATGCAGATTGCCAGCTGAGCAATCCTATTTTCTATGACTTAAAGCC
AATCACAGGCTGGGCGTGGTGGCTCATACCTGTAGTCCCAGCACTTTGGGAGGCCGAGGC
AGGCGGATCACTTGTGCTCAGGAGTTCCAGACCAGCCTGGCCAACATGGTGAAACCCTGT
CTCTACTGAGAAAATACAAAAATTAGCCGGGCGTGGTGGCGGGCGCCTGTAATCCCAGCT

4874

GGTTAAAGAGCAATCTGAGTGTGATTCACCTAAAATAATACATTTTATAAAATCCTAAGC
CTTTTAGATCCTTCACGATTGTGTCTCTAAGCCACAATCTACAGCAGCTTTGGACTGTTT
TCCAAGGCGTGATGGAGAATAGTGAGGGGTGAGCTTGAGTCTCAGTCTGGAGTTGAAACC
CAGTCTGGGTGGGTGTGACCTCTCTTCATCCTAAACTGTCACTACAGGAACATAAGTTTG
CTTTTAAGTGCTCTTTCGCCCTCATTCCGAATTCTCTCAGGCCCCAAACAAGCACCCGCA

FIGURE 3LL

[G,A]
GAGTACTGAACTTTTTGGGGGGTGGGCAGAGGGGATCTGTATGCAGATTGCCAGCTGAGC
AATCCTATTTTCTATGACTTAAAGCCAATCACAGGCTGGGCGTGGTGGCTCATACCTGTA
GTCCCAGCACTTTGGGAGGCCGAGGCAGGCGGATCACTTGTGCTCAGGAGTTCCAGACCA
GCCTGGCCAACATGGTGAAACCCTGTCTCTACTGAGAAAATACAAAAATTAGCCGGGCGT
GGTGGCGGGCGCCTGTAATCCCAGCTTCTCAGGAGGCTGAGGCAGAGGAATTGCTTGCAC

5255 AAAGCCAATCACAGGCTGGGCGTGGTGGCTCATACCTGTAGTCCCAGCACTTTGGGAGGC
CGAGGCAGGCGGATCACTTGTGCTCAGGAGTTCCAGACCAGCCTGGCCAACATGGTGAAA
CCCTGTCTCTACTGAGAAAATACAAAAATTAGCCGGGCGTGGTGGCGGGCGCCTGTAATC
CCAGCTTCTCAGGAGGCTGAGGCAGAGGAATTGCTTGCACCCAGGAGGCAGAGGTTGCAG
TAAGCCAAGATCACACCACTGCGCTCCAGCCTGGGCGACAGAGAGAAAAAGAAACTTGTC
[G,A]
GCGTTCTAGATTGACCAGTTTTCCTCAAGGTCAGGTAGTTAGGAAGAAAGAGTGCAGTTT
GCAGTTGTGAAAAGTCTGATAATGGATTCTTTTTTTCTTTTTTATGCGTGAAGGGATTCT
GGAGTACGTCTGGTCTAAAGGCCGATTTCGTTTTAGGAACTTTGGATCAGAACAGTCATA
CTAGTCCTCAGAGAAAAAATGGTTTTCAATCTGGTTCTTCAAATTTCTTGTTCATATAAC
CAAGCCATGCTTGTTCCTATGATGGAGAACAATTGTGCTTTAAAAAAAGAAATTTCAGGG

6268 TCCTTTCTCTATATATCAGATAAAAAATACTTGGGTTTTTTCCCAGAAGTGTCCTTATGG
AATCATTTGGCATCTACAACCCAGTGCTTGCTTGTCATGGGTACCCCAAGTGTTAACCTG
TCAGGAAGGAGGTAATTCAACAGGTAAACCAGTGGCCAGGCCTTGGGTCCACATTTCATT
TTCCTTTTCTCAGCCTAGTTCTGCATTTACTCATCTACAGAGGGAAATAATGACGGAACC
TGTCCTACACGATGACGATGAGGAAGACTCCAAAGTTCCTAGACCCCTATTAAAAATATA
[T,C]
ATTTTTTGAAATACAGACTCACAGGGGATTTCAAAAACAGTACCTGGAGTCTCATGGACC
CTTCAGCCAACTTCCCCATGGTGACGTCTTCATATCCGTGGGACAATATCAGAACCATGT
CATCGATGTTGGTATATCCTTATTAAAGAGAACACATACCTCGTTCAGCTTTTTTTTTTT
TTTTTTTTTGAGACAGGGTCTCACTCTGTTGCCCAGTCTGGAGTGCAGTGGTGCGATCTC
GGCTCACTCCAGCCTTGAACTCCTGGGCTCAAGCAATCCTCCTGCCTTGGCCTCCCAAAG

6438 ACATTTCATTTTCCTTTTCTCAGCCTAGTTCTGCATTTACTCATCTACAGAGGGAAATAA
TGACGGAACCTGTCCTACACGATGACGATGAGGAAGACTCCAAAGTTCCTAGACCCCTAT
TAAAAATATATATTTTTTGAAATACAGACTCACAGGGGATTTCAAAAACAGTACCTGGAG
TCTCATGGACCCTTCAGCCAACTTCCCCATGGTGACGTCTTCATATCCGTGGGACAATAT
CAGAACCATGTCATCGATGTTGGTATATCCTTATTAAAGAGAACACATACCTCGTTCAGC
[-,T]
TTTTTTTTTTTTTTTTTTTTGAGACAGGGTCTCACTCTGTTGCCCAGTCTGGAGTGCAGTG
GTGCGATCTCGGCTCACTCCAGCCTTGAACTCCTGGGCTCAAGCAATCCTCCTGCCTTGG
CCTCCCAAAGTGCTGGGACTATATACAGGCATGAGCCATCGTGCCCGGCTTGTTCAGGCT
TTATTAGTTTTCAAAAGGTGCTCATTTGTGTTTGCGAGTGTGTGTGTAGAGTTCTGTGCA
GTTTTACCCAGTGTGTGGATTTGGCAGCTACCACCCTCCAAACCATGGTGCAGGATGAAT

6457 TCAGCCTAGTTCTGCATTTACTCATCTACAGAGGGAAATAATGACGGAACCTGTCCTACA
CGATGACGATGAGGAAGACTCCAAAGTTCCTAGACCCCTATTAAAAATATATATTTTTTG
AAATACAGACTCACAGGGGATTTCAAAAACAGTACCTGGAGTCTCATGGACCCTTCAGCC
AACTTCCCCATGGTGACGTCTTCATATCCGTGGGACAATATCAGAACCATGTCATCGATG
TTGGTATATCCTTATTAAAGAGAACACATACCTCGTTCAGCTTTTTTTTTTTTTTTTTTT
[-,T]
GAGACAGGGTCTCACTCTGTTGCCCAGTCTGGAGTGCAGTGGTGCGATCTCGGCTCACTC
CAGCCTTGAACTCCTGGGCTCAAGCAATCCTCCTGCCTTGGCCTCCCAAAGTGCTGGGAC
TATATACAGGCATGAGCCATCGTGCCCGGCTTGTTCAGGCTTTATTAGTTTTCAAAAGGT
GCTCATTTGTGTTTGCGAGTGTGTGTGTAGAGTTCTGTGCAGTTTTACCCAGTGTGTGGA
TTTGGCAGCTACCACCCTCCAAACCATGGTGCAGGATGAATTCCCTCACCACAGAACACC

8486 CATCCAAAGAACAGACCCGGCACTTAGTGTGTGCCCAAGACCATCCACCGCATGAATAGA
GAAATCAACCCTCCTCATGTGCCTGGGGTTTCCTGAGGTGGGAAACCTTCAGTGCTAGCT
GGGAGAGTCGCAGGCAGAGACAGGGACAAGCTGGTCACTCTGTGTGTGAATAAATAAATG
AATGGATGATGGCATTATCGGCAGTTGTTCTTTATGACACTCACTGATGCCAAGTACTGG

FIGURE 3MM

ACGGGTACAATATGTACATTAGTTTCTCTATGGGCAGAAGCTCCACCATGACAACATTAG
[T,C]
GTTATTTTCTTTTTGCTTTTTTGTTTAGAGACAGGGTCTTACTCTGTCGCCCAGGCTGGG
GTGCCGTGGTGCAATCAACAGCTCACTGCAGCCTCGACCTCCCAGGCTCAAGCAATCTTC
CCACCTCAGTCTCCCAAGTAGCTGGGACTGCAGACGTGCACCACCACACTCAGCTAATTT
ATGTATTTATTTTTGTAGAGATGGGCATTGCTATGTTGCCCAGGCTGGTCTCGAGCTCCT
GGGCTCAAGTGATCCTCCCGCCTCAGCCTCCCACGTAGCTGGGACTACAGGTGCATCCAC

8534 CGCATGAATAGAGAAATCAACCCTCCTCATGTGCCTGGGGTTTCCTGAGGTGGGAAACCT
TCAGTGCTAGCTGGGAGAGTCGCAGGCAGAGACAGGGACAAGCTGGTCACTCTGTGTGTG
AATAAATAAATGAATGGATGATGGCATTATCGGCAGTTGTTCTTTATGACACTCACTGAT
GCCAAGTACTGGACGGGTACAATATGTACATTAGTTTCTCTATGGGCAGAAGCTCCACCA
TGACAACATTAGTGTTATTTTCTTTTTGCTTTTTTGTTTAGAGACAGGGTCTTACTCTGT
[C,T]
GCCCAGGCTGGGGTGCCGTGGTGCAATCAACAGCTCACTGCAGCCTCGACCTCCCAGGCT
CAAGCAATCTTCCCACCTCAGTCTCCCAAGTAGCTGGGACTGCAGACGTGCACCACCACA
CTCAGCTAATTTATGTATTTATTTTTGTAGAGATGGGCATTGCTATGTTGCCCAGGCTGG
TCTCGAGCTCCTGGGCTCAAGTGATCCTCCCGCCTCAGCCTCCCACGTAGCTGGGACTAC
AGGTGCATCCACCATGCTTGTAGCCTTATTTTCTTAATGGGAAAGAGGGTCTGAGAGAAG

8995 TGCTATGTTGCCCAGGCTGGTCTCGAGCTCCTGGGCTCAAGTGATCCTCCCGCCTCAGCC
TCCCACGTAGCTGGGACTACAGGTGCATCCACCATGCTTGTAGCCTTATTTTCTTAATGG
GAAAGAGGGTCTGAGAGAAGGGATGCTGTGTGCCCAATGGGTTTCGCCTGCAGCACGCTG
CCTCCTCCCCGGGAAAGCAGGGCGTGCACATTGGGATTGGACGACAAAAGCAGAGTCATC
TACAGTTCATGGGCACGCTGCAAAGAAGGGAGACGTTAAACTCTCGAAAGCAGCAGACAC
[C,G]
CCCCACCAGGAAGAGACATACTTGTAAAAATCAAAGGAGGGCGAAGGCATGAGAATCGCT
TGAGCCCAGGAGGTTGAGGTTGCAGTGGGCTGAGATCGTGCTACTGCATTCCAGCCTGGG
TGACAGAGACCTTGTCTCAAAAAATAAAAATTCAAGGGAGGCCAGGTGTGGAGGCTCACG
CCTGTACCCAGCACTTTGGGACTCTGAGGTGGAGGATCACTTGAGCCCAAGAGCTCAAG
ATCTGTCTGGACAATATAGCACTACCCCATCGCTACAAAAAAAAATTTTTTTAAGTAGCT

9623 CAGCTACTAGGGAGGCTGAGGCAGGAGGATTGCTTGAGCCCAGGAGGTGGAGACTGCACT
GAGCCATGATGGTGCCACTGTGTTCCAGCCTGGGCAACAGAGCAAGACCCTATGTCAAAA
ATAAAGAAAGTATCAAGGGAGATGAGTACACAGTGCCTGGCACACTGTAGGGTCTCCAAA
AAGTAAACCTTTTCTATCCATCAGTTTCCTCTTCTCTCCAGCATGAAATCGCATATGTAA
AGTTGAAAAAAAGAGTGAGAGATATATCTTAAAAAGGTAGTAATGTTGATGACATTGTGG
[T,-]
TTTTTTTTTTTTTTTTAAAGAAAAACCGGCCGGGTGCGGTGGCTCATGCCTGTAATCCCAG
CACTTTGGGAGGCTGAGGCAGGCGGGTCATGAAGTGTCAGGAGATCGAGACCATCCTGGC
TAACACGGTGAAACCCCGTCTCTACTAAAAATACAAAAAAAAATTAGCCGGGTGTGGTGG
CGGGCGCCTGTTAGTCCCAGCTGCTGGGGAGGCTGAGGCAGCGGAATGGCATGAACCCGG
GAGGTGGAGCTTGCAGTGAGCCGAGATCACACCACTGCACTCCAGCCTGGGCGACAGAGC

13172 TTGGTTTGGGTGGGATTTGGCCAGCTTCTTTACCGCAACCTGTTTTATCAGCAAGCTCCT
TATGACCGGCATCTTGTGCTGACCTCCTATCTCATCCCGTGACTTAGAATGCCTTAACCA
TCTGGGCATGCAGCCCAACAGGCTTCAGCTTCATTTTACCCAGCTCCTCTTCAAGATGGA
GTTGCTCTGGTTCAGATGCCGCTGACAGAACTAGCTTATGGTTGGAGACAATGTCATAGG
GAATTATTCTTCAAAGATCGCAAAATCCAGCTTGGATGAGATTCCAAAAATCAAAAGGTG
[C,T]
TGAGAAAGCAACTTGTCTAGAATTTCCTCTTCATGGGCTGGTTGATTTTGTTTACAATGA
CACCTTCAGAAAAAGTAGGCGACACACAGTGGCTCACGCCTATAATCCTAGTGCTTTGGG
AGGTCAAGGAGGGAGAATCATTTGAGGCTAGCAGTTCTAGACTAGCCTGGACAACATAGT
GAGACCTTGTCTTTACAAAAAATAAAATCAGCCGTGTGTGGTGGCGCATACCTATAATCC
CAGCTGTTCAGGAGGCTGAGGCAGGAGGATCATTTGAGCCCAGGAGTTGGAGGCTGCAGT

14802 AGGAAAACTGTTAGGAAACTCCATCCCTTTTGACCTTCAAAGGTCACCGCCTAATTTTGG
TGTTTTGTAGTCTGATGTGTTCATAGCTTGTGACTATTAGGCTCTGATTGAGCTCTGCTT
TTTTTTAAGTTTCTCTTACTCAGCTGGTGCTGTTTTAGCTCCAGCTTCCTCCTCTGTGTA

FIGURE 3NN

ATCAACACTCCCAGTCTCCTCTTCACCCAAAAAGCCACAGAAATAAGTGCAGAAAACAAG
GCAGCCGCCACCTGCTACAGAGGCATGTCCTTAAATACGATGCATTTCAGGACAGCTGTG
[C,T]
GAGTTCCGGGAGCTTGTCTTCCTTCAAAGGGAAAAGTAAAAATAAACAGGAAGGTTGCAC
TGAAAGCATTCTCAATTGAAATTGTGCCATTTGGCTGTAGTGTTTCTGATGCTCATTTAG
AACTTTGGAAGTTGTGGGATGGTGGGCAAGTGTGTGACCTGGGATGGAGATTCTCTACCT
CTTTAAGAGTGAAACCCTGGCTGGGCGCCGTGGCTCACTCCTGTCATCCCAGCACTTTGG
GAGGCCAAGGCGGGTGGATCACCTGAGGTCAGGAGTTTGAGACCATCCTGGCCATAATGG

20393 TTTCTGCATCTCCCAGCTCCTGGGGGCTCCAGGCATCCCTGGGCTTGTGGCTGTATCACT
CCAGTCTGCCTCCGTCTCCATGTGGCCTTCTCCTCTGTGTCTGTGTCTCCTCATCTGGCT
CTTTATTTTTTTAAATTATTTATTTATTTATTTATTTTTTATTTTTTTTGGTGACGGAGT
TTCGCTCTTTTGCCCAGGCTGGAGTGCAGTGGCATCATCTCGGCTCACTGTAACCTCTGC
CTCCCGGGTTCAAATGATTCTCCTGCCTCAGCCTCCTCAGTAGCTGGGATTATAGGCACC
[C,T]
GACACCACGCCTGGCTTATTTTTTATGTTTTTAGTGGAGACGGGATTTCACCATGTTGGC
CAGGCTGGTCTCGAACTCCTGTCCTCAGGTGATCCGCCCGCCTTGGCCTCCCAAAGTGCT
GGGATTACAGGTGTGAGCCACCATGCTCACTGGCCATTTTTTATTATTACTCTTTTTTCC
TCTTCTGTCTCTTAGAAGGACACCCGTTGTTGGATTTAGGTCCCACCCTAAATCCAGGAT
GGCCTTATCTGGAGATTGTTTACTTAATAGAAACTACAAAGACCCTATTTTCTTTTCTTT

22234 TCTCTACTAGAAATACAAAAAATTAGCCAGGCGTGGTGGTGGGTGCCTGTAGTCCCAGCT
ACTCAGGAGGCTGAGGCAGGAGAATGGCGTGAACCTGGGAGACGGAGCTTGCAGTGAGCT
GAGATCGCGCCACTGCACTCCAGCCTGGGTGACAGAGCGAGACTCCGTCTCAAAAAAAAA
AAAAAAAAAGTTCAGTTGCTTACTCTCCATAGCCTCAATTCAAATCCTCAGTAGCCACTT
GTGAGCTTGTGGCTACCATTTTGGACAGTGCAGATAGAGAACATTCCTATCATTGCAGGC
[G,A]
ATACTACGGGCAGTGCTTGCTCCAAAACAGGGGGTCTCAACTGGGGGCCGGCCTTCCCCC
ACAGGGCACTTGACAGTGTCTGGGGACAGTTGTGGTTGTCACTACTGGGGGTGGATGCTG
ATGGCGTGTGGTGAGTGGAGCCCAGGGACGCCGCTCTGCAGGTTTGCAGTGCACAGGATG
GCCCTACAGAGAATCATCCAGCCTCAAATGTCGGCAGTGCTAGGCTGAGAGAACCTGCTT
TAGCGTGAGAGTCAGTCTCTCTCTTTCTGTCTCTCTCTCTCTCTCCCCCTCTCTCCCCTC

22253 AAATTAGCCAGGCGTGGTGGTGGGTGCCTGTAGTCCCAGCTACTCAGGAGGCTGAGGCAG
GAGAATGGCGTGAACCTGGGAGACGGAGCTTGCAGTGAGCTGAGATCGCGCCACTGCACT
CCAGCCTGGGTGACAGAGCGAGACTCCGTCTCAAAAAAAAAAAAAAAAAAGTTCAGTTGC
TTACTCTCCATAGCCTCAATTCAAATCCTCAGTAGCCACTTGTGAGCTTGTGGCTACCAT
TTTGGACAGTGCAGATAGAGAACATTCCTATCATTGCAGGCGATACTACGGGCAGTGCTT
[G,T]
CTCCAAAACAGGGGGTCTCAACTGGGGGCCGGCCTTCCCCCACAGGGCACTTGACAGTGT
CTGGGGACAGTTGTGGTTGTCACTACTGGGGGTGGATGCTGATGGCGTGTGGTGAGTGGA
GCCCAGGGACGCCGCTCTGCAGGTTTGCAGTGCACAGGATGGCCCTACAGAGAATCATCC
AGCCTCAAATGTCGGCAGTGCTAGGCTGAGAGAACCTGCTTTAGCGTGAGAGTCAGTCTC
TCTCTTTCTGTCTCTCTCTCTCTCTCCCCCTCTCTCCCCTCCCCACTCTCGCTCTCCCTC

25890 ACCTGTGCAGAATTTGCCCTCTCCTTCCACCCAGGTGCCCATATTAATGTGTCTTGTATA
TTTCTCCAAAGTCCTTTCTCAATATAGAAGCAAATTATCACTTATGGAGAAGAGCCTCAC
TTTTTTTTTTTTTTTTTAAACAGATGGGGGTCCCGCTCTTTTGCCCAGGCTGGAATGCAG
TGGTACTATCATAATTCACTGCAGCCTCCAACTCCCGGGCTCAAGCAATTCTCCCATCTC
TGCCTCATGAGTAGCTGGGACTACTGGAGCATACCACCACACCCGGCTCATTAAAAAAAA
[A,T]
TTTTTTTTTTTATAGATGGTGTCTGGCTATGTTGCCCAGGCTAGTCTCGATCTCCTGGGC
TCAAGTGATCCTTCTGCTTCAGCCTTCTAAAGTGCTGGGATTACAGGCATGAGCCACTGC
TCCTGGCCTCCACCCATCTATAGGTGTGGAACAAGAGCATGTTCCCTCCCAAGCTAATGT
GGCAGGTAACTGGCCTCCCAGGCTGTAGACAAGATGGATGGGGGCTGTGCCCACTTCTTG
AGTTAACCTTTTTTTTTTTCTTTGGAGACAGAGTCTCGCTCTGTCGCCCAGGCTGGAATGC

25891 CCTGTGCAGAATTTGCCCTCTCCTTCCACCCAGGTGCCCATATTAATGTGTCTTGTATAT
TTCTCCAAAGTCCTTTCTCAATATAGAAGCAAATTATCACTTATGGAGAAGAGCCTCACT

FIGURE 3OO

TTTTTTTTTTTTTTTTAAACAGATGGGGGTCCCGCTCTTTTGCCCAGGCTGGAATGCAGT
GGTACTATCATAATTCACTGCAGCCTCCAACTCCCGGGCTCAAGCAATTCTCCCATCTCT
GCCTCATGAGTAGCTGGGACTACTGGAGCATACCACCACACCCGGCTCATTAAAAAAAT
[A,T]
TTTTTTTTTTATAGATGGTGTCTGGCTATGTTGCCCAGGCTAGTCTCGATCTCCTGGGCT
CAAGTGATCCTTCTGCTTCAGCCTTCTAAAGTGCTGGGATTACAGGCATGAGCCACTGCT
CCTGGCCTCCACCCATCTATAGGTGTGGAACAAGAGCATGTTCCCTCCCAAGCTAATGTG
GCAGGTAACTGGCCTCCCAGGCTGTAGACAAGATGGATGGGGGCTGTGCCCACTTCTTGA
GTTAACCTTTTTTTTTTCTTTGGAGACAGAGTCTCGCTCTGTCGCCCAGGCTGGAATGCA

25894 GTGCAGAATTTGCCCTCTCCTTCCACCCAGGTGCCCATATTAATGTGTCTTGTATATTTC
TCCAAAGTCCTTTCTCAATATAGAAGCAAATTATCACTTATGGAGAAGAGCCTCACTTTT
TTTTTTTTTTTTTAAACAGATGGGGGTCCCGCTCTTTTGCCCAGGCTGGAATGCAGTGGT
ACTATCATAATTCACTGCAGCCTCCAACTCCCGGGCTCAAGCAATTCTCCCATCTCTGCC
TCATGAGTAGCTGGGACTACTGGAGCATACCACCACACCCGGCTCATTAAAAAAATTTT
[T,C]
TTTTTTTATAGATGGTGTCTGGCTATGTTGCCCAGGCTAGTCTCGATCTCCTGGGCTCAA
GTGATCCTTCTGCTTCAGCCTTCTAAAGTGCTGGGATTACAGGCATGAGCCACTGCTCCT
GGCCTCCACCCATCTATAGGTGTGGAACAAGAGCATGTTCCCTCCCAAGCTAATGTGGCA
GGTAACTGGCCTCCCAGGCTGTAGACAAGATGGATGGGGGCTGTGCCCACTTCTTGAGTT
AACCTTTTTTTTTTCTTTGGAGACAGAGTCTCGCTCTGTCGCCCAGGCTGGAATGCAGTG

27386 GACTGGCATTTACAGTTTATTAAGGCACTTACCTCTTAGGTGTATAATCCTCAAAACATC
TAAAAAATTAGTGATTTTTGTTATCCAAGTTACTTTGACATCAGCCATTTGCTGTCTCAC
CCACATGATTTCTCATTATGTTACCTTATTATTGGCTAAGTTAATCTGCTTACTGAGGAC
CTGCATGTGACTTTTCCCATTAAAAGTAAGTTAAGTCTGGGCGCAGTGGCTCATGCCTGT
AATTCTAGCACTTTGGGAGGCTGAGGTGGGAGGATCCCTTGACTTTGAGACCAGCCTGGG
[T,C]
GAAAAAGTGAGATCTCAAAAACAAAATTAGCCAGACATGGTGGCGCATGCCTGTAGTACC
AGCTACTTGGGAGGCTGAGGTGGGCTGATGGCTTGAGCCCAGGAGTTTATGCTGCAGTGA
GCCGAGATTGCATCACTGCACTCTAGCCTGTGGCACAGAGTGAGACCTGTCTCTTAAAAA
AAATTAATTAATTAATTAAAAATAAATAAAAGTAAGTCCAAGTGGAGATGGTTGGTGGTG
TTGGTTGGATAACATTGTGAATGTATTTAACACCGTTAATCTGTACACTTCAAAATGGTT

28861 TCTTGCTCTGTCTCCCAGGCTGGAGTGCAGTGGTGCAGTCATGGCACTCATTGCAGCCTC
TACCTCCTGGGCTCAAGAGATCCTCCCTGCTCAGCCTCCTGCGTAACTGGGACCACAGAT
GTGCGCCACCATGCCCAGCTAATTTTTAAATTTTTTGTAGAGACAGGGTTTCACCATGTT
GCCTGGGCTGGTCTTGGACGCCTGGGCTCCAGTGATCCACCTGCCTTGGCCTTCCAAAGT
GCTGGGATTACAGACATGCGCCACCGAGCCTGGTTTTGCTTACTTTTTCTTTTTTTTTTT
[-,T,A]
AATTCCTCTTAGCCTATCTTGGGGGAGGCGGGTCAGTGTTATTCCGGTGTACATACAACA
AAATCACCCATTTGAAGTGCACACTGGGAGGAGTCCTTGCCAAATGGATAGGGCTGGGTA
ACCACTGCCACATGGACATTTGGGAAGCCGATGTTTGAATGTTTTCACGCTTACAGATG
CATTCATTTACTACGTTTATTATTCTGTGTGATGTGCTTTCTGTGTGTTATTTCACTTAA
ACCCAGTGGGGGTAAAGATTATGATCCCTATTTGGTAGATGAATTTTAGAGAGGTTAGGG

30916 ACTGTGCCTGGCCAACTACCTTGTTTTTTTTTGGATGAAAATGTGGTTCTTACCTCAGTAA
AGATTATGAAGGGATTTATGTACAGATGACTAAAATATCAGCCATTAGTTTCCTATTTGT
TTTTGTTGTTGTCATTTTTTTGTTTTGAGACAGGGTCTTGCTCTGTTGCCCAGGCTGGAGT
GCAGTGATGCGATCTTAGCTCACTGCAGCCTCGACCTCCCAGGCTCAGGCAATCCTCCCA
CCTCAGCCTCCCAAGTAGTTGGGACGACGGCTGTGCACCACCACACCTGGGTAATTTTTT
[G,A]
TTTTTATTTTTGTAGCTGGGATCTCGCTATGTTGCCCAGGCAGGTCTTGAACTCCCGGCC
TCAAGTGATCCCACCATCTAGGCCTCCCAAAGTGCTGGACTTACAAGCGTGAGCCACCCT
GCCCAGCCTAGTTTACAATTTGAACTTGGTTTTTCATCTCGGCTCCTTTGAAGACTTCTG
TCTTCTCCCATGTTTGGGGCAGCTGTGTGTTGTGGACATTCCTTAGTGATCGGCCTGGGA
AGGCTCAGACATGTCTAGGCTGCCTTTGTAGGAATAGGGATTAGTAGCTCCTTAGCCCCA

30959 GGTTCTTACCTCAGTAAAGATTATGAAGGGATTTATGTACAGATGACTAAAATATCAGCC

FIGURE 3PP

ATTAGTTTCCTATTTGTTTTTGTTGTTGTCATTTTTTGTTTTGAGACAGGGTCTTGCTCT
GTTGCCCAGGCTGGAGTGCAGTGATGCGATCTTAGCTCACTGCAGCCTCGACCTCCCAGG
CTCAGGCAATCCTCCCACCTCAGCCTCCCAAGTAGTTGGGACGACGGCTGTGCACCACCA
CACCTGGGTAATTTTTTATTTTTATTTTTGTAGCTGGGATCTCGCTATGTTGCCCAGGCA
[A,G]
GTCTTGAACTCCCGGCCTCAAGTGATCCCACCATCTAGGCCTCCCAAAGTGCTGGACTTA
CAAGCGTGAGCCACCCTGCCCAGCCTAGTTTACAATTTGAACTTGGTTTTTCATCTCGGC
TCCTTTGAAGACTTCTGTCTTCTCCCATGTTTGGGGCAGCTGTGTGTTGTGGACATTCCT
TAGTGATCGGCCTGGGAAGGCTCAGACATGTCTAGGCTGCCTTTGTAGGAATAGGGATTA
GTAGCTCCTTAGCCCCACTCTTTCCTGGGATGTTGCTGTTTGCTGAGGTCTGCACAGTTC

34435
CCAGACAGAAAGCTGGGATGTGGCCAGGTGCAGTGGCTCATGCCTGTACTCCTAGCACTT
TGGGAGGCCGAGGTGGGTGGATCACTTGAGGTCAGGAGTTTGAGACCAGCCTGGCCAACA
TGGTGAAACCCTGTCACTACTAAAAATACAAAAATTAGCCAGGCGGGGTGGCGGGCACCG
GTAATCCCAGCTACTTTGGAGGCTGAGGCAGGAGAATCGCTTGAACCCAGGAGGCAGAGG
TTGCAGTGAACTGAGATTGCGCCATTGCACTCCAGCCTGGGCGACAGAGTGAGACTCTGT
[-,A]
ACAACAACAACAACAACAACAACAACAACAACAGGCCAGGATGTGTTTGTGTGTGAGTTG
GACCCAAGGGCTTGGGAAGGATGGATAGGGTAGGGGAGGAGGGATAGATGGATGAGGGAA
TGCAGAGAGAGTGGCCACACTGTCAGAGGCTTTCAAAAAGCAGGAGGTTCTCCAGTGGGA
GAGAGGAGACCTGAGTCCACCCCGCATTAATGTTTACAGATCAGAATTGCACACATAGAA
TGGCTCATAAATCTGATCCACCTTCCTCGTCTGGCACTTGGCTGGAGAAACAACTCTTTG

36813
AGTGGCCATAGTCAAACACCTAAACTGTATCAGTTCACAGTCCTCAAAGCCCTTCTCCCA
CTTCCTGTCTTTGACCTGATTCCACCTAATTTTGTCCACACCATGTTGTACTGTAATAAA
ACCTATTTTATTTCCAAATTAACTAAGAGAATATACTTTAAAAATGTGTTACTATTTCAT
TATTTGTTTACTTTTTTTAAAGAAATATTTAACACCTGTCAGCTATTGACATTGTTTCCT
TCTTACACTTTTTCTTTATCTTGTAGTTCACTTTCTATTTCTGCCATAATAAAATATTCA
[G,T]
TATCGGAAACTTCACTTAAAAAGCAAAGGTTACTTCTCCTCCTCCCTTCCCAGTCTGCCC
TATAAGCTAGTAAATTCATCATTCATTAGCTTAGATATTTTACAACATGGGGATTTTAGT
TTACAGCAAATACTCTAAGTAAAATTGGTAGCTTAAGTACAACTTTTTCTTTTCACGTTA
CCATGTGCAATCAATGGCATTCCAGACTCTTGGAAGGAAATCCATTGTATGGTTGTGGTC
TTTTTTTTTCCTTCTCAAACCAGTCAAAAATACCCAGTCACAATTTAAAAAATTATCCGC

37063
TTTCTTTATCTTGTAGTTCACTTTCTATTTCTGCCATAATAAAATATTCAGTATCGGAAA
CTTCACTTAAAAAGCAAAGGTTACTTCTCCTCCTCCCTTCCCAGTCTGCCCTATAAGCTA
GTAAATTCATCATTCATTAGCTTAGATATTTTACAACATGGGGATTTTAGTTTACAGCAA
ATACTCTAAGTAAAATTGGTAGCTTAAGTACAACTTTTTCTTTTCACGTTACCATGTGCA
ATCAATGGCATTCCAGACTCTTGGAAGGAAATCCATTGTATGGTTGTGGTCTTTTTTTTT
[C,T]
CTTCTCAAACCAGTCAAAAATACCCAGTCACAATTTAAAAAATTATCCGCCCTTGGTGGT
GCACGCCTGTAGTCCCAACTATTTGGGCTGAGGTGGGAGGGTCACTTGAGCCTGGCAGGT
CAAGGCTGCAGTGAGCTATTGATTGTGCCATTGCACTTCAGCCTGGGCAACAGAGAGAGA
CCCTGTCTCAAAAAAAAAAAAAAAAAAAAGACAAAACAATATAATGTGATCTACCCTCTAA
GCAAATTTTCATATATACAATTTTACTATTGTATATGTGAGCTATTTATATATAAAATTT

37569
AAAGACAAAACAATATAATGTGATCTACCCTCTAAGCAAATTTTCATATATACAATTTTA
CTATTGTATATGTGAGCTATTTATATATAAAATTTCATTTATCAGTTCAGTATTGTTAAC
TATATGAACTAGGTGTATGGTAGATCTCCATGGTTTATCTTGTTCAACTAAAACTTTGTA
TCCTTTGACCAATATATTTCCCCTTCCCCCTCAAGCCCTACCCTCTGATAACTACCTCTC
TACTCTCTGCTTCTATGAGTTTGACTATTGTAGATTCTGCATTAGTCCATTCTCATGCTG
[C,T]
TAATGAAGACATACCTGAGACTGGTTAATTTATAAAGGAAAGAGGTTTAATGGACTCACA
GTTCCACATGGCTGCGGAGGTTCCGACAGTCATGGCAGAAGGTAAAAGGAGGAGCAAAGT
CACGTCTTACATGACAGCAGGCAAGAAGAGAGCCCGAGCAGGGAAACTCCCATTTATTAA
AACATCTGATCTCGTGAGACTTATTCACTATCAGGAGGACAGCATGGGAAAACCCACCCC
CATGATTCAGTTACCTCCCACCTGGTCTCTCCCACAACACGTGGGGATTATGGGAGCCAC

FIGURE 3QQ

37905 AGGAAAGAGGTTTAATGGACTCACAGTTCCACATGGCTGCGGAGGTTCCGACAGTCATGG
CAGAAGGTAAAAGGAGGAGCAAAGTCACGTCTTACATGACAGCAGGCAAGAAGAGAGCCC
GAGCAGGGAAACTCCCATTTATTAAAACATCTGATCTCGTGAGACTTATTCACTATCAGG
AGGACAGCATGGGAAAACCCACCCCCATGATTCAGTTACCTCCCACCTGGTCTCTCCCAC
AACACGTGGGGATTATGGGAGCCACACTTCAAGATTAGACTTGGGTGGGGACACAGCCAA
[A,G]
CCATGTCAGATTCCTTGTATAAGTGAGATCATGCAATATTTAATATTTGTTTTTCTGTGC
CTATCTTATTTCACTGAACATAATGGCCTCCAGTTCCATCCATGTTGCTGCAAATGCCAG
AGTTTCCTTCTTTTTTAGGGCTGAATGGTATTCCATCGTGTATATGTACCATGTTTTCTT
TATCCATTTGCCCTTGGACGGACACTGAGGTTGTTTCCACGCCTTGGCTGTTGTGAATAG
TGCTGTCATAAACATGGGAGTGCAGGTGTCTGGAAGATCCTGGTTCTCTTGGGTTTTGCA

41617 TCTCCCAGGCCACCCTTCTTTGACAGGCCTCCTTCTTTGCTCTCATCATTGTCCTTCACT
TCCCCCATCTAAGAAACACCTACCTGTTTTCCCTCATTCACCTGCTGTCCCCGGGACACA
GGGTGCCTCCCATCATGTTCTTGAAGCACCTCGTGTGTACTGGAACAAGTGCACCTGCCT
TCTCCTCTAGACCCAATGCTGCCTAAGCTCCGAACAAAATCATATGCAGAGGATGGGCGC
GGTGGCTCCCTTCCTCCCTTCCTTTCTTCCTTTCTGCATTTCTCTTTCTTTCTTGACAGG
[T,G]
TCTCACTCCTTCTTGCCCAGGCTGGAATTCAGTGGCACAATCATGGCCCACTGCAGCCTC
TGCCGCCTCCCAACTAGTTGAGACTACAGGTATATGCCACCATGCCTGACCAACTTTTAA
AAGTTTTTGTAGGATGAAGTCTTGCTGTGTTGCCCAGGCTGGTCTCAAACTCCTGGCCTG
AAGCAGTCCTCCAGCCTCAGCCTCCCAAAGTGCTGGGATTGCAGGTGTCAGCCCCTGCAC
CTGGACTGAGAATGCATGTCTGTTGTCTGCCGCGTCCCTCCACCCCAACCCCCAGTTTGT

42444 AGAACAGAGCTTTAGTTAGGTAGTTCTCCTTTCTTCAAGGCAGGATAGCTCAAGACTGTT
TTCCTTGGCAGATAAGGTGCATTCCTGCAGGGACGTGGATTCTGATTTTGATATTCCCTG
CTTTCAATTAAGGAACAAAGTCGTTTATATTTCTTAAGTCTTATATAAAGCCCTAGAGAC
TTTAGAAATTCTATTCAAAGTTACCTATGTTGGTTTATTTTTATCTTTTATATAAAAAAG
TATATATATAGATTTACATTTAGAGACGGGTTTTGCTCTGTGGCCCATCTTGGAGTGCAA
[C,T]
GGTGCAATCACAGCTCACTGCGGCCCCAACCTCCCGGGCTTAAGCCATCCTCCTTCCTCA
GCCTCCAGAGTAGCCGGGACTACAGGCACCCATCACTACACCCTGCTAATGTTTTTATTT
ATTTTTAATTTTTAAAAAACATATGTATATATTTTTCACAACCTCTTTGGTGAAGATAAT
GTTTTTGTTTTTTCTCTATGAACAGGGTCTTGCTATGTTGCCCAGGCTGGTCTTGAACTT
TAGGCTGCAAGCAATCCACTTGCCTTGGCCTCCTGACATGCTGGGATTACAGGTGTGCAC

46230 ACTTGGAAGGCAAGAGGTCTCTCCACTCCGGGCCACATCCTTCTAGTTCCTGGATGACCG
CTCGTTTCTCCATGGAGAGGAGTTCATGCCAGAACCTCTTCTTCGGGGAGAGTGGATGCA
TCTCTTGGAAACATCTTTTTTTTAAAGTCTGCAGACTTGAGTGTGGTCCCCATTGTCATTG
GTACTTGTTGGGGGTAGGAGTAAAATCATTCCTTTGTTTTACTGAGAGTTCAGGAAGAAA
GAACACCATGTTCTCTCCTTTTATTTATTTATTTATTTTGCTCTCTATTTGAATTTTAAA
[G,A]
GCAAAAATCTAGAAATAGCGCTTCTTGCTCTGTCATCACTGCCTGCAAAGCACAGAGACC
AGAGTGAAGGCAGGCAGCTCCTGGGTCTTCTCTTCCTCTTCTTTGTCCAAAAAATGATAC
ATTGCATGTTTAGTATTTGGGGCAAAGCAGACGCTTCAAAAAGGGAGGCTTATTTTATTA
TCTATATTTTTCTTTTTTATTATTTTTTACCTTGATTCCCTTTTTCTATGTATGAAAAGG
GAGGTTTAAGTTCTTGCAAGAGAATGCAACTGTAGTGTCTTCTGAATGGAGTTTTCCATT

48604 CCTCAGCTACTTGGGAGGCTGAGGCAGGAGAACGGCATGAACCTGGGAGGCAGAGTTTGC
AGTGAGCCAAGATCGCACCACTGCACTCCAGCCTGAGTAACAGAGCGAGACTCTGTCTCA
AAAAAAAAAAAAAAAAAATGTACAGTTCACTACTCGGGAGGCTGAGGCAGGAGGATCAC
TTCAACCCAGGAGGCGGAGATTGCAGTGAGCTGAGATTGTGTCGCTGCACTCTATCCTGG
GCAACAGAGTAAGACTCTGTCTCAAAAAAAAAAAACAGAAAACAAAAAAAACAAAACACT
[T,A,G]
TTTAGTGGCATGGAGCACATTCATGTTTCTGTGCAACCGCCACCCCATCCCCATCCCCAT
CCCCATCCATCTCCAGAACTCCTTTTCATCTTCCCCAACTGAAACTCTGTCCTCATGAAA
CACGCCTTATTGCCCCTCCCTCCAGCCCTGCCCTGGCAACCTCCCTCGTACTCTCTGCTC
TATGAATTTGGTGATTCTAGGAGCCTTATATAGGCAGAATCATACGGCATTTGTCCTTTT
GCGACTGGCTTCTTTCAGTTACTGTAATGTCCTTCAGATTCCCCCGTCCTGTAGAAAGGA

FIGURE 3RR

48867
AAAAAAAAAAAACAGAAAACAAAAAAAACAAAACACTGTTTAGTGGCATGGAGCACATTC
ATGTTTCTGTGCAACCGCCACCCCATCCCCATCCCCATCCCCATCCATCTCCAGAACTCC
TTTTCATCTTCCCCAACTGAAACTCTGTCCTCATGAAACACGCCTTATTGCCCCTCCCTC
CAGCCCTGCCCTGGCAACCTCCCTCGTACTCTCTGCTCTATGAATTTGGTGATTCTAGGA
GCCTTATATAGGCAGAATCATACGGCATTTGTCCTTTTGCGACTGGCTTCTTTCAGTTAC
[T,C]
GTAATGTCCTTCAGATTCCCCGTCCTGTAGAAAGGAATTTCCCTCCTTTCTAAGCCTGA
GTACTATTCCATCGTATAGAGGATACAGCATGTTGTGTTTACCCATTCATTCATCCTTGG
ACACTGGGGTGCCTTCCACCTCTTGGCTGTAGTGAATAATGCTGCTATGAACAAGGTTTG
GCAAATATCTGTCCAGTGCCTGATTTCAGCTGCTTGAATACATTGTTTTAATTTATTATT
ATTATTTTTTAGAGATGGAGTCTCGCTCTGTCACCCCAGCTGGAGTGCAGTGTTGTGATC

51123
TTTGCACTTCCCCATTTCATAGGTGGTCCTTCCAGCTCTTGGGGCTCACCCAGGAACCAT
TTTTTATTCCTTTTCTTTGACTCTGCATTCACTGTAATCCTGAGTCCTGCCCTTTTAACT
TTTTTTTTTTTTTTTTTTTTTTAAGAGATGTGGTCTTGCCGTCTCATCCAGGCTGGAGTGC
AGTGGTGCAATCATGGCTCACTGCATCCTTGACCTCCTGGGCTCAAGAGATCCTCCCACC
TCAGCCTCCCAAGTAGCTGGGACCACAAGTGCACACCACTATGTCCAGCTAATTGAATTT
[T,G]
TGTGTGTGTGTGTGTGTGTGTGTGTGTGTGTGTGTGTGTGTGTGTGTAGGGACAAGATCTCA
CTGTGTTGCTCAGGCTGGTCTCAAACTCATAATTTCAAGCATTTCCCCTGCCTCAGCCTC
CTAAGTAGCTAGGATTATAGGTGCACACCGCCATGCCTTGCCCCTTTCCAATTCTCAAAC
ACATCTCCAGAGCCCATCCACATCAATGATGTCTTCACAGAAGCTGCCATAGCTTATCTA
AATTCCCTCCCCTTCTCTCCACTGATCTCTGATCTCTGCTGAACTCACCCCTTCCTGCTG

51212
CACTGTAATCCTGAGTCCTGCCCTTTTAACTTTTTTTTTTTTTTTTTTTTTTTTAAGAGATG
TGGTCTTGCCGTCTCATCCAGGCTGGAGTGCAGTGGTGCAATCATGGCTCACTGCATCCT
TGACCTCCTGGGCTCAAGAGATCCTCCCACCTCAGCCTCCCAAGTAGCTGGGACCACAAG
TGCACACCACTATGTCCAGCTAATTGAATTTTTTGTGTGTGTGTGTGTGTGTGTGTGTGTG
TGTGTGTGTGTGTGTGTAGGGACAAGATCTCACTGTGTTGCTCAGGCTGGTCTCAAACTC
[A,G]
TAATTTCAAGCATTTCCCCTGCCTCAGCCTCCTAAGTAGCTAGGATTATAGGTGCACACC
GCCATGCCTTGCCCCTTTCCAATTCTCAAACACATCTCCAGAGCCCATCCACATCAATGA
TGTCTTCACAGAAGCTGCCATAGCTTATCTAAATTCCCTCCCCTTCTCTCCACTGATCTC
TGATCTCTGCTGAACTCACCCCTTCCTGCTGTATCAGCCCAAACGTTTCTGATGTGAAAA
TAGGCAGGGCGTAGTGGCTCATGCCTATAATCTCAGCACTGTCAGAGGCTGAGGTGAGAG

52308
AGTAGCTGGGACTACAGGCGCCCGCCACCACATCCAGCTAATACTTTGTATTTTTAGTAG
AGATGGGGTTTCACCATGTTAGCCAGGATGGTCTCGATCTCCTGACCTCGTGATCCACCT
ACCTTGGCCTCCCAAAGTGCTGGGATTACAGGCATGAGCCACTGCGCCTGGCCCTAATTT
TTAATTTTTTGTAGAGACGTGATCTTGCTTTGTTGCCTAGGCTGGTTTTGAGCTCCTGGG
CTCAAGCGATCTGCCACCTTGGCCCCGCAAAGTGCCGGAATTACAGACGTGAGCCACCGC
[C,T,A]
CCTGGCCTCCAGCTCTTTTGTGTCCCTCCCCAATCTTCCTTTGGCCTTCAGCTGTGGGGA
CAGAGATGCCCCCTGCCTCCCTGTCCCCACCTTCTACCTGGTCTTACAGGACCCCCTCCA
GCCATCCTTCCAAGTTTACTATGTAATGTCTGTTCCACATCAAGCCTGCAAAGCTCATGA
CAGTCACAAGATCTGCCGTTCCTGATACTATGTACCGAGAACATTACTTGGCACATAAGG
GGCCCTTGTCCAAAACATTTGGAAACCAATAAAGAATGTGGCTGGTGAGTTACTGATTAA

52333
CACCACATCCAGCTAATACTTTGTATTTTTAGTAGAGATGGGGTTTCACCATGTTAGCCA
GGATGGTCTCGATCTCCTGACCTCGTGATCCACCTACCTTGGCCTCCCAAAGTGCTGGGA
TTACAGGCATGAGCCACTGCGCCTGGCCCTAATTTTTAATTTTTTGTAGAGACGTGATCT
TGCTTTGTTGCCTAGGCTGGTTTTGAGCTCCTGGGCTCAAGCGATCTGCCACCTTGGCCC
CGCAAAGTGCCGGAATTACAGACGTGAGCCACCGCACCTGGCCTCCAGCTCTTTTGTGTC
[C,T]
CTCCCCAATCTTCCTTTGGCCTTCAGCTGTGGGGACAGAGATGCCCCCTGCCTCCCTGTC
CCCACCTTCTACCTGGTCTTACAGGACCCCCTCCAGCCATCCTTCCAAGTTTACTATGTA
ATGTCTGTTCCACATCAAGCCTGCAAAGCTCATGACAGTCACAAGATCTGCCGTTCCTGA
TACTATGTACCGAGAACATTACTTGGCACATAAGGGGCCCTTGTCCAAAACATTTGGAAA

FIGURE 3SS

```
          CCAATAAAGAATGTGGCTGGTGAGTTACTGATTAATGTGTTGATGAATTCATTGATTGCT

53079     GATGCATTGGTTTCTAATTTTCTAAGCTCAGATTTGAAATCACCTGTGGTCACTAAACTC
          GTCCTATCCCACAGCCCCTGCACATGATGACTTAAGTTTTGTGAATGTTTTTTGGAGATA
          GTAAAGTCAGTATCTCTTTCAACATTTTGTTCCTTATCTTTAGTGATACCCAGCTCTGTA
          CAAATTCTGTCCACGTAAGCAAAGTCTTTTTTTTTTTTTCCAGATAGGGTCTGGCTCTGT
          CACTGAGGCTGGAGTGCAGAGGTTCAGTCATAGCTTCAACTCCTGGGCTCAGGCTGTCCT
          [G,C]
          CTGCCTCAGCCTCTTAAGTACCTGGGACTACAGGCCTGCACAACCACACCTAGCTAATCT
          TTTTATTTTTTGCAGAGACAGAGTCTCCCTATTTTGCCCAGGCTAGTCTCAAACTCTTGG
          TCTCAAGTGATCCTCCTGCCTCAGTTTCCCAAAGTGCTGGGATTACAGGTGTGAGCCACC
          ACACTCGCCTGCAAAGTCTTACTGATAAAAGATTTGAAGGAAGGATGTGTCAGAGAACTT
          CTTTTTTCTTATAATATTTACTTAATCTTATTGGTTTGGGGAAGGGCAAGAGAATCCCAG

62141     TTCCCATATAGTCACATTCTGAAGTTCTGGGGGTTAGGACTGCAGCATATAAGGTTTAAG
          GGATACATTTCAGCCTGGAACAAGTATATATAGATATGTTTCCGTACACACACATACTCC
          ATTGAGGAGAAAACAGTTATCCTTTTTTGTTTGTTTTTTTGTTTTTTTTTTGGGACGAAGT
          CTCGCTCTGTCGTCCAGGCTGGAGTGCAGTGGCACAATCTCGGCTCACTGCAACCTCCGC
          CTCCCAGATTCAAGTGATTCTCCTGCCTCAGCCTCCCAAGTAGCTGGGATTACAGGTGCC
          [T,C]
          GCCACCAGGCCTAGCTAACTTTTTTTTTTTTTTTTGAGATGGAGTCTGGCTCTGTCGCCC
          AGGCTGGAGTATAGTGGCATGATCTCAGCTCACTGCAAGCTCTGCCTCCCGAGTTCACGC
          CATTCTCCTGCCTCAGCCCCCCAAGTAGCTGGGACTACGGGCGCCCGCCACCACGCCCGG
          CTAATTTTTTGTATTTTTAGTAGAGACGGGATTTCACTGTGTTAGCCAGGATGGTCTCAA
          TCTCCTGACCTTGTGATGCGCCCACCTTGGCATCCCAAAGTGCTAGGATTACAGGTGTGA

70339     TTCCATACTTAGCTCTAACCTGCAGATAGAGAGTAAGTCCCTTCCACATGCTTCCATGGG
          AGGAGAACTCAATTTCTCTCCTTGTCTTCTTTCCTGGTTTCCTGATTTATATCTGCTACA
          TCCTGCAGTAATTTTTTTTTTTTTTTTTTTTTTTTGAGACAGTGTCTTGCTCTGTTGCTC
          AGGCTGGAGTACAGTGACACTATCATGCTCCCTGCAGTGTTGACCTCCTGGGCTCAAGTG
          ATCCTTCCATCTCAGCCTCCCGACTAGCTGAGACTACAAGTGCACTTCAGCACACCTGGC
          [-,T]
          TTTTTTTTTTTTTTTTTTTTGTAAAGGAGTGGTCTTGCTGTGTTGTCCAAGCTGGTCTGA
          AACTCCTAGCCTAAAGCAATCCTCCTGCCTCAACCTCCCAAAGTACTAGGATTACAGGTG
          TGAACTACCATGCCTGACCTTGTGGTACTTTTATTTCATGGATGGCCGACAGAATTTGAA
          ATTTGGATGGCAGCCAGTTTGTTGTTATCCCAAGGGCTTACAGATTAGTGTGGAAAAGTC
          TGTTGTCTGGAAAGAGATGGGGTATGGAGGTGTGGTGGGGAAGGGAAGGAAAGATAACAG

70379     CTTCCACATGCTTCCATGGGAGGAGAACTCAATTTCTCTCCTTGTCTTCTTTCCTGGTTT
          CCTGATTTATATCTGCTACATCCTGCAGTAATTTTTTTTTTTTTTTTTTTTTTTTGAGAC
          AGTGTCTTGCTCTGTTGCTCAGGCTGGAGTACAGTGACACTATCATGCTCCCTGCAGTGT
          TGACCTCCTGGGCTCAAGTGATCCTTCCATCTCAGCCTCCCGACTAGCTGAGACTACAAG
          TGCACTTCAGCACACCTGGCTTTTTTTTTTTTTTTTTTTTGTAAAGGAGTGGTCTTGCT
          [A,G]
          TGTTGTCCAAGCTGGTCTGAAACTCCTAGCCTAAAGCAATCCTCCTGCCTCAACCTCCCA
          AAGTACTAGGATTACAGGTGTGAACTACCATGCCTGACCTTGTGGTACTTTTATTTCATG
          GATGGCCGACAGAATTTGAAATTTGGATGGCAGCCAGTTTGTTGTTATCCCAAGGGCTTA
          CAGATTAGTGTGGAAAAGTCTGTTGTCTGGAAAGAGATGGGGTATGGAGGTGTGGTGGGG
          AAGGGAAGGAAAGATAACAGTAACAACATTTTGGGTGGGTTCCTGCAAGCAGGAAGCTGA

76074     ACCTCCCTACCTATCCATCTATCAATCATCTATCTACCTATTCATCTATCTGCTTTTCTA
          TATATCTATGTATTTATCAATCATCTACTTACCTACCTATCCCTCTATCTCTACCTTTCT
          GTCTATCTAGCTATCAATAATCTACCTACCTACCGGCCTGTTGGTCTTTTGAATTTTCCA
          TTACTCTTTGCTGAGACATGCCTACAAGTCATATAGAACCAAACTTCTCAATATGCACCC
          TAGCCCATTATGTCCTAGGCAAACCCAAAAGGTTAAAAATAACTTAGGCATATTGATCAG
          [C,T]
          GTCCACCCAAGGAAAAGCACCACATTTTCCTTCGGTGATAACACTGACCACACGAGGGCA
          GCATTGCCTGAGGATCGTTGTATCCTGTAGTCTAATGGTTTTAAATAGAGTGAGGTTCGT
          GTGCCCCAAATTTTATTGATTCTAGGATAGAGTAGACTATTATTAGAATACAATATACTA
```

FIGURE 3TT

TTAGGACATAATATTGTTAGAATACAACATAGAATTATTAGACTATAATTAAAACAGAAT
ATTAGTCTCAGGGTACGCTGAAGTTAAAAATACATAAAAATACATTTAAAAAGAATAGAA

77336

GGTGTCTTGAGAGTTACCAGCTTCGCCGACCCCAACTCTCCCAGGCATTCCTGTGCTCTT
CCCCAGCTCCAGCCGGCCTGAGCTCGCCTGGACCACCCCAAGCCTTCTCAGTCTCCTGCA
TCCCCTCCTGCCTGCAGTACATTTTCCTGGAAGCAGCTGCAGGCATCCTGTCCACGTACC
CATCAGCTGTGTCCCTATTCCCTGGGAGCCCGCTTGTTGCTTCCCGGATGACTGGAGCAG
AATCGGAGGCTCGTTATCATATGAGGTTCTGAGACGGTCTGCCTGTGGGTTGTCCACCCC
[C,T]
CTTAGACAACAGCCTGGCCCCTCCTTGTCTTCCCACTGCTTTTTAAACGTGCCAGGAAGC
CTGACCTGTCCCCCTGCCCAAAGGCTGGCTTCCTTCCTCCTTCTTTTCTTTTTCCCTTTC
CTTTCCTTCCCTTTCCTTTCCTCCCTCCCTCCCTCTCTCCTTCCTTCCTCTCTCCCTCCC
TCTCTCTCTCTCTCTCCTTCCTCCCTTCCCTTTCCCTTCCCTTCTTCCTTTCCTTTTCCT
TTCCCGTCTCCCTCTTCCTTTCCCCTTTCCCTTTTCCCCTTTCCCCTTTTTCCTTTCCTT

77582

AGGCTCGTTATCATATGAGGTTCTGAGACGGTCTGCCTGTGGGTTGTCCACCCCTCTTAG
ACAACAGCCTGGCCCCTCCTTGTCTTCCCACTGCTTTTTAAACGTGCCAGGAAGCCTGAC
CTGTCCCCCTGCCCAAAGGCTGGCTTCCTTCCTCCTTCTTTTCTTTTTCCCTTTCCTTTC
CTTCCCTTTCCTTTCCTCCCTCCCTCCCTCTCTCCTTCCTTCCTCTCTCCCTCCCTCTCT
CTCTCTCTCTCCTTCCTCCCTTCCCTTTCCCTTCCCTTCTTCCTTTCCTTTTCCTTTCCC
[G,C]
TCTCCCTCTTCCTTTCCCCTTTCCCTTTTCCCCTTTCCCCTTTTTCCTTTCCTTTCCTTT
CATTTCCTTTCCTTCTTCCTTTCCTTTCTGTTCCGCCTCGCTCTGTCACCCAGGCTGGAG
TGCAGTGGCACAATCTTGGCTCACTGTAACCTCTGCTTTCTTGTCTCGCTCTGTCACCCA
GGCTGGACTGCAGTGGCGCAAATCTTGGTTCACTGCAACCTCTGCTTCCCAGGTTCAAGC
AATTCTCCTTCCTCAGCCTCCTGAGTAGCTGGGATTACAGGTGTGCGCCACCACGCCCAG

78010

GCACAATCTTGGCTCACTGTAACCTCTGCTTTCTTGTCTCGCTCTGTCACCCAGGCTGGA
CTGCAGTGGCGCAAATCTTGGTTCACTGCAACCTCTGCTTCCCAGGTTCAAGCAATTCTC
CTTCCTCAGCCTCCTGAGTAGCTGGGATTACAGGTGTGCGCCACCACGCCCAGCTAATTT
TTGTATTTTTAGTAGAGAGGGGGTTTCACCATATTGGCCAGGCTGGCCTCAAACTCCTGA
CCTCAAGTGATCCACCTGCTTCGGCCTCCCAAAGTGCTGGGGTTACAGGCGTGAGCCACC
[C,T,A]
CACCCAGCCAGGGCTGGCCCTTTCTCTTCCACTGCACATGCTGCAGGCTCACCTGTCACC
TGCTCCCACAGCCCTCTGGGGCCTCCCCTGTTCTCCTGGGCCATGCCCTGTCCGACCAGC
CCATCTGTTTTCTTTATACTGATTAGCAGCTCTGAAACCATCTAAATTTTGTATGTGTTG
ACTGCCTCTGAGAGCAATGCTCCCAAGCTGCTCTCCTCACCTCCTTGAACCCAGAAACTT
CTGGTGGCTGGAGGGAGGGCACTGCTGCACATACAAGTGGAGCCGGCCTGCAGTCAGAGT

78011

CACAATCTTGGCTCACTGTAACCTCTGCTTTCTTGTCTCGCTCTGTCACCCAGGCTGGAC
TGCAGTGGCGCAAATCTTGGTTCACTGCAACCTCTGCTTCCCAGGTTCAAGCAATTCTCC
TTCCTCAGCCTCCTGAGTAGCTGGGATTACAGGTGTGCGCCACCACGCCCAGCTAATTTT
TGTATTTTTAGTAGAGAGGGGGTTTCACCATATTGGCCAGGCTGGCCTCAAACTCCTGAC
CTCAAGTGATCCACCTGCTTCGGCCTCCCAAAGTGCTGGGGTTACAGGCGTGAGCCACCA
[A,G,C]
ACCCAGCCAGGGCTGGCCCTTTCTCTTCCACTGCACATGCTGCAGGCTCACCTGTCACCT
GCTCCCACAGCCCTCTGGGGCCTCCCCTGTTCTCCTGGGCCATGCCCTGTCCGACCAGCC
CATCTGTTTTCTTTATACTGATTAGCAGCTCTGAAACCATCTAAATTTTGTATGTGTTGA
CTGCCTCTGAGAGCAATGCTCCCAAGCTGCTCTCCTCACCTCCTTGAACCCAGAAACTTC
TGGTGGCTGGAGGGAGGGCACTGCTGCACATACAAGTGGAGCCGGCCTGCAGTCAGAGTC

79557

GACAGGGTGCAGAAGATCCTAGAGAAGGTGGAATTTGGCTGCAGTGGAGCCTCTTCCACG
GGGAGCATTAGGCATTGCGCAGTGGTTCTCAAACATGTTGGCCTCGGGAACCCTTCAACA
CACAGCTCAAAGTTATTAACAACCCACAGAACTTTCATTTCTGTGTGTTACAGCTGTCCG
CGCTGACTACATTTGAAATTAAAGTAGAGACTGAAATATAAACCAACAGAATACATAAAT
AATATATATGAGAAGTTAAATAATCAGAGGAGAACATAAATAGCATTTTTAAATGAAAAA
[G,A]
ATGTGTAACCACACTTTCTAGAATTAAAACCATTCAGGCTGGACATGGTGGCTCACGCCT
GTAATCCTAGCACTTCAGGAGGCTGAGGTGGGAGGATCACTTGAGCCCAGGAGTTGGAGG

FIGURE 3UU

CCAGCCTGGGCAACATAGTGAGACCCCATTTCTACAAAAAATAAAATGAAATAAATAAAC
CAATTAGCTGAGCATGATGGTACACGCCCAGGGTCCCAGTACTTTGGGAGGCTGAGGTGG
GAGGATCACTGAGGCTGGGAGGTCAACGCTGCGGTGAGCTGTGGTCTCGTCACTACACTC

79617

GGGAGCATTAGGCATTGCGCAGTGGTTCTCAAACATGTTGGCCTCGGGAACCCTTCAACA
CACAGCTCAAAGTTATTAACAACCCACAGAACTTTCATTTCTGTGTGTTACAGCTGTCCG
CGCTGACTACATTTGAAATTAAAGTAGAGACTGAAATATAAACCAACAGAATACATAAAT
AATATATATGAGAAGTTAAATAATCAGAGGAGAACATAAATAGCATTTTTAAATGAAAAA
AATGTGTAACCACACTTTCTAGAATTAAAACCATTCAGGCTGGACATGGTGGCTCACGCC
[T,C]
GTAATCCTAGCACTTCAGGAGGCTGAGGTGGGAGGATCACTTGAGCCCAGGAGTTGGAGG
CCAGCCTGGGCAACATAGTGAGACCCCATTTCTACAAAAAATAAAATGAAATAAATAAAC
CAATTAGCTGAGCATGATGGTACACGCCCAGGGTCCCAGTACTTTGGGAGGCTGAGGTGG
GAGGATCACTGAGGCTGGGAGGTCAACGCTGCGGTGAGCTGTGGTCTCGTCACTACACTC
CAGCCTGGGTGACAGAGAGACCCTGTCTCTAAAAAGAGAGAAAACATTTGTGAGGAGGTT

84900

TTTCAAGGCTGTATTTGCATGTATTTCTGTCTTTTTCCTGGTCTCCAGGGGTCAAGAAAT
GGTTTTCTTGGGGCAAAGAGCTTCGGTCAGCTTTGCAGACTACCCAGTCTCAGTTACAAG
TACAGACTCTGCTCCTGCACCTTAAAAAGTAGTCACATAGTGAGACCGCATCCCTATAGA
AAGTCAAAAAATTAGCCAGACATGGTGGCACACACCTGTGGTCCCCGCTACATGGAGCC
TGAGGTGGGAGGATGGCCTCCTGGGGGAGGTCAAGGCTACAGTGAGCTATGATTGCACCA
[C,G]
TGCACTCCAGCCTGGGTGACAGAGTCAAACCCTGTCTCAAAACAAAAGAAAAATATGATA
TCTCAGGCTCTTTCATTTGGCCTGTACACATTTATTGAGCACCTGTTGTGTGCCACATAC
TGTTCCATGAATGAGGAATATAAAGAAATTCAGTAATGGGTGTGGTGGCTCACATCTGTA
GTCCCATTACTTTGGAAGGCTGAAGTGGGAGGATCACTTGAGCCCAAGCGTTTGAGACCA
GCCTGGGCAACATAGTGAGACCTTGTCTCTACCAAAAATTAAAAAAAAAAAAAAAACAAA

100529

CTGAGTAGCTGGGATTACAGACGCCCAGCTAATTTTTGTATTTTTACTAGAGACGGGGTT
TCACCATGTTGGCCAGGCTGGTCTCAATCTCCTAACCTCAAGTGATCCACCAGCCTCAGT
CTCCCAAAGAAGTGCTGGGATTACAGGCATGAGCCGCTGCACCCGGCCTGGCTTAGTTTA
CTTAACATGATGGTCTCCCATTCCATTCGTGGTGCTATAAATGACAGGATTTCATTCCAT
TTTATGGCCGGATAGTTTTTCATTGTGTGTATGGACCACACTTTCTTTATCCTTTCATCC
[A,G]
TTGGTGGACACTTAGGTTGATTCCATATCTTGGCTTTTGTGAACACTCTGAACTGCATAT
GTTACTGATGGGAGTGGTCAATGGTAGTGTTTTCACCTTTGCACTTCAGAGTTAAAAGAA
TGGAGAATGCTTAGAAATGCTTATTCCTAGTCCTCAGCTCAGACCAGAGTTTCTGGGGCT
GGAGCCTGGGATGATACGCTTCTTTTTTTTTTTTTTTTTTTTTTTTTTGAGATGGAGTCT
CACTTTGTCGCTCAGGCTCGGGGTGTAGTGCAGTGGAGTGATCTCAACTCACTGCAACCT

100997

AGTTTCTGGGGCTGGAGCCTGGGATGATACGCTTCTTTTTTTTTTTTTTTTTTTTTTTTT
TGAGATGGAGTCTCACTTTGTCGCTCAGGCTCGGGGTGTAGTGCAGTGGAGTGATCTCAA
CTCACTGCAACCTCCACCTCTTGGATTCAAGTGATTCTTCTGCCTCAGCCTCCCAAGTAG
CTGGGATTACAGGTGTGCGCCACCACATCCAGCTAATTTTTTTGTGTGTTTTTAGAAGAG
ATGGGGTTTCACTATGTTGGCCAGGCTGGTTTCGAACTCATGACCTCAAATGATCCACTC
[-,T]
CCTCGGCCTCCCAAAGTGCTGGGATTACAGGTGTCAGCCACTGGGCCTGGGCTGATGCAT
CATTTTGTTCAAAGTTTTACCTTTTCAAATACTTTATTGTATTAAATTGCATTAAAAAAA
CAATTTGAATACGTTTTATCTATCCACATTGGTCAAAAACCAAGTCAATATTAAAACAGA
TATATTGCCAAGTCTCCCTCTTACCCCCTCCAAGCCACCTGTAGGTAATCACCTTTTATT
GTTTTTCTGTGTATCCTTCTAGAGTTTCTTTGTGCTAATAAAAACCCACATGGATACATG

101864

CTCCCAAGTAGCTGGGATTACAGGCACCCACCACTATGCCCGGCTAATTTTTGTCTTTTC
GGTAGAGACAGGGTTTCTCCATGGCCAGGCTGTTCTCGAACTCCTGACCTCAGATGATC
CTCCCACCTTGGCCTCCCAAAGTGCTGGGATTACAGGCATGAGCCACTGCGCCTAGCCAG
CTTCCTCATTTTAAAAAATACTGCATTGTATTCCATCACATGACTGTACCATAGCTTACT
TAATACTATATATATATATATTTTGAGACAGGATCTCACTCAGTCATTCAGGCTGGAATGCA
[C,G]
TGGTGCAATCATGGCTCACTTGGAGTATCGACCTCCTGGGCTCAAGCAGTTCTCCCACCT

FIGURE 3VV

CAGCCTACTGAGTAGCTGAGACTGCAGGCACACAGCACCACACCCGGCTAGTTGTATTTT
TTGTAGAGACAGGGGACTCCCTGTGTTCCCCAGGCTGGTCTCAAACTTCTGAGGCTCAAG
CAACCCTCCCGCCTCACCTTCTTAAAGTGTTGGGATTACAGGTGTGAGTCCCCACACGCA
GCCTCATTCACAATATTTTAATTCAAAGATTGCCGCTTTCATAAATGAAGGGAAGACAGC

101915 TGTCTTTTCGGTAGAGACAGGGTTTCTCCATGGGCCAGGCTGTTCTCGAACTCCTGACCT
CAGATGATCCTCCCACCTTGGCCTCCCAAAGTGCTGGGATTACAGGCATGAGCCACTGCG
CCTAGCCAGCTTCCTCATTTTAAAAAATACTGCATTGTATTCCATCACATGACTGTACCA
TAGCTTACTTAATACTATATATATATATTTTGAGACAGGATCTCACTCAGTCATTCAGGC
TGGAATGCAGTGGTGCAATCATGGCTCACTTGGAGTATCGACCTCCTGGGCTCAAGCAGT
[C,T]
CTCCCACCTCAGCCTACTGAGTAGCTGAGACTGCAGGCACACAGCACCACACCCGGCTAG
TTGTATTTTTTGTAGAGACAGGGGACTCCCTGTGTTCCCCAGGCTGGTCTCAAACTTCTG
AGGCTCAAGCAACCCTCCCGCCTCACCTTCTTAAAGTGTTGGGATTACAGGTGTGAGTCC
CCACACGCAGCCTCATTCACAATATTTTAATTCAAAGATTGCCGCTTTCATAAATGAAGG
GAAGACAGCTTTAGTGTTTTGCAAATCATTTTCATTTTTAGGTACAGTGACAGAAATAAA

102141 TCAGTCATTCAGGCTGGAATGCAGTGGTGCAATCATGGCTCACTTGGAGTATCGACCTCC
TGGGCTCAAGCAGTTCTCCCACCTCAGCCTACTGAGTAGCTGAGACTGCAGGCACACAGC
ACCACACCCGGCTAGTTGTATTTTTTGTAGAGACAGGGGACTCCCTGTGTTCCCCAGGCT
GGTCTCAAACTTCTGAGGCTCAAGCAACCCTCCCGCCTCACCTTCTTAAAGTGTTGGGAT
TACAGGTGTGAGTCCCCACACGCAGCCTCATTCACAATATTTTAATTCAAAGATTGCCGC
[G,T]
TTCATAAATGAAGGGAAGACAGCTTTAGTGTTTTGCAAATCATTTTCATTTTTAGGTACA
GTGACAGAAATAAAGCGGTGTGTGCAGCATCCAAGTGTCCCGTCCCTTTCTAACCATGCC
TTTGTGCTTCGGCCATGTCTCACAGCCTCCCATCGTGCCCAAGATAGCTGGTGACGGCGA
CACTTCCAACTTCGAAACTTACCCTGAGAATGACTGGGACACAGCCGCGCCCGTGCCGCA
GAAGGATTTAGAAATCTTCAAGAATTTCTGAGGACAGGAGCTCACATCTGGAAGGTATAT

102459 GACAGCTTTAGTGTTTTGCAAATCATTTTCATTTTTAGGTACAGTGACAGAAATAAAGCG
GTGTGTGCAGCATCCAAGTGTCCCGTCCCTTTCTAACCATGCCTTTGTGCTTCGGCCATG
TCTCACAGCCTCCCATCGTGCCCAAGATAGCTGGTGACGGCGACACTTCCAACTTCGAAA
CTTACCCTGAGAATGACTGGGACACAGCCGCGCCCGTGCCGCAGAAGGATTTAGAAATCT
TCAAGAATTTCTGAGGACAGGAGCTCACATCTGGAAGGTATATCTTTATATTTAGTAATT
[A,C]
CCAAAAAATGAGACTGACTCGACCCCACATCCAGGTGAGGCTGCGTTTACTGAGTGGGGC
TTAACCTCATGCACACAGAGGTCAGCAGTGAAGCAGAGCAAAGGGGATTGATTGCAAGGG
TCAGCGAAATAAACACAGCCATGCCTGTGACTCCAGGTCAGCATGTGACCGTCAGAGGCA
TCAGCATGACAGTCCAGAATCCATGTTCTGCATCAGAACCTGCATGTCTAAATAAGACCG
CTAGGTGGTTTGTGTGTGCCTGAATATTTGAGAAGCCCAGCTCCTCTGGTCCCTGTTCCA

102724 CACATCTGGAAGGTATATCTTTATATTTAGTAATTCCCAAAAAATGAGACTGACTCGACC
CCACATCCAGGTGAGGCTGCGTTTACTGAGTGGGGCTTAACCTCATGCACACAGAGGTCA
GCAGTGAAGCAGAGCAAAGGGGATTGATTGCAAGGGTCAGCGAAATAAACACAGCCATGC
CTGTGACTCCAGGTCAGCATGTGACCGTCAGAGGCATCAGCATGACAGTCCAGAATCCAT
GTTCTGCATCAGAACCTGCATGTCTAAATAAGACCGCTAGGTGGTTTGTGTGTGCCTGAA
[C,T]
ATTTGAGAAGCCCAGCTCCTCTGGTCCCTGTTCCAGAAACCCTGAGTGACAGGCGAGCTT
CCTTAGAATAATTAACAAGTATTTTCAAAAGTCTCTTTAGGTCTCCTTTGGTTAAAAAAT
AAGAAGAAGAAATATGCCCTCATAGGAAATTTGCTAAGCTTAATTGAAGATGACTGGAAA
AGGATTTTGAGTCTATTACTTCTTTGAGCCTTTGAAGGTCTATTATTAGTTTTTAAATAA
TAATAATATTTTTTAGAATCCCTCATGAAATTTGCTAAGCTTTAATTTAAGATGACTGAA

FIGURE 3WW

ISOLATED HUMAN KINASE PROTEINS, NUCLEIC ACID MOLECULES ENCODING HUMAN KINASE PROTEINS, AND USES THEREOF

This application claims priority to U.S. Provisional Application No. 60/377,592, filed May 6, 2002.

FIELD OF THE INVENTION

The present invention is in the field of kinase proteins that are related to the serine/threonine kinase subfamily, recombinant DNA molecules, and protein production. The present invention specifically provides a novel alternative splice form of a known kinase, novel splice form peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin.

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell. Biol.* 8:463–93). Regulation of PTK activity may therefore be an important strategy in controlling some types of cancer.

Serine/Threonine Kinases (STKs)

The novel human protein of the present invention is a novel alternative splice form that is related to the X-linked protein kinases (referred to as PRKX and PKX1). These X-linked protein kinases represent a novel subtype of serine/threonine kinases that are related to the catalytic subunit of the cAMP-dependent protein kinases, which play important roles in regulating cellular responses to the second messenger cAMP. See Klink et al., *Hum. Molec. Genet.* 4: 869–878, 1995 and Schiebel et al., *Cytogenet. Cell Genet.* 76: 49–52, 1997 for further information on X-linked protein kinases.

The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Kinase proteins, particularly members of the serine/threonine kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the serine/threonine kinase subfamily.

SUMMARY OF THE INVENTION

The present invention is based in part on the identification of amino acid sequences of human kinase peptides and proteins representing a novel alternative splice form of the serine/threonine kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma.

DESCRIPTION OF THE FIGURE SHEETS

FIGS. 1A–1B provide the nucleotide sequence of a cDNA molecule or transcript sequence that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma.

FIGS. 2A–2E provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence. FIG. 2 also provides EST alignments supporting the alternative splicing region of the present novel alternative splice form.

FIGS. 3A–3WW provide genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 57 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the serine/threonine kinase subfamily. Utilizing these sequences, additional genomic sequences were assembled and transcript and/or cDNA sequences were isolated and characterized. Based on this analysis, the present invention provides amino acid sequences of human kinase peptides and proteins that represent a novel alternative splice form of the serine/threonine kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the serine/threonine kinase subfamily and the expression pattern observed. Experimental data as provided in FIG. 1 indicates expression in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known serine/threonine kinase family or subfamily of kinase proteins.

Specific Embodiments

Peptide Molecules

The present invention provides nucleic acid sequences that encode protein molecules that have been identified as being members of the kinase family of proteins and are related to the serine/threonine kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988*; Biocomputing: Informatics and Genome Projects*, Smith, D. W., ed., Academic Press, New York, 1993*; Computer Analysis of Sequence Data, Part* 1, Griffin, A. M., and Griffin, H. G., eds., Humana Press, New Jersey, 1994*; Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol. (*48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res*. 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated in FIG. 3, the map position was determined to be on chromosome X.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated in FIG. 3, the map position was determined to be on chromosome X. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found at 57 different nucleotide positions in the gene encoding the kinase proteins of the present invention.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science*244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol*. 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma, as indicated by virtual northern blot analysis. A large percentage of pharmaceutical agents are being developed that modulate the activity of kinase proteins, particularly members of the serine/threonine kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma. Such uses can readily be determined using the information provided herein, that which is known in the art, and routine experimentation.

The proteins of the present invention (including variants and fragments that may have been disclosed prior to the present invention) are useful for biological assays related to kinases that are related to members of the serine/threonine kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma, as indicated by virtual northern blot analysis.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma, as indicated by virtual northern blot analysis.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}S$-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem*. 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (Clin. Chem. 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma, as indicated by virtual northern blot analysis. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding-sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated in FIG. 3, the map position was determined to be on chromosome X.

FIG. 3 provides information on SNPs that have been found at 57 different nucleotide positions in the gene encoding the kinase proteins of the present invention.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C, followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 57 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated in FIG. 3, the map position was determined to be on chromosome X.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma, as indicated by virtual northern blot analysis. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma, as indicated by virtual northern blot analysis.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma, as indicated by virtual northern blot analysis. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found at 57 different nucleotide positions in the gene encoding the kinase proteins of the present invention. As indicated in FIG. 3, the map position was determined to be on chromosome X. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv.*

*Chromatogr*. 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found at 57 different nucleotide positions in the gene encoding the kinase proteins of the present invention.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in lung squamous cell carcinoma and large cell carcinoma, kidney, B-cell chronic lymphatic leukemia, kidney tumors, breast, ovary fibrotheoma, brain anaplastic oligodendroglioma, head, stomach, testis embryonal carcinoma, and lymphoma, as indicated by virtual northern blot analysis. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application W095/11995 (Chee et al), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found at 57 different nucleotide positions in the gene encoding the kinase proteins of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res*. 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J*. 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can, also be expressed in insect cells using, for example, baculovirus expression vectors. Baculovirus vectors available for expression of proteins in cultured insect cells (e.g., Sf9 cells) include the pAc series (Smith et al., *Mol. Cell Biol*. 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufmnan et al., *EMBO J*. 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell- free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal.

Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgemc animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter G. phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule, wherein the nucleotide sequence of said nucleic acid molecule consists of a nucleotide sequence selected from the group consisting of:

(a) a nucleotide sequence that encodes a polypeptide having an amino acid sequence comprising SEQ ID NO:2;

(b) SEQ ID NO:1;

(c) SEQ ID NO:3;

(d) nucleotides 2388–102412 of SEQ ID NO:3; and (e) a nucleotide sequence that is completely complementary to the nucleotide sequence of (a), (b), (c), or (d).

2. An isolated nucleic acid molecule comprising a nucleotide sequence selected from the group consisting of:

(a) a transcript or cDNA sequence that encodes a polypeptide having an amino acid sequence comprising SEQ ID NO:2;

(b) SEQ ID NO:1; and (c) a nucleotide sequence that is completely complementary to the nucleotide sequence of (a) or (b).

3. An isolated nucleic acid molecule, wherein the nucleotide sequence of said nucleic acid molecule consists of SEQ ID NO:1 or the complete complement thereof.

4. An isolated nucleic acid molecule having a nucleotide sequence comprising SEQ ID NO:1 or the complete complement thereof.

5. An isolated nucleic acid molecule, wherein the nucleotide sequence of said nucleic acid molecule consists of SEQ ID NO:3 or the complete complement thereof.

6. An isolated nucleic acid molecule, wherein the nucleotide sequence of said nucleic acid molecule consists of nucleotides 2388–102412 of SEQ ID NO:3 or the complete complement thereof.

7. An isolated nucleic acid molecule, wherein the nucleotide sequence of said nucleic acid molecule consists of a nucleotide sequence that encodes a polypeptide comprising SEQ ID NO:2, or the complete complement of said nucleotide sequence.

8. An isolated transcript or cDNA nucleic acid molecule comprising a nucleotide sequence that encodes a polypeptide comprising SEQ ID NO:2, or the complete complement of said nucleotide sequence.

9. A nucleic acid construct comprising the nucleic acid molecule of claim 1 or 2 fused to a heterologous nucleotide sequence.

10. The nucleic acid construct of claim 9, wherein the heterologous nucleotide sequence encodes a heterologous amino acid sequence.

11. A vector comprising the nucleic acid molecule of claim 1 or 2.

12. An isolated host cell containing the vector of claim 11.

13. A process for producing a polypeptide, the process comprising culturing the host cell of claim 12 under conditions sufficient for the production of said polypeptide, and recovering said polypeptide.

14. The vector of claim 11, wherein said vector is selected from the group consisting of a plasmid, a virus, and a bacteriophage.

15. The vector of claim 11, wherein said nucleic acid molecule is inserted into said vector in proper orientation and correct reading frame such that a polypeptide comprising SEQ ID NO:2 is expressed by a cell transformed with said vector.

16. The vector of claim 15, wherein said isolated nucleic acid molecule is operatively linked to a promoter sequence.

* * * * *

SEQUENCE LISTING

```
<160> NUMBER OF SEQ ID NOS: 8

<210> SEQ ID NO 1
<211> LENGTH: 957
<212> TYPE: DNA
<213> ORGANISM: Homo sapiens

<400> SEQUENCE: 1

atggaggcgc ccgggctggc ccaggcggcc gcggcggaga gcgactcccg caaggtggcg     60

gaggagaccc ccgacggggc gcccgcgctc tgccccagcc ctgaggcgct gtcgccggag    120

ccgcctgtgt acagcctgca ggactttgac acgctggcca ccgtgggcac tgggacgttc    180

gggcgggtgc acctggtgaa ggagaagaca gccaagcatt tcttcgccct caaggtgatg    240

agcattcccg acgtcatccg cctaaagcag gagcaacacg tacacaatga gaagtctgtc    300
```

-continued

```
ctgaaggaag tcagccaccc gttcctcatc aggctgttct ggacgtggca tgacgagcgc    360

ttcctctaca tgctcatgga gtacgtgccg ggcggcgagc tcttcagcta cctgcgcaac    420

cgggggcgct tctccagcac cacggggctc ttctactctg cagagatcat ctgtgccatc    480

gagtacctgc actccaaaga gatcgtctac agggacttga agccagagaa catcctgctg    540

gatagggatg gccacattaa gctcacggac tttgggttcg ccaagaagct ggtagacagg    600

tttcctccgt tttttgatga caacccgttt ggcatttatc agaaaattct tgcaggcaaa    660

atagatttcc ccagacattt ggatttccat gtaaaagacc tcattaagaa actgctcgtg    720

gttgacagaa caaggcgatt aggaaacatg aagaacgggg cgaatgatgt gaagcatcat    780

cggtggttcc gctccgtgga ctgggaagct gttccgcaga gaaaactgaa gcctcccatc    840

gtgcccaaga tagctggtga cggcgacact tccaacttcg aaacttaccc tgagaatgac    900

tgggacacag ccgcgcccgt gccgcagaag gatttagaaa tcttcaagaa tttctga      957
```

<210> SEQ ID NO 2
<211> LENGTH: 318
<212> TYPE: PRT
<213> ORGANISM: Homo sapiens

<400> SEQUENCE: 2

```
Met Glu Ala Pro Gly Leu Ala Gln Ala Ala Ala Ala Glu Ser Asp Ser
 1               5                  10                  15

Arg Lys Val Ala Glu Glu Thr Pro Asp Gly Ala Pro Ala Leu Cys Pro
            20                  25                  30

Ser Pro Glu Ala Leu Ser Pro Glu Pro Pro Val Tyr Ser Leu Gln Asp
        35                  40                  45

Phe Asp Thr Leu Ala Thr Val Gly Thr Gly Thr Phe Gly Arg Val His
    50                  55                  60

Leu Val Lys Glu Lys Thr Ala Lys His Phe Phe Ala Leu Lys Val Met
65                  70                  75                  80

Ser Ile Pro Asp Val Ile Arg Leu Lys Gln Glu Gln His Val His Asn
                85                  90                  95

Glu Lys Ser Val Leu Lys Glu Val Ser His Pro Phe Leu Ile Arg Leu
            100                 105                 110

Phe Trp Thr Trp His Asp Glu Arg Phe Leu Tyr Met Leu Met Glu Tyr
        115                 120                 125

Val Pro Gly Gly Glu Leu Phe Ser Tyr Leu Arg Asn Arg Gly Arg Phe
    130                 135                 140

Ser Ser Thr Thr Gly Leu Phe Tyr Ser Ala Glu Ile Ile Cys Ala Ile
145                 150                 155                 160

Glu Tyr Leu His Ser Lys Glu Ile Val Tyr Arg Asp Leu Lys Pro Glu
                165                 170                 175

Asn Ile Leu Leu Asp Arg Asp Gly His Ile Lys Leu Thr Asp Phe Gly
            180                 185                 190

Phe Ala Lys Lys Leu Val Asp Arg Phe Pro Pro Phe Phe Asp Asp Asn
        195                 200                 205

Pro Phe Gly Ile Tyr Gln Lys Ile Leu Ala Gly Lys Ile Asp Phe Pro
    210                 215                 220

Arg His Leu Asp Phe His Val Lys Asp Leu Ile Lys Lys Leu Leu Val
225                 230                 235                 240

Val Asp Arg Thr Arg Arg Leu Gly Asn Met Lys Asn Gly Ala Asn Asp
                245                 250                 255

Val Lys His His Arg Trp Phe Arg Ser Val Asp Trp Glu Ala Val Pro
```

-continued

```
            260                 265                 270

Gln Arg Lys Leu Lys Pro Pro Ile Val Pro Lys Ile Ala Gly Asp Gly
        275                 280                 285

Asp Thr Ser Asn Phe Glu Thr Tyr Pro Glu Asn Asp Trp Asp Thr Ala
    290                 295                 300

Ala Pro Val Pro Gln Lys Asp Leu Glu Ile Phe Lys Asn Phe
305                 310                 315


<210> SEQ ID NO 3
<211> LENGTH: 105413
<212> TYPE: DNA
<213> ORGANISM: Homo sapiens
<220> FEATURE:
<221> NAME/KEY: misc_feature
<222> LOCATION: (1)...(105413)
<223> OTHER INFORMATION: n = A,T,C or G

<400> SEQUENCE: 3

caagcaaggt gttgtgaaac gtgcagggtc tatttataag aagaggtagc tatgcggtca     60

agttcagggt gggttcggtg gaatcagacc aaccagcagc tcaagcagag tttaacgctg    120

caaatctgtg ccacgttctt cttcctgcgt gcaatttgca ggcaaggaca tctgcttaat    180

tgggtgtgaa acccgggcct tgattaaaag gactttatga ggccgcagcc ttgcatttcc    240

aaggtcaggc cctagtggag agggcgcgcg ttccgcgggg agacacgaac ttttcctgag    300

tgcgcgttcc ttgctggccc tgaacccctc ggccaggcag ggcttggcag ggccgtttcc    360

tgtcctaacc aggatcaagg gattgcgcgg cttgctggtg aagcttggca gggccgtgac    420

ctgtcctaac caggctcagg ggatggcagg ggcctgctgg tgtcgcatat gttttgcatt    480

ccagctcagg attttgcaga gcatagggag cgggtgtcac ccccgggggg aaatgccacc    540

cacaaaatgc aggtggaggc tgggcgaggc tggcagccag gggccagaaa tccaaagcct    600

gagccaggtt cagacttcct gactccccct ccccgttagc tgtggaagga tggctcggcc    660

tggtccccct aaaaatgtgt ccgttctgac ttagaggccg ctttggctct cggaaagccc    720

ccctgacctg cggactgagg gactggagac cccctccaat cgcagaatcg ctgagatccc    780

tcaaaacaaa ggcgtttgca gtttgacccc ttgctgctca aactgtggtc ggcgaaccgg    840

cagcctgggc cgccctggtc gcgggtcagg ggcgcagcgt ccaggccgtg ccaggcccgc    900

aagttaagca ctgtctgcat ttccctgggg aaaggggtga ccaaatatct agctatattt    960

gcatttcaaa tccacacgga tatgggtttt aaatataagt atgtccaact attgcctgag   1020

ccacacttaa gccaggaaaa aaaaatcttt ggggtttctg aaattgaaat gcctctgcac   1080

aattctttat agggttgtcg ccggggtgtt tgaaacagtg accaatcaag tttcacgcac   1140

tacatttggt cgggcgatct ctcaaatctg tctttcccta gttttttaaa ggaatgttta   1200

tttgtaaaga attctagatc cacaggaagc tgcaaagaaa cgcacagggt cgagcccgcc   1260

cttccccgcc ccttccaagt agaaatctag aatcaccaga gtcctacagc aaaaccagga   1320

cgctgaactc atcccgaaga cccggcagcc cctcttgggg atccgccctc attccaaatt   1380

ctctcaggtc ccaaacaagc acccgcagga gtactgaact ttttgggggg agggcagagg   1440

ggatctgtat gcagattgcc agctgagcaa tcctattttc tatgacttaa agccaatcag   1500

aggctgggcg tggtggctta tacctgtagt cccagcactt tgggagaacg aggcaggcgg   1560

ttcacttgtg ctcaggagtt ccagaccagc ctggccaaca tggtgaaacc ctgtctctac   1620

tgagaaaata caaaaattag ccgggctaat ccgagcccct ctcttcacca aacgccagtt   1680
```

-continued

```
tcacttttta gttttgaact tcacttctgc tgagctacgc cctccctgtc cccgggcccc   1740
ctcgcctccc catcttccgg gcttgggtgc agcgacgcgg gtggcccgcc agtgcgtccc   1800
cgaggagaag tcagcctggg tcccacccca ggggtgcccc gggcgcggag ggggcgtggg   1860
cacctcccca gcgccgcacg cccgggtctc cggctcctgg gctgggtcgg ggcgggggcg   1920
gacgcgcgcg cgaaggcgac gccccccagc cccgcggccg ggttagggcg gggagaggcg   1980
cggtcacgcc caggcggctt ccgcccgccc caacagcgcg cacgcggcta ccgagctgga   2040
ggaggcggcg ggcgcgagac ccggaatgcg caggggcccc gcctcgcccc ccccagcccg   2100
ggccgcggcc cccgccttcc ccgcagtcgt cccgcactcg gtgcccgccc cccgaggccg   2160
gcggctgctc ccactcgggg ccgttgctgc ttgtgccgtg agcgccgccc agccattgtc   2220
cccgtcgctc cgtcagccgc gccggaccgc gcaccaggag gcgagagcgc gcatggggag   2280
cctctgttga tgccgccgcc gcgccgccct ccgaggctgc gtcccgggaa gcccggctcc   2340
ccgagcgctc cggcctggcc cggtgccccg gacctgagtg cgtccccatg gaggcgcccg   2400
ggctggccca ggcggccgcg gcggagagcg actcccgcaa ggtggcggag gagacccccg   2460
acggggcgcc cgcgctctgc cccagccctg aggcgctgtc gccggagccg cctgtgtaca   2520
gcctgcagga ctttgacacg ctggccaccg tgggtgagtg agtgcgggcg gggactcggc   2580
ccacaggggc gcgcggcgtg gccgggacgt tgtagtagga caaagggccc tgggtgccga   2640
cctcctgggg agggccctga cccgctactt cggctcggag tccccgtgcg gggctgcacc   2700
tgcgccccgg gtcttcccgg gtggagcgca ctccccagcc ccccagccca ggcaagtacc   2760
cccgaccggc cgggtgccta acctgaaatg ccgacggctc ctctcggaga ccaccctcca   2820
cccccagcac acacagcact ctggggcctg ggccgtccga cgtcacaaaa cctcctgcgg   2880
gtcacctcgc ctgggggacc tcgtgctccc tccctggcag cggccccagg gacactggcg   2940
cggggtgcga agacccctgc aggcctcccc taggccagcc tccctgtgtg cccagaggca   3000
gggaatgtac agatttctcc aggggctgca ggagcagctg ggctgtgggg gacaggtgtc   3060
ccggggcgct gtggggacga ggacggcagc gctggggacg gatcctaaca tgtcctgaca   3120
ccgcctgtgc tcttcgtctt gtgcctctga aatgggtaat tcttgtatcg gacgctttat   3180
ccgtttcctt tgtcctctgt ctttgaactt aaccccgaat gggcagcttg acagagaggt   3240
ttcgagttct cggtgctctt gcatccggac acgcgctgct ttatggagca gccctgagtg   3300
ggtcagaata tcccaactga acgtgggcgc tggatttaaa cagttgtcat cggcccgcct   3360
gtgccactta gggactccgt atggctaagt ggggtgttgg ctgtcaagaa aataaatggg   3420
agagtagagg gggctgtcct gggtgtgttg gtgaggcgtc ggctctcagg ccctctaact   3480
cctgtttgtc ctcattttgg aaaggaggaa gctgggctgg gaagcccaag ggctcgaggc   3540
catagcttat gacttaggaa gaccagcggg catagccagt ggggccttta gaaccgctga   3600
ggaagagggg acttagcttc cttcagtgac ctctttgcca cttagacctt gaggaagggc   3660
ccacgaggaa agcctgaatt tggaaggaca gagtgggagg aggccctctc tctttctcct   3720
ctccctccct cctcctcttt atctcattct ctctctcttt tctctgtttc tcttctctct   3780
ccctctttct gtctctgttc aagtctctct gcatttctcc tcctctgtct cttggtgtct   3840
ctctccctgt ccccttccgg tcttggtttt tctgtctccc tccctcctct ctctctgcct   3900
tccccccttgt cttggtcccc ccggaaagct gtcctggtct aatcttagag ctgggtgtgt   3960
tttgcgcgga agaagggtgg ggcaggaacc ctgactggcg cagccgccac agtaggtgga   4020
aatacaactc gacaatggaa aattgatgag gtccagccgt tccttggcac tcagcaccag   4080
```

-continued

```
cgtttgtcat tctttggggc acccacatgg gtcccttggg aaaggtggag ctggggctgg   4140
aggccggggc agagagcagg atgcgggcag gagggcggca gaggtgaggg gttctggtgt   4200
cacagggggc cactcagttt gacgtcaagt cagcttaggg tgcccagcgg gtaacctcat   4260
ctttaaaaat agagtgtcgc tgcctctggg gaccaagctg gctgggcggg gagtcagctt   4320
ttttttcag tccagtcagt gctctcttaa tgaggatgag gatgatgctc ctttctcaag    4380
gataacttcc tgtgagctcc aacgatgtga caggagggct aggtatccca cactcattgg   4440
acagcagggg accaggaccc aggggtgtgt gtgtgtatgt ttgcatgcac gtctggaaca   4500
ctctctcatg acaactgcac agctttggtg acattatctg caacctttta tccaagcccg   4560
tttctttatt gttggttaaa gagcaatctg agtgtgattc acctaaaata atacatttta   4620
taaaatccta agccttttag atccttcacg attgtgtctc taagccacaa tctacagcag   4680
ctttggactg ttttccaagg cgtgatggag aatagtgagg ggtgagcttg agtctcagtc   4740
tggagttgaa acccagtctg ggtgggtgtg acctctcttc atcctaaact gtcactacag   4800
gaacataagt ttgcttttaa gtgctctttc gccctcattc cgaattctct caggccccaa   4860
acaagcaccc gcaggagtac tgaacttttt ggggggtggg cagaggggat ctgtatgcag   4920
attgccagct gagcaatcct attttctatg acttaaagcc aatcacaggc tgggcgtggt   4980
ggctcatacc tgtagtccca gcactttggg aggccgaggc aggcggatca cttgtgctca   5040
ggagttccag accagcctgg ccaacatggt gaaaccctgt ctctactgag aaaatacaaa   5100
aattagccgg gcgtggtggc gggcgcctgt aatcccagct tctcaggagg ctgaggcaga   5160
ggaattgctt gcacccagga ggcagaggtt gcagtaagcc aagatcacac cactgcgctc   5220
cagcctgggc gacagagaga aaaagaaact tgtcagcgtt ctagattgac cagttttcct   5280
caaggtcagg tagttaggaa gaaagagtgc agtttgcagt tgtgaaaagt ctgataatgg   5340
attctttttt tctttttat gcgtgaaggg attctggagt acgtctggtc taaaggccga    5400
tttcgtttta ggaactttgg atcagaacag tcatactagt cctcagagaa aaaatggttt   5460
tcaatctggt tcttcaaatt tcttgttcat ataaccaagc catgcttgtt cctatgatgg   5520
agaacaattg tgctttaaaa aaagaaattt cagggccagg tacagtggtg cgtgcctgta   5580
gtcccagcta tttgggaggt cgcggtggga ggatgacttg aggccgggag ttccagacca   5640
gcctgggcaa tatagtgaga ccctcatctc ttaaaaaaaa tagtagtaat agttagctgg   5700
gcatggtggc gcatacctga gttacctggg aagctgaggc aagaggatca cttgagccca   5760
ggaggtcaag gctgcagtca accacaatcg cgccaccgta ctccagcctg ggtgatagag   5820
cgagatcctc tctataaaaa ataaaataag aaaatgatat tatggaaatg aaaaactcac   5880
cctatgtaga gagaagagga tgaatctgtg cagccatcta ccagccttat tttaccaatt   5940
tcctacttaa aatgaccact tgagaattcc tttctctata tatcagataa aaaatacttg   6000
ggttttttcc cagaagtgtc cttatggaat catttggcat ctacaaccca gtgcttgctt   6060
gtcatgggta ccccaagtgt taacctgtca ggaaggaggt aattcaacag gtaaaccagt   6120
ggccaggcct tgggtccaca tttcattttc cttttctcag cctagttctg catttactca   6180
tctacagagg gaaataatga cggaacctgt cctacacgat gacgatgagg aagactccaa   6240
agttcctaga cccctattaa aaatatatat tttttgaaat acagactcac aggggatttc   6300
aaaaacagta cctggagtct catggaccct tcagccaact tccccatggt gacgtcttca   6360
tatccgtggg acaatatcag aaccatgtca tcgatgttgg tatatcctta ttaaagagaa   6420
```

-continued

```
cacatacctc gttcagcttt tttttttttt tttttttgag acagggtctc actctgttgc   6480
ccagtctgga gtgcagtggt gcgatctcgg ctcactccag ccttgaactc ctgggctcaa   6540
gcaatcctcc tgccttggcc tcccaaagtg ctgggactat atacaggcat gagccatcgt   6600
gcccggcttg ttcaggcttt attagttttc aaaaggtgct catttgtgtt tgcgagtgtg   6660
tgtgtagagt tctgtgcagt tttacccagt gtgtggattt ggcagctacc accctccaaa   6720
ccatggtgca ggatgaattc cctcaccaca gaacacccct cggtcttgct cgacactttt   6780
tttttttttt tgagacagag tttcactctt gttgcccagc ctggagtgta ttgaccacaa   6840
cctctgcttc ccgggttcaa gcgattctcc tgcctcagcc tcccgaggag ctgggattac   6900
aggcatgtgc caccatgcct ggctaatttt atatttttag tagagatggg gtttctccat   6960
gttgattagg ctggtctcaa actcctgacc tcaggcgatc cgcccgcctt ggcctcccaa   7020
agaggtggga ttgcaggtgt gagccaccgt gcctggccag acactttttt tttttttaaa   7080
ctttcacaca ctatacaatc tgaaaatatt ttattttctt aagagctagg agatcttcat   7140
aattaatgat acatggttct cagatctaaa gtgcttatac tggtaggttt tctcttgtcc   7200
ttggttctcc tgaattggcc agaatttcct ttcctctcct tgttgctggg ttcttattaa   7260
tgcctcaagt tagtcggttc aggcagttgt agcaaaacac caccgactgg gtggcttata   7320
aaccacagac atttattcac agttcagagg ctggaggtcc aagatgaagg catggcagat   7380
ttggtgtctg gtggggacct gcttcctggt tcatagatgg tgccttctcg ctgtgtcctc   7440
acatggtgga aggggtgagg gagctctctg gggccccttt ataagggcag tgatcccatt   7500
catgaggctc caacctcacg acctcatcac ctccctaggg cctcacctcc tgacaccatt   7560
accttgcagg tgaggatttc aacacaggaa ttttaggggg acacagacat tgagtccacg   7620
gcatccccac cctgtctgtc acacagcatg ctgccgggac gaatggcatc tgaactggtg   7680
agattctact gtgtgcataa atcagcagcc ttgtgggcag tgttgacata gcaattagga   7740
gtgttgtttg tagcctaaca atacacagaa agtggagctc agccctttga tcttatttac   7800
cttatgtggg tgctccgtgt gagacaggct catgcatgtg tgaatgacag tttcctttaa   7860
gtgcatcacg caaatgccaa gagatgagat caaatattac acatcagaga acatttccaa   7920
ggatagaagt cctgccggtt tctcctcttc attgtttatt tcattttatt tttttaattt   7980
aagttaaaat acatgttaaa ttaaatttaa gttaaattaa gatacatgtg caggacttat   8040
tttaaataaa agagacaggg tctcgctgtg ttgcccaggc tagacttgaa cccctgggct   8100
caagcattct gcctgcctcc gctgctggca cataaatgcc aagtgtgcag ggacctctgt   8160
gtgttggagc cactttcatc tcccacatcc aaagaacaga cccggcactt agtgtgtgcc   8220
caagaccatc caccgcatga atagagaaat caaccctcct catgtgcctg gggtttcctg   8280
aggtgggaaa ccttcagtgc tagctgggag agtcgcaggc agagacaggg acaagctggt   8340
cactctgtgt gtgaataaat aaatgaatgg atgatggcat tatcggcagt tgttctttat   8400
gacactcact gatgccaagt actggacggg tacaatatgt acattagttt ctctatgggc   8460
agaagctcca ccatgacaac attagtgtta ttttcttttt gctttttttgt ttagagacag   8520
ggtcttactc tgtcgcccag gctggggtgc cgtggtgcaa tcaacagctc actgcagcct   8580
cgacctccca ggctcaagca atcttcccac ctcagtctcc caagtagctg ggactgcaga   8640
cgtgcaccac cacactcagc taatttatgt atttattttt gtagagatgg gcattgctat   8700
gttgcccagg ctggtctcga gctcctgggc tcaagtgatc ctcccgcctc agcctcccac   8760
gtagctggga ctacaggtgc atccaccatg cttgtagcct tattttctta atgggaaaga   8820
```

-continued

```
gggtctgaga gaagggatgc tgtgtgccca atgggtttcg cctgcagcac gctgcctcct   8880
ccccgggaaa gcagggcgtg cacattggga ttggacgaca aaagcagagt catctacagt   8940
tcatgggcac gctgcaaaga agggagacgt taaactctcg aaagcagcag acaccccccca   9000
ccaggaagag acatacttgt aaaaatcaaa ggagggcgaa ggcatgagaa tcgcttgagc   9060
ccaggaggtt gaggttgcag tgggctgaga tcgtgctact gcattccagc ctgggtgaca   9120
gagaccttgt ctcaaaaaat aaaaattcaa gggaggccag gtgtggaggc tcacgcctgt   9180
acccagcact ttgggactct gaggtgggag gatcacttga gcccaagagc tcaagatctg   9240
tctggacaat atagcactac cccatcgcta caaaaaaaaa ttttttaag tagctgggtg   9300
tgatggaatg cacctgtagt cccagctact agggaggctg aggcaggagg attgcttgag   9360
cccaggaggt ggagactgca ctgagccatg atggtgccac tgtgttccag cctgggcaac   9420
agagcaagac cctatgtcaa aaataaagaa agtatcaagg gagatgagta cacagtgcct   9480
ggcacactgt agggtctcca aaaagtaaac cttttctatc catcagtttc ctcttctctc   9540
cagcatgaaa tcgcatatgt aaagttgaaa aaaagagtga gagatatatc ttaaaaaggt   9600
agtaatgttg atgacattgt ggtttttttt tttttttaa agaaaaaccg gccgggtgcg   9660
gtggctcatg cctgtaatcc cagcactttg ggaggctgag gcaggcgggt catgaagtgt   9720
caggagatcg agaccatcct ggctaacacg gtgaaacccc gtctctacta aaaatacaaa   9780
aaaaaattag ccgggtgtgg tggcgggcgc ctgttagtcc cagctgctgg ggaggctgag   9840
gcagcggaat ggcatgaacc cgggaggtgg agcttgcagt gagccgagat cacaccactg   9900
cactccagcc tgggcgacag agcaagactc tgtctcaaaa aaaaaaaaag aaaagaaaaa   9960
ccttggggga aatacagagg aagccctaag gcatcccttc caaaaagctg aaagtgcttt  10020
acttagaatt gtgacctcgt tttccctgtt agaaaagtct gtggttagaa gcttcctggt  10080
aagcccagtg tgagaaggtg gaaccgatgt ttctgtgtga cgggttccct ctgcctgttt  10140
ctccaggtgg cctccccgtg gtcctctact gtggtgggtc cagtcccaaa accaagtctg  10200
gggccaccat catcatattt gtgtccccca ccccaagatt cttatgtcaa aaccctaatc  10260
cccaaggtaa tggtgttagg aggtggggct tttaggaggt gatggggtca ctagggtggg  10320
gtctcatgaa tgggatcaat gtccttataa aagggacccc agagagctcc ctcacccctt  10380
ccactatatg aggacacagt gagatggcac cgtctgttaa ttagaaagcc ggtccccacc  10440
aaactctgaa tctcccatac cttcatcttg gacttgtagc ctccaggact gacagcggta  10500
aatgtctgtt gtttctaagc cccagtctgc cgtgttttgt gatggcagcc gaaatggatt  10560
tagatggggc tctattcacc ccacgcggca gggtccatgg aaaggcagct gcaatgcgct  10620
ggtctatcat tacctctttt atgctctttc acactgtctt agtcttgcgt ggctgctgga  10680
atgaaggacc gcaaatatag tagcttaaaa ccacatacag tgaagagata cctgcactcc  10740
caggttcact gcagcacgag tcacacaaca gccaagatag ggcaacaacc cacttgcccg  10800
tcagcagatg actgggtgaa gaaaatgtgg tctctacaca atggagtact attcagcctg  10860
taaaaagaat aaagtcctgt catttgcaac aatgtagatg caactggagg tcattatgct  10920
ctgagaaatg agccaggcac agagagacaa atacggcatt atctcactcc tttttttttt  10980
ggacagggtc tcactcggac acccaggctg gagtgcagtg acgtggtgtc actgcagcat  11040
tgacgtccca ggctcaaggg atcctctcac ctcagcctcc tgaggagctg ggactgcagg  11100
tgtgcatcac cacgccaggc tattgttttg atttnnnnnn nnnnnnnnnn nnnnnnnnnn  11160
```

-continued

```
nnnnnnnnnn nnnnnnnnnn nnnnnnnnnn nnnnnnnnnn nnnnnnnnnn nnnnnnnnnn  11220
nnnnnnnnnn nnnnnnnnnn nnnnnnnnnn nnnnnnnnnn nnnnnnnnnn nnnnnnnnnn  11280
nnnnnnnnnn nnnnnnnnnn nnnnnnnnnn nnnnnnnnnn nnnnnnnnnn nnnnnnnnnn  11340
nnnnnnnnnn nnnnnnnnnn nnnnnnnnnn nnnnnnnnnn nnnnnnnnnn nnnnnnnnnn  11400
nnnnnnnnnn nnnnnnnnnn nnnnnnnnnn nnnnnnnnnn nnnnnnnnnn nnnnnnnnnn  11460
nnnnnnnnnn nnnnnnnnnn nnnnnnnnnn nnnnnnnnnn nnnnnnnnnn nnnnnnnnnn  11520
nnnnnnnnnn nnnnnnnnnn nnnnnnnnnn nnnnnnnnnn nnnnnnnnnn nnnnnnnnnn  11580
nnnnnnnnnn nnnnnnnnnn nnnnnnnnnn nnnnnnnnnn nnnnnnnnnn nnnnnnnnnn  11640
nnnnnnnnnn nnnnnnnnnn nnnnnnnnnn nnnnnnnnnn nnnnnnnnnn nnnnnnnnnn  11700
nnnnnnnnnn nnnnnnnnnn nnnnnnnnnn nnnnnnnnnn nnnnnnnnnn nnnnnnnnnn  11760
nnnnnnnnnn nnnnnnnnnn nnnnnnnnnn nnnnnnnnnn nnnnnnnnnn nnnnnnnnnn  11820
nnnnnnnnnn nnnnnnnnnn nnnnnnnnnn nnnnnnnnnn nnnnnnnnnn nnnnnnnnnn  11880
nnnnnnnnnn nnnnnnnnnn nnnnnnnnnn nnnnnnnnnn nnnnnnnnnn nnnnnnnnnn  11940
nnnnnnnnnn nnnnnnnnnn nnnnnnnnnn nnnnnnnnnn nnnnnnnnnn nnnnnnnnnn  12000
nnnnnnnnnn nnnnnnnnnn nnnnnnnnnn nnnnnnnnnn nnnnnnnnnn nnnnnnnnnn  12060
nnnnnnnnnn nnnnnnnnnn nnnnnnnnnn nnnnnnnnnn nnnnnnnnnn nnnnnnnnnn  12120
nnnnnnnnnn nnnnnnnnnn nnnnnnnnnn nnnnnnnnnn nnnnnnnnnn nnnnnnnnnn  12180
nnnnnnnnnn nnnnnnnnnn nnnnnnnnnn nnnnnnnnnn nnnnnnnnnn nnnnnnnnnn  12240
nnnnnnnnnn nnnnnnnnnn nnnnnnnnnn nnnnnnnnnn nnnnnnnnnn nnnnnnnnnn  12300
nnnnnnnnnn nnnnnnnnnn nnnnnnnnnn nnnnnnnnnn nnnnnnnnnn nnnnnnnnnn  12360
nnnnnnnnnn nnnnnnnnnn nnnnnnnnnn nnnnnnnnnn nnnnnnnnnn nnnnnnnnnn  12420
nnnnnnnnnn nnnnnnnnnn nnnnnnnnnn nnnnnnnnnn nnnnnnnnnn nnnnnnnnnn  12480
nnnnnnnnnn nnnnnnnnnn nnnnnnnnnn nnnnnnnnnn nnnnnnnnnn nnnnnnnnnn  12540
nnnnnnnnnn nnnnnnnnnn nnnnnnnnnn nnnnnnnnnn nnnnnnnnnn nnnnnnnnnn  12600
nnnnnnnnnn nnnnnnnnnn nnnnnnnnnn nnnnnnnnnn nnnnnnnnnn nnnnnnnnnn  12660
nnnnnnnnnn nnnnnnnnnn nnnnnnnnnn nnnnnnnnnn nnnnnnnnnn nnnnnnnnnn  12720
nnnnnnnnnn nnnnnnnnnn nnnnnnnnnn nnnnnnnnnn nnnnnnnnnn nnnnnnnnnn  12780
nnnnnnnnnn nnnnnnnnnn nnnnnnnnnn nnnnnnnnnn nnnnnnnnnn nnnnnnnnnn  12840
nnngacaacc agagtcactc ttgtcaccat cttggtttgg gtgggatttg gccagcttct  12900
ttaccgcaac ctgttttatc agcaagctcc ttatgaccgg catcttgtgc tgacctccta  12960
tctcatcccg tgacttagaa tgccttaacc atctgggcat gcagcccaac aggcttcagc  13020
ttcattttac ccagctcctc ttcaagatgg agttgctctg gttcagatgc cgctgacaga  13080
actagcttat ggttggagac aatgtcatag ggaattattc ttcaaagatc gcaaaatcca  13140
gcttggatga gattccaaaa atcaaaaggt gctgagaaag caacttgtct agaatttcct  13200
cttcatgggc tggttgattt tgtttacaat gacaccttca gaaaaagtag gcgacacaca  13260
gtggctcacg cctataatcc tagtgctttg ggaggtcaag gagggagaat catttgaggc  13320
tagcagttct agactagcct ggacaacata gtgagacctt gtctttacaa aaaataaaat  13380
cagccgtgtg tggtggcgca tacctataat cccagctgtt caggaggctg aggcaggagg  13440
atcatttgag cccaggagtt ggaggctgca gtgagctatg atggcgccac tgcactccag  13500
ccttagtgac agagcaacat tctgaaagaa aagaaagaaa agaaaaaaag aaaaggaaat  13560
```

```
aaaagatgaa gaaagaaaac agaagaaaaa aataatttat atagaaaaaa agtccataat  13620
gactcaaaat attccctgga cactggaata gaatgatttt gtttattaaa gcttttcttt  13680
agttcgtcct taaacagttt agtattttct tttgaaaaca gattgtgtct tgtcaacttc  13740
attgattttc gggctgggct tggtggctga acacctgtaa tcccccaaca ctttgggagg  13800
ttgaggtggg tggagcgctt gaggccaggg gttcgagact agcctctagc ctcggcaaca  13860
tggtgaaaac ctgtctctac aaacaacaac aacaacaaca acaaacaatt agctgggcgt  13920
ggtggcacgt gcctgtagtc ccagcaactt gggaggccga ggtgggagga tcacttgagc  13980
ccaagaggtc gaggtcgaag tgagctatga ttgcaccatt gtactccagc ctgggtgaca  14040
gagtgagacc atgaaagaaa agaaagaaaa gaaaaaagag aaagaagaag gaaaaaaaaa  14100
gagaagaaaa aagtaaaaga aaaacataga aaaaaaatca gtaacgactc aaaatattcc  14160
ctggatagtt gaatacaaat agttgttgtt ggacgtgatt ttatgtatta aggcttttgt  14220
ttagtttatc cttaaatagg ttaggatttt attttgagaa tagattctgg tttatcaatt  14280
tcatcagtct ttgcaaagaa acagcttagg gtttccttta tgtttctccg ttaacttcct  14340
gttttcagtt acattgcgtt ttgctctggt ttttctttcg ttttttccac tcgttttagg  14400
tttctggaat ttcctgaaac attgtatttt gatacagatt ctgagctggt gctttggctg  14460
tcacaagcca gagggtccta gaagaagtag aattgtaacc gaggaaaact gttaggaaac  14520
tccatccctt ttgaccttca aaggtcaccg cctaattttg gtgttttgta gtctgatgtg  14580
ttcatagctt gtgactatta ggctctgatt gagctctgct tttttttaag tttctcttac  14640
tcagctggtg ctgttttagc tccagcttcc tcctctgtgt aatcaacact cccagtctcc  14700
tcttcaccca aaaagccaca gaaataagtg cagaaaacaa ggcagccgcc acctgctaca  14760
gaggcatgtc cttaaatacg atgcatttca ggacagctgt gtgagttccg ggagcttgtc  14820
ttccttcaaa gggaaaagta aaaataaaca ggaaggttgc actgaaagca ttctcaattg  14880
aaattgtgcc atttggctgt agtgtttctg atgctcattt agaactttgg aagttgtggg  14940
atggtgggca agtgtgtgac ctgggatgga gattctctac ctctttaaga gtgaaaccct  15000
ggctgggcgc cgtggctcac tcctgtcatc ccagcacttt gggaggccaa ggcgggtgga  15060
tcacctgagg tcaggagttt gagaccatcc tggccataat ggtgaaaccc cgtctctact  15120
aaaaatacaa aaaaatagct gggcgtggtg gcaggtgctt gtaatcccag ctacttggga  15180
ggctgacgtg agagaatcac ttgaacccgg caggcggtgg ttgcagtgag ctgagattgt  15240
gccactgcac tccagcctgg gtgacagagt gagactccac ctcaaaaaaa gaaaagaaaa  15300
agaaaaactt taaaaaatgc cggcacggt ggctcccgcc tgtaatccca gcactttggg  15360
aggctgaggt gggtggattg cctgagctta ggagtttgag accagcctgg gcaacatggt  15420
gaaaccccgt ctctcctaaa atgcaaaaaa ttagccgggc gtagtggtgc acgcctgtag  15480
tcccagctgc ttgggaagct gaggcaggag aattgcttga acctgggagg cagagattgc  15540
agtgaaccga gatggtgccg ctgtactcca gcctgggcga cagagtgaca ctctgtctca  15600
aaaaaaaaaa taaaataaaa attagctggg cgtggtggca cacatctgtg acagagcgag  15660
actccatctc aaaaaaaaaa aaaaaagaat tttggaagtt gtgggatggt gggcgagtgt  15720
gtggtctggg atagattctc cacctctcta aaagtgaaaa cctggttggg tggggtggct  15780
cacatctgta atcccagcac tttgggaagc tgaggtgggc ggatcacttg aagtcaggag  15840
tttgagacca gcctggccaa catggtgaaa ctctgtctct accaaaacta caaaaattag  15900
```

-continued

```
ccgggtgtgt ggtggcgggc atctgtaatc ccagctactc gggaggctga gacacgaaaa  15960
tcgcttcaac ccggaaggcg gaggttgcag tgagccgaga tcacaccact gtgtatgcca  16020
ctgcactcca gcctgagcgg cagtgagacc ctgtctcaaa aaatacacac acacacaaaa  16080
acaaaaaaca aaacacatgt agaaaaaacc acaaagacaa aaacaaaaca acaacaacaa  16140
caacaaaaag tgaaaaccta cttctttttc tggacacggt ggctcatgcc tgtaattgca  16200
ccattttggg aggccgaggt gggaggatca ctctcacctt tcaaggccca ggagttcgag  16260
accagcctgg gcaacacagc aaaaccccat ctctctaaaa ataaaaaaga gaaaaagaga  16320
aaaattgctt ctttctatgt agttggtgag ttttttcagt aggatgcttt gcatttcttc  16380
ctgcgtctgt ggctctgtgg tatgccagca tatacgatag tcactacaag atccgtagtt  16440
gtacacccag ccatacgcat cacaggtttt tggctgattt catgacaacg cttaaggctg  16500
ctgaaaacac tctaattctt tggatgttgg caaatgttca gatgaaacta agcggctggc  16560
ccacccacct gctcaggaaa gaatggccgc attgtgtggg aaaggaatcc tctgttccct  16620
agctggctgc ctggtgttct tgttgagtga gcagaacaga gagtgcccct gggtagacct  16680
gtgtgtgctc caaaaggcga ttttgtcaat tgttcccttg ggatgccctt gttccagaaa  16740
gcatgttctg tgtgactctc agctggggtt cccagactgt gtaaagaaaa catggtgatt  16800
catggctgtg tgcggttgcc catgcctgtc atcccagcat tttgcgcggc cgaggcggga  16860
ggactgcttg agcctgggag gtcaacgcca gcctaggcaa cacagtaaga acctgtctct  16920
acaaaaacaa aacaaaaaaa gtgtagccgg gcatggcgac gagcacctgt ggtcccagct  16980
actcaggagg ctgacgcagg acgatcgcct gagcctggaa gttggaactg cagtgagcca  17040
taatcacacc actctactcc agcctgggtg acagagtgag accgcatctt aaaaaaaaaa  17100
gaaaaaaaaa aggacattgt gattaatgaa aacaaacatt gcctggtgat aaggaaagta  17160
agaagtagga ttgttctcag attagtgacc caggagataa aggagtaaca gagtgtgcag  17220
gaagcaggtc tccaatttaa tagcaggatg gtgaagatag agcaagtgac ttctttctat  17280
tttttttaga aactgggtgt tgctttgtca cccaggctgg agtgcagtgg cgtaatcata  17340
gctgactgca gccttcacct cctgggctca agcagtcctc gtgccgcacc ttcccgagta  17400
gctgagacta caggcacata ccaccatact tggttaattt tttgtatttt tagtagacat  17460
gggggtgtgg ggatggtttg ccgtattatc caagctggtc tcagacttct ggcctcaaat  17520
aatcctcctg cctcggcctc ccaaagtgtt gggattacag gcatgagcca ctgtgcctgg  17580
tgagtaggta gctttttgtt tgtctgtttg tttgttctgt ttgtttgttt ttgagacagt  17640
ctcgctctgt cgcccaggct ggagtgcagt gatgcaatct tggctcaccc caacctccac  17700
ctcccgggtt caagtgattc tcgtgcctca gcctctcaag taggtgggat tacaggcaca  17760
tgccaccatg cttggctatt ttttgttttt ttagtaggga cagagttttg ccttgttggc  17820
caggctggtc tcaaactcct gacctcaagt gatccgcctc cctcggcctc ccaaagagct  17880
gggattacag ttgtgagcca ccgtgtccag ccaaacaaaa aaaagtctgt cttataaaga  17940
agatccctaa tttatgatga ttccatttat gatggtttga gttatggtag tttgagttag  18000
gatagttcga ttgaagattt tttgatttta cgatggtgag aaagacacag tccgtggaac  18060
ccgggcttcg agtacccatg caactgttct gtttttaact tgcagtgcag tattcagtaa  18120
attacatgag gcattcaata cttgattgta aactaggctt cacgttaggt gattttgccc  18180
agttgtaggc taatgtaaat gttgcgagca cgtttagggc aggctgggct aagctgtgat  18240
gttcgtaagt taggtgtatt cgatgcattt ttgacttacc atattttcaa cttacaaagg  18300
```

-continued

```
gtttatgggg tgtaatgtca tcattgtaag ttgaggagtg tctgtatcat agactggggg  18360
gcttaaacag acatttattg ctcccagttc tggaggctgg gagtcacaga tcaaggcgtg  18420
gcacattcgg tgtctggtga gggcttcctg gttcatagac ggcgccttct cactgtgtcc  18480
tcacatggtg gaaagggtga gggagctctc tagggtccct ttaataagga cattgatccc  18540
attcatgagg ctccaccctc atgacctcaa cacctcccaa aggccccacc tgctaacatc  18600
atcatcttgg ggatgaggat tcaacacggg aattttggga ggatgcaagc tttcaccagt  18660
agggttttct ttgtaaagaa atagaaggaa atgaaaaggc aggcactggg taggagagag  18720
ctacagaaga cagcggggtg gtggcactcc aggatagtgc tgtcccccag catcatttac  18780
accgaagaaa cctgaggcag tctttctgat gtgtcattct taggaaaacc accatgaatc  18840
tggcatctag ctatcagtga aactgtggga gagcttaatg gaagtaaaga catgtggtcc  18900
cagaaatgac agatcattcg gagaacctaa gagaggatta aaagcaaaag ggggtcatgt  18960
gcgctgtgac tcaaactttg ggaggtcgag tgggaagatt gcttgagccc agaagtttga  19020
gaccagcctg ggcaacatag ggagacccta tctctacaaa aaatacaaaa attagctgag  19080
tgtggtggca cacaccttag tcccagctac tcaggagtct gaggtgggag gattgcttga  19140
gcctgggagt tcaaggctgc actgagctaa gattgcgcca ctgcactcca gcctgggcga  19200
cagaacaaga tcctgtctca aaaacaaaaa caaaagcaaa acaaaacaag aaaatccaaa  19260
agggaaatat aagagaaaac aaaaaatctc actttgagac atctttttttg aagagttgga  19320
gaggatattg tctccatcca caaaaatagg atgttacaat aaaagagaaa gaggaaggaa  19380
gagctttata tgggactgct gaaagttaaa agaaaaacat tgcattaaat aaattagaag  19440
ggtgatctca tctgtgcctg tgacttcagt tatcatctta aggctttggg tctcaaagca  19500
cacatctagt ttagaccttt cttaggagcc ctgaagggtg cattgccaac tactgcccgt  19560
tggagggtcc atttttccca agatatccag caacactctt atatgagtgt cctgctccat  19620
tgtctcaaat taccataaac tggggaacgc aagcaacaga aatttatgct ctcccaggcc  19680
tggacaccag gagtctgaaa tcaaagtgca ggcaggattg tgctccctct ggaggctctg  19740
ggggaggaag cttcctgcct ctcccggctc ctgggggctc caggcatccc tgggcttgtg  19800
gccacagcac tccagtctct gcctctgtct ccacgtggcc ttctcatctg tgcctgtgtc  19860
tcctcttctg tctcttagaa gtacactggt cattggattt agggcccacc cttttccagc  19920
gcgatctcat ctcaagatcc ctagcttaat cacgtttgca aagttcctta tttccaaata  19980
agttcccatt ccaggttctg gacatgagga tgtgaatata tctttgtggg gaccacagtt  20040
cagtctacta gagttgtatg cagttccttc tggaggctct aggggaggat cctttctgca  20100
tctcccagct cctgggggct ccaggcatcc ctgggcttgt ggctgtatca ctccagtctg  20160
cctccgtctc catgtggcct tctcctctgt gtctgtgtct cctcatctgg ctctttattt  20220
ttttaaatta tttatttatt tatttatttt ttattttttt tggtgacgga gtttcgctct  20280
tttgcccagg ctggagtgca gtggcatcat ctcggctcac tgtaacctct gcctcccggg  20340
ttcaaatgat tctcctgcct cagcctcctc agtagctggg attataggca cccgacacca  20400
cgcctggctt attttttatg tttttagtgg agacgggatt tcaccatgtt ggccaggctg  20460
gtctcgaact cctgtcctca ggtgatccgc ccgccttggc ctcccaaagt gctgggatta  20520
caggtgtgag ccaccatgct cactggccat tttttattat tactcttttt tcctcttctg  20580
tctcttagaa ggacacccgt tgttggattt aggtcccacc ctaaatccag gatggcctta  20640
```

-continued

```
tctggagatt gtttacttaa tagaaactac aaagacccta ttttcttttc tttttttttt  20700
tttttttttt gagacggagt ctccctctgt tgtccaggct ggagtgcagt ggcgcaatct  20760
cggctcactg caagctccac ctcccgggtt cacgccattc tcctgcctca gcctcccaag  20820
tagctgggac tacaggcacc cgccaccaca cccggctaat tttttttgt atttttagta  20880
gagacgcggt ttcacctcgt tagccaggat ggtctctatc tcctgacctc gtgatccgtc  20940
cgcctcggcc tcccaaagtg ctgggattac aggcgtgagc caccgcgccc ggcctcaaaa  21000
accctatttt caaataagac gccattcaca ggcaccaggg gttaggatgt agacatattt  21060
ttgggggca ccattcaacc tagtctatcc ctcaatctca atacatcccc tgggttaaac  21120
atgaaatgtg tccccttctt cccccaaatc aaagcaaccc aaaagacccc tgtgcacctg  21180
cacaccttgc ctaagtcggc agcactcact gcgtagatgc ccaaacccta agctgtgatc  21240
atctccaccc tccctcttgc agcctaattg agcccattct ctgcccaagc accttatgaa  21300
caggacttta accctccatc tccaccacct tcccattttc actggaaatt ttacttctta  21360
aagaggcctt ccctgacccc ttgaccaagg ttagatgcat cccaatgttc tcctatggat  21420
atgttgtttg aagtcctcaa gtctgaacaa actcatgtga ggtcacccaa gttgttagac  21480
ttactgtcat taatgcttcc tgccctcctt ccagcccgac tggaactaaa caaaactaaa  21540
tgagggacca accttgtgtt gttcattgca gtttctcgga ggtagacagc acctgagacc  21600
caggaaaata tcaatcatga tggaagtgat gcattcattt attatattga ctcctttttt  21660
ttcccaaaag ctattttgtg ttcaaaacct ggactgcata aaccacttca ttgtggttat  21720
ggagtgttag aagccgacac ctaatcaaag aattcagtgt gtctcagtgg taggaactct  21780
aaagccatct aacattaaat gcaataaaag ttcagttgct tacgacctgg cgccgtggct  21840
cacgcctgta atcccagcac tttgggaggc tgaggcgggt ggaccacgag gtcaggagat  21900
tgagaccatc ctggctaacg tggtgaaact ctgtctctac tagaaataca aaaaattagc  21960
caggcgtggt ggtgggtgcc tgtagtccca gctactcagg aggctgaggc aggagaatgg  22020
cgtgaacctg ggagacggag cttgcagtga gctgagatcg cgccactgca ctccagcctg  22080
ggtgacagag cgagactccg tctcaaaaaa aaaaaaaaaa aagttcagtt gcttactctc  22140
catagcctca attcaaatcc tcagtagcca cttgtgagct tgtggctacc attttggaca  22200
gtgcagatag agaacattcc tatcattgca ggcgatacta cgggcagtgc ttgctccaaa  22260
acaggggtc tcaactgggg gccggccttc ccccacaggg cacttgacag tgtctgggga  22320
cagttgtggt tgtcactact gggggtggat gctgatggcg tgtggtgagt ggagcccagg  22380
gacgccgctc tgcaggtttg cagtgcacag gatggcccta cagagaatca tccagcctca  22440
aatgtcggca gtgctaggct gagagaacct gctttagcgt gagagtcagt ctctctcttt  22500
ctgtctctct ctctctctcc ccctctctcc cctccccact ctcgctctcc ctccctcccc  22560
cctccaccca tcccatctgt tatctaccta cctacctacc tatcaattat ctaaccatcc  22620
taattatcta tgtatcacct atctatccta tctgttacct atctacctac ccacctaccc  22680
atccatccat ccatccaatc aattaatcag tgtatcatct ttctctttcc atgtatgtat  22740
catacccatt gtccatccat ccatccatcc atccagtcag tcattcaatc aatcaatcaa  22800
tcatctttct atctatccat ctatctgtct atcataccca tctacctatc tttctatctg  22860
tctgtggcag agattctctg ccaatggcaa ttcagctcca tcagggagat acttcttccc  22920
tggacaagtc tggagacatt tttgttgtca cagctcaggt aggtgctact gataacaggt  22980
gggtggagtc cagggtcact gcttgccacc ttacagtgca caggatggcc ccaccacaga  23040
```

```
gaatcatcca gctccaaatg ttaatggact cagtttgaga agctgatctc aagggtaatt  23100
cgggggagtc ctgcgggatt gttgcatcct attgaagggg aaattaatga attttgtaag  23160
tgtaatgggg cggggggact gggttaagag agaatactaa ctgcttatcc ctcctctatg  23220
cccagagagg cttatctgtg ttccatcgtt ttacattcct tgaggcacgg cgagttcttg  23280
cttccctccc tagtgcagct gtaaagtcac aaggttgaca agcaattgct gcaaaagtat  23340
gtattcccaa gaatgtaaga cgtacggtgt aacaaatgca aaagagtaat taactgcctt  23400
tgttctcgct tctgcaagta tgctttctgc agcacgtaac tcccgccaca aactgcttaa  23460
aaggtgattg atccctctgt acggggctca gactttctag accctagtcc gactgagctg  23520
gtgatcacct taataattat aattataatg gtcatctcct aactgtgctc ggtctctacc  23580
gtctctgatt tatcccgcaa cactatcgtg gaggtaggct aggatgtatc tttaacctgg  23640
ctggattgta ttgtagatgt gtgaaaacca gcccttgttt ttcttggtag agttgcactc  23700
aaatgttatt gaaagctgca catactgtgc ttgtataaat acactgagcc agaaatcacg  23760
aacctttccc tggcttcaca tctgttagtg ttgtgggaga agatgagaat ttcttgtttt  23820
tcttttcact tctgtgatta tacattttgt attttgttgt tgttttttgg gacagggtct  23880
cgctctgtca cctaggctgg agtgcagtgg tgtgatcata gctcactgca accccccgccc  23940
ccaggctcaa gtgatcctcc tgcctcagcc tcccaagtag ctgggactat agtcgcatgc  24000
caccatgcct ggctgttttt tgtgttttta gtagagatgg ggttttgctt tgttgtctag  24060
cctggtcttg aactcctgtg ctcaagtgat ccgcccacct tggcttccca actgtgggga  24120
ttacaggtgt gagccactac tcacggccac attttgtatt tctgatgaga aagtgtaatt  24180
taatacactg tacatcggag agtgtagttc tgaaacatct gcatctttta aattaggaca  24240
gtgtaaaaat ggaatgttgt ttgactcagc aaaattttga gggagtttgt ttccaactgt  24300
ctagaccagt gaactcacca aactatctac cacacactgc ttggctgaat tggctctact  24360
gtttttaact gaagtttgaa gtaaatattc caagcttaaa aatatatctt gttcctcccc  24420
cacccactgg ttatagcagc aatataaata aaaaatacct tcccaagaat atccaaagca  24480
tacattcttt tctaaagtaa acattgttta tagagataca atttctatac cataagattc  24540
accctttaaa aacacatagt tctttagttt tcagtttatt cacagagtaa gcacactgtt  24600
ttttgtttgt tttgtttttt tcgagacaga gtcttgctct gtcacgcagg ctggagtgca  24660
gtggtgccat ctcggctcac tgcaagctct gcctcccggg ttcacgccat cctcctgccc  24720
cagcctcccg agtagctggg actacaggct tccgccacca cactcggcta atttttttgta  24780
tttttagtgg agacagggtt tcaccgtgtt agccaggatg gtctcgatct cctgaccttg  24840
tgatccgccc gccttggcct cccaaagtgt tgggattaca ggtgtgagcc accgcgccca  24900
gcccattcat tcatttttttg agacagagtc ttgctctctc acccaagtta gagcacaggg  24960
gtgcgatcac tactcactgc tgtcttgaac tcctgggctc aagtgatcct cctgcctcag  25020
cttcccaggt aacttggact gcaggtgtgt aaccaccacg ccctgctaat tttttgatct  25080
tttaatagag acggggtctc gttatgttac ccaggctggt ctaggactcc tgaactgatg  25140
tccttccgtg gcctcccaaa gttctgggat tataggcacg agccaccatg cctggcaaca  25200
cacactcttt tttaaaaata ctttttaaca gcttttttttc ctgtctataa aatagaaggt  25260
cattatactt gtttgcagca gtaattccaa aaatcgactt cgtaaagaag aactgcgtgt  25320
ttcacacact tatttcctcc atggtagcat ttaatgttct tttattgatt ttacccaggg  25380
```

-continued

```
gggaaaatgt caaggaaaag aactgagttt gaggatgata aatgtgtacg ttctgatatc  25440
attattttga aacaattatt taatgcaatg cgtcggtttc acttatcaat ttaacataaa  25500
ttgaacctat gttgatgaac tatttctata gtcataaatt ttaaaaggtg agaaagttat  25560
atagtgaaat gcatctgttt ttgtgcctca cctgtgcaga atttgccctc tccttccacc  25620
caggtgccca tattaatgtg tcttgtatat ttctccaaag tcctttctca atatagaagc  25680
aaattatcac ttatggagaa gagcctcact tttttttttt ttttttaaac agatgggggt  25740
cccgctcttt tgcccaggct ggaatgcagt ggtactatca taattcactg cagcctccaa  25800
ctcccgggct caagcaattc tcccatctct gcctcatgag tagctgggac tactggagca  25860
taccaccaca cccggctcat taaaaaaaat tttttttttt tatagatggt gtctggctat  25920
gttgcccagg ctagtctcga tctcctgggc tcaagtgatc cttctgcttc agccttctaa  25980
agtgctggga ttacaggcat gagccactgc tcctggcctc cacccatcta taggtgtgga  26040
acaagagcat gttccctccc aagctaatgt ggcaggtaac tggcctccca ggctgtagac  26100
aagatggatg gggctgtgc ccacttcttg agttaacctt tttttttct ttggagacag  26160
agtctcgctc tgtcgcccag gctggaatgc agtggtgtga tcttggctca ctgcagcctc  26220
cgcttcccag gtttaagcaa ttctcctgcc tcagcctcct gagtagctgg ggttacaggt  26280
gcctgccacc atgcccggct aatcgttgta tttttagtag agatggggtt tcaccatgtt  26340
ggctgggctg gtctcgaact cttggcctca gatcatccac ctgcctcggc ctcccaaagt  26400
gctgggatta caggcgtgag ccagcgcgcc cagctgggtt ttaccttttt tgtttgtttg  26460
ttttttgaga cagagtcttg ctctgtcgcc caggctggag tgcagtggtg tgatcttgcc  26520
tcattgtagt ctctgcctcc tgggttcaag caattctcct gcctcagcct cccaagtagc  26580
tgggattaca ggcatgtgct gtcacgccca gccaattttt tgtattttta gtagagatgg  26640
ggttttccca tgttggccag gatggggttt taccttttt gaagtgtatt ttccatgtag  26700
ccacctctct tggagtgtcc atgaggaaca cgatgctgtc cttggtgtct cagcggagcc  26760
actgtgacgc tctcctcttg caaagatttc tggtcatgat gtctcaacat tggcctgttt  26820
ggggtttttt ttctcctgca ttttagggag aattagggct catccaccct caccttctct  26880
cccccattga attggtgcat cctgtttttt tttagcccct gggatgccca tgttcaagat  26940
tccttaagca tcacagttta aggaaagaaa tgcagattat ttaaaatatg tggggtgagt  27000
gtgcagggtg gtgatggaca atgcatgtgt ttaattcagg gactgttgtg ccagctgtgt  27060
ttgagcctta ggaattctta tagttgactg gcatttacag tttattaagg cacttacctc  27120
ttaggtgtat aatcctcaaa acatctaaaa aattagtgat ttttgttatc caagttactt  27180
tgacatcagc catttgctgt ctcacccaca tgatttctca ttatgttacc ttattattgg  27240
ctaagttaat ctgcttactg aggacctgca tgtgactttt cccattaaaa gtaagttaag  27300
tctgggcgca gtggctcatg cctgtaattc tagcactttg ggaggctgag gtgggaggat  27360
cccttgactt tgagaccagc ctgggtgaaa aagtgagatc tcaaaaacaa aattagccag  27420
acatggtggc gcatgcctgt agtaccagct acttgggagg ctgaggtggg ctgatggctt  27480
gagcccagga gtttatgctg cagtgagccg agattgcatc actgcactct agcctgtggc  27540
acagagtgag acctgtctct taaaaaaaat taattaatta attaaaaata aataaaagta  27600
agtccaagtg gagatggttg gtggtgttgg ttggataaca ttgtgaatgt atttaacacc  27660
gttaatctgt acacttcaaa atggttaatt aagatggtaa attttatgtt gtgcgtattt  27720
taccataatt aaaaaataga tttggtctgc gtgatggctc acgcctgtga tcccagcact  27780
```

-continued

```
ttgggaggcg aggtgggcgg atcacctgag gtcaggagtt ggagaccagc ctggccaaca  27840
tggtgaaacc ccgtgtctac taaaactaca agaattagtc gggcgtagtg gcaggcacct  27900
gtaatcccag ctactctgga ggctgaggca gaaaaatcgc ttgaacccag gaggtggagg  27960
ttgcagtgag ctgagatcgc gccactgaac tccagcctgg gtgacagaat gagactctgt  28020
ctcaaaaaaa aaaaaagatt taaaacaaag taactatgtt caaggccagg tgtagtggct  28080
cacgcttgca attctgacac tttggggcgc tgaggtggaa gattgcttga agccaggagt  28140
tcaagaccag cctgggcaac agagtgagac cccatgtcca aaaaaaaaaa aaaaatcatc  28200
agctttcatt ctgggatcgt aagtagagac attgtttccc agacctggta cagatggaac  28260
ctgcctacgt gtcttcaatg ggcatcttaa gacttatgtt ttggacatat cagacttttg  28320
gaataaagga gctgagttgg gagtacaaac tcctcttctt atccatttcc ctgtggcagg  28380
agattttgct ctcagccccc acttactggt gtgagatcct tgattctgga aggtgagctg  28440
tgctgttcag cccacaggtc ctcatgaatg tctacattca gtgccacgca gaataagaag  28500
aaacacacac cagctctgct tctgtgaagc ttacttttttg ttgttgttgt tgagaggggg  28560
tcttgctctg tctcccaggc tggagtgcag tggtgcagtc atggcactca ttgcagcctc  28620
tacctcctgg gctcaagaga tcctccctgc tcagcctcct gcgtaactgg gaccacagat  28680
gtgcgccacc atgcccagct aatttttaaa ttttttgtag agacagggtt tcaccatgtt  28740
gcctgggctg gtcttggacg cctgggctcc agtgatccac ctgccttggc cttccaaagt  28800
gctgggatta cagacatgcg ccaccgagcc tggttttgct tactttttct tttttttttt  28860
aaattcctct tagcctatct tgggggaggc gggtcagtgt tattccggtg tacatacaac  28920
aaaatcaccc atttgaagtg cacactggga ggagtccttg ccaaatggat agggctgggt  28980
aaccactgcc acatgggaca tttgggaagc cgatgtttga atgttttcac gcttacagat  29040
gcattcattt actacgttta ttattctgtg tgatgtgctt tctgtgtgtt atttcactta  29100
aacccagtgg gggtaaagat tatgatccct atttggtaga tgaattttag agaggttagg  29160
gggcttgtca aggtcacaca gcttttaacc gtgatgggat gacgcctctt gaatgaggct  29220
tagtagtgag atggctgagg aaggaaaaaa gtaggaagga gagaaagaga gaaggaggga  29280
aggaagaaag tagggagaaa ggaaggaaag gagagggaag gaagggagaa aggaggatgg  29340
aaagatggaa tgagaggaaa gaaggaagga aaccgatgaa agaaggaggg aagggctgaa  29400
ggaaggaaca ggtgccctgt tcaggtgggt ttatcctcag gaaggaccca agatggaaag  29460
tgtgtatgca agaattattt taggccaggc gttgtggctc atgcgtgtaa tcccagcact  29520
ttgagaggct gaggcaggcg aatcacttga ggtcaggagt ttgagaccag cctggccaac  29580
atggttaaac cccatctcta ctaaaaatac aaaaattagc tggctgtggt ggcacatgcc  29640
tgtaatccca gctacttggg aggctgaggc cggaggatcg cttgaaccca ggaggtggag  29700
gttgcagtga gctgtgatcg tgccactaca ctccagtctg ggccacagag caggactcta  29760
tctcacaaag tagaaataaa taaaaaataa ataaaaacag agatgaggac acagacgcac  29820
atagaggacg accctgtgag gacacaggga gaagatggca tcgacaagcc taggagagag  29880
gcctcaggag gaaccagccc tgcccacacc tgggtctccg acttccagcc tccaggactg  29940
tgagagaaga aagttctctt taagtcctcc agtctgtgtt aggttattac agtagttcga  30000
gcaaagtact ttatttacat agaagtctgc cacaattatg agccctgaaa ccctttccca  30060
ggatgaaccg aggtcagagt gtaattaata ggtacttttt ttcatttacg tttagccact  30120
```

-continued

```
agatttttt tttcaacaga gagtagcgaa tactgcagaa gctgaatgag atgaagctta  30180
agtcagatct ttatgcacct cagaatattt gtactgatga aaagaaataa ccaacacttg  30240
atagagggaa agattgagac ccagaaagta atctctccct gtgaccactc ctaccaaatt  30300
cttgcttaac taccttattt tgttcgtttg tttgtttttg tttttttgag acggagtctc  30360
gctctgttgc ccaggctgga gtgcagtggc gcaatcttgg ctcactgtaa cctccacctc  30420
ccgggttcaa gcgattctcc tgtctcagcc tcctgagtag ctgggattac aggagcgcgc  30480
cactaccacc cggctaattt ttgtattttt agtagagacg gggtttcacc atgttggtca  30540
ggctgatctt gaactcctga ccttgtgatc cacctgcctt ggcctcccga agtgctggga  30600
ttacaggtgt gagccactgt gcctggccaa ctaccttgtt ttttttggat gaaaatgtgg  30660
ttcttacctc agtaaagatt atgaagggat ttatgtacag atgactaaaa tatcagccat  30720
tagtttccta tttgtttttg ttgttgtcat tttttgtttt gagacagggt cttgctctgt  30780
tgcccaggct ggagtgcagt gatgcgatct tagctcactg cagcctcgac ctcccaggct  30840
caggcaatcc tcccacctca gcctcccaag tagttgggac gacggctgtg caccaccaca  30900
cctgggtaat tttttatttt tatttttgta gctgggatct cgctatgttg cccaggcagg  30960
tcttgaactc ccggcctcaa gtgatcccac catctaggcc tcccaaagtg ctggacttac  31020
aagcgtgagc caccctgccc agcctagttt acaatttgaa cttggttttt catctcggct  31080
cctttgaaga cttctgtctt ctcccatgtt tggggcagct gtgtgttgtg gacattcctt  31140
agtgatcggc ctgggaaggc tcagacatgt ctaggctgcc tttgtaggaa tagggattag  31200
tagctcctta gccccactct ttcctgggat gttgctgttt gctgaggtct gcacagttca  31260
gaccaccctg gaagcctctc tcaggttctc agagatggtg gagttatacc tttgaccgtg  31320
agctcgcagc attgctaggg aatgtacttg gctaaatttg gaactatttg gttgaatttg  31380
taccccttgg gcatatttgc tttggtaaca taccacagac tgggtgcctt aaaataacag  31440
aagttaattg tttcacagtc ctggagacca caactctgaa gtgcagatgc ggcagggctg  31500
tgctccctct gcgggctcta ggggaggctc cttcctgcct ctcccagctc ctgggggctc  31560
caggcgtccc tgagcttgtg gccgcatcac tgcggtctct gcctccgtct ccacatggcc  31620
ttctcctctg tgtctgtgtc ttctcttctt ctcttacagg aacacccgtc attgtgttta  31680
gggtccactc caattttgga tgacctcacc ttgagatctt taacttaatt acatctgcaa  31740
agaccctttt cccaaatgag gtctcattta caggttctgt gggtcaggac atggacatat  31800
ctttctggga gaccatagtt cagtccacta cagttgtatc cagttgtttc tggaggctcc  31860
aggggaagct ccttcctgcc tctcccagct gctgggggct ccaagtgtcc ctgggcttgt  31920
ggccgcatca ctgtactctc tgcctctttc tccacgtggc cttcccctct gcgtctgtgt  31980
ctccttatta gttcaccact catattgcac caccttcagg atgacctcac cttaatatat  32040
accttttttt ttatttcatt ttttaaaaaa gtggagctga ggtcttgctg tgttgcccag  32100
gctggtctca aactcctgtg ctgggattac aggggtgagc cactgtgccc agcctttgtg  32160
tatatcttaa tcacatctgc aaagaccctg tttgcaacta aggtcccatt cacaggtacc  32220
aaggattagg atgtcaacgt atcttttcca gggcacccca ttcaatgcac acaaagtggg  32280
gagaggggag attggctgtg tttaggtgac ctgtgaaagg ccgagctagc tgtgcggcgt  32340
tgctcttgca gcacagagga agaactgggc tcagatggtg tcagctgttg gtgtctgaga  32400
tcatccgtga atctactccc gggaatgtgc tgcagtgaga cacggtcctt ctcccgtcac  32460
cttcctgacc ccatcccata tacccacgga ccccaaggga aagtactcag ggttggttgg  32520
```

-continued

```
tttcttttcc gttttgtgac cgcgtgaaat tccatgtcac ggtccctgtg tttattccat  32580
acagctctcc tgaagtgttt tgagttctag caaaatttaa aaatataacc aaagaaactt  32640
aaatccgtgt ttctcctctt tctggacact tctttagtat gaatgggcat cgtgatgata  32700
aacacggtgg cctgctgtct ttgcttctct ctctgctggc cgcctccttc cttccctcca  32760
aagtcacagg caagagggat ttagggtttg ctgggcttga ggaagagagg aaaaggccat  32820
ctcttttcac agtgagaaat gtgttttctg ttctttctca tacctcgctt tgtacattta  32880
aaaaaattat ttctctttag atttttgaac caagagagat atatttatta tttaaaaaaa  32940
attttttttt gagacaaaat ctccctctgt tgcccaggct gcagtgcagt ggtgcaatct  33000
cagctctctg caacctcctg ctccctggtt caagacattc tcatgccttt ggagtagctg  33060
ggattacagg tacccgccac catgcctggc taattttttt gtatttttag tagaggctgg  33120
ggtctcactg tgttgtccag gctgatctca aactcctggg ctcaagcgat cctcccatgt  33180
tggcctccca aagcactggg attacaggtg tgagctactg tgcccggcct atttcttttc  33240
taaatagagg cagggtctca ctatgttgcc ctggctggtc tcaacctcct gggctcaagc  33300
aatcctcctg cttcggcctc ttgagcagtt gggactccag gtgcacacaa ccatgcctgg  33360
ctaattttttg tatttttttcg tagagatagg gatctcacca tgttgcccag gctggtcggg  33420
aattcctggg ctcaagcagt cctctgacct cagccttcca gtgtgctggg attacaggtg  33480
tgcaccactg tgcctggcct tatttatttt ttatttattt atttttggag acagggtttc  33540
attctgttgc ccagactgca gtgcggtggc aaccatagct cactgcagcc tccacctcct  33600
gggctcaagt gatcctccca cttcagcctc cccagtagct gggactgcag gagtgcatca  33660
tgactcctgg ctaatttctt ttaataggga tgagatctct atgtttttgt agacaagggg  33720
ctctcgctgt gttgcccaag ctggtcgaga actcctggcc tgaagccatc ctcttgcctt  33780
ggcctcccaa agtgctggga ttacagttgc gagctacggt gcctggctgt agattccccc  33840
cagcccccaa gccgccagtt gtgagtcttc actaacaagg gaacctttca gcattttcca  33900
tggtcatggt gattcaccta atattttagt tctgctgagt tgtctaaaca ttcgggataa  33960
aggctgtcat tttttggtga ccgtaatgtg tatgtgtatg tttacagtta cacatgcctg  34020
tatttgggtg gagctcagaa gatgcccatg gcatttttct gggaaagttg aagtttatga  34080
tgtttgctct ttattgggag tgtggaggtc gtctttctcc ttcttcccat ccctccagac  34140
agaaagctgg gatgtggcca ggtgcagtgg ctcatgcctg tactcctagc actttgggag  34200
gccgaggtgg gtggatcact tgaggtcagg agtttgagac cagcctggcc aacatggtga  34260
aaccctgtca ctactaaaaa tacaaaaatt agccaggcgg ggtggcgggc accggtaatc  34320
ccagctactt tggaggctga ggcaggagaa tcgcttgaac ccaggaggca gaggttgcag  34380
tgaactgaga ttgcgccatt gcactccagc ctgggcgaca gagtgagact ctgtaacaac  34440
aacaacaaca acaacaacaa caacaacagg ccaggatgtg tttgtgtgtg agttggaccc  34500
aagggcttgg gaaggatgga tagggtaggg gaggagggat agatggatga gggaatgcag  34560
agagagtggc cacactgtca gaggctttca aaaagcagga ggttctccag tgggagagag  34620
gagacctgag tccaccccgc attaatgttt acagatcaga attgcacaca tagaatggct  34680
cataaatctg atccaccttc ctcgtctggc acttggctgg agaaacaact ctttgaatgt  34740
tggaggaaaa gcccactgta ttgcacctgc tataaaaagg gcgtgcccac cttaaaagta  34800
gccacacctt cccgagattg ccatggtcct tctaagtctc tgaaatgtat agatcaggta  34860
```

-continued

```
tatttgggaa tttggggatt tttctaaatt tgggatgaga atgggtgcat gtccttttta  34920
attatacaac accctcagca gagtctgggc tggatgttgt tatcaagaca agaatatttc  34980
tgtagtgaaa taggtagata ttcaccccaa ggaggatcaa gcctgaacag tctcacgtta  35040
ggcaaggtcc agttttgcgg ccaggtgtgt tgatgaagac actttgagta ttcagagcct  35100
ttagctttag ccactgtggg taagggattg tagaacccat acttaagctt tccccttaaa  35160
gctttgactt taatctccac attgcagccc tgcaaaagaa cagaatcgtg tcctttgcag  35220
caaagtggat gcagctggag gctgctatcc taaacaaatt catgcaaaaa atcgagagcc  35280
agatattgca tgttctcact tataagtggg atctaaacac tgagtacttc atggacacaa  35340
agatgggaac aataaacact ggggattcca aaaagaggaa gggagggagt ggggaaaaga  35400
ctgaaaaact tcctattaga aactgtttac tacttgggca acgggatcat tagaagccga  35460
aacctcagca tcatgcaata tacccatgta atgaacctgc acatggaccc cctgaatcta  35520
aaattaaaag aaaagacata aactccacat ctgatttccc tcgtgcataa cactactact  35580
tagcttggag agagatggag gggatctcta gggtggggaa tggaccactt accttcaaga  35640
tctcccttat caggaaggaa agagctgacc tgcctagaaa cacttgaaaa cactcttttt  35700
ttatgtctta ttgggcaaag ctgggtcaga tggccaccct tagctgcaga gaaggctaca  35760
aatagacatt ttctcctcaa gtgggataat gataactggg gaatgtgtac tggagagcct  35820
tccaacacca agcggggaag atctaccagc accattaaat gttgcctttg tcttctgtgc  35880
acttaagctg ataaacctta aacattacag catgccactt ctgtctgctt tgaataaggt  35940
tgtttaccga catacttctg cagtctgatt gtggcgttgg cgggactgac aatatctccc  36000
agggtagcgc aaagatccgc tgcagtgcat aagtaacgtg ttttgagttt tgtatgttta  36060
taatgcacac agctcagaga aagctttaaa gaagtcacag aagtgtaaaa aatctgttga  36120
gtcatagctg ttgttcttaa agtaggcatg gagaattctc tctgttgagg gtcaaataca  36180
agtactaaga cagaatgtta tgcagtaaac acagccaagt aatgaatggg ttccttgggg  36240
tgggtgatag agaaagataa ataaggagga aggaaccaga tagaggaaga aaagtcaagg  36300
accatattca ttgcattatt agaattttag ggtgtggcaa gaatttaatg tttcctaata  36360
atatgcaagt tctgttggaa agaagagcaa caggagacta aaaggttaaa aggttactct  36420
gttgcccatt tcataggtcc aatggcagga taagcttggg ttggatgcca gtgttcctga  36480
ttcctaattg tgttttatcc aattgaaaca tcagtggcca tagtcaaaca cctaaactgt  36540
atcagttcac agtcctcaaa gcccttctcc cacttcctgt ctttgacctg attccaccta  36600
attttgtcca caccatgttg tactgtaata aaacctattt tatttccaaa ttaactaaga  36660
gaatatactt taaaaatgtg ttactatttc attatttgtt tacttttttt aaagaaatat  36720
ttaacacctg tcagctattg acattgtttc cttcttacac tttttcttta tcttgtagtt  36780
cactttctat ttctgccata ataaaatatt cagtatcgga aacttcactt aaaaagcaaa  36840
ggttacttct cctcctccct tcccagtctg ccctataagc tagtaaattc atcattcatt  36900
agcttagata ttttacaaca tggggatttt agtttacagc aaatactcta agtaaaattg  36960
gtagcttaag tacaactttt tcttttcacg ttaccatgtg caatcaatgg cattccagac  37020
tcttggaagg aaatccattg tatggttgtg gtcttttttt ttccttctca aaccagtcaa  37080
aaatacccag tcacaattta aaaaattatc cgcccttggt ggtgcacgcc tgtagtccca  37140
actatttggg ctgaggtggg agggtcactt gagcctggca ggtcaaggct gcagtgagct  37200
attgattgtg ccattgcact tcagcctggg caacagagag agaccctgtc tcaaaaaaaa  37260
```

-continued

```
aaaaaaaaaa agacaaaaca atataatgtg atctaccctc taagcaaatt ttcatatata  37320
caattttact attgtatatg tgagctattt atatataaaa tttcatttat cagttcagta  37380
ttgttaacta tatgaactag gtgtatggta gatctccatg gtttatcttg ttcaactaaa  37440
actttgtatc ctttgaccaa tatatttccc cttccccctc aagccctacc ctctgataac  37500
tacctctcta ctctctgctt ctatgagttt gactattgta gattctgcat tagtccattc  37560
tcatgctgtt aatgaagaca tacctgagac tggttaattt ataaaggaaa gaggtttaat  37620
ggactcacag ttccacatgg ctgcggaggt tccgacagtc atggcagaag gtaaaaggag  37680
gagcaaagtc acgtcttaca tgacagcagg caagaagaga gcccgagcag ggaaactccc  37740
atttattaaa acatctgatc tcgtgagact tattcactat caggaggaca gcatgggaaa  37800
acccaccccc atgattcagt tacctcccac ctggtctctc ccacaacacg tggggattat  37860
gggagccaca cttcaagatt agacttgggt ggggacacag ccaagccatg tcagattcct  37920
tgtataagtg agatcatgca atatttaata tttgtttttc tgtgcctatc ttatttcact  37980
gaacataatg gcctccagtt ccatccatgt tgctgcaaat gccagagttt ccttcttttt  38040
tagggctgaa tggtattcca tcgtgtatat gtaccatgtt ttctttatcc atttgccctt  38100
ggacggacac tgaggttgtt tccacgcctt ggctgttgtg aatagtgctg tcataaacat  38160
gggagtgcag gtgtctggaa gatcctggtt ctcttgggtt ttgcaatcta gcataaagca  38220
ggcacaggag taccagccaa tgaatggata ggtaaatgga tcaatattga tcggtgagat  38280
ttgctcgtca acagatgttg gttcctcaga aggatacact tccaaaccat cctttctctg  38340
aatgtcagtt tctgagaagc ctctctgctg tttggggtgg gtgtgatcac ataatacggg  38400
agggcagttt tgttttagtt gctcatctct gtctgcagct gtgaatgcgt tgtttaaaaa  38460
tattgctgag gaatgacttg catgtcagta aggggctgct gacgctggga tcaaggtacg  38520
tcaaaggcaa tttagggata ctctagaaat cctgcatcag ttgcagtggc tcatgcctgt  38580
agtcccagca ctttgggagg ccgaagcagg aggatcactt gagcccagga gttcaaggct  38640
agcctgagca acgcagtgtg accccctctt tacaaaaagt acaaaaatta actgggtagg  38700
ctgaggcggg aagattgctt gagcccagga ggtagaggct acagtgagct gtgatggcgc  38760
cactgcacta ttcgttccat taacccaaga acatttatgc tacgtgaaga atatttcaat  38820
atgtgcgtga acacgtgcac accttgtagg atcagtgtgt tacaggaaga ggaggaggat  38880
gaagaggaag aagaggagag ggaggaggag aaaggaggag gaggaacaag caaagcttgt  38940
ttagagattt tgattttctt ttatatctca ttgactatta gatttcttca tttacatgca  39000
ccccagtggg aggaagagga gggagaggag gaggagatgg aggaggagga agaagtggaa  39060
aagaaaagga tgtagaggag aaggaagaga tgaaagagaa ggaggagaag attgaggaag  39120
agaaaaaaga gaaggaagag atggaggagg ggaaggagga gaagagagtg tttggattga  39180
aaatgtccca gcagaataca gtagagctat tggttttctt ttatatttgt agtggttgca  39240
gttgttgttg ttgttttgtt ttctgtttgt gggcacctat atagcacttc atcccaaccc  39300
acgccagatt gtagaatacg gactccgtac tttgagcaag ccttaatgtg cgttaaggaa  39360
acagccgtgt tgaggagggc tgtgtgtttt acaccctgtc tgtatttctg ataaaaccag  39420
agagcctgaa gagaaaaagg catgttatat aaatacattt actattactc taatgcttct  39480
ccatgtgggt gtgtggggcg tgtgggtgtg ctgtgtgcga agactgatct gcagaaatta  39540
tggccagttt gtccccaaat tgaggaacca ttcagaggca gatggctctc tctgtctccc  39600
```

-continued

```
tctctctccc tctttctctc tctgcaattt ctgtattcag tggaaaattc caggtgagcg  39660
cctctcacta aatgccatca gcccacgtgc accatgacac aaagtctctg aaagtttcac  39720
ttggggtctg tgtttgccgt cctggtgcag ccccccgctg attgcatggc tgtggtggtt  39780
tcttcctttg tcggaagact taatgacctc tgtcgatttc ttctctctcc aggcactggg  39840
acgttcgggc gggtgcacct ggtgaaggag aagacagcca agcatttctt cgccctcaag  39900
gtgatgagca ttcccgacgt catccgccta aagcaggagc aacacgtaca caatgagaag  39960
tctgtcctga aggaagtcag ccacccgttc ctcatcaggc tgtgagtccc ctcctgaagc  40020
ctctccccac gcactctccc tagacccctg tgtgtctctt cttataagaa gctgggtggg  40080
ccgagaccat ggcctgcgtg caaagcctta ggccacagca gtctccacct gtcaggtctt  40140
atcagcctct gatcttagag ctggaatacc tccagggctc ctgacctcca tggctgacca  40200
ggtccaaaaa gaaacgctct gtgttcagaa gtccgtgccc aaggcccctt gctcctctcc  40260
tgggtgaacc aagtatctct gcccggaaaa ggatgcagaa atctttgtct cctcacctcc  40320
ttgggttctg catctatagc tctcggcaga actggttaag ttggttttta agggaccaca  40380
gtcacgtgga cggggctggg cttcaggttt cgttgggttt ctggttgact gtggatgaga  40440
gataccccgt tgagatgcag cccacacact tccagctgat ggtacacaac agtcttatgt  40500
cctagggtag gtgtgatagt ccattcaggc tgctataaca aaggatctta gactcggtaa  40560
tttacaaatg acagacattt gcctcatggt tctggaggct ggaaagtcca agatcaagac  40620
acggtggatt cagtgtctgg cgaggacccg cttcctggtt catagatggc gccttttcac  40680
tgtgtcctca catggtggaa ggggtgaggg atctctctgg ggtccctttt ataagggcac  40740
tcgtcccatt catgagactt caccctcatg acctcccaaa ggacacaaca cctaacacca  40800
tcaccttggg ggtgaggatc caacataggg atttgggagg acacaagata ttcagaccat  40860
tccagcaggg taattccatt tccacccaga tgccttagac aaggatgtcc tgcgtgtctc  40920
tcctttccct ccatgggtgc cttccatcca attcccacgt cttccctccg ccatcttgct  40980
accatgcctc tcctgtccac ctatccatct tctgctttat ctgggtcccg tctctctgcc  41040
ctgattttct gtactggctt ccctcctacc tggtctttct ctcccagcct tgctcccctt  41100
gaagacattc ctcactttat agcctcactg gtcctcccag gtacctctgc aatgacctgc  41160
ctctctcctt tcatcctcag ggtactcctg aagtatccca tataaagccc cagcaatgca  41220
gcatcctcct accagtatcc tcgtggactg gccccctgcc accacctccc tacaggagaa  41280
ggtagaaggt gctgttcaca cactcattcc ggggcttctc ccaggccacc cttctttgac  41340
aggcctcctt ctttgctctc atcattgtcc ttcacttccc ccatctaaga aacacctacc  41400
tgttttccct cattcacctg ctgtccccgg gacacagggt gcctcccatc atgttcttga  41460
agcacctcgt gtgtactgga acaagtgcac ctgccttctc ctctagaccc aatgctgcct  41520
aagctccgaa caaaatcata tgcagaggat gggcgcggtg gctcccttcc tcccttcctt  41580
tcttcctttc tgcatttctc tttctttctt gacagggtct cactccttct tgcccaggct  41640
ggaattcagt ggcacaatca tggcccactg cagcctctgc cgcctcccaa ctagttgaga  41700
ctacaggtat atgccaccat gcctgaccaa cttttaaaag tttttgtagg atgaagtctt  41760
gctgtgttgc ccaggctggt ctcaaactcc tggcctgaag cagtcctcca gcctcagcct  41820
cccaaagtgc tgggattgca ggtgtcagcc cctgcacctg gactgagaat gcatgtctgt  41880
tgtctgccgc gtccctccac cccaaccccc agtttgtggt actttgttaa tgatagccct  41940
gaggaactca cacacacccc ctgcgcctcc tggagcagga gagcagccga gacgatgggc  42000
```

-continued

```
tcctgagtac tctacagttc agaaatctaa aatcccacag aagaaccgca tggacatggg  42060
agtgggtgga gtatacaagt gagagaattc cccaggatgg aattcttgag ctcccgcaag  42120
ttaaaaaata gggaggagct tgtagaacag agctttagtt aggtagttct cctttcttca  42180
aggcaggata gctcaagact gttttccttg gcagataagg tgcattcctg cagggacgtg  42240
gattctgatt ttgatattcc ctgctttcaa ttaaggaaca aagtcgttta tatttcttaa  42300
gtcttatata aagccctaga gactttagaa attctattca aagttaccta tgttggttta  42360
tttttatctt ttatataaaa aagtatatat atagatttac atttagagac gggttttgct  42420
ctgtggccca tcttggagtg caacggtgca atcacagctc actgcggccc caacctcccg  42480
ggcttaagcc atcctccttc ctcagcctcc agagtagccg ggactacagg cacccatcac  42540
tacaccctgc taatgttttt atttattttt aatttttaaa aaacatatgt atatattttt  42600
cacaacctct ttggtgaaga taatgttttt gtttttttctc tatgaacagg gtcttgctat  42660
gttgcccagg ctggtcttga actttaggct gcaagcaatc cacttgcctt ggcctcctga  42720
catgctggga ttacaggtgt gcaccaccac acctacctca ttttaaaatt ttctgtagag  42780
atgggatctt actttgctgc ccaggctagt ctcaaactcc tgggctcaaa tgatcttccc  42840
acctcggcct cccaacatgc tgagattata gatgtgagcc accgtgcctg gcctatttct  42900
aacttttaag gagtgaaatt tctctgcacc gtgacagctt ttgaagagga cattttggat  42960
gcttcatggg ttgtcctttg cccgtacagc tcaccggctc ctccgagtgc tggttacagt  43020
cgaatgtgag ctgttatttg tatgtcaggt ccgcctggtg gtgttgccaa aaagcatgaa  43080
tttttcctca tcatttaaag tctacatgga atttaaggcc actttcgata ttattcttgg  43140
gaggatttta ttcagtgttt tgggagaaca tggcaggggc tcatttcaga attctctgat  43200
ttggggccga gctcggtggc tcacacctgt aatccctgca tttttggagg ccaaggcgga  43260
aggatcactt gagaccagga gttccagacc agcctgggca acatagtgag atctcgtctc  43320
ttaagaaaaa aaattaaaaa gaaaattcta gcctggccaa tatggggaaa ccctgtctct  43380
actaaaaata caaaaattag ctgggcgtgg tggcgcacgt ctataaccca gctacttggg  43440
aggctggggc actagaatct cttgagcctg ggaggcagag cttgcagtga gccaagatcg  43500
tgccactgca ctgcagcctg ggtgacagag caagactttg tctcaaaaaa taataataaa  43560
taaaaataaa taaataaata cagttctttg attttgaaat agtgcagaaa acaaggcagg  43620
ccctgaagtc cacagctctc atgaaaagtt ttggatctag ggaagtgatt gtcaacaatg  43680
agcctttaaa gacttaatgg tgatagcaat ttacaggtga cttttcccaa aaaatgacag  43740
aaaatgagtt tgccacttgg gcatgttgac tcacacttat aatcccagca ttttaggaag  43800
ctgaggtggg agtgtccctt gcacccagga gtttgagacc agcctgggca acatggcaag  43860
accctgtctc tacaaaaagt acaaaaatta gctgggtgtg gtgggggggc ctgtagtccc  43920
tgctactcag gaggctgagg taggggggatc gcttgatcct gggaggcgga gattgcagtg  43980
agccgagatt gtgccactgc actccagcct gggggacaga gcaagaccct gtctcaaaaa  44040
agaatccgaa aaacaatgta gacttggagg gggtgatgta acttagccca tgagaccgcc  44100
ttagtgactt gctgataatt gatctttcgg tgccctgcag tattatgata acctgctata  44160
gcattttgct ttttctgtgc attaacactt tagggaccaa gtggctttaa gaactggatt  44220
aaagttgatc cagtgcattc agacacttgg cattccctgt acataacacg agagagcacg  44280
ccgggtctgg ccagccccat ggataagatg ctggagggtg tccaacgttg catgctgagg  44340
```

-continued

```
agcatgtctt agaggagaat cctagatcct ctgtgaagaa tgaatttcat cctcccagct  44400
gtgcagcttc tcttctaaat gtaagttgcc ttgctcaaca tctgcttccc atacgggcag  44460
ttttaggcct tggacttctt gatgaaggta taaaacgagg actttcagcg gaggtgcctc  44520
ccatttatgg ctggaggagt ctctggggtg gggccgtcct gcacacttca gggtgttggg  44580
gagtgtccct gggctccacc caccagcggc caggagcagc aacctcagtt atgaaaagca  44640
gaaatgtctc catacataac caagtgttcc ttcagggagg gagggcaaag ttttctccac  44700
tagtgaacca ctgtgataga cagacgacgg acagagagag atgatagata cgataggtag  44760
gtatatgttg agatggatag gtgatagata atagatatta agataggtgt aaatgatggg  44820
tgattgatag gtgagtagat agatgatggg tagctaatag atgatattaa gataggtgat  44880
agataataga tactaatata tacagctata gatgatagat gatattgagg tgggtaggtg  44940
attgattgat agattaatga ccgattgcat gtaggcagag ctctcatgct aaaagagagt  45000
ttctcaacct cagcagtgct gacacatggg gcgggatcat ggaggactct gtggtggggc  45060
atcctgtgca ctgtagggtg ttgagcagcg tccctggact ccacccagca gatgccaaga  45120
gcacccatcc catctatgac gagtatctaa agatgtctct agatactgct aagttccccc  45180
tatgggggga caaaaagtta tccccagttg tgaaccactg tgacagatag ttgatggatg  45240
gatggatgga tggatggatg gatggatgga tggatggaga tcaacattga gacagatatt  45300
tgatagatga cagatattga ggtagatgat agctatagat gatagatggt tgatagatat  45360
tagataagtg attgatagat gatagctata gatgatagct gattgataga tagctggtag  45420
ctatagatgg tagatggttg atagatattg agatagatag gtgattgatt gatagattga  45480
tgatggaacg tattagtaga gtttctcaac ctcagcactg ctgacatttg gggctggagg  45540
attctctgcg gtggaaccgc cctgtgcact gtagggtgct gagcaatgtc tctgggctcc  45600
acccaccaga tgcctctagc acccccactc cagcgtgaca gccaaagatg tctccagaca  45660
ttgtccagtg tttattgtgg ggagcagaat cagctccatt gacacccact gtagcggatg  45720
cacagacaga taaatacctg tgcgtgtgga gtccctttct ccctttctg ccccagcccc  45780
tgagcctgca gccccactct tctgtcatga ttgattggct tatgggccaa acagtggttc  45840
cagtgccata ttatctatgg cacagcagcc gagccaagcc agtgggtttg gtctgtggtt  45900
gcagggctta gccagctttc ttctacagaa cttggaaggc aagaggtctc tccactccgg  45960
gccacatcct tctagttcct ggatgaccgc tcgtttctcc atggagagga gttcatgcca  46020
gaacctcttc ttcggggaga gtggatgcat ctcttggaaa catctttttt taaagtctgc  46080
agacttgagt gtggtcccca ttgtcattgg tacttgttgg gggtaggagt aaaatcattc  46140
ctttgtttta ctgagagttc aggaagaaag aacaccatgt tctctccttt tatttattta  46200
tttattttgc tctctatttg aattttaaag gcaaaaatct agaaatagcg cttcttgctc  46260
tgtcatcact gcctgcaaag cacagagacc agagtgaagg caggcagctc ctgggtcttc  46320
tcttcctctt ctttgtccaa aaaatgatac attgcatgtt tagtatttgg ggcaaagcag  46380
acgcttcaaa aagggaggct tattttatta tctatatttt tctttttat tattttttac  46440
cttgattccc tttttctatg tatgaaaagg gaggtttaag ttcttgcaag agaatgcaac  46500
tgtagtgtct tctgaatgga gttttccatt tgatgccaag ccttccagtg ccttggtcta  46560
aggagaactg cgtagggtga gaagagtccc agcgatacgt ggaaaagggg ccttaccagc  46620
tctggagggc aagaggtagg gggtgaagac gcagtggaca cctaaggaga attttgcagg  46680
aggagtaggg gtttattggc tgaaaggggt gggtggtgga aactcattct agacagggag  46740
```

-continued

```
tgacacggaa gccatgggtc actacggggc aggagggaca tgggggagaa actcaaatct  46800
gagttcagcc aggaggtgga cacaggaatg cagtgaaccc agatgtgtag gagactgcca  46860
tggggactgg ggtatgagga aggactggct ctggctcggc tgtgcatata aggaaggact  46920
ggctctggct cagctgtgca tttgggctgc tggacagtga ggagatccag ggagagagag  46980
tgcattccaa tttgggaaac tttgagggca aaacatctgc agcaactgtc tcagaagaga  47040
gcctgaggca gggtccttgg agggaggaag ccacaggtgg atggagccac cgagggctgc  47100
taggtcacct tggttaaggg ctagttgcag tgcagccagg tcggaaagta gagccgttct  47160
ggagcctcac gtggcataga tgttggagga gatgggatga ggatggctca ttttcttctt  47220
ctcaccacaa aagcccagct ttatggcggg ctctggagag aggaggacca acttctacgg  47280
taaggcgtct ccaaattagt gaggctgatt tgcctgttca taaaaacaaa aacaaaagca  47340
aaaaaatccc ttagaggaca agccatcccc gcagaccctg caaataaaag actgcagatc  47400
agcttcgcgg atggaaaagt gctgctgtca gctaaagatg aggacagagc tgctcagctg  47460
aggtcactgg agaggatggg gaggggactt ggaaacctcc cttgtctcag tcgttgttga  47520
cgacattgac tctttcttca tgttgacttt ccccccgttc atagattcat agattgctct  47580
ctatgctgga aaacattctt taaaatttaa ttttttttatt ttgttaacat atatcacata  47640
acagtttact attttaactt cctttttttt tttttttttt tttaaaagaa atgaggtctt  47700
gctctgttgc ccaggctgca gtgtactggt gcaatcatgg cccactgcag cctcaacctc  47760
ctgggctcag gtgatcctcc tgcctcagcc tcccaagtag ctgggactac aggtgcgcac  47820
taccacgcct ggctaatttt ttaatttttg gtagagacag ggtctcgctg tgttgcacag  47880
gctgatctcc aactaccagg ctcaagcagt cctcctacct caggctctca agttgagctg  47940
ggactatagg cacatgccac catgcccagt taatatttta atttttggca aacatgtgat  48000
cttgctttgt tgcccaggct gttctcaaac tcctgatctc actcaatcct cctgccttgg  48060
cctctcaaag tgctgagatt acaggcatga gcgtccatgc ccggcctcat tttaaccatt  48120
tttaaaatgt acagttcacg gctgggcgtg gtggctcacg cctgtaatcc cagcactttg  48180
ggaggccgag gtggacggat cacgaggtca ggagatcaag accatcctgg ctaacacagt  48240
gagaccccgt ctctactaaa aatacaaaaa aattagctgg gcgtggtggc gggtgcctgt  48300
agtcctcagc tacttgggag gctgaggcag gagaacggca tgaacctggg aggcagagtt  48360
tgcagtgagc caagatcgca ccactgcact ccagcctgag taacagagcg agactctgtc  48420
tcaaaaaaaa aaaaaaaaaa aatgtacagt tcactactcg ggaggctgag gcaggaggat  48480
cacttcaacc caggaggcgg agattgcagt gagctgagat tgtgtcgctg cactctatcc  48540
tgggcaacag agtaagactc tgtctcaaaa aaaaaaaaca gaaaacaaaa aaaacaaaac  48600
actgtttagt ggcatggagc acattcatgt ttctgtgcaa ccgccacccc atccccatcc  48660
ccatccccat ccatctccag aactcctttt catcttcccc aactgaaact ctgtcctcat  48720
gaaacacgcc ttattgcccc tccctccagc cctgccctgg caacctccct cgtactctct  48780
gctctatgaa tttggtgatt ctaggagcct tatataggca gaatcatacg gcatttgtcc  48840
ttttgcgact ggcttctttc agttactgta atgtccttca gattcccccg tcctgtagaa  48900
aggaatttcc ctcctttcta agcctgagta ctattccatc gtatagagga tacagcatgt  48960
tgtgtttacc cattcattca tccttggaca ctggggtgcc ttccacctct tggctgtagt  49020
gaataatgct gctatgaaca aggtttggca aatatctgtc cagtgcctga tttcagctgc  49080
```

-continued

```
ttgaatacat tgttttaatt tattattatt attttttaga gatggagtct cgctctgtca 49140
ccccagctgg agtgcagtgt tgtgatcttg ggtcactgca acctgtgcct cctgggttca 49200
agcgattctt ccaactcagc ctcctgagta gctgggatta caggcatgca ccaccacccc 49260
cagctaattt tgtactttta gtaaatatgg gttttcacct tgttgactgg gctgatctgg 49320
aattcctcat tgccaggtaa ctatttcaca gcctggtatg gatccttctg tacttttctt 49380
tgtgttaaaa aagccccctc acacaaacgc acacacacaa gcacgcacac acacaagcac 49440
acacacgtgc acgtgcacac acacatgcac gcacacatat atgcatgcac acacacacac 49500
gcgcgcgccc cgtgcagttt tggcctcatg ccactagagt atgcatcatt tttgtctctt 49560
gttttcttgg agatccctct ggggtatttt gaggaggaga agttgtatta ttattgtgtt 49620
gttgttaatc tttagacatt cagggataca cgtggacgtt tggtacatgg atgtatcatg 49680
ttatggtgag ctttgggctt ctagggtacc ccttacccga atagtgaaca ttgtacccaa 49740
taggttattt ctcagccctc aaccccttcc cagccttccc cttttgggag tccccgtatc 49800
tgttatttcc atttctgtgt ccatgtggac ccactgttga gctcctactt ttgagtgaga 49860
ctatgcggta tttgactttc tgtgtctcag ttattttact taggatagtg gtttccagtt 49920
ccatccctgt cgttgcaaaa gacatgattt tattttttat ggtggtgtcg atatactaca 49980
ttttctgtga cttttatata ctaaattttc tttatccagt catctattgg aatggctgtt 50040
acaaaaactc aaaaaaatcc aggcatggtg gcccacgcct ataatcccag cactttgaga 50100
gacccaggca ggaggatcgc ttgagcccag gagttttaga acagcctggg caatataggg 50160
agaccctgtc tctacaaaaa gctcgaagaa atagcgaggg atggtgttgc acgcctatag 50220
tcacagttct tcaggaggct gaggtgggag aattgctcga gctcaggagt tgaaggttgc 50280
agtgatctat ggttgcgcca ctgcactcca gcctatgcaa caacagagcg agaccctatc 50340
taggaaaaaa acaaaaaagt aagaaaacaa cagatgttgg tgtggaagtg gaggaaaggg 50400
gccatggatg cgctgctggt gcggaggagg tcttccagtg cgtgcagcag gggaggtgac 50460
ctcacttctc ctcgagagga gctcagctgt gcaaggcagt gttgcagagg atgggagggt 50520
gcatgtgacc ctaggagcaa ggctgtgtgc ctgtgggcat gtacttcctg gtgacgtttc 50580
cttggacccc acagtgggaa acaggagccc ctctgccctc tcattcctct ttctctgtat 50640
ttgcattcgc tgtcttgctg gtctcaagat tcccaagcgc tgctgccagc ccaccccttc 50700
agcctgccaa gctacatgtg tgcgcccact tgaccactct ctgagccttc tgctcagatg 50760
cctctcacca aaaatgagtt cctgctcttc ctccttgccc ctcagcccta atcagttcct 50820
catttgcact tccccatttc ataggtggtc cttccagctc ttggggctca cccaggaacc 50880
attttttatt ccttttcttt gactctgcat tcactgtaat cctgagtcct gcccttttaa 50940
cttttttttt ttttttttt tttaagagat gtggtcttgc cgtctcatcc aggctggagt 51000
gcagtggtgc aatcatggct cactgcatcc ttgacctcct gggctcaaga gatcctccca 51060
cctcagcctc ccaagtagct gggaccacaa gtgcacacca ctatgtccag ctaattgaat 51120
ttttgtgtgt gtgtgtgtgt gtgtgtgtgt gtgtgtgtgt gtgtgtgtag ggacaagatc 51180
tcactgtgtt gctcaggctg gtctcaaact cataatttca agcatttccc ctgcctcagc 51240
ctcctaagta gctaggatta taggtgcaca ccgccatgcc ttgccccttt ccaattctca 51300
aacacatctc cagagcccat ccacatcaat gatgtcttca cagaagctgc catagcttat 51360
ctaaattccc tccccttctc tccactgatc tctgatctct gctgaactca ccccttcctg 51420
ctgtatcagc ccaaacgttt ctgatgtgaa aataggcagg gcgtagtggc tcatgcctat 51480
```

```
aatctcagca ctgtcagagg ctgaggtgag aggattgctt gaggccagga gtttgagacc  51540
aacctgggca tcttagtgag accccatctc taattttttt tttttttttt tttttaaaga  51600
cagggccttt ctctgttgcc caagatggag tgcagtggtg ccatcatagt tcactgcagc  51660
ctcattctcc tgggcccaag ttatcctccc acctcagcct cccagatagt tgggactaca  51720
ggcctgcacc accaagcctg gctgattttt aaattttggg ggtcttgcta tgttgcccag  51780
gctgatcttg aactcctggg cacaagtgat tctgctacct ctgtctctca agtagatagg  51840
agtacaggtg catatcacca tgcccaccta atttttaatt tttttttttt ttttttttg   51900
agatggagtc tcactctgtc ccccaggctg gagtgcagtg gtgtgatctt ggttcactgc  51960
aagctccgcc tcccaggttc acgccattct cctgcctcag cctcccaagt agctgggact  52020
acaggcgccc gccaccacat ccagctaata ctttgtattt ttagtagaga tggggtttca  52080
ccatgttagc caggatggtc tcgatctcct gacctcgtga tccacctacc ttggcctccc  52140
aaagtgctgg gattacaggc atgagccact gcgcctggcc ctaattttta attttttgta  52200
gagacgtgat cttgctttgt tgcctaggct ggttttgagc tcctgggctc aagcgatctg  52260
ccaccttggc cccgcaaagt gccggaatta cagacgtgag ccaccgcacc tggcctccag  52320
ctcttttgtg tccctcccca atcttccttt ggccttcagc tgtggggaca gagatgcccc  52380
ctgcctccct gtccccacct tctacctggt cttacaggac cccctccagc catccttcca  52440
agtttactat gtaatgtctg ttccacatca agcctgcaaa gctcatgaca gtcacaagat  52500
ctgccgttcc tgatactatg taccgagaac attacttggc acataagggg cccttgtcca  52560
aaacatttgg aaaccaataa agaatgtggc tggtgagtta ctgattaatg tgttgatgaa  52620
ttcattgatt gctgaggcta gtatgtacag taagtgttag atcttgaaca tacttctcat  52680
atccattgtg ataaaccctc ttatcttcta ttgcttttga acttttatag acttgatgtc  52740
aggggcagag tccctcaggt aactggaatc attgaactga tgcattggtt tctaattttc  52800
taagctcaga tttgaaatca cctgtggtca ctaaactcgt cctatcccac agcccctgca  52860
catgatgact taagttttgt gaatgttttt tggagatagt aaagtcagta tctctttcaa  52920
cattttgttc cttatcttta gtgataccca gctctgtaca aattctgtcc acgtaagcaa  52980
agtctttttt tttttttcca gatagggtct ggctctgtca ctgaggctgg agtgcagagg  53040
ttcagtcata gcttcaactc ctgggctcag gctgtcctgc tgcctcagcc tcttaagtac  53100
ctgggactac aggcctgcac aaccacacct agctaatctt tttatttttt gcagagacag  53160
agtctcccta ttttgcccag gctagtctca aactcttggt ctcaagtgat cctcctgcct  53220
cagtttccca aagtgctggg attacaggtg tgagccacca cactcgcctg caaagtctta  53280
ctgataaaag atttgaagga aggatgtgtc agagaacttc ttttttctta taatatttac  53340
ttaatcttat tggtttgggg aagggcaaga gaatcccagt tatctagatt tttcttttc   53400
ttaaaggagt atgtttttac ttgctaactc tctttgtaaa ctgttacttc ttaaagatgc  53460
tgaagggtga tcccgcatta gtgtataggt aaaaatgatg tctccatttc atatatactg  53520
ataaggtgac tttattaagc cttgtggttt gttgatgttg attttactga gacacttgtg  53580
gaacagatgt attttcatac aaccttacac atctcagtag ttttccccac tcgtgcagta  53640
actttttctc ccctgctttc tctcctcctc tccccacctc ttcttccttc ccctcctctc  53700
ctcgtccctt ccctcctctt ctcatttgat acaaagccct aactctcttc ctctacagat  53760
catcctaccc atggttgaaa ttgcaacttc ccctgcaagc caagtgaccg aacctgagat  53820
```

-continued

```
gtttgtattg tcagggcttg cgtattctac atgcctgtgt aatcctcaaa gttctttcat  53880
tccttgcttc taacctaccc aaatccttct aatctcccac catggttaat tatctctgat  53940
gctcctgaaa ggtgacctgc tgctacattg tgacaaggtg atgcattatt cttaagagga  54000
tctgtgcaga ttattatccc agagtgaggt agatgggggga ggatacagga tatatccaaa  54060
aatgtgttgc aagctaattg atagagagag agagagtgtg tttgtatgtg tgtgtgtaag  54120
catgcgtcca tctttttctt acatatttga gccataggga agtagagcca tgtatattct  54180
cttcaaccaa attaacagtt gtagacagtg gtcttgctat tgctttgact attaatggta  54240
ttttcaagag ctcagtgtta cccccaaatg ttcagtatca caccttggct ggtcagtcgt  54300
agctaaattt tccttccacc ttgcgccctg aagaaattta gaaagtcacc agctgacaca  54360
gaagtttatt gtaaaagttc actagtacga tagtatttgg accttggaaa atatttcccc  54420
accagaacag tgaaatcatg aaatcatggt tgtcttctaa gctcatccac aaaagtacag  54480
tttgactgtc atgcatttga gatgccatgt gcttaatcac gaaatattac tgagaggaac  54540
actcttgccc aaccaataac ggtgcaaagc agaaaaacag ggcatttagc tgggagaaaa  54600
tgagtcgaga tgtcagtgat aagatggaag gaatgtgggt atgtgctggg tcttttagaa  54660
ctccagcaga ttgctctgga aaacagccac tacataccaa aagtagccgg tcatggtggc  54720
atgcgcctgt aatcccagct actcgggagg ctgaggcggg agaatcactt gaactcggga  54780
ggcggaggtt gcagtgagcc aagatcgtgc cattgcactc caagcctggg tgacagagca  54840
agactgtctc aaaaaaaaaa aaaacaaaaa aaaaaacaaa aaaaacacca ctccaacaaa  54900
atacttctcc ttcctcatat agtgtccctg cttcccttta tgcctcaaga ccacacattt  54960
tgaacttgct gagctataag aagtgaatgg agaggtggga cacaggtgca cagccttcag  55020
taactgaagg aaaaaaaaca gaagaaatgt ctaaccctga gcttcctgag ctcccttcag  55080
ccacccagct gctgaggggc aggaatccag cagcaaggtg gagagcagaa ggcattcctg  55140
caacctgtat gtgtgggtca ttagtccccc acctccagca tcattgcaga atctgcaaat  55200
ttaaaagtgc gttaggtaag agcctttttt ataagaggcc catatttttg ctaatacata  55260
aaaacattgt gattagtcaa ataaatgttc atttaaaatt cacagtagca tgtgtctatt  55320
tttttttttt tttcctttta gaaatgaggt cttgctctgt cacccaggtt ggagtacagt  55380
gatgttgtga tcatagctca ctgcagcctc caattcctgg gctcaaatga tcttcccacc  55440
tcagcctccc gaattgctgg gatgccacca tgcctggctg attcttttat tgtagagacg  55500
ggatcttgct gtgctgctca tgctgctttc caacacctgg cctcaagtga tcctcctgcc  55560
ttggcttccc aaagtgctgg aatgacaggc attgagccgc cgtgcccagc ctatgatttt  55620
tcttagcatt aatctctgtg tcattgcaag ctgtctccca cgtccttgcc ttcattctac  55680
attgttttgg tggaatggcc tgtgctagca gacaagacca tccggtcgac cttgagcatc  55740
cttccctgtc ctcagggaag gtttcctggg cctcattttg ttttctttgt ataccagcgg  55800
ggtgcagctc atttgaatga gcttgcaggg gagcatctgt gatagcatca tgatcagatg  55860
agacaaaact ggcacgggtc ctggtcatgg ttgaagacct ttatgctcct gattctattg  55920
ggtgtcttct actggtgaag gctcatgtgc tcatgggaac acgggcatgc tggtgtcttc  55980
cgagtcctct ccaaaaacaa agcccaggtc aggtacagtg gctcacgttt gtaatcccag  56040
cacttcggga ggatgaggcg ggaggattgc tggagccctg gagttcaaaa ccagcctggg  56100
caacacagtg agaccctgtc tctacaaata acagtaaata aaaattagcc aggcatggtg  56160
gcatgcacct gtagtcctag ctacttggga ggctgaggtg agaggattgc tcgagcccgg  56220
```

-continued

```
gaagttgagg ctgcatgagc cttacctgca ccactgcact ccagcctggc agacagaata  56280
agaacctgtt tcagaaacaa acagaccggg cacggtggct catgcctgta atcccagcat  56340
ttctggaggc cgaggcgggt ggatcgcctg aggtcaggag ttcgagaccg gcctggccaa  56400
catggtgaag ccccatctct actaaaaata caaaaattag ctgggcgtgg tggtgggcgc  56460
ctataatccc aactacttgg gaggctgagg caggagaatc gcttgcaccc aggaggcgga  56520
ggttgcagtg agccgagatt gcaccgttgc actccagcct gggcaacaag agcaaaactc  56580
tctgaaaaac aaacaaacaa aaatcccaaa gcccttagtt ccaaatcttg cctcataccc  56640
cacccgtccc atctttaggt gaaaacgttc tttcattatc agtgcgtatc tctccaaact  56700
gtatttgtaa cttgtgctga gatgttgaat gcacagacgc acctcagtat cttctgttcc  56760
ttctttcatc cctaccccca ccttcctcaa tctctcattg ctgcgttttc ttccattaat  56820
caacaccttt gtaaggagaa gcacctcagg caagctccca caagcaagtg cttcgaaata  56880
cttcatttgg ggctttttaa aagggctacc ttttcctagc aggtttggga tgcagtctgc  56940
tagtttattg ttaattctca ggcttaatga tagttccagg ttactgaatc aggtgtgatc  57000
tctgaagatg tgtgtgttgt aggttagtta gttagtgctg ccataacaaa gtagcataga  57060
cggtgtggat taaacaacac tgatttattg ttttataatt tttgaggcta gaattttgag  57120
aagaacgtct taacagggct ggtgcctcct gagccctctc tccttggctt gcagacgctg  57180
tcttctccct gtgtcctcac gtggtcgtcc ctctgtgtgt gtctgtgtcc tcatctcctc  57240
ttcttaggac tccagtcctg ttggaatagg gcccattcta gtgaccacat tttaccgtaa  57300
tcacctgttt acatgacctg tctccaaata cagtggatat tggaaggaca cagttcagcc  57360
catagcatac tgttggctgg tttattatga gaccatgata tttactattc attcatccca  57420
agacaatgag accttttacc catgtcccag gatacacata tcttaacatc tgctgttgtc  57480
tgaatacgtc ctttccaaat tcatatattg agacagtaac ccccaaagct atggaattaa  57540
aaggtggagc tttgggggaa gtgattagat cgtgagggtg aagccgctga acaggaccag  57600
tgccctcggt gaaggggcct gagggagccc gtttcccctt ggtccatggg aggacagcga  57660
gaagggccct tccctcagga atgggccctt accacgcagt tcatcagcag gcgccccgac  57720
ctcggacttc cagcctccag aactgagggt aatacatttt tcttatttgt aagaccccct  57780
agtatatggt atttttgtga tagcagccag aatggactaa gacaacatct atgtaacatc  57840
tgtggaactt gtactttaat gtccatctat atgcttatcc cagtatctga ttatacacct  57900
cttaacatct acacacgtct tagcatctac ctatactgat gaattacacc tttctatatg  57960
cagacctcag cacctgtcta tacctgtaga gtcacatcta cacacacgca tatcctaaca  58020
tctgtctgta tgcacacctt agcatctgtc tatcacatat attagcatct atctacacct  58080
acatattaac atctacttcc acccatatcc taatatctgt ctgcacccac agagcaacac  58140
cggtctacac gtctataccc atatcctaac atctctctat acctctgtta atatctatct  58200
acgttcatat tctaacatct gtctttacgt gtatattaac atctctctac acccatatcc  58260
tactatccat ctacacccat attgtaacat ctgtctcttc ctatatgtta acatctctct  58320
acacccatat tctaacatct atgtccatat attaacctct gtctacaccc gtatcctgac  58380
atccatctac acccatattg taacatctat acgtatagat atcatctgtc ttcacctata  58440
ttgtaacatt gatctctatc catattctaa cgtctgccta catccatatc ctaacatcta  58500
tacctacata ttaacatctg tctacaccta tattccaaca tttatctatc tgtattttat  58560
```

-continued

```
ttgtctatgc ccatacatta acacctgtct acacccataa tctaacatcc atctgcaccc  58620
atatactaac acctgtctac atccatctac acccatatat taatacctgt ctacatccat  58680
ctacacccat atcctaacat ctctctatac ctacatatta acatctgtct acacctgtat  58740
tccaacactt atccatatcc atattgtaat atctgtctgc aaccatatcc taacatctat  58800
ctataactac atattaacat ctttctatac ctatatgcta acatatatct atatccatat  58860
ttaataccat atggtaacac tgtttacacc catgtatcag ccccgatgta cacccatatc  58920
ctaacatctg tctctaagca catcgtaaca tctgtatgta cgtgcattcg aacacctatc  58980
tgtacccata tattaacatc cgtctttacc catgtgctga tatctgtgtg ctccatgtcc  59040
cgacatctgt ccccagctat tactgtctgt ctgtacacac attttggtat ctagctgcat  59100
ctgtacccca acacctagct gacggcgtac cccctgccct gccttggcgg ggccctgagc  59160
atgtgctgtc tgtccccgca ggttctggac gtggcatgac gagcgcttcc tctacatgct  59220
catggagtac gtgccgggcg gcgagctctt cagctacctg cgcaaccggg ggcgcttctc  59280
cagcaccacg gggctcttct actctgcaga gatcatctgt gccatcgagt acctgcactc  59340
caaagagatc gtctacaggg acttgaagcc agagaacatc ctgctggata gggatggcca  59400
cattaagctc acggactttg ggttcgccaa gaagctggta gacaggtaag aggaacgtga  59460
actccgatgg aatctacact gcttggcaat gagaaaggtg gtggtagttg tggcaggtca  59520
ggcagggaaa gattgggaac cagagtttaa ctctcatgtg taggagacac ttgcaaccag  59580
ggatgagaga gccaggttga cccacagctc gttttaggtg ggctgcgatt gctggcaaag  59640
agccagtggg caggaagtca gtctccttca ctggcaccgt ggaggaaatc agaacaccac  59700
atatccgcta ttgatccgaa atgatgagga aatgagtcat atccaagttt gaattgccct  59760
gactataaaa tagatctgca tcgaatagga tacaatatct cttaaaatta aatgccaggt  59820
gctgtggctc acacctgtaa tcccagcact ttgggacgcc gaggtgggag aatcatttga  59880
gcccaggagt ttgagaccac tgtggacaac ctagtgagac cccgtctcta cagaaatata  59940
tatatttaaa aaaaagttga ttatggtggt ggatccctgt agtcccagct acttaggagg  60000
ctgaggttgg aggattattt gagccccgga agttgaggct gcagtgagct gtgattatac  60060
cactgcactc cagcctgggt aaaagagcaa gatcctatct caaaaaaaaa caaaacaaaa  60120
aaaaaaaaaa aaaaaaccaa attgaatatt ccatacacac ctgctcacac acacgtgcac  60180
ttattttttt ctgttatcta tatttctatt atgtatatat atatttccac tatatatgta  60240
tattaaatag aaatatatat aatactatat tattgtatat aacatatagt atattttatg  60300
tacatatgat atagtattat atatgtatag tatatattat actatatatt atatagtata  60360
caatgactat gatatagtat catataggta tactatatat tataatatat aatatatatt  60420
atatagcata cctatatcat actatatcat acatatcact atactctata tagtatatat  60480
tatacgtatt atatattaca catactacat atatatatta tatagtatat tatactatat  60540
aatatatata atatatatat tacatagtat ataatatata tagtatatat cacatagtat  60600
ataatatata taatatatat atcacatagt atataatata tattatatat atcacatagt  60660
atataatata tattatatat atcacatagt atataatata tataatatat atatcacata  60720
gtatataata tataatatat atatcacata gtatataata tataatatat atatcacata  60780
gtatataata tatattatat atatcacata gtatataata tatattatat atatcacata  60840
gtatattata tatattatat atatcacata gtatattata tatattatat atatcacata  60900
gtatattata tatattatat atatcacata gtatattata tatattatat atatcacata  60960
```

-continued

```
gtatattata tataatatat atattacata gtatataata tatatagtat acctatatca  61020
tactatatga catgtatgat atatgtgttt cttttctgga aacacacaga catacccccaa  61080
aacagtgttt gaacaaacat ctgggcaccc cacggcccat caacacatga aacaaaccat  61140
tacatgtcgt ctcagccagt gcgggctgca ctaacacaca ctcatagact gggcagcctc  61200
aacagcagac attcatggct cacagctctg gaggctggaa gtccgagatc gaggtgcgac  61260
agattctgta cctggaggga accagcttcc tggttcgtag acggcgcctt ctcgctgtgt  61320
cctcacatgg tggaaggggc gagggggctc tctggggccc cttttgtaag ggcactcatc  61380
ccattcatga gactccacct ttgtgacctc atcacctccc aaaggcccca cctcctaatc  61440
ctatcacttt ggggatgatg atttcaacat aggaattttg gcggggggca catacattca  61500
gcttataata catgtatatg tatttttttt tccatgattg gattcattta accagtctgt  61560
cttgacaaaa gaccacacac tgggcatttt aaagaataga ccttttcctc tcactgtcat  61620
ggaggctaag gtctgagatc caggtgtggg cagggctggt tcctcctgaa gcctctctcc  61680
ttggcttgga gacgctgtct cctccctgtg tcctcacagg attgtcctct gtgcatgtct  61740
gtatcctcat ctcctcttct tatgaggaca ccagtcctct tggatcagga cccaccctag  61800
tgacctcgtt ttaccttaat gacctcttta aagatgctct ttcccatata gtcacattct  61860
gaagttctgg gggttaggac tgcagcatat aaggtttaag ggatacattt cagcctggaa  61920
caagtatata tagatatgtt tccgtacaca cacatactcc attgaggaga aaacagttat  61980
ccttttttgt ttgttttttt gttttttttt gggacgaagt ctcgctctgt cgtccaggct  62040
ggagtgcagt ggcacaatct cggctcactg caacctccgc ctcccagatt caagtgattc  62100
tcctgcctca gcctcccaag tagctgggat tacaggtgcc cgccaccagg cctagctaac  62160
tttttttttt ttttttgaga tggagtctgg ctctgtcgcc caggctggag tatagtggca  62220
tgatctcagc tcactgcaag ctctgcctcc cgagttcacg ccattctcct gcctcagccc  62280
cccaagtagc tgggactacg ggcgcccgcc accacgcccg gctaattttt tgtattttta  62340
gtagagacgg gatttcactg tgttagccag gatggtctca atctcctgac cttgtgatgc  62400
gcccaccttg gcatcccaaa gtgctaggat tacaggtgtg agccaccgca cccggcccca  62460
gtatgtagtc ttttatctct cacccacctc ccaccctta ccccaagtcc ttgaagtccg  62520
ttgtatggtt cttatgcctc agcgtcctca tagcttagct cccaatggat ctttaattta  62580
cattcataaa atcaacagtc ataaaaagta aattcacacg cccaagctgc tgaaaaatac  62640
tcagaaagat ttttggtaac tacactgagt gtcagttttt caattagatt aaattaatga  62700
aagtagaatt agataatgac atccgttcct tggtagacaa gctacatttc aaatacccag  62760
gattgcacat ggctatcggc ttctgtcttg gtcagacaag cctagaaaat acattttata  62820
tttccatatt ctttgatgtg gtggggttgg gtaaggtgat aattacacta attatactcc  62880
taacattgta aaaccgtctg cattttgaga aacttgatgt gggggcagtt ttacactaaa  62940
tgactctctt ctctggcagc ttttagaaaa gggctctcct aggaaaattt tatgatgcgt  63000
ttacattcaa tctgattttc ccctatagta tttcttgtac tacatttcca aaaataaggc  63060
acatggaaat taggtgcatt ttacatggag taggaaagat gcaggatttt ttaaaatatt  63120
gatttatagc atctgtgctg ccctctcttg gcagcacacg gtatattagt aaattctttt  63180
aaagtcattt tatttgcaag tctaattcaa agaaaacaga taaaatattt catatattca  63240
cttgtttata agtttgacaa accatgttac tgtccagtta attcatcata tctatttaaa  63300
```

-continued

```
tggacgaaaa tggtttcgta tataacatgc agcaattatt ttacttaatg aacatgtgaa  63360
aatcttagaa aatgtctcat taccatattg atagattgct tttgcaaaga actgcatctt  63420
cctctgtatg ggtagtgtag cttctggaaa cttttttttt gtgggggctt ttttctcctt  63480
tttttttttg accatcattg taacgaagca tctctctgct ggcccggccc cagggaagtt  63540
gtgttcatgg gggcagatac atggccctgc ctctgattca ggattcaaac agtacctgtg  63600
ccttttgaat aaaactgaaa ttcaccactg tatcgtggac cactacagaa tagatggaac  63660
taaacaggga ggcctcatct tgaataattt tttttttttt tttttttttt ttttaaagac  63720
agggtcttac tctgtcactc aggctggagt gcagtggtgg gatcttggct cactgcaacc  63780
ttggcctcct gggctcaagc gatcctccca tttcagcctc ccaagtagct gggattacag  63840
gcatgtacca ccacacctgg ctaatttttg tatttttagt agagacctgg tttcaccatg  63900
ttgcctaggc tggtcttgaa cagctggcct caagtgatcc acctgccgcg accttccaaa  63960
gcattgggat tacaggcgtg agccaccgtg cccggccttg aataacattt ttgaacatat  64020
cccagaaaga agtctgtttc tcatttttct ctcttttttt tttttttttt tttggagagg  64080
agtctcgctc tgtcgcccag gctggagtgc agtggtgcga tctcggctca ctgcaagctc  64140
tgcctcccgg gttcacgcca ttctcctgcc tcagcctccc aagtagctgg gactacaggc  64200
gcccaccacc acgcccggct aatttttgt gtttttagta gagacggggt ttcactgtgt  64260
tagccaggat ggtctcgatc tcctgacctc gtgatccgcc cgcctcggcc tcccagagtg  64320
ctgggattac aggcgtgagc caccgtgccc cgccattttt ctcttatagc atggggtaaa  64380
aacatactta agcatgttgt aatgtaatct actcactaca tgaatttctt tctttgtttt  64440
ttgtttcttt tttgagacag ggtctcactc tgtcacccag gctggagtgc agtagtgcaa  64500
ccatggctca ccacagcctc gaacttgcag gctcaagcaa tcctcctgtc tctcagcctc  64560
ccaagtagct gcaactacag gcttgcacac cctgcctggc taatttttgg attttttgta  64620
gagacggggt ttcactatgt tgccagggct ggtcttgaac tcctaaactg aagcagtcct  64680
ccaaccttgg ccccccaaag ttttgggatt acaggcggga gctacggtac tcagcctctc  64740
cctcccttcc ttccttcctt cctccctccc tccctccctc cctcctttcc tctccctccc  64800
ctccctccct tccttcctcc cctcccctcc cctcccattc cttcccctc cctcccctcc  64860
cattctttcc ccttccctcc cctcccattc cttcccctc cctcccctcc cattccttcg  64920
cctcccctcc cctcctctat cctcccctcc cctcccctcg cctcctctaa ccctcccctc  64980
ccctcccctc ccctcccctc ccctagcaac cctgttaact ggatgacttg taccctactt  65040
attttaaacc actgctcttg gtgacttgat ttctgacttt cctaggttgt cagtatgttc  65100
agatggtgtt cttttgtgac ttgcgttcac caggctcttg ttttctaaca gcaatattac  65160
gtttgtattg taaatatttt gcacacacac tttatgttat ctagatagct cccctaaaag  65220
atttggtggc aaactagaat tatttctggt tttatgaaat ggtcaaaata aaatactgat  65280
gtgtttaatt tgattttata attcaaatgc ataacacaag catcccttac ctgaaatact  65340
tcagaccaga attgttttgg attttagatt tttttcagat tgtggaatat ttgaattaca  65400
cttacctgtg agcatcccta atttgaaaat ctgaaatcca agatgctcca gtgaggattt  65460
cctttgcgct gtgagcctca tgtcggtgct ggaaaagtat tgacttttgg agcatttggg  65520
atttcagatt tggattaaag atgctcaacc tttatacatc tgtctttaaa ccataacaga  65580
tggttttctt tctctgcaac agctcttttt tgtttgtttt tggtgttttt tatttctctg  65640
cgacagcttt ttgtttgttt gtgttttttt gtgtttcttt tgagacaggg tcccactatg  65700
```

-continued

```
ttggccagga tagtcttgaa ctcctggcct caagcaatcc ttccacctcg gcctcccaaa  65760
gtgccaggat ggtagccgtg agccaccatg ccaggtgcaa cagctctttc ctagttcctc  65820
tgttgtagca ttttaaatcc agatgttaca ttgattactg tcctctggat ttttatttct  65880
agccttatag ggataacatt gaacctagtc tttcaaaatt actacttacc cctttcacac  65940
acacacacac acacacacac acacacacac acacacacac acacacagga gtagagagag  66000
taattcacat tgaaacctta tggccccatc acccagcttc gattgttatc aaagctttgt  66060
cactttgttt tttttctctt tgcccatttg tttcttgagt tattttaaag caggtgcact  66120
ttatcctatc tttaacagat aactcccttt aaaaaagaac ttcagtgcca ttatcacatc  66180
tgacaactat ttaaaaaaaa aaaacccagc ctgggtaaca tagcaagacc tcatctctac  66240
aaaacatcaa aaacaaaaaa attagccttg cataggttaa atccagcccc ctatgtgtct  66300
gttaataaag ttttattgga acacagtcac atcttggggg cttttgagct accgtagcag  66360
agctggatat ttgtaacaga gaccatgtga ttcacaaggc ctaaaatatt tgccgtctgg  66420
ctctttacag aaaatatttg cccacccctg agccaggcca tttgctttgt gaactggtta  66480
aaattggcca ggagctctgt ctgtgcagtg gaatattatt tggccttgaa aaggaatata  66540
attctgacac attctacgcg ttgataaacc ttgaaaacat gatattggac gaaataagcc  66600
agaccaaaaa ggtctcatgt cgtgtgattc tacttgtagg agggccctag attcttccaa  66660
atcataagga cagaaagtag aatggtgggt gccaggggcc ggggaggtgc agggaagggg  66720
aagatgctgt ttaatgagga tggagtttct gtttggaatg atgaagaagt tccagcagtg  66780
gacggtaggg agggttgaac acgaaggtca gtggacttcc caccaccgaa ctatacaatt  66840
aaaaatgctt aaaatggaaa attctatgct gtgtgtattt taccacatta gaaaatcata  66900
catataaaat cataattatg tatataatta taaataacta tataattgta atatttacac  66960
ataaataata tatccgacat taaatttata tatttaaata tatttatctc tttaatatat  67020
taaatatttt agtatattca tatataaatt taatacataa agatattaat gtaatgtgtt  67080
aattactaat ataacaatgt atgtatatat taatatacta atatattcta attataatta  67140
tatattaaat atgtaatttt tagttaaaca taattatatt taaaaaataa tttaatacaa  67200
ttaaatatat aataaatgga tacagtttta tatttaatat tacatattta attttataaa  67260
catggctacc aaataattat atgtgctcat aaattatggt ataaatatgt ttagaaagtt  67320
atatgtagct ataattatac attattatcc atagttttat atataatttt ataaatatat  67380
atttattttt aaaatttaaa tttatatatt agtatgtgtt acacatttag tgtttagatt  67440
ataagttcaa atttaaacat atacatttat aaatacataa tcgttttata tatatttcat  67500
aacaccagaa aagtctttct agttacttta gaccttttcc cctagcttct tactttgagt  67560
atttaacgga agtcaaggag ggcctgagat gtcgagtctg tttgcagtcg gtgttgttac  67620
tttcccttga gccccttttta attttgctgt agttcatact aggacgtggg tattactgtg  67680
ccgaggttgg tgacaggcac ccttctccct gctgatcagt ggtgcctagg agccattgtc  67740
accgaggaaa cccctcccag ggcctgggct ggccatcgga agctgtccca tgctcgcaaa  67800
cacacacctt ctcccttcac gggcctgaaa ttctcaactg tttgtcccca tcagacagtt  67860
ctaggaactg tgattgtgtc cccataaaaa aaaagatgac aaaatcttcc ctttttatga  67920
aaaaccccac accctgctgc tttattgcaa cccaagatcc tataagaaaa ggcaatgtag  67980
tattttcacc atgagtactg agcgaacatc tatttcctgc attaccaaac ccagacaaaa  68040
```

-continued

```
cactggctca tacttttctg ataaaaaggg aaaaaatgca tttgtatctg taatcaagtg  68100
taaaagctgt aatcagctgt ccttcctcct gagccctacc atgcccctgt tagctgagtg  68160
acatgctcac catgtcataa agccatgagg agagacagaa agtgaggctg gtgacgccac  68220
ctgctaggac gtaagaggga ctggactgaa actcagcttg gagatgtcat ccgtttctct  68280
ctgtctctct ctcttttttt ttgagacgga gtctcactct gttgcccagg ctggagtgca  68340
gtggtgcgat ctcggctcac tgcaacctct gccacccagg ttcaagtgat tctcctgcct  68400
cagcctccgg agtagctggg attacaggtg cctgccaccg cgcccagctg atttttgtag  68460
tttttagtag agacagggtt tcaccatctt ggccaggctg gtcttgaact cctgttcatg  68520
atccacttgc ctcggcctcc caaagtgttg ggattatagg catgaaccac cgtgcctggc  68580
ctctttttct ctttttattg tggtaaaata cacttaaaat gtaccatcgt aaccatcttt  68640
attaacattt tttatgtttc agaatagggt cttcctctgt cagccaggct ggagtgcagt  68700
ggtacgatca tggctcactg cagcttccaa tgcctgggct gaagcaatcc tcctccctca  68760
gcctcctgag tacttgagac tagaggtgtg agccaccatg actggctaac tttgaaatat  68820
ttttgtacag acagggtctt gctatgttgc cttggctggt ctggaactct gaggctcaag  68880
tgatcctccc accttggcct cccaaagcgt tgagattata ggcatgagcc actgtaccca  68940
gcctgtttga accatcttgc cgtgcacaat tgagtggcat ttattgcatt taccatgtcg  69000
tgcaaccatc acctctctct agttccagaa cattttcacg atcccaaaag agaacttgta  69060
tctgttaagc aattattccc catcctaagc caggatgatc tcatcttaac ttgattgcag  69120
ctacaaagat cgtgtttgca cataaggtcc cactcacaaa tactggggtt taggactttg  69180
gggggtgcac agttcaacca gtgcaggtgt ggcggaaggc gtgggcatta agaacacagg  69240
agtcattgga tatctatact ttatagataa tcctatcctt agctctgttt ctccttcgtt  69300
aacatggcct cctccctccc ctccccccgg ccatagtgaa actaagaaca gtgagaaaac  69360
tgagaacagc aggtgtcacc ttccttctac ccaaaagcca ggtgagcaaa aggagacagg  69420
agcagggaag tggataattc actgcccaga ccagtggtct cgacataaca ctcaggctgt  69480
ctcatctcat attcattcac gcagtcagca tctctccata gcagcgtatg tctctctgta  69540
cattcagcta ggcgttgggg ctttttgcag gaaggagtga ctctaacagg gcaggagtcc  69600
tcctgaggca agttagaacc tggatactta tacagcctca tacaacctca ggtgtgtgtc  69660
cttaccctaa cacggagcca aaaagagcct catctttcaa aaggtaagtg gagaagttgc  69720
agctaatgcc tgtagcatga cctgtggcct ctacctgggc ttcatatcag ctaagatcta  69780
ggcttttagc tactttcagg ccactttgga tgggctagaa aggtggaaat acaaaactag  69840
caggccagta agtcgctcgt cttgcagaat gacagaagtg tcgtgcattg aagcagccag  69900
ggtgtacttg gagttgattc aactgctggg cagggcaggg gagagcgtgt ttctaaaata  69960
gtgcgcattg tactttccat ttgtagactt aattctaatg agtgagaagc acttaacagg  70020
accacaaggt ggtccctgtt ccatacttag ctctaacctg cagatagaga gtaagtccct  70080
tccacatgct tccatgggag gagaactcaa tttctctcct tgtcttcttt cctggtttcc  70140
tgatttatat ctgctacatc ctgcagtaat tttttttttt tttttttttt tttgagacag  70200
tgtcttgctc tgttgctcag gctggagtac agtgacacta tcatgctccc tgcagtgttg  70260
acctcctggg ctcaagtgat ccttccatct cagcctcccg actagctgag actacaagtg  70320
cacttcagca cacctggctt tttttttttt tttttttttg taaaggagtg gtcttgctgt  70380
gttgtccaag ctggtctgaa actcctagcc taaagcaatc ctcctgcctc aacctcccaa  70440
```

-continued

```
agtactagga ttacaggtgt gaactaccat gcctgacctt gtggtacttt tatttcatgg  70500
atggccgaca gaatttgaaa tttggatggc agccagtttg ttgttatccc aagggcttac  70560
agattagtgt ggaaaagtct gttgtctgga aagagatggg gtatggaggt gtggtgggga  70620
agggaaggaa agataacagt aacaacattt tgggtgggtt cctgcaagca ggaagctgag  70680
gagctgaagc caagatacgt gcccacacca ctgcaaacag tgcggactca ggcaagatgt  70740
gctgggtata aaataggctt tgcacatgct tgatacattg tgcaaagaac ttgagagtgg  70800
ataaacatgt atattaccag actctgtgga acttgttttt tgttctcttt acattcaact  70860
tacaaaataa gggtttcttc tttcattgat ctgagtggtg ggagggaagg gtcttttgca  70920
aagcatctat atattttttc cctctgaggg tgttgcttct ttctgcctgt ctacagacag  70980
gctccacaca ccagggcagc acttggcagg aagggtggat gtggcccgca tttgtgctac  71040
aggtctgaat tgctgaaagc ccgaagcgac attctaccca gcagtagagc gccaatggag  71100
tacggcccag acaaggcccc ctctctgggg ttactgatac tcagctcctt tccagcccat  71160
gagtcttcca gcttctgctg cagtccttgt tatcttgccc tgactttatt tagcagattc  71220
ttctgtaacc aaaatgcagg ttcagccgct cgccgtttgc agagtgcaat tagcaagagc  71280
gaggtctagt gtaaagaaag tgatttttta ttccagagct ttcttagggg aagaagtaca  71340
ggcttcctgc ttgaggccac ccctttgctt ttggagcaca aagcaggcac ctttaaagga  71400
aaatggtatg caggggagga agtgtatttc tgtctttaca ctggtttcca gggggcaaga  71460
aatgtttttt tggggggtgg gggtgtaaag agccaaagag aacatacgta agctttgcaa  71520
accatccagt ctcagttaca agtacaaacc cagctcttgc accttttttt tttttttttt  71580
ttttttttga gagagagtct cactctgtcg cccaggttgg agtgtaaagt gcagtggcgc  71640
attcttggct cactgcaacc tccgcctcct gggttcaaac atttctcctg cctcagcctc  71700
cggagtagct tggactatag gcatgcatca ccatgcctgg ctaattttgt atttttagta  71760
gagatggggt ttcaccatgt tggccaggct ggtcttgaac tcctggcctc aagtaatctg  71820
cccaccttgg cttctcaaag tgctgggatt ataggtgtga gccaccatgc ccggcctaag  71880
cgagttcttg aattattctt ttcactgcca cttttttttt tggataaagg attttctttt  71940
tacttaattt tatttattta tttatttaaa gaacttttag gttcaggggt acacgtgcag  72000
gtttgttaca tgggtaaact gtatgacact tggtgtactg attattttgt cacctgggta  72060
ataagcatca tacctgacag gtagattttc catcctcatc cttctcctgt gcttctcctt  72120
ccagcggcca ggtgtctgct tttccccctc tctgtgtctg tgtgtcccca gtgtttagct  72180
cccacataca agtgagaaca tgtgagtcca cttaggagaa tggcctctcc acctccgtcc  72240
atgttgctgc agaggacatg atctcgttct ttttccttta attaattaat tttattcttt  72300
atgatttata ctaaggtata aataactcaa aaaaaatgag gttttttttt gcttctgagt  72360
aacagtggta acagtaccag caacaggagc aaggatgata aaaccaattc ttagcttcca  72420
agcccgttaa gaaatgtttc tatggaaagg aatcagcgaa aacaatgtta ctgtctttac  72480
acattaaaat atgtgcacag gagggtaaac ggagcgtggt tttactcaac gaagttattg  72540
taacaatcag agcttctaag gtgactgcat tagccaagca ccactgagtg ttgtgggggc  72600
ctgtctctgt cgcccatata ggacttggac cctctgtgga acacccggag tacctagccc  72660
ccgaagtcat tcagagcaag ggccacggaa gggccgtgga ctggtgggcc ctcggcatcc  72720
tgatattcga gatgctttcg gggtaagtag agtctctgta gagaatcttc atcttacagg  72780
```

-continued

```
ccagcacccc ccttccccca cccattcgtc cactcggcat ttctgtaacc ttgaaaacag  72840
tacgtgagtg tcgcaaacac acagtgtggc tgcacacaca tctgctgccc tgctgaggtt  72900
ggcaatgtga attagcaatt gagcttgtgt gaataagagg caaaaaaccc aaacttgtga  72960
aggaaccacc catgcatgcc cattgagatt tttatattga aatatccata tcttctttaa  73020
atatacaatt aacattctgg gctgctctga aggtagtgag ttatctcagt tgattttcac  73080
agtcagctac agattgaact ccttgctcta ctcttttccc cccttatcac ttctgcgctt  73140
gtttagtctt aaaaagaatt taaaaattaa attaaaaaat gaatcttctg cacagaccct  73200
ttctgaagta acctgcagag ctcagggggg cacaggttgg gtcaaggtaa atcagccaaa  73260
tacagttcag tggtttctgg atgaacagct ggcaaggaag gcgagaatat gttctttcct  73320
aaaaccgtat gtctgtggta caggaaaggg gtcccgaccc acaccccagc acagggttct  73380
tggatctctc gcaataaaga atttggggaa agtccataaa gtgaaagcaa gtttattaag  73440
aaagtaaaag aataaaagta tggttactcc ttaggcagag cagccctgag ggctgctgtt  73500
tggctatttc gatggttatt tcttgactat atgctaaaca aggggtggat ttttcgtgag  73560
ttttccggga aagtggtggg caattcctgg agctgagggt tcctcccctt tttagagcat  73620
acagggtaac atcctgacct tgtcatggca ttcgtaaact gtcatggccc ttgtgggagt  73680
gtcttttagt acctaatgca ttataattaa tgtataatga gccatgaaga cgatcagagg  73740
tcacttgtcg ccatcttggt tttggtggca tttggccggc tttactgcag tctgttttat  73800
cagcagggtc tttgtgacct gtatcttgtg ctgacctcct atcttgtcct gtgacttaga  73860
atgccttaac cgtctgggag tgcagcccag taggtctcag cctcatttta cccggcccct  73920
gttcaggatg gagttactct cgttccaacg cctgtgatac ctgtgttggg tgagatttgg  73980
aagtcaggag aggtgccatc caccctgcaa ccacataaca gaggtcggtc atttgttggg  74040
acgtcagcat gattgagtgt tcaagtctag catatgcctg agacagctcc actatgacta  74100
gaccagaaac gcaaaggaag cacgcaacac ttggaaaccc aggacgtggg cgtcatcctc  74160
gttccgttgt tagtgctaag atgacacagt agcgtggcac ttttccagat aggaacctgt  74220
aggaaggagt gagctacgtg tcagaggaac tgttgcacca tgtggctctg cacgaaaggc  74280
tcttctctct gggatgaaga cgagaggaag cccagccagc gagggcccag aacaccggtt  74340
gggggagcct ctgccgcgct ttgccacagc cgacactctg cctcctaggt tctctctttt  74400
cctgtttcct tctttcttct gcttgcccct gagtctcaaa gacagacacc agcgtatcct  74460
ctgagtggcc tccattgtcg caaaagccag atcctctctc acatctctct gattccctgc  74520
agggggtaaa gaccagagtt ttactgggga accttccctt tcagttggaa acaaaggagg  74580
gaaggaagag aggcattctc ctgcctggaa ggcgtgtcta agccaggtcc tgctggtggg  74640
gagcaccgag cgcttgttcc tgggggtgtg gagcatgtga cattctaaca tccacctcag  74700
gaaatccagg cagtcgctga ctttgtttgg ggagcagaca ggggtcatcg tcccatgtgc  74760
ttatctctgc cctcttttat aaagaaagtg aatccgttaa ttcccacact agcttaggga  74820
tcagaacgat gttgaacaag cactaccaaa gaattccacc acaaaaccgg agcctgagat  74880
gccgcaggag gagagtggaa cccgtaaaaa cctgtatttc attgtctagc tatccatgtg  74940
tattgtttat catccatcca tccatctacc cacctgtcta tttatctatg tttatatact  75000
tttccatcca tccacccacc taccccccaa ccccttcatc catccaccca cccaccccgt  75060
catccatcca cccacccact ccttcatcca tccatgtacc cactccccca ccccctaccc  75120
cttcatccat ccaccccccc accccttcat ccatccaccc ccaccccttc atccatccat  75180
```

-continued

```
gcacccaccc ccccacccct ctaccccttc atccatctac caccccaccc cttcatccat  75240
ccacccccac cccttcatcc atctaccacc ccaccccttc atccatccac cccccgaccc  75300
ccccacccct tcatccatcc atccatccat ccatccaccc acctacccct tcatccatcc  75360
acccacccac cccttcatcc atccacccac ctgcccaccc accgcttcat ccatccaccc  75420
accccttcat ccatccatcc atccacccac ccttccatcc atccatccat ccacccaccc  75480
acccacccac acacctatcc ctgtctatct ctatggtcta cctattttgt aagtatgtat  75540
gtatctgttt atccatttat ccttatctat catctaagtt gtcatttata tatttatata  75600
tccatctctc tccatctctt tatctctacg atctttttat ctgcctacct acctgttatc  75660
tatgtattta cctatcatct atctgtcatt catgtaccaa tctatccatc tacttcctat  75720
ttatctatgt gcctatccat ctatttatca tctgtctttc tatgtaactg tttacctccc  75780
tacctatcca tctatcaatc atctatctac ctattcatct atctgctttt ctatatatct  75840
atgtatttat caatcatcta cttacctacc tatccctcta tctctacctt tctgtctatc  75900
tagctatcaa taatctacct acctaccggc ctgttggtct tttgaatttt ccattactct  75960
ttgctgagac atgcctacaa gtcatataga accaaacttc tcaatatgca ccctagccca  76020
ttatgtccta ggcaaaccca aaaggttaaa aataacttag gcatattgat cagcgtccac  76080
ccaaggaaaa gcaccacatt ttccttcggt gataacactg accacacgag ggcagcattg  76140
cctgaggatc gttgtatcct gtagtctaat ggttttaaat agagtgaggt tcgtgtgccc  76200
caaattttat tgattctagg atagagtaga ctattattag aatacaatat actattagga  76260
cataatattg ttagaataca acatagaatt attagactat aattaaaaca gaatattagt  76320
ctcagggtac gctgaagtta aaaatacata aaaatacatt taaaaagaat agaatattac  76380
actcttagaa tgactgtatt cgaattatat aaagttacca gaattgttaa taggctataa  76440
cattggaata tttaaatata ttagaataca atagaataga aaataaccta attgtaatgt  76500
aataaatcat taggctaatt gaaaatgaat aattaggcca ggcaccatgg ctcacacctg  76560
taatcccaac actttgggag gccgaggtgg ttggatcacc tgaggtcagg agttcgagac  76620
cagcctggcc aaaatggtaa aaccccgtct ctactacaca tacaaaaaaa agccaggcat  76680
ggtgcctgta atcctagcta ctcgggagtc tgaggcacga gaatcgcttg aacctaggag  76740
gcgggtaggt tgcggtgagc cgagatcgca ccactgcact ccagcctggg caacagaggt  76800
gagactccat ctcaaaaaga aaaaaaaaaa aaagaaagaa aatgaataat taaattaaat  76860
gaataaccgt ctcccaatca aagcccagtc tgctgacctg tgcatttcat gaggcaggga  76920
gctattgatt cacagtaagc ctatttttat tttccttttt tctaattaga gtctatttct  76980
gggtgaatat tgtttttttca atttctcagc agccctgtgt ctcttcacat gggtgggtgt  77040
cttgagagtt accagcttcg ccgaccccaa ctctcccagg cattcctgtg ctcttcccca  77100
gctccagccg gcctgagctc gcctggacca ccccaagcct tctcagtctc ctgcatcccc  77160
tcctgcctgc agtacatttt cctggaagca gctgcaggca tcctgtccac gtacccatca  77220
gctgtgtccc tattccctgg gagcccgctt gttgcttccc ggatgactgg agcagaatcg  77280
gaggctcgtt atcatatgag gttctgagac ggtctgcctg tgggttgtcc acccctctta  77340
gacaacagcc tggcccctcc ttgtcttccc actgcttttt aaacgtgcca ggaagcctga  77400
cctgtccccc tgcccaaagg ctggcttcct tcctccttct tttctttttc cctttccttt  77460
ccttcccttt cctttcctcc ctccctccct ctctccttcc ttcctctctc cctccctctc  77520
```

-continued

```
tctctctctc tccttcctcc cttccctttc ccttcccttc ttcctttcct tttcctttcc  77580
cgtctccctc ttcctttccc ctttcccttt tcccctttcc cctttttcct ttcctttcct  77640
ttcatttcct ttccttcttc ctttcctttc tgttccgcct cgctctgtca cccaggctgg  77700
agtgcagtgg cacaatcttg gctcactgta acctctgctt tcttgtctcg ctctgtcacc  77760
caggctggac tgcagtggcg caaatcttgg ttcactgcaa cctctgcttc ccaggttcaa  77820
gcaattctcc ttcctcagcc tcctgagtag ctgggattac aggtgtgcgc caccacgccc  77880
agctaatttt tgtattttta gtagagaggg ggtttcacca tattggccag gctggcctca  77940
aactcctgac ctcaagtgat ccacctgctt cggcctccca aagtgctggg gttacaggcg  78000
tgagccacca cacccagcca gggctggccc tttctcttcc actgcacatg ctgcaggctc  78060
acctgtcacc tgctcccaca gccctctggg gcctcccctg ttctcctggg ccatgccctg  78120
tccgaccagc ccatctgttt tctttatact gattagcagc tctgaaacca tctaaatttt  78180
gtatgtgttg actgcctctg agagcaatgc tcccaagctg ctctcctcac ctccttgaac  78240
ccagaaactt ctggtggctg gagggagggc actgctgcac atacaagtgg agccggcctg  78300
cagtcagagt cttcctgctc ccttcgcagc ctgtgtctgc acctttccta tcgcagctcc  78360
atttgctgga ttcccactct tagcaggatc aagtgagact gtgccttgtc tgtgttattg  78420
ctttaagtga ttatctcaat cttccactaa gcacagggaa aaccatctat ttggtaaaat  78480
ctgccatgtg attaggaagg agatcatatc atgatgcaga ttttattttc atggaatgag  78540
acatgtttag gtcagatgaa aattgtgtgg cacattctgg aacaaaatca ctcatgcact  78600
ttccaaggac ccaagctcag ctccgatttc ttccatccta ttctctttcc tcatccattt  78660
ctgtggtttt attctcccag agagtttaac tcaagagtca ggtaaaggct ggacgtggtg  78720
gttcatgcct gtcatcccag cactttggga ggctgagaca gaagaactgc ttaagcccaa  78780
gagttcaaga ccagcctggg caacatagtg ggaccccatc tctacaaaaa ataaaaataa  78840
aactagctgg gtgtggttgt atgttcctgt agtcccagct actcaggagg ctgaggtggg  78900
aggattgctt cagcccagga agtcgaggct gcagtgagct gagattgcac cagtgcacat  78960
cagcttgggt aacagagcaa gacactgtct cagaaaaaga aaaaaaaaaa tcagctaaag  79020
catcaagaac aaaacacagg gacacacaag acatacagca gagtgcaggg taagagaaag  79080
cccctgggcc atcttgtctt agttgtgaca gcagtgattc tcaaagtggc atcccagagg  79140
actatggggt tcccgaagtg tgtttcagca gatgagtgag atcatttttc caatgacaga  79200
tctgaatagt gatgaatttt cttcataggt gtcaactaag acaatacagc atagcagaca  79260
gggtgcagaa gatcctagag aaggtggaat ttggctgcag tggagcctct tccacgggga  79320
gcattaggca ttgcgcagtg gttctcaaac atgttggcct cgggaaccct tcaacacaca  79380
gctcaaagtt attaacaacc cacagaactt tcatttctgt gtgttacagc tgtccgcgct  79440
gactacattt gaaattaaag tagagactga aatataaacc aacagaatac ataaataata  79500
tatatgagaa gttaaataat cagaggagaa cataaatagc atttttaaat gaaaaaaatg  79560
tgtaaccaca ctttctagaa ttaaaaccat tcaggctgga catggtggct cacgcctgta  79620
atcctagcac ttcaggaggc tgaggtggga ggatcacttg agcccaggag ttggaggcca  79680
gcctgggcaa catagtgaga ccccatttct acaaaaaata aaatgaaata aataaaccaa  79740
ttagctgagc atgatggtac acgcccaggg tcccagtact ttgggaggct gaggtgggag  79800
gatcactgag gctgggaggt caacgctgcg gtgagctgtg gtctcgtcac tacactccag  79860
cctgggtgac agagagaccc tgtctctaaa aagagagaaa acatttgtga ggaggttggc  79920
```

-continued

```
tgtattttct gggttttgtg aatctcttta gtgtccagct ttcacaaggg ctgctggcct  79980
ctcctccctc tgtctgcagc ctgtctgctg tgctgcgtgg cacgttgttt agttgaggca  80040
taggagaaaa ttcatcacta ttctgaactg gagtcagaaa aacgatctca gccatcccta  80100
aactgaggtc gggaagccac cctgggactc cactttgagg gccactgctg tgatgcccaa  80160
gtcaacgtgc ccggggctat attttcaccc tctactctgc cccaaccctc acacacccca  80220
gtgcctgctc cttccgcttt aactggccct caagttcccc tttctcatct cccacctcag  80280
cctccctgat tcatctgagg agcacagatt ttatatttat ttattaatta ttattatttt  80340
ttttctttag agggacccct gctctgtcac ccaggctgga gtgtagtggc gcgatctcgg  80400
ctcactgcaa cctctgtctc ctgggttcaa gcaattctcc tgcctcagcc tgccgagtag  80460
ctggggttac aggtgcgtgc caccgtgcct ggctaatttt tgtattttta gtagagatgg  80520
ggtttcgcca tgttggccag cctgctctca aactcctgac ctcgagtgat tcacctgcct  80580
cagcctcaca aagtgctgag attacaggtg tgagccacca cgcctggcct aaattttagt  80640
ttttaatctg aaggtatcgg gacaaggatt tttgaggaag aagtcaaggt gggatgaaat  80700
tctagtgaaa ttctagtgac ggctttcttc ttttctctaa aaacctctgc cttccttttc  80760
ttgaatgcat ttccaaagca cctgtcttcc aaggccagcc ccggtcctca gaactggagc  80820
aggtagtgtg tcagctgata gtttaggagg gtgtttttcc agctgagtag gagggagaac  80880
atcagctcac agcgcccagg gtatctctgc ctgcaccatc cactttactg gaagatgtaa  80940
ataggcggaa tggttacatt caaattttac tggcaaatga tagagctagt ggcacaattg  81000
gtgtaaattt ttttcatttt tctttttttg tttttgcaga cagttttgct ctgttgccca  81060
gtcaggagtg cagtggtgca gtcacagctc actgcagcct ggacctcctg ggctcaagca  81120
aacccccacc tccgcctctt gagtagctgg gatgacaggt acacgtcact gtgcctggct  81180
aagtttttaa aatttttttg tagagatagg gtcttgctat gttacccagg ctgatttcaa  81240
attcctaggc tcaagtgatc cacctgcctc ggcctcccaa agtgctggga tgacagccgt  81300
gagccactgc atgagcgttt tttttgtttt tttttttttt cttttgagac agggtcttgt  81360
tctgtgtcca gattggaatg cagtggtgca gtcatagctt actgaagcct cgacctcctg  81420
ggctcaagcg atcctcctgc ctcagcctcc tgggactaca gaggctgtag ctggggaccg  81480
cagaggctgt agctgggaac acaggcacac accagcacgt ccagataatt tttaaatttt  81540
ttgtagagac gaggtctcac tgtgttgtcc aggctggtct tgaactcctg ggctcaagca  81600
gtcctcccgc gttggcctcc ccaaatgctg ggatgacagg catgagccac tgtgcctagc  81660
ctgggcatga atttttcagg cgaaaatctg gagcttgcat tcatgctgat tagcagattg  81720
tccttgcaag tgtagctgtc accacagatc aatttaactt gcttaataat gccaaatgcc  81780
atataatgag aatttattct ccacttggta agaattggaa gcagtctgta tgtttagaga  81840
cagaaatttg agggtttcag agggcactgc ccaggcgtcc gggggagtgc tgtttctcag  81900
acacacacac acactgtctc tgctttttct ttcaggcaag atcatcagtt agtgctcact  81960
tattatttat ctttttccgc ttattaatac ctttcccatg atcttatgta atgtctactg  82020
tccaagagca cttcgtttaa tattctccat aaatgttttt aggtatgtat ggcacatttc  82080
ctcctggagt ttaatgctcc attcctgtat ttgtgcatta ttcacacagc tgaatgtatt  82140
cagacagggt cgccacccaa acccagagag aaacaggaat acaactcccc caactactgt  82200
tacagagaac gctgcgggca ggtgagggag gacgggctcg ggaggttgtt aacgtctgag  82260
```

-continued gcggcagggt tggcgcagat cgcatgagtg tctgtactca gagctctgct tcccagcctg 82320
gcctgggtgg tttttcagta cgttgtggtg gctcgtaact ccaggaccag cggcccaaag 82380
agataccta ttgggaaact caccttcatg ctaaagtgca aaacaagcaa ctgaaatgtt 82440
atttaagaag gaagaaatgc tgtgttaggg ccacgtcgca cgcacctaat catttacctt 82500
tctctggtaa ctttcatttc ctcatgtaac ccaccccac ttctctgtca cctctcccat 82560
tgatttccat ttttgtactt catatttctc ctctttgttt ttctttgaat ttttctccac 82620
tgcagtgtat tggacagttc atgtgtgtag ttctacgtat gaatgtcctg acgctgctgt 82680
tagaaactac cacagactga aaggtttaaa caagagaact ttatcctctc ttagtccggg 82740
agaccagaag tttgagatca aagtgtctca ggactgtact ccagggaagg atcctttctg 82800
cctctcccag ttcctggggg ctccagcatc cctgggcttg tggccacatc actgcagtct 82860
ctgcctccac cttcatgtgg ccttctcctc tatgtctctg tctcctcttc agtctcttag 82920
aaggaaggcc acctgtcatt ggatttaggg ccatcctaat ccaggacgat ctcatctcaa 82980
gatccttcaa ttaatcacat ctgcaaagac cctattgctg aataaggtct cattccaggt 83040
ctgggcatta ggacgtggac agatctttct gagggccaca gttcaatcca ctacacgtgt 83100
atccagttcc ctctggaggc tctaggggag gatactccct gcctctccca gctcctgggg 83160
gctccaggca tccctgggct tgtggccgca tcactgctgt ctctgcctct gtccccatgt 83220
ggccttctcc tctgtgtgtg tgcctcctct tgagtctctt atgaggatac ctgtcattgg 83280
atttgggcct accctgttcc aggatgatct catctgaagc tccttaattc tatctgtgaa 83340
aaccctgttt cccaataagg tcccattcac aggttgttgg ggtaagatca tggatgtatc 83400
tttttgggga cctctcattc cgtccactcc actgaatttt gttaaggtca ggaagtgatt 83460
tggaatctac aggagaatta tttttgctca tggacatttc tgataatcaa tgagggtgtc 83520
atttgaaagc tccgttttat aaggtatttc cgttgctagc atacctgaat tagaatatct 83580
taagtcaaaa gaagctaaat ggaaaacatg actttgagcc aatatgagta tctgtcctga 83640
tcaatatgag aaaatctcag aagtacaact tgtgccacgg acatgtaagt gtctagtata 83700
cacttactgg ttgatgaaat ggtttggctt tgtgtcccca cccaaatctc atgtttaaat 83760
gtaatcccca gtgttggagg tgggacctgg tgagaggtgg ttggatcatg ggagtggttt 83820
ctgacagttt agcaacattg ccctagtaca gtctcatgat agagttctca ggagatctga 83880
tggttttaaa gtgtagtact tgcccctttg ctcgctttca ctcatctgcc accatgtaaa 83940
tgtgccttgc ttccccttcg ccttccacca tgattgtaag tttcctgagg cctccccagc 84000
catgcggaac tgtgagtcaa ctcaatctct tttcttttct tttttgtttt ttgagacaga 84060
gtcttgctct gtcgcccagg ctcgagtgca gtggcgtgat ctcggctcac tgcaagctcc 84120
gcctcccggg ttcacgccat tctgctgcct cagcctcctg agtggctggg attacaggct 84180
tccgccacca cgcctggcta attttttgta tttttagtag agacagggtt tcactgtgtt 84240
agccaggatg gtctcgatct cctgacctcg tgatccgccc accttggcct cccaaagtgt 84300
tgggattaca ggcgtgagcc accgcacctg gcctaaatct tttttcttta taaattaccc 84360
agtctcaggt agttctttat agcagactga aaatggacta atacagttga cttctagatg 84420
ttcttggatt tatcttggtc tttgcagttt taagtatata tattttttta gtttgtttca 84480
catattttga acatttctag gtattagtaa agtctgctgg tttctgcagc aggactgtaa 84540
tctttttact acagtcaaca aagcatagta tgacaatctt gtttttacac atgcaccatt 84600
ttcaaggctg tatttgcatg tatttctgtc tttttcctgg tctccagggg tcaagaaatg 84660

-continued

```
gttttcttgg ggcaaagagc ttcggtcagc tttgcagact acccagtctc agttacaagt  84720
acagactctg ctcctgcacc ttaaaaagta gtcacatagt gagaccgcat ccctatagaa  84780
agtcaaaaaa ttagccagac atggtggcac acacctgtgg tccccgctac atgggagcct  84840
gaggtgggag gatggcctcc tgggggaggt caaggctaca gtgagctatg attgcaccac  84900
tgcactccag cctgggtgac agagtcaaac cctgtctcaa aacaaaagaa aaatatgata  84960
tctcaggctc tttcatttgg cctgtacaca tttattgagc acctgttgtg tgccacatac  85020
tgttccatga atgaggaata taaagaaatt cagtaatggg tgtggtggct cacatctgta  85080
gtcccattac tttggaaggc tgaagtggga ggatcacttg agcccaagcg tttgagacca  85140
gcctgggcaa catagtgaga ccttgtctct accaaaaatt aaaaaaaaaa aaaaaacaaa  85200
accctggcgt ggtggtgcag acctgtagcc ccagctgctc aggaggctga agtaggagca  85260
tagcttgagc cctggaggtg aaggctgagt gcactgagcc aggatcacgc tgcagtactc  85320
cagcctgggg gcaacagagc aagaccctgt ctcaaaaaaa aaaagtagtt cactgacatt  85380
cacttgcagt ttattgagga tgccttatag tgccgtgcaa gcaggctcag taccgggctg  85440
gacataatca ggtattgctc gtgctgtaga gtgaaggaag cctcgagaaa ggtgtcctgt  85500
tcttggccat agtggcgtat tcaccactgt aaactttatt ttaacaatta ttttatattt  85560
catttcattt atgtactcca tctctctctg tcacccaggc tggagtgcag tggcacgatc  85620
tcagctcact gcaacctctg cctctcaggt tcaagcaatt ctcctggccc agcctcctga  85680
gtagctgaga ttacaagcac cggggaccat gcccagctaa tttttgtatt tttagtagag  85740
acgggtttca ccatgttggc caggctggtc tggaactcct gacctaaagt gacctgcctg  85800
cctcagcctc tcaaagtgtt gggattgcag gcatgaccca cagcatccag cctattttat  85860
attttatttt attttgagac aaggtctcac tctgtcaccc aggctggagt gtggtggtgt  85920
gatcacagct cactgcagcc ttgacctcct gtgctcaagc gatcctcccc cctcagcctc  85980
ccaagtagct gggaccacac atatgcacca ccacactcag ctaatatata ttttttttaag  86040
actgggtttt gccatatttc ccaggcttat tttatttttt aaattgacac ataataattg  86100
tacatattca tggggtagac agtgatgctt tgatacaaag aatggagtaa tcagatcagg  86160
gtaattagca tatccatttc aattatttac catttctttg tgttaggaac attcaatatc  86220
ctctatgtat ttgaaacaat acgacatgtt attgctaatt atagtcaccc tacaagacta  86280
tagaacactg gaacatattc ctcctatctg cttgtaattt tgtatccttt aacaaacctc  86340
tccctatctc tcacttcttc ccttcccagc gtctagtatc ctctgttctt ctttatcctt  86400
tcaggagatc agcttttttt tagctttcat gtatgagtaa gcacaagtgc tgtttaatgt  86460
tcttttcctg gcttatttca cctaacataa tgtcctccag tttcatccat gttgctgcca  86520
gtcagaggat tgtattcctt ttcatggctg aatagtattc tactgtgtgt agataccacc  86580
ttttctttac ctatctgctc atctgttgat ggacatctac gctgattccc tatcttggct  86640
gttgtgaatg gtgctgtggt aaacatgggc gtgccgatgt ctctccagta tcatgacttc  86700
ctttcctttg aacagatacc tagtaatgtg atggctgggt catatgggag ttctatttct  86760
agcttttctg aggaacctcc atactcttct ctatggtggc tctactagtt tacgttccca  86820
ccaacattgc gtaagagttc ccttttggc caggcacagt ggctcacgct ggtaatccta  86880
gcactttgag agaccaagct gggtggatca cttgagccca ggacttcaag accagcctag  86940
gcaacatggt gaaacccccg ctctacaaaa aaaaatacaa aaattagctg gcatggtggc  87000
```

-continued

```
agatacctgt gatcccagct acttggaagg ctgaggcagg tagatcgctt gagcctggga  87060
ggcagaggtt gcagtgagct gagattgcac cgctgcactc cagcctggga gacagagcga  87120
gatcctgtct caaaaaaaaa aagagttccc ttttctccac atcctcacca gcatttctta  87180
tttttgtgtg tatgtgtctt tttttttttt ttttttaatt ttttttgaga cagagtttca  87240
ctcttgtttc ccaggctgaa gtgcaatggc atgatctcgg ctcactgcaa cctccacctt  87300
ccgggttcaa gtgattctcc tgcctcagcc tcccaagtag ctgggattac ggacgcgtgc  87360
caccacgcct ggctaatttt tgtattttta gtagagatgg ggtttcacca tgtcggccag  87420
actggtctca aactcctgac gtcaggttat ccacccgcct cggcctccca aagtgctggg  87480
attacagtgt ctttttgata atggccgtct taattgggtt gagatgattg acacctcatt  87540
gaggttttga tttgcatttc cctgatgatt agtgacgttg agcatttttt ttcatataca  87600
tgttggcctt ttccatgtct tcttttgaga aatgtctgtg aagaccacct gtccattttt  87660
taattggagt gcttatcttt tcgctcttga gacatttgag ttccatgctt ggtcatggtg  87720
gtggattcac cccggtaaac atgagagagc attgctgtcc agtgtttagt gcacagttaa  87780
ggaatgggct ggtggcccct caataagatg cccaaaggag ttgccttctg ctcagcagac  87840
gcctctcaaa tggtctttat attctctcca agggagcttc ccctgcatcg gactgtggca  87900
cacgatgcct tgcctcttag aaccatctga ctgtcacgtg ctttcagatc gtgacaactt  87960
cagtgtgcgg ggaagagcat gtgaaataaa ttaccttctg cctgtgtgaa gcagaaatag  88020
ctatcgttac aaagcaggga tttttttcca tgcttactcc ccactaaaaa tacatgtttg  88080
tttttctaac aggtttcctc cgtttttttga tgacaacccg tttggcattt atcagaaaat  88140
tcttgcaggc aaaatagatt tccccagaca tttggatttc catgtaaagt aagtaaaccg  88200
tttgcctcat catgaggtgt gtttattttt aaagtgtcta aaatcaccgt gaaagcacgc  88260
actcagcagg ataccatatt gtgttattaa atgtgctgcg cataaactat tttggacagt  88320
tgtcttttcc acaagaaaag aaaaagattt tcagtattct actttaatga tagcttcaca  88380
ttttaatgag tcttggccgt attgtgttct tttggtggta tgttatattt aaaatgagcc  88440
aatgaacgag tttgtcatcg tattttataa gagagcagtt ttggaatttg acaagaagga  88500
tcctcctagt tctgtggcta acagaactgt tgatgggttt agcagagttt tatcctttct  88560
ctcctgctta aattatgctc aacctctaag tcctttttaa cgtcaacatt ttcagttctg  88620
agcatgttgc ttcaaggata tttacagttg ctggatattg gcaactttgg atgcacattt  88680
tataaaggtc gtggcagtag ggaaaaaata tattattttc ttaaatataa gaacgcggct  88740
gggcgtggtg gctcatgcct gtaatcccag cactttggga ggttgaggtg ggtggaacac  88800
gaggtcagga gatcgagacc atcctgggaa acacggtgaa acctcggctc tactgaaaat  88860
ataaaaaatt agctgggtgt ggtggtgggc gcctgtagtc tcagctactt gggaggctga  88920
gacagcggaa tcgcttgaac ccaggaggcg gaggttgcag tgagctgaga tcgcaccact  88980
acattccagc ctgggcgaca gagcaagatt ctgtctcaaa aaaaaaagaa tgcttttggt  89040
tttctggcta ccttacccaa tctggtcaac tggtagccat ttttactgta ataagcactg  89100
atttctgttt gtttcactgt atttttcaga tgagttgatg ggtgcaccag ccccctgggc  89160
acaaactaga gctaaatgca tctagttgag aattaaactt tttcttttcc atggtctatt  89220
ttcttatgag ccggtggaag ttcagttcag agaagactta tttcagggcg atggagcagg  89280
ttgttttgaa tatgcccctt atggggccac tggctacgtt cagttgagtt tcttggtggt  89340
gaacgcaccc catcctaacc agaggttctt agtctgaaca gaagataagg tcgtgtttta  89400
```

-continued

```
ttggcttgag catgtgttgt gtttgacaca ctaagaggca ggctttaaaa gactttagca  89460
agaaaacgag gctccgctta acaatgagtc gcctagaagg gacaccctgt ccagtgaatg  89520
gtaagacagg gaggtgtcag gggaaacagc acctcagaag ccgactgctc tggaaggaaa  89580
tagaaaggat tatatagaac ctctctctca ggccccaaat cccatctgag ttgagtgaca  89640
ttatattaag tggatggcaa agcactttta tgatcgagtt tggccaggtg aggtgctcat  89700
gcctgtaatc ccagcacttc aggagcaatc cgaagtggga ggattgcttg gggccaatcc  89760
aatagtttga ggccagcctg gacaatgtag caagacccca tgtctacaaa aaatttaaaa  89820
attagctggg catggtagca agtgcctgta gtcccagcta ctagggaggc tgagatggga  89880
ggactgcttg agcccaggaa gtcgaggctg cagtgaccta tgattgcacc actgcactcc  89940
agactggatg aaagagtgaa actctgtgtc aagaaaagaa aaaataataa aattaaaaga  90000
tataattata tatatatatg gggggggttt ccaatgttct gtggaaacaa caacaaaaaa  90060
aggaattgca gaaatagaat aaaccagaag cgtaatcaaa gtctggtctc ttgccacttg  90120
tccttctttc tctcctagtt tatcttcttt gagagtaggg aaccagcagc gaccatcttg  90180
gtactgtctg atctaacatg cctctcttta tgcagctccc agccccttcc agtgttcccc  90240
acagtgcccc tgtttcttta catacccagt gtgggttccc caagagcaga aacagtgata  90300
gatagaagtg aactgacagt tcacttcttc ccattatttg ttaaatctta tcaaattggc  90360
tgagaagcaa gacctcaatg actcatatct ttcctttttt tggtagagat gggtatgggg  90420
atcttgctgc attgcctagg ctgcttttga actcctgggc tcaactgatc ctcctgcctt  90480
gtcctcccca agtgttggga ttacaggcgt gaaccactgc acctggcctt aatgaggcat  90540
ttttcttatc caaatcactg tccctggttg tccatgatgc tagaattttg attctctgct  90600
ttttaaagtc atatgttggt tcctgcaact tttatcattt gaccaggtaa acatgtcgcc  90660
tgggcaaatg gcacatcagg attgacattc cttatagaaa taaatatcat ttaaaacaaa  90720
acaccaaaac aaagctttgg gacttgttgc caattcagta gaggtattat ctgccggtgt  90780
tttttacaac acctgaaagt acctgcatct gagaggagcc agctggtgcc aggatcgtaa  90840
ataaaatgta gaattttggc tacagtgcat caaaagagtg ccggcagatg tgtcgcttat  90900
cccggggtca agggacccat ctacagctgt ggacacttct gtcgttcctt tatagggctt  90960
tgcatcttca ggggcctctt ctcatccata ctctttactt tctagactgc tttataagag  91020
tttgctttgg tattttactt tttcttttaa agagacgggt gtcttgctct gtcaccccgg  91080
ctggagtgca gtggcacaat catagctcac tgcagcctcg acgtcctggg ctcaaatgac  91140
actcccacct cagcctcccg agtaactggt gctacaggca tgcaccacca tgcctggcca  91200
atgttttgat attttgtaga aacgagggtc ttactatgtt gcccatgctg gtttcgaact  91260
cttggtctca cgtggtcttc ccacttcagc ccactgcata gctgggatta caagccactg  91320
tcccctgtat tttaaataaa tcttcatttt cttacatgcc aaacaccaaa aaaatttaaa  91380
aaaaaattca aggtcatcaa acattttgtt ttcttacatg acacacacac acacacacac  91440
acacacacac acacacgttg aaatttatca ggtgatcacc aaaacattct gaaataaaca  91500
tagggctttt tttccccccct ataatttaca ccactgcctg ccccattagc gtatacactt  91560
aaagctgatt ggactgggat tataagaaaa caaaggttta tctaaaatat aaaagcataa  91620
ataaacctgt cttataattg cactccagtg agctttaagt gtgtgtggta agggggcagg  91680
cagtggtgta aatcacgtgg gggacgaagc cccacattta tttgggaatg ttttggggt  91740
```

-continued

```
atagtgtttg ataaccttga ttttttttg gcagggggga gcatgtcaaa ataatgaagg  91800
agaaactcac taagtagtgg aaaggtttct aacttttagg tgatttttat attccccatc  91860
ctgctcaaag cttttcagcc ttacaggatg gatacaaaat cctagcctta ggtgggcgga  91920
cagatggtct ctgagtttta ctttgtggca gagaagcggt gaagtctgac aagcatccca  91980
tcctaattca gaaagcatgg tggcaggaaa ctgtaaaatt tccgatcaga cagcactggc  92040
gagattcaca atctagatgg tggagtctga ccctaggacg tcacctggct tgtcggagac  92100
tccacagtct gtcacagaac ctgggagtgg ctcagtccaa gttcgtgcta cttaccttgg  92160
ggcatagttt atgctgggaa agcctagacg cttacaccgg ggtcatgggt attggattgt  92220
tttgggggac ttcaatatat tatattatta tatcatatta tgtatgttat tatacataat  92280
gtactctgtg tattttatgt gtacacacag acacacatga tcatttctac ttccataaat  92340
atgcatcttt tagaactcac ctaatctcct ggaagtcttc aacatcatct ccaactaccc  92400
atcctaattg aagcagcttg ctgtttttttg ttgtcgttgt tgttgtttgt ttttgttttt  92460
ttttgagact gactctacct ctgtcaccca gactggagtg cagtggctca gtctcagctc  92520
actgcaacct tcgcctcctg ggttcaagcg gttcttgtgc ctcagcctcc caagtagctg  92580
ggaccacagt tgtgtgccag catgcccagc gaatttcttt ttcttttttt ttgtagagat  92640
ggggtttcac catgttggcc aggctggtct caaactcctc acgtcaagtg atccacccgc  92700
ctcggcctcc ccacagtgct gggattactg gtgtgagcca gtatgcccaa cctccccacc  92760
tgctgtactt ctgacatggt ctgttattta aaaggaagat tataagtgaa gaagcagact  92820
taggagactc atcctaatgt gtgtgcttat gggaaagcca gccttttaaa acaggaatcc  92880
catcaataag cagaccccca ggacagcgcg tgagtgttga tgttggtgaa agcagatgtc  92940
ttctattttg cagggacagc ctgacaggca tgtttacgtt aagtgtctgg atcctccctg  93000
caggcacata taaatttcac ccttttctac tcagaggtgt attttcttta caaagatgta  93060
atcaaccccc ttcccttagc ttcagccttg cacggggcaa cccagccttg cataggtgat  93120
ttaagagccg gtgatggtag gaaataagca ctagaaagtg ttttgccaaa gtggaaattg  93180
aactgcggtc ctcatgtcag atagatctta tctctgttgc catgctgcgt ttgctgatgt  93240
tgatatataa tctgtgtact tttttttttt ttgtctcctt ccccaacata gagacctcat  93300
taagaaactg ctcgtggttg acagaacaag gcgattagga aacatgaagg tcagtatttg  93360
atcccgtggg tattcagtgg tacccgatgt gcgtgtctgc cgtctaacac ccacattggc  93420
atgtgcaggt ataaaccaag gcttagcggt cgtatttaat cactgcccaa atttcaaatc  93480
tggtgtttta tttatttttt taaattttac ttgaaactgc caggaaagat ctatcaaatc  93540
tcggtttctg ggcccacaac gtcaaactgg gtctacaccg tatctcccct cccctcaagc  93600
aaggttaata gagcaataac aatgtataag ttattactca ttattttgtt tacttattta  93660
ttttattttt taaacagttt tacggagagt gaattcacac gccatgccat ttacccatct  93720
aaaatgtgca attcggtggc ttttagtata cacacgatta tgtacagcca cccctgtggt  93780
taatcttaga acatcttcat cagttcaaaa aaagaaaccc tgcacccttc agttatcact  93840
gtgctattct ttcatcctct cttgccctaa gccagcggtc cccgaccttt ttggcaccag  93900
gggccagttt tgtggaagac agtttttcca cagaccgcac aacctaaatc ccttagttgc  93960
gcagttcaca atagggtgtg tgctcctatg agaatctaat gccactgctg atctgacagg  94020
aggcggagct caggtgctaa tgccagccat ggggagcagc tgtcagtaca ggtgaagctt  94080
cgctcacctg cctgctgctc acctcctggt gtgcggccca ttttggttcc tcataggccg  94140
```

-continued

```
tggaccacta ccagtttgtg gcccaggggc tggggacccc taccctaagc agccactaat  94200
ctactgactt tctctgtagg gttcggtgtt ctgggctctg ctaaaaatgg aattgtacaa  94260
aatgtaagct tttgcctctg gcttctttct ctgagcacga tgtcttcaag gttcatccag  94320
gctgtagccc gtgtcagagc ttccttcctt ttcctgactg catagtattc gattgtgtgg  94380
gcagacctcg ttttgtttat ccattcatct atggatggac atctgggctg tttccacctt  94440
ttggcttttg tgaatggttc tgccatggac atgagagtag gtgttttgtg tgcgcaggtg  94500
atgattttaa aagttgtgca tcaggtatga tttccacaaa ctttttgtgt ggaggcaagt  94560
atataattga caaacagact attccttaag tagtatcata cctgatatgc gtgttttgac  94620
atccctgaat ttgacagaat tcatggactt tttgttggcc atttctagct ctggacaacc  94680
tcagagggac ttatacatgg aggaacttcc atatacgtct tgaccctgta aattacagtc  94740
tggagagaca cagtacaccg gggtgtgagg cttgaaccac ttggctctct tggggccctc  94800
tgtgtggttt acgagtctcc agtagctgcc ataagaactg accacaaact aggggcttaa  94860
acaacaggaa tttctgcttt ccccatcctg gagacgagga gtctgagatc aaggtgtctc  94920
aggcctccag aggctctagg ggaggatcat tcctgcctct cccagcccct gggggctccg  94980
ggcatccctg ggcttatggc cgcatcactc cagtctctgt ctttcttcac gtggccttct  95040
ctgtgtctgt gtctcctctt ctgtctctca gaaggatgcc tgtcattggg tttagggtca  95100
tcctaatgca ggattatctc ttctcaagag ccttccctta attacattta caaagaccct  95160
atttgcatgt agggttccat tcccaggtac tgggagtcag gacatgggca tatattttga  95220
gggccactgc ccaatgtgtg ataattgtgt ctgcttcctg ctagaggctc tagtggggga  95280
tccttcctgc ctctcccagc tcctgggggc tccaggcatc cctaggcttg tggccacacc  95340
actgcagtct ccacctccat tttcacatgg ccttctctat gtttgtgtct cctcctctgt  95400
ctcttatgag gacacctgtc actggattta gggcccaccc ttctccagga tgatgtcatc  95460
tcaagaacct taatttagtt acatctgcaa agaccctatt tccaaataaa gtgatattca  95520
caggcactgg gggataggga tgtgcacata tctttttgag ggacattgtt taccctataa  95580
cagtagtcaa gcttctgtcc tttacattat ttgcggacag caacgggata ccttcaggtc  95640
tccgaggagc ctatccagcc aggttgcacg gtgtggactc atctgtgcca cggctcttca  95700
taagattgga cgagtcctgt tttaatgcca cagccattta gaaaagagct gggtctcttg  95760
ctgggactgc agggaatcac agacgaccca tatctagaat ctgctgggaa tggcgtagtg  95820
accatcatag gtaccttcca agggggaaga acaagtttcc caatcaaagg aattggggaa  95880
aagctcacaa actcccaagc taggtcttaa agtctagtta aagcttcctg atatggagat  95940
aaactgaaag agactcaaga aaacactgac tttatatttt ttttaaatta acacatgaaa  96000
atggtattat ttagcatgta caacatgaag ttttgaaata tgtacccatt gtggaatggg  96060
tccattgagt tcattaacat atgcattacc tcacataatt accatttatt tgtggtgaga  96120
acacttaaga tctactcttt gaaaaaaatt gtttttaaga gttggggtct tgatgtgttg  96180
cccaggctgg tctcgagctc ctgagctcaa gtgatccgcc caccttggcc tcataaagtg  96240
ctaggattac aggcaagagc cactgcaccc agcaagatct actcttccag agattcttga  96300
gaatacatca ttagttatag tcaccgagct gtgcaagcca ctgactgaac ttgttcctcc  96360
tgtctctctc actttgtctc ttttgaccaa tgacttccca tctcagcccc ttcccagccc  96420
ctggtatcca ccattctact ctctgcttct atgagttcaa ctttttttaga tttcccatgt  96480
```

-continued

```
aagtgaggtc aggcggtatt tgtctatctc tacctggctt atttctctct ctctctctct  96540
cttttttttt tttttttttg agacacagca aggcggaggt tgcagtgagc caagatggcg  96600
ccatgccctc cagcctggat gatggagtga aactctgtcc attgccccgc ccccccaaaa  96660
agaacataga gtatagtaaa tagataaacc agggacatag tcatttatta tcattaccaa  96720
gtattaggtg ccgtaggtaa cgtatgtgtt agactgttac acgcctggca gcgtaacagg  96780
agggatgcat tgtcctgtgg ttacaatggc catggcgtca ctaggggata ggagttttta  96840
agatcattat aatcttacag gagcaacact gtatatgtca tccattgttg actgaagcat  96900
cattttgagg ctcatgactg tagatacaca cccacacaca cacttttttt atttttattt  96960
tttcaagaca ggatcttgct ctgtcatcca ggctggagtg cagtggtgcg atcacagctc  97020
actgcagcct tgacctcctg gcgtcaagtg atcctcccac ctccgcctcc cgagtagctg  97080
ggactcagtg catgcaccac caaggctggc taattttta tgtttttttg tagagaccag  97140
gtcttacttt gttgcccagg ttagtctcaa actcctgggt tcaagcagtc ctcctgcctc  97200
ggcctcccaa agtgctggaa tataaacgtg agccactgct cccaccccc tcacacacac  97260
tttatataac acacacacac tagtttggat actaatgtga atctcggtat atacatatac  97320
tttgtactct acatataaag tgtgtaaagt acatatgtat atgtgtatat atatatataa  97380
tacatgtgta tatattaacg tgtatgtata taagtatgtg tatatttaat gtgtatatat  97440
taacgtgtgt atgtatataa gtatgtgtat atataaatat atgtgtgtat atattaacgt  97500
gtatatgtgt ataagtatgt atatattaac gtgtgtatgt ctataagtat gtgtatatat  97560
taatgtgtgt atgtgtataa gtatgtatat atcaatctat gtgtgtatat atgtatgtgt  97620
gtgtgtatat attactatgt atgcatgtga gtatatacag acacacacat cctttagtat  97680
ccaaattaga attttatctg atggataaaa tttattttat tctcttattc acagcactct  97740
tatttattct tattcacaac attgctgaag ggaaaactca acagctattg tttgttgcct  97800
gacttagcta tagatcaaaa atacctgttt tgcaataaga aaagaaaaag ttgtcaaaac  97860
aactggatgg gaaaacaata gaaaaaattc acattactgt ttccttttga agatatggtc  97920
gtggacgtat tcctctttaa ggataagaaa tttgaaacta cagtaatgct aactgataga  97980
cgcgttaaat tcagatgtac tggcttctgt ttcatggaac ctacgtttat ttcttctgct  98040
gtcccacatt taattgataa cgacatcact acaagtataa gaaaaggaag cagagtgagg  98100
tttacggatg agcacttggg agggatttca gaggtcgtga tggccacagt gtgagccagc  98160
gatgcctggt gctacccttg agcatgaagc aggccgactt gaacgcacct tgttaattgc  98220
caggccgtgc aatgtcgttc ctaaggtctc ttaaactgga catccttggt ttgagttccc  98280
agtcttgtta tttacttgct gggtcctacg gagcaaatta acatcattcc ttgaacccta  98340
gtttctatgt ctgtaaaata ctgagtaagt ttgccaagat gaaaacagga gacaaactga  98400
gaaactactg gctgtccaat tttatgtcga gagatggaat cgtatttacc tttttcgtct  98460
ttggtccgga atgcaaatgc attgcacagg agcagaatga ctggatttgt ttctgcggca  98520
aaaaagggca aacaaaacac taacagcttt gcttgcaggt tttcctggca gctcaccctc  98580
caggcacagt tctccaaaat gcagcaaact tggtctgttt gtttcaatac taaaataatg  98640
tagagattct ttggggtatt tttctttcct gccctgtcaa aattctgtac gctgacgaca  98700
tgtgttgttt cttttgaaga acggggcgaa tgatgtgaag catcatcggt ggttccgctc  98760
cgtggactgg gaagctgttc cgcagagaaa actgaaggta caacacatat cagtgggtga  98820
ctcagtatgc ccgagctctt ccattagcag ggactgcctc tgaatcctgg gacttcttta  98880
```

-continued

```
ttgatggctg acatgtgatt aatttatata atacaactat ttgtctaaaa ctgttcataa  98940
gccaagttcc ccactctttg agtgtcttag tgctaaccat ctacctagct cccacaaagg  99000
caggagccac cacacccagt catataccac atgttctttg tccattcatc cctggatgga  99060
cacttatccc agattttgaa gcagatttta ggagacctgg cctgattcct gactagctct  99120
gtgactgcta aaccctactc cctcctcttt agtggaaagc ggtcaacagg attacagaga  99180
taagcaagcg tctagcacca tggtcatcat tcagtgatgg tggtgtatta catggagaat  99240
attctttgga acgtttctgg ccaaactgcc tatttttaaa catctggctt tttggctggg  99300
tgctgtggct cacgcctata attccagtac tttgagaggc caactcaggc agatcactgg  99360
aacccacgag tttgagacta gcctgggcaa tatggtgaaa tcccgcctct acagaaaata  99420
ccaaaattag ccaggcgtgg tggcatatgc ttgtggtacc agctacttgg gaggctgagg  99480
cacaagaatt gcttgatacc aggaggcgga ggttgcagtg agccaagatt atgccactgc  99540
actccagcct gggcgacaga gccagaccct gtctcaaaaa aaaaaaaaaa aaaaaaaaaa  99600
tctggcattt ttttcaatgt ataatacttg tccattttat aaatgaggag actgtgctca  99660
gagaagttaa gcaatgtgtg gaaggttaca cagctgctaa gcagtgtaac tatcacaggt  99720
acatatttat gggggtacat gttatatttt gacacacgca tagaatgtgt aatgatcaac  99780
tgagggtaac cagggtatcc atcagctcaa acatttatca tttttatggg ttgggaatat  99840
tgcaaatcta gctattctga aatatacaat atattgttaa ctctgcccac ccaactatgc  99900
tgtcaaacac tggaacttat tccttttatc taacattatg tttatgcaat atttcttcat  99960
ctccccttca tcccctagct atacacactt cccaccctct ggtaactatc attctactct 100020
caaccttcat gacatccatt tttttagctc ccacatatga gtgggaacac gctgtgtttc 100080
tcattctgcg tctggcttag tttattattt attatttatt ttttgagaca gcgtcttgct 100140
ctgttgccca ggctggagtg cagtggcacg atcttgctca ctgcagcctc cacctcctgg 100200
cttcaagcag ttctcatgcc tcagcccccct gagtagctgg gattacagac gcccagctaa 100260
tttttgtatt tttactagag acggggtttc accatgttgg ccaggctggt ctcaatctcc 100320
taacctcaag tgatccacca gcctcagtct cccaaagaag tgctgggatt acaggcatga 100380
gccgctgcac ccggcctggc ttagtttact taacatgatg gtctcccatt ccattcgtgg 100440
tgctataaat gacaggattt cattccattt tatggccgga tagtttttca ttgtgtgtat 100500
ggaccacact ttctttatcc tttcatccat tggtggacac ttaggttgat tccatatctt 100560
ggcttttgtg aacactctga actgcatatg ttactgatgg gagtggtcaa tggtagtgtt 100620
ttcacctttg cacttcagag ttaaaagaat ggagaatgct tagaaatgct tattcctagt 100680
cctcagctca gaccagagtt tctggggctg gagcctggga tgatacgctt cttttttttt 100740
tttttttttt tttttttgag atggagtctc actttgtcgc tcaggctcgg ggtgtagtgc 100800
agtggagtga tctcaactca ctgcaacctc cacctcttgg attcaagtga ttcttctgcc 100860
tcagcctccc aagtagctgg gattacaggt gtgcgccacc acatccagct aatttttttg 100920
tgtgttttta gaagagatgg ggtttcacta tgttggccag gctggtttcg aactcatgac 100980
ctcaaatgat ccactctcct cggcctccca aagtgctggg attacaggtg tcagccactg 101040
ggcctgggct gatgcatcat tttgttcaaa gttttacctt ttcaaatact ttattgtatt 101100
aaattgcatt aaaaaaacaa tttgaatacg ttttatctat ccacattggt caaaaaccaa 101160
gtcaatatta aaacagatat attgccaagt ctccctctta ccccctccaa gccacctgta 101220
```

-continued

```
ggtaatcacc ttttattgtt tttctgtgta tccttctaga gtttctttgt gctaataaaa 101280
acccacatgg atacatgcat tcttattttt gccactcatt tatacaaatc tagagtagcg 101340
tagtatgtac attattatag tcttgctttt tgcacttgac tatataatct ggagacctgt 101400
ctacatacct ggctagcttc ctcatttttt tttttttttt tttttttttt tttttttttt 101460
tgagacgaag tcttgctccg ttgcccaggc tggagttcag tggtgcgatc tcggctcact 101520
gcaacctccg cctcccaggt tcaagcgatt ctcctgcctc agcctcccaa gtagctggga 101580
ttacaggcac ccaccactat gcccggctaa tttttgtctt ttcggtagag acagggtttc 101640
tccatgggcc aggctgttct cgaactcctg acctcagatg atcctcccac cttggcctcc 101700
caaagtgctg ggattacagg catgagccac tgcgcctagc cagcttcctc attttaaaaa 101760
atactgcatt gtattccatc acatgactgt accatagctt acttaatact atatatatat 101820
attttgagac aggatctcac tcagtcattc aggctggaat gcagtggtgc aatcatggct 101880
cacttggagt atcgacctcc tgggctcaag cagttctccc acctcagcct actgagtagc 101940
tgagactgca ggcacacagc accacacccg gctagttgta ttttttgtag agacagggga 102000
ctccctgtgt tccccaggct ggtctcaaac ttctgaggct caagcaaccc tcccgcctca 102060
ccttcttaaa gtgttgggat tacaggtgtg agtccccaca cgcagcctca ttcacaatat 102120
tttaattcaa agattgccgc tttcataaat gaagggaaga cagctttagt gttttgcaaa 102180
tcattttcat ttttaggtac agtgacagaa ataaagcggt gtgtgcagca tccaagtgtc 102240
ccgtcccttt ctaaccatgc ctttgtgctt cggccatgtc tcacagcctc ccatcgtgcc 102300
caagatagct ggtgacggcg acacttccaa cttcgaaact taccctgaga atgactggga 102360
cacagccgcg cccgtgccgc agaaggattt agaaatcttc aagaatttct gaggacagga 102420
gctcacatct ggaaggtata tctttatatt tagtaattcc caaaaaatga gactgactcg 102480
accccacatc caggtgaggc tgcgtttact gagtggggct taacctcatg cacacagagg 102540
tcagcagtga agcagagcaa aggggattga ttgcaagggt cagcgaaata aacacagcca 102600
tgcctgtgac tccaggtcag catgtgaccg tcagaggcat cagcatgaca gtccagaatc 102660
catgttctgc atcagaacct gcatgtctaa ataagaccgc taggtggttt gtgtgtgcct 102720
gaatatttga gaagcccagc tcctctggtc cctgttccag aaaccctgag tgacaggcga 102780
gcttccttag aataattaac aagtattttc aaaagtctct ttaggtctcc tttggttaaa 102840
aaataagaag aagaaatatg ccctcatagg aaatttgcta agcttaattg aagatgactg 102900
gaaaaggatt ttgagtctat tacttctttg agcctttgaa ggtctattat tagtttttaa 102960
ataataataa tattttttag aatccctcat gaaatttgct aagctttaat ttaagatgac 103020
tgaaaaaggg ttttgactgt gttatttcct tgagcctttg aaaatctatt attagttttt 103080
aagtatggat taaaaagagc tttcagttac tcctcaattc taaattgctc ggttatatgg 103140
cttcaattag atctttcttc ctgtaacaca cgagcaagaa acataccagt gaagcaaaat 103200
attgtcagtg atgtgtctat tcattgacat agcttgtttt tcccattttg atttccattc 103260
ccgtaatttt cctgtagtct tcccagttat gtgaagtgga aagccaattg gctaaccaac 103320
accattcgaa acagacacca aatgtcacaa ttgctgactg gggagaggaa ccaacctgct 103380
gaaagacgtg gtgaatgaga gccctccatc ctgggcaggt gtttacatgg atgtaccaag 103440
aggaaagctg gatacaaatt gaaataatag acaacaaaat gatagaggaa taggtggcta 103500
tgacctcgag aagataacct gtctccatgg catggcttca cctctcagtg tgtgatgaac 103560
gctttcacag tggtgactgg tttgtattaa catgagagcg tgtaacttta ccaacttcat 103620
```

-continued

```
aaacgctcat gaaatccagt tgcgggtttt aaaaatcata agatgttcct gaatgtgttt 103680

acttcttttt gtttctctgc tctactctgg ggcttacatt ttagctgact cgcccataac 103740

atcttacaaa ttgtgtctct ccaggaaatc tttaaaatga tgtaaagact tggtttgctt 103800

tagtatgaag gacccctagt tgataagcca caaaaataga acctttctct aatagagacc 103860

cctcaattgt aaaatttact taaagaacaa aaaagcttcc atttgatgga tttttgtcat 103920

ataatcagtg aacaatttca ttacatcctg tccccagctg cccctacttt ccctgaaaaa 103980

gattccacac gtaggaataa cctttctcca tctggtatgc attgttgaga aagtatgtgt 104040

aagtaagtat tatttttgct aagtggaatc atttttaata tagtttggct agtggttggg 104100

gctctgttta atgaattttt ttttcttttt gagacagagt ctcgctcggt tgcccaggct 104160

ggattgcagt ggtgcgatct cagctcactg caacctccgc ctcctgggtt caagtgattc 104220

tcctgcctca gcctcccgag tagctgggat tacaggtgcc tgccaccaca ccaggctaat 104280

tgttttgtat ttttagtaga gatgggtttt gccatgttgg ccaggctggt cttgaactcc 104340

tgaactcagg caatctgccc acctcggcct cccaaagtgc tgggattaca ggcatgagcc 104400

actgtgcctg gcccagatgc aatattttaa tccgtcttag taattttatc aagtaatttg 104460

cacaccaaac acatccctgg cattttcagc aacgagcgat tagttgcagg aattttatgc 104520

aggaagatat ttcttcatga agccaaatct tctcctgtaa ataagacacc agttcagatg 104580

aatcactgca cttgagggca gcttagaaac tatgctgtag ccgttcatct ttgtttgaat 104640

caccctgtat gcctttctga atgtggagga ggaatttaag agaactgact cactatgtct 104700

tttattttac tttgtaataa aatattttct gtcttgctgt aaggttctct gaggaagcat 104760

gttgaattgg ggatcccatt tttcttgtgc agttcatcat ctattggtgg atacatttat 104820

ctatttatgg ataagcgtat gatagaacat tcttcaggct ggatgtggtg gctcctacct 104880

gtaatcccgg cactttggga ggccgagttg ggaggctcac ttgaggtcag gagtttgaga 104940

tcaagcctgg gcaacatagt gagaccccat ctctacaaaa aataaaaaag ttagccaggc 105000

gtagtgatac atacctattg tcacagctat tctagaggct gaggtgagag gctcgcttgg 105060

gcctggaaag ttgaggctgc agtgagccgt gattgtgcct gtactccggc ctggatggca 105120

gagttagacc tcatctcaaa aatgaaaaca gggctgggcg aggtggctca tgcctgtaat 105180

cccagcacct tgggaggccg aggcgcatgg atcatctgag gtcaggagtt cgagaccagc 105240

ctggcaaaca tggtgaaatc ccatctctac caaaaataca aaaattaccc aggcgtggtg 105300

gcgggcacct gtaaccccag ctactcagga ggctgaggta ggagaatcac ttgaacatgg 105360

aggcggaggt tgcagtgagc tgagatcaca ccactgtact ccagcctggg caa        105413
```

```
<210> SEQ ID NO 4
<211> LENGTH: 358
<212> TYPE: PRT
<213> ORGANISM: Homo sapiens

<400> SEQUENCE: 4

Met Glu Ala Pro Gly Leu Ala Gln Ala Ala Ala Ala Glu Ser Asp Ser
 1               5                  10                  15

Arg Lys Val Ala Glu Glu Thr Pro Asp Gly Ala Pro Ala Leu Cys Pro
            20                  25                  30

Ser Pro Glu Ala Leu Ser Pro Glu Pro Pro Val Tyr Ser Leu Gln Asp
        35                  40                  45

Phe Asp Thr Leu Ala Thr Val Gly Thr Gly Thr Phe Gly Arg Val His
```

```
    50                  55                  60

Leu Val Lys Glu Lys Thr Ala Lys His Phe Phe Ala Leu Lys Val Met
65                  70                  75                  80

Ser Ile Pro Asp Val Ile Arg Leu Lys Gln Glu Gln His Val His Asn
                85                  90                  95

Glu Lys Ser Val Leu Lys Glu Val Ser His Pro Phe Leu Ile Arg Leu
            100                 105                 110

Phe Trp Thr Trp His Asp Glu Arg Phe Leu Tyr Met Leu Met Glu Tyr
        115                 120                 125

Val Pro Gly Gly Glu Leu Phe Ser Tyr Leu Arg Asn Arg Gly Arg Phe
    130                 135                 140

Ser Ser Thr Thr Gly Leu Phe Tyr Ser Ala Glu Ile Ile Cys Ala Ile
145                 150                 155                 160

Glu Tyr Leu His Ser Lys Glu Ile Val Tyr Arg Asp Leu Lys Pro Glu
                165                 170                 175

Asn Ile Leu Leu Asp Arg Asp Gly His Ile Lys Leu Thr Asp Phe Gly
            180                 185                 190

Phe Ala Lys Lys Leu Val Asp Arg Thr Trp Thr Leu Cys Gly Thr Pro
        195                 200                 205

Glu Tyr Leu Ala Pro Glu Val Ile Gln Ser Lys Gly His Gly Arg Ala
    210                 215                 220

Val Asp Trp Trp Ala Leu Gly Ile Leu Ile Phe Glu Met Leu Ser Gly
225                 230                 235                 240

Phe Pro Pro Phe Phe Asp Asp Asn Pro Phe Gly Ile Tyr Gln Lys Ile
                245                 250                 255

Leu Ala Gly Lys Ile Asp Phe Pro Arg His Leu Asp Phe His Val Lys
            260                 265                 270

Asp Leu Ile Lys Lys Leu Leu Val Val Asp Arg Thr Arg Arg Leu Gly
        275                 280                 285

Asn Met Lys Asn Gly Ala Asn Asp Val Lys His His Arg Trp Phe Arg
    290                 295                 300

Ser Val Asp Trp Glu Ala Val Pro Gln Arg Lys Leu Lys Pro Pro Ile
305                 310                 315                 320

Val Pro Lys Ile Ala Gly Asp Gly Asp Thr Ser Asn Phe Glu Thr Tyr
                325                 330                 335

Pro Glu Asn Asp Trp Asp Thr Ala Ala Pro Val Pro Gln Lys Asp Leu
            340                 345                 350

Glu Ile Phe Lys Asn Phe
        355
```

<210> SEQ ID NO 5
<211> LENGTH: 945
<212> TYPE: DNA
<213> ORGANISM: Homo sapiens

<400> SEQUENCE: 5

```
ggagagcgac tcccgcaagg tggcggagga gacccccgac ggggcgcccg cgctctgccc      60

cagccctgag gcgctgtcgc cggagccgcc tgtgtacagc ctgcaggact ttgacacgct     120

ggccaccgtg ggcactggga cgttcgggcg ggtgcacctg gtgaaggaga agacagccaa     180

gcatttcttc gccctcaagg tgatgagcat tcccgacgtc atccgcctaa agcaggagca     240

acacgtacac aatgagaagt ctgtcctgaa ggaagtcagc cacccgttcc tcatcaggct     300

gttctggacg tggcatgacg agcgcttcct ctacatgctc atggagtacg tgccgggcgg     360
```

-continued

```
cgagctcttc agctacctgc gcaaccgggg gcgcttctcc agcaccacgg ggctcttcta    420

ctctgcagag atcatctgtg ccatcgagta cctgcactcc aaagagatcg tctacaggga    480

cttgaagcca gagaacatcc tgctggatag ggatggccac attaagctca cggactttgg    540

gttcgccaag aagctggtag acaggtttcc tccgtttttt gatgacaacc cgtttggcat    600

ttatcagaaa attcttgcag gcaaaataga tttccccaga catttggatt tccatgtaaa    660

agacctcatt aagaaactgc tcgtggttga cagaacaagg cgattaggaa acatgaagaa    720

cggggcgaat gatgtgaagc atcatcggtg gttccgctcc gtggactggg aagctgttcc    780

gcagagaaaa ctgaagcctc ccatcgtgcc caagatagct ggtgacggcg acacttccaa    840

cttcgaaact taccctgaga atgactggga cacagccgcg cccgtgccgc agaaggattt    900

agaaatcttc aagaatttct gaggacagga gctcacatct ggaag                   945
```

```
<210> SEQ ID NO 6
<211> LENGTH: 944
<212> TYPE: DNA
<213> ORGANISM: Homo sapiens

<400> SEQUENCE: 6

ggagagcgac tcccgcaagg tggcggagga gacccccgac ggtcgcccgc gtctgcccca     60

gccctgagcg ctgtcgcgga tgccgcctgc gtacagcctg caggactttg acacgctggc    120

caccgtgggc actgggacgt tcgggcgggt gcacctggtg aaggagaaga cagccaagca    180

tttcttcgcc ctcaaggtga tgagcattcc cgacgtcatc cgcctaaagc aggagcaaca    240

cgtacacaat gagaagtctg tcctgaagga agtcagccac ccgttcctca tcaggctgtt    300

ctggacgtgg catgacgagc gcttcctcta catgctcatg gagtacgtgc cgggcggcga    360

gctcttcagc tacctgcgca accgggggcg cttctccagc accacggggc tcttctactc    420

tgcagagatc atctgtgcca tcgagtacct gcactccaaa gagatcgtct acagggactt    480

gaagccagag aacatcctgc tggataggga tggccacatt aagctcacgg actttgggtt    540

cgccaagaag ctggtagaca ggtttcctcc gtttttgat gacaacccgt ttggcattta    600

tcagaaaatt ckt gcaggca aaatagatkt ccccagacat ttggatttcc atgtaaaaga    660

cctcattaag aaactgctcg tggttgacag aacaaggcga ttaggaaaca tgaagaacgg    720

ggcgaatgat gtgacagcat catcggtggt tccgctccgt ggactgggaa gctgttccgc    780

agagaaaact gaagcctccc atcgtgccca agatagctgg tgacggcgac acttccaact    840

tcgaaactta ccctgagaat gactgggaca cagccgcgcc cgtgccgcag aaggacttta    900

caaatcttca agaatttctg aggacaggag ctcacatctg gaag                   944
```

```
<210> SEQ ID NO 7
<211> LENGTH: 556
<212> TYPE: DNA
<213> ORGANISM: Homo sapiens

<400> SEQUENCE: 7

tctgccccag ccctgaggcg ctgtcgccgg agccgcctgt gtacagcctg caggactttg     60

acacgctggc caccgtgggc actgggacgt tcgggcgggt gcacctggtg aaggagaaga    120

cagccaagca tttcttcgcc ctcaaggtga tgagcattcc cgacgtcatc cgcctaaagc    180

aggagcaaca cgtacacaat gagaagtctg tcctgaagga agtcagccac ccgttcctca    240

tcaggctgtt ctggacgtgg catgacgagc gcttcctcta catgctcatg gagtacgtgc    300

cgggcggcga gctcttcagc tacctgcgca accgggggcg cttctccagc accacggggc    360
```

-continued

```
tcttctactc tgcagagatc atctgtgcca tcgagtacct gcactccaaa gagatcgtct    420

acagggactt gaagccagag aacatcctgc tggataggga tggccacatt aagctcacgg    480

actttgggtt cgccaagaag ctggtagaca ggtttcctcc gttttttgat gacaacccgt    540

ttggcattta tcagaa                                                    556


<210> SEQ ID NO 8
<211> LENGTH: 555
<212> TYPE: DNA
<213> ORGANISM: Homo sapiens

<400> SEQUENCE: 8

tctgccccag ccctgagcgc tgtcgcggat gccgcctgcg tacagcctgc aggactttga     60

cacgctggcc accgtgggca ctgggacgtt cgggcgggtg cacctggtga aggagaagac    120

agccaagcat ttcttcgccc tcaaggtgat gagcattccc gacgtcatcc gcctaaagca    180

ggagcaacac gtacacaatg agaagtctgt cctgaaggaa gtcagccacc cgttcctcat    240

caggctgttc tggacgtggc atgacgagcg cttcctctac atgctcatgg agtacgtgcc    300

gggcggcgag ctcttcagct acctgcgcaa ccgggggcgc ttctccagca ccacggggct    360

cttctactct gcagagatca tctgtgccat cgagtacctg cactccaaag agatcgtcta    420

cagggacttg aagccagaga acatcctgct ggatagggat ggccacatta agctcacgga    480

ctttgggttc gccaagaagc tggtagacag gtttcctccg tttttgatg acaacccgtt     540

tggcatttat cagaa                                                     555
```